United States Patent
Anandan et al.

(10) Patent No.: US 7,772,245 B2
(45) Date of Patent: Aug. 10, 2010

(54) INHIBITORS OF HISTONE DEACETYLASE

(75) Inventors: Sampath K. Anandan, Fremont, CA (US); Xiao-Yi Xiao, San Diego, CA (US); John S. Ward, Redwood City, CA (US); Dinesh V. Patel, Fremont, CA (US)

(73) Assignee: Miikana Therapeutics, Inc., Rockville, MD (US)

( * ) Notice: Subject to any disclaimer, the term of this patent is extended or adjusted under 35 U.S.C. 154(b) by 1096 days.

(21) Appl. No.: 11/354,594

(22) Filed: Feb. 14, 2006

(65) Prior Publication Data

US 2006/0199829 A1    Sep. 7, 2006

Related U.S. Application Data

(60) Provisional application No. 60/652,870, filed on Feb. 14, 2005.

(51) Int. Cl.
*A61K 31/506* (2006.01)
*C07D 471/02* (2006.01)

(52) U.S. Cl. ........... 514/275; 514/232.8; 514/269; 544/126; 544/333

(58) Field of Classification Search ........... 514/232.8, 514/269, 275; 544/126, 333
See application file for complete search history.

(56) References Cited

U.S. PATENT DOCUMENTS

| | | | |
|---|---|---|---|
| 5,700,811 A | 12/1997 | Breslow et al. | |
| 5,925,672 A | 7/1999 | Piomelli et al. | |
| 5,993,845 A | 11/1999 | Geerts et al. | |
| 6,087,367 A | 7/2000 | Breslow et al. | |
| 6,124,495 A | 9/2000 | Neiss et al. | |
| 6,541,661 B1 | 4/2003 | Delorme et al. | |
| 6,552,065 B2 | 4/2003 | Remiszewski et al. | |
| 6,706,686 B2 | 3/2004 | Long et al. | |
| 7,345,043 B2 | 3/2008 | Anandan et al. | |
| 2003/0082666 A1 | 5/2003 | Kammer et al. | |
| 2003/0206946 A1 | 11/2003 | Chung | |
| 2003/0235588 A1 | 12/2003 | Richon et al. | |
| 2004/0029903 A1 | 2/2004 | Lan-Hargest et al. | |
| 2004/0058868 A1 | 3/2004 | James et al. | |
| 2004/0077591 A1 | 4/2004 | Dangond | |
| 2004/0087657 A1 | 5/2004 | Richon et al. | |
| 2004/0092431 A1 | 5/2004 | Hellberg | |
| 2004/0092558 A1 | 5/2004 | Klimko et al. | |
| 2004/0167184 A1 | 8/2004 | Wiech et al. | |
| 2005/0137232 A1 | 6/2005 | Bressi et al. | |
| 2005/0197336 A1 | 9/2005 | Anandan et al. | |
| 2005/0234033 A1 | 10/2005 | Anandan et al. | |
| 2005/0250784 A1 | 11/2005 | Anandan et al. | |

FOREIGN PATENT DOCUMENTS

| | | |
|---|---|---|
| EP | 0 827 743 A1 | 3/1998 |
| EP | 0827742 | 3/1998 |
| WO | WO 01/38322 | 5/2001 |
| WO | WO 02/051842 A1 | 7/2002 |
| WO | WO 01/024482 | 3/2003 |
| WO | WO 03/076422 | 8/2003 |
| WO | WO 03/075929 | 9/2003 |
| WO | WO 03/075929 A1 | 9/2003 |
| WO | WO 03/076395 A1 | 9/2003 |
| WO | WO 03/087066 A1 | 10/2003 |
| WO | WO 2004/013130 | 2/2004 |
| WO | WO 2004/063169 A1 | 7/2004 |
| WO | WO 2004/082638 | 9/2004 |
| WO | WO 2004/092115 | 10/2004 |
| WO | WO 2004/113336 A1 | 12/2004 |

OTHER PUBLICATIONS

Yoshida et al. "Histone deacetylase . . ." Cancer Chem. Pharm. v. 48, p. 520-526 (2001).*
Bouchain et al. "Novel hydroxamate and . . ." Current Medicinal Chem. v.10, p. 2359-2372 (2003).*
Miller et al. "histone deacetylase . . ." J. Med. chem. v.46(24) p. 5097-5116 (2003).*
Marks et al. "Histone Deacetylases and Cancer: Causes and Therapies" *Nature Reviews: Cancer* 1:194-202 (2001).
Finnin et al. "Structures of a histone deacetylase homologue bound to the TSA and SAHA inhibitors" *Nature* 401:188-193 (1999).
McLaughlin et al. "Histone Deacetylase Inhibitors in Psoriasis Therapy" *Current Drug Targets—Inflammation & Allergy* 3:213-219 (2004).
Office Action—U.S. Appl. No. 11/075,603, pp. 1-11, Jun. 16, 2008.
Bertino et al., Principles of Cancer Therapy, 21st Edition, *Oncology XIV* Vol/Iss: 21st Ed, vol. 1, pp. 1060-1074, Jan. 1, 2000.
Krontiris, Chapter 71: Molecular and Cellular Biology of Cancer, *Internal Medicine* Vol/Iss: 4th Ed., pp. 699-729, Jan. 1, 1994.
Carey et al., Histone Deacetylase Inhibitors: Gathering Pace, *Current Opinion in Pharmacology* Vol/Iss: 6 (4), pp. 369-375, 2006.
U.S. Appl. No. 11/075,603—Office Action, *U.S. Patent & Trademark Office* pp. 1-11, Mar. 19, 2009.

(Continued)

*Primary Examiner*—Celia Chang
(74) *Attorney, Agent, or Firm*—Sima Singadia Kulkarni; Zara A. Doddridge; Johnson & Associates

(57) ABSTRACT

Disclosed are compounds of formula I that inhibit histone deacetylase (HDAC) enzymatic activity, pharmaceutical compositions comprising such compounds, as well as methods to treat conditions, particularly proliferative conditions, mediated at least in part by HDAC, wherein A, W, $W^1$, $W^2$, $Ar^2$, and G are described herein.

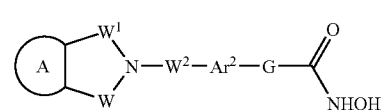

8 Claims, No Drawings

OTHER PUBLICATIONS

Banker et al., *Modern Pharmaceutics* Vol/Iss. 3rd Ed., pp. 596, 1996.
Hamada et al., An Improved Synthesis of Arylsulfonyl Chlorides from Aryl Halides, *Synthesis-Communication* pp. 852-854, 1986.
Huang et al., Design, Synthesis and Structure-Activity Relationships of Benzoxazinone-Based Factor Xa Inhibitors, *Bioorganic and Medicinal Chemistry Letters* Vol/Iss: 13, pp. 561-566, 2003.
Morimoto et al., Potent and Selective ET-A Antagonists. 2. Discovery and Evaluation of Potent and Water Soluble N-(6-(2-(Aryl-loxyl)ethoxyl)-4-pyrimidinyl)sulfonamide Derivatives, *J. Med. Chem.*, Vol/Iss: 44, pp. 3369-3377, 2001.
Wolff, M., *Burger's Medicinal Chemistry* Vol/Iss: 5th ed., Part 1, pp. 975-977, 1995.

* cited by examiner

INHIBITORS OF HISTONE DEACETYLASE

CROSS-REFERENCE TO RELATED APPLICATION

This application claims the benefit under 35 U.S.C. 119(e) to co-pending provisional application U.S. Ser. No. 60/652,870 filed on Feb. 14, 2005, which is incorporated herein by reference in its entirety.

BACKGROUND OF THE INVENTION

1. Field of the Invention

This invention relates to compounds which inhibit histone deacetylase (HDAC) enzymatic activity. This invention is also directed to pharmaceutical compositions comprising such compounds as well as to their use to treat conditions, particularly proliferative conditions, mediated at least in part by HDAC.

2. References

The following publications are cited in this application as superscript numbers:

[1] Marks, et al., Nature Reviews: Cancer 1:194-202 (2001)
[2] Finnin, et al., Nature, 401:188-193 (1999)
[3] Geerts, et al., European Patent Application Publication No. 0 827 742, published Mar. 11, 1998

All of the above publications are incorporated herein by reference in their entirety to the same extent as if each individual publication, patent or patent application was specifically and individually indicated to be incorporated by reference in its entirety.

3. State of the Art

In all eukaryotic cells, genomic DNA in chromatin associates with histones to form nucleosomes. Each nucleosome consists of a protein octamer made up of two copies of each histone: H2A, H2B, H3 and H4. DNA winds around this protein core, with the basic amino acids of the histones interacting with the negatively charged phosphate groups of the DNA. The most common posttranslational modification of these core histones is the reversible acetylation of the ε-amino groups of conserved highly basic N-terminal lysine residues. The steady state of histone acetylation is established by the dynamic equilibrium between competing histone acetyltransferase(s) and histone deacetylase(s) herein referred to as HDAC. Histone acetylation and deacetylation has long been linked to transcriptional control. The recent cloning of the genes encoding different histone acetyltransferases and histone deacetylases provides a possible explanation for the relationship between histone acetylation and transcriptional control. The reversible acetylation of histones can result in chromatin remodeling and as such act as a control mechanism for gene transcription. In general, hyperacetylation of histones facilitates gene expression, whereas histone deacetylation is correlated with transcriptional repression. Histone acetyltransferases were shown to act as transcriptional coactivators, whereas deacetylases were found to belong to transcriptional repression pathways.

The dynamic equilibrium between histone acetylation and deacetylation is essential for normal cell growth. Inhibition of histone deacetylation results in cell cycle arrest, cellular differentiation, apoptosis and reversal of the transformed phenotype. Therefore, HDAC inhibitors can have great therapeutic potential in the treatment of cell proliferative diseases or conditions.[1]

The study of inhibitors of histone deacetylases (HDAC) indicates that indeed these enzymes play an important role in cell proliferation and differentiation. The inhibitor Trichostatin A (TSA) causes cell cycle arrest at both the G1 and G2 phases, reverts the transformed phenotype of different cell lines, and induces differentiation of Friend leukemia cells and others. TSA and sub-roylanilide hydroxamic acid (SAHA) have been reported to inhibit cell growth, induce terminal differentiation, and prevent formation of tumors in mice.[2]

Trichostatin A has also been reported to be useful in the treatment of fibrosis, e.g., liver fibrosis and liver chirrhosis.[3]

In view of the above, there is an ongoing need for inhibitors/antagonists of HDAC.

SUMMARY OF THE INVENTION

This invention is directed to compounds, compositions, and methods for treating diseases mediated, at least in part, by histone deacetylases.

Specifically, this invention is directed to compounds, stereoisomers, tautomers, or pharmaceutically acceptable salts of formula I and the related compositions and methods:

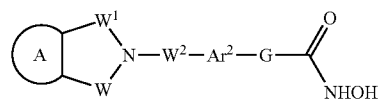

wherein:

is $Ar^1$ which is selected from the group consisting of substituted 1,2-fused aryl, 1,2-fused heteroaryl, substituted 1,2-fused heteroaryl, 1,2-fused heterocyclic; and substituted 1,2-fused heterocyclic;

$Ar^1$ is fused to the ring containing $W^1$ and W;

W and $W^1$ are independently $[-C(R^1)(R^2)-]_m$;

$W^2$ is a bond or $[-C(R^1)(R^2)-]_p$;

$R^1$ and $R^2$ are independently selected from the group consisting of hydrogen, alkyl, substituted alkyl, aryl, substituted aryl, heteroaryl, substituted heteroaryl, heterocyclic, and substituted heterocyclic;

each m is independently 1 or 2; and p is 1, 2, 3, or 4;

$Ar^2$ is selected from the group consisting of arylene, substituted arylene, heteroarylene, and substituted heteroarylene; and G is selected from the group consisting of a bond, alkylene, substituted alkylene, alkenylene, substituted alkenylene, alkynylene, and substituted alkynylene;

provided that when $Ar^2$ is arylene or substituted arylene, then G is not alkenylene or substituted alkenylene.

DETAILED DESCRIPTION

Throughout this application, the text refers to various embodiments of the present compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

In one embodiment, the invention provides a compound of formula I, a stereoisomer, tautomer, prodrug, or pharmaceutically acceptable salt thereof:

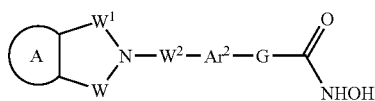

I wherein:

is $Ar^1$ which is selected from the group consisting of substituted 1,2-fused aryl, 1,2-fused heteroaryl, substituted 1,2-fused heteroaryl, 1,2-fused heterocyclic, and substituted 1,2-fused heterocyclic;

$Ar^1$ is fused to the ring containing $W^1$ and W;

W and $W^1$ are independently $[-C(R^1)(R^2)-]_m$;

$W^2$ is a bond or $[-C(R^1)(R^2)-]_p$;

$R^1$ and $R^2$ are independently selected from the group consisting of hydrogen, alkyl, substituted alkyl, aryl, substituted aryl, heteroaryl, substituted heteroaryl, heterocyclic, and substituted heterocyclic;

each m is independently 1 or 2;

p is 1, 2, 3, or 4;

$Ar^2$ is selected from the group consisting of arylene, substituted arylene, heteroarylene, and substituted heteroarylene; and G is selected from the group consisting of a bond, alkylene, substituted alkylene, alkenylene, substituted alkenylene, alkynylene, and substituted alkynylene; provided that when $Ar^2$ is arylene or substituted arylene, then G is not alkenylene or substituted alkenylene.

In one embodiment, $Ar^1$ is 1,2-fused heteroaryl, substituted 1,2-fused heteroaryl, 1,2-fused heterocyclic, or substituted 1,2-fused heterocyclic. In some aspects of the embodiment, $Ar^1$ and the ring containing $W^1$ and W to which it is fused together form the optionally substituted groups in the following table:

| Structure | Name |
|---|---|
| | 1,3,4,9-tetrahydro-2H-b-carbolin-2-yl |
| | 1,3,4,4a,9,9a-hexahydro-2H-b-carbolin-2-yl |
| 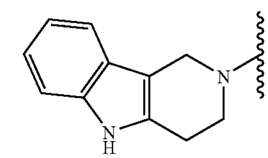 | 1,3,4,5-tetrahydro-2H-pyrido[4,3-b]indol-2-yl |
| | 1,1a,3,4,4a,5-hexahydro-2H-pyrido[4,3-b]indol2-yl |
| 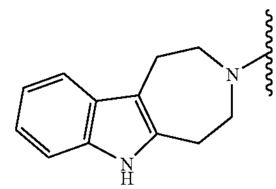 | 1,4,5,6-tetrahydroazepino[4,5-b]indol-3(2H)-yl |
| 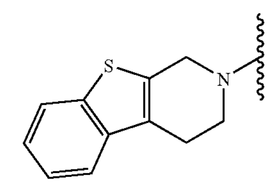 | 3,4-dihydro[1]benzothieno[2,3-c]pyridin-2(1H)-yl |
| 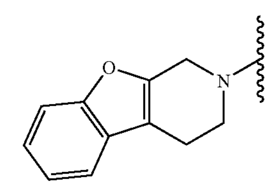 | 3,4-dihydro[1]benzofuro[2,3-c]pyridin-2(1H)-yl |
| | 10-oxo-3,4,5,10-tetrahydrobenzo[b]-1,6-naphthyridin-2(1H)-yl. |

In one embodiment, $Ar^1$ is substituted 1,2-fused aryl. In some aspects of the embodiment, $Ar^1$ and the ring containing $W^1$ and W to which it is fused together form a substituted 3,4-dihydroisoquinolin-2(1H)-yl group, where 3,4-dihydroisoquinolin-2(1H)-yl group is shown in the following table in its unsubstituted form:

| Structure | Name |
|---|---|
| 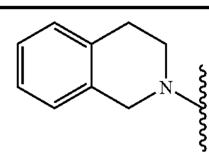 | 3,4-dihydroisoquinolin-2(1H)-yl |

In one embodiment, W and $W^1$ are optionally substituted methylene. In one embodiment, W is optionally substituted methylene and $W^1$ is optionally substituted ethylene. In one embodiment, W is optionally substituted ethylene and W¹ is optionally substituted methylene. In one embodiment, W and W¹ are optionally substituted ethylene. As used herein, "optionally substituted methylene" refers to —CR¹R²— and "optionally substituted ethylene" refers to —CR¹R²CR¹R²— where R¹ and R² are as defined above. In one preferred embodiment, W is methylene and W¹ is ethylene. In another preferred embodiment, W is ethylene and W¹ is methylene. In another preferred embodiment, W and W¹ are ethylene.

In one embodiment, W² is a bond. In one embodiment, W² is optionally substituted alkylene of the formula [—C(R¹)(R²)—]$_p$. Preferably, W² either is a bond or is methylene.

In one embodiment, Ar² is heteroarylene or substituted heteroarylene. Examples of —Ar²-G-C(O)NHOH include, for example, 5-[-G-C(O)NHOH]-pyrimid-2-ylene, 5-[-G-C(O)NHOH]-thiazol-2-ylene, 5-[-G-C(O)NHOH]-pyrid-2-ylene, and 5-[-G-C(O)NHOH]-thien-2-ylene wherein attachment to —W²—Ar¹— is in all cases at the 2-position as shown in the following diagram.

| Structure | Name |
|---|---|
| ![structure] | 5-[-G-C(O)NHOH]-pyrimid-2-ylene |
| ![structure] | 5-[-G-C(O)NHOH]-thiazol-2-ylene |
| ![structure] | 5-[-G-C(O)NHOH]-pyrid-2-ylene |
| ![structure] | 5-[-G-C(O)NHOH]-thien-2-ylene |

In one embodiment, Ar² is arylene or substituted arylene. An example of an arylene group is 4-phenylene.

Preferred —Ar²-G-C(O)NHOH groups include the 5-[-G-C(O)NHOH]-pyrimid-2-ylene and the 5-[-G-C(O)NHOH]-pyrid-2-ylene (and the N-oxide thereof). A particularly preferred Ar² group is 5-[-G-C(O)NHOH]-pyrimid-2-ylene.

In one embodiment, G is a bond. In one embodiment, G is optionally substituted alkylene. In one embodiment, G is optionally substituted alkenylene; examples of which include, for instance, E-vinylene and Z-vinylene. In one embodiment, G is optionally substituted alkynylene.

In another of its compound aspects, this invention is directed to a compound of formula II:

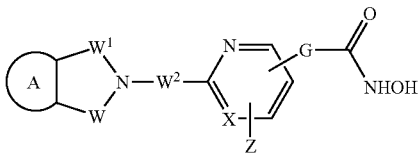

wherein:

is Ar¹ which is selected from the group consisting of substituted 1,2-fused aryl, 1,2-fused heteroaryl, substituted 1,2-fused heteroaryl, 1,2-fused heterocyclic, and substituted 1,2-fused heterocyclic;

Ar¹ is fused to the ring containing W¹ and W;

W and W¹ are independently [—C(R¹)(R²)—]$_m$;

W² is a bond or [—C(R¹)(R²)—]$_p$;

R¹ and R² are independently selected from the group consisting of hydrogen, alkyl, substituted alkyl, aryl, substituted aryl, heteroaryl, substituted heteroaryl, heterocyclic, and substituted heterocyclic;

each m is independently 1 or 2;

p is 1, 2, 3, or 4;

X is CH or N;

Z is absent or is selected from the group consisting of halo, alkyl, and substituted alkyl; and G is selected from the group consisting of a bond, alkylene, substituted alkylene, alkenylene, substituted alkenylene, alkynylene, and substituted alkynylene, or a tautomer, stereoisomer, prodrug, or pharmaceutically acceptable salt thereof.

In one embodiment, Ar¹ is 1,2-fused heteroaryl, substituted 1,2-fused heteroaryl, 1,2-fused heterocyclic, or substituted 1,2-fused heterocyclic. In some aspects of the embodiment, Ar¹ and the ring containing W¹ and W to which it is fused together form the optionally substituted groups in the following table:

| Structure | Name |
|---|---|
| ![structure] | 1,3,4,9-tetrahydro-2H-b-carbolin-2-yl |
| ![structure] | 1,3,4,4a,9,9a-hexahydro-2H-b-carbolin-2-yl |

-continued

| Structure | Name |
|---|---|
| 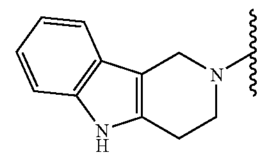 | 1,3,4,5-tetrahydro-2H-pyrido[4,3-b]indol-2-yl |
| 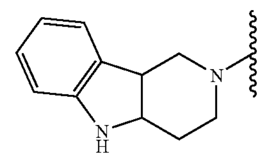 | 1,1a,3,4,4a,5-hexahydro-2H-pyrido-[4,3-b]indol2-yl |
| 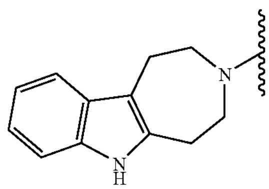 | 1,4,5,6-tetrahydroazepino[4,5-b]indol-3(2H)-yl |
| 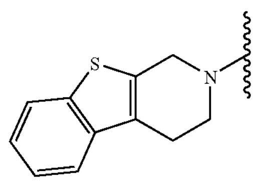 | 3,4-dihydro[1]benzothieno[2,3-c]pyridin-2(1H)-yl |
| 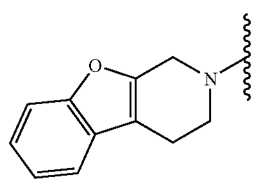 | 3,4-dihydro[1]benzofuro[2,3-c]pyridin-2(1H)-yl |
| 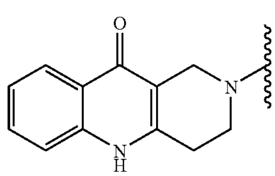 | 10-oxo-3,4,5,10-tetrahydrobenzo-[b]-1,6-naphthyridin-2(1H)-yl. |

In one embodiment, $Ar^1$ is substituted 1,2-fused aryl. In some aspects of the embodiment, $Ar^1$ and the ring containing $W^1$ and W to which it is fused together form a substituted 3,4-dihydroisoquinolin-2(1H)-yl group. In one embodiment, W and $W^1$ are optionally substituted methylene. In one embodiment, W is optionally substituted methylene and $W^1$ is optionally substituted ethylene. In one embodiment, W is optionally substituted ethylene and $W^1$ is optionally substituted methylene. In one embodiment, W and $W^1$ are optionally substituted ethylene. As used herein, "optionally substituted methylene" refers to —$CR^1R^2$— and "optionally substituted ethylene" refers to —$CR^1R^2CR^1R^2$— where $R^1$ and $R^2$ are as defined above. In one preferred embodiment, W is methylene and $W^1$ is ethylene. In another preferred embodiment, W is ethylene and $W^1$ is methylene. In another preferred embodiment, W and $W^1$ are ethylene.

In one embodiment, $W^2$ is a bond. In one embodiment, $W^2$ is optionally substituted alkylene of the formula [—$C(R^1)(R^2)$—]$_p$. Preferably, $W^2$ either is a bond or is methylene.

In one embodiment, X is CH (i.e., pyridyl). Preferred pyridyl groups include 5-[-G-C(O)NHOH]-pyrid-2-yl and the N-oxide thereof. In another embodiment, X is nitrogen (i.e., pyrimidinyl). Particularly preferred pyrimidinyl groups include 5-[-G-C(O)NHOH]-pyrimidin-2-yl.

In one embodiment, Z is absent. In another embodiment, Z is halogen, alkyl or substituted alkyl (e.g., trifluoromethyl).

In one embodiment, G is a bond. In one embodiment, G is optionally substituted alkylene. In one embodiment, G is optionally substituted alkenylene; examples of which include E-vinylene and Z-vinylene. In one embodiment, G is optionally substituted alkynylene.

In still another of its compound aspects, this invention is directed to a compound of formula III:

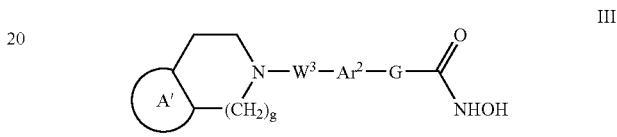

III wherein

is $Ar^3$ wherein $Ar^3$ is substituted 1,2-fused aryl, 1,2-fused heteroaryl, substituted 1,2-fused heteroaryl, 1,2-fused heterocyclic, and substituted 1,2-fused heterocyclic;

$Ar^3$ is fused to the adjacent piperidinyl or homopiperidinyl ring;

$W^3$ is a bond or [—$C(R^1)(R^2)$—]$_p$;

g is 1 or 2;

$R^1$, $R^2$, p, $Ar^2$, and G are as defined above;

or a tautomer, stereoisomer, prodrug, or pharmaceutically acceptable salts thereof;

provided that when $Ar^2$ is arylene or substituted arylene, then G is not alkenylene or substituted alkenylene.

In one embodiment, the compound of formula III is a compound of formula IIIa

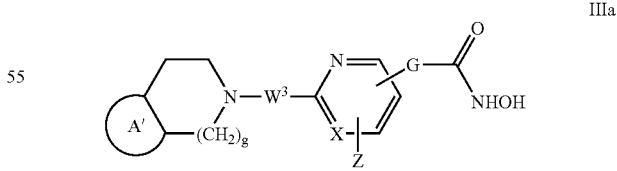

IIIa wherein A', g, $W^3$ are defined above for III and X, Z, and G are as defined above for II.

In one embodiment, $Ar^3$ is 1,2-fused heteroaryl, substituted 1,2-fused heteroaryl, 1,2-fused heterocyclic, or substituted 1,2-fused heterocyclic. Examples of such $Ar^3$ groups coupled to the piperidinyl or homopiperidinyl ring as represented by

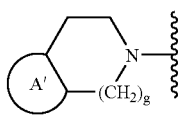

include optionally substituted:

| Structure | Name |
| --- | --- |
| 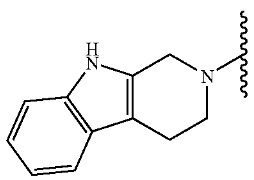 | 1,3,4,9-tetrahydro-2H-b-carbolin-2-yl |
| 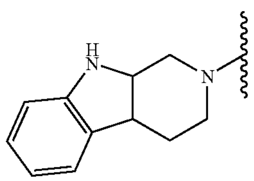 | 1,3,4,4a,9,9a-hexahydro-2H-b-carbolin-2-yl |
| 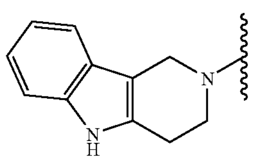 | 1,3,4,5-tetrahydro-2H-pyrido[4,3-b]indol-2-yl |
| | 1,1a,3,4,4a,5-hexahydro-2H-pyrido[4,3-b]indol2-yl |
| 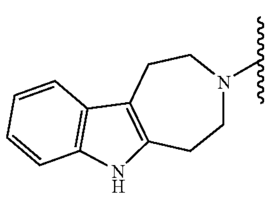 | 1,4,5,6-tetrahydroazepino[4,5-b]indol-3(2H)-yl |
| 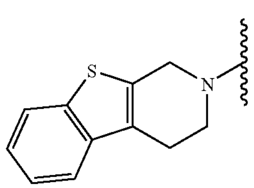 | 3,4-dihydro[1]benzothieno[2,3-c]pyridin-2(1H)-yl |
| 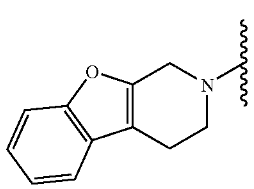 | 3,4-dihydro[1]benzofuro[2,3-c]pyridin-2(1H)-yl |

-continued

| Structure | Name |
| --- | --- |
| 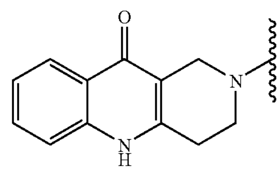 | 10-oxo-3,4,5,10-tetrahydrobenzo-[b]-1,6-naphthyridin-2(1H)-yl. |

In one embodiment, $Ar^3$ is substituted 1,2-fused aryl. In some aspects of the embodiment, $Ar^3$ is a substituted 3,4-dihydroisoquinolin-2(1H)-yl group. In one embodiment, $W^3$ is a bond. In one embodiment, $W^3$ is optionally substituted alkylene of the formula $[-C(R^1)(R^2)-]_p$. Preferably, $W^3$ either is a bond or is methylene.

In one embodiment, g is one. In another embodiment, g is two.

In one embodiment, $Ar^2$ is heteroarylene or substituted heteroarylene. Examples of $-Ar^2$-G-C(O)NHOH groups include, for example, 5-[-G-C(O)NHOH]-pyrimid-2-ylene, 5-[-G-C(O)NHOH]-thiazol-2-ylene, 5-[-G-C(O)NHOH]-pyrid-2-ylene, and 5-[-G-C(O)NHOH]thien-2-ylene wherein attachment to $W^3$ is in all cases at the 2-position.

In one embodiment, $Ar^2$ is arylene or substituted arylene. An example of an arylene group is 4-phenylene.

Preferred $-Ar^2$-G-C(O)NHOH groups include 5-[-G-C(O)NHOH]-pyrimid-2-ylene and 5-[-G-C(O)NHOH]-pyrid-2-ylene (and the N-oxide thereof). A particularly preferred $-Ar^2$-G-C(O)NHOH group is 5-[-G-C(O)NHOH]-pyrimid-2-ylene.

In one embodiment, G is a bond. In one embodiment, G is optionally substituted alkylene. In one embodiment, G is optionally substituted alkenylene; examples of which include E-vinylene and Z-vinylene. In one embodiment, G is optionally substituted alkynylene.

In still another of its compound aspects, this invention is directed to a compound of formula IV or a tautomer, stereoisomer, prodrug, or pharmaceutically acceptable salt thereof:

IV

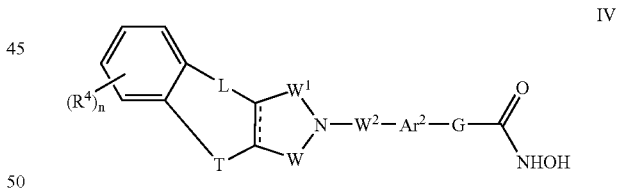

wherein:

L is a bond or C(O), such that when L is a bond the central ring containing L is a five membered ring and when L is C(O) the central ring containing L is a six membered ring;

the dashed line ---- represents a single or double bond;

T is O, S, or $-N-(Y)_q-R^3$;

Y is selected from the group consisting of $-C(O)-$ and $-S(O)_2-$;

q is equal to 0 or 1;

$R^3$ is selected from the group consisting of hydrogen, alkyl, substituted alkyl, aryl, substituted aryl, heteroaryl, substituted heteroaryl, heterocyclic and substituted heterocyclic;

$R^4$ is selected from the group consisting of acyl, acylamino, alkyl, substituted alkyl, alkoxy, substituted alkoxy, amino, substituted amino, aminoacyl, aminocarbonyloxy, oxycarbonylamino, aryl, substituted aryl, carboxyl, carboxyl ester, cyano, halo, heteroaryl, substituted heteroaryl, heterocyclic, substituted heterocyclic, hydroxyl, nitro, thiol, thioalkyl, and substituted thioalkyl;

n is 0, 1, 2, or 3;

W and $W^1$ are independently $[-C(R^1)(R^2)-]_m$;

$W^2$ is a bond or $[-C(R^1)(R^2)-]_p$;

$R^1$ and $R^2$ are independently selected from the group consisting of hydrogen, alkyl, substituted alkyl, aryl, substituted aryl, heteroaryl, substituted heteroaryl, heterocyclic, and substituted heterocyclic;

each m is independently 1 or 2;

p is 1, 2, 3 or 4;

$Ar^2$ is selected from the group consisting of arylene, substituted arylene, heteroarylene, and substituted heteroarylene; and G is selected from the group consisting of a bond, alkylene, substituted alkylene, alkenylene, substituted alkenylene, alkynylene, and substituted alkynylene;

provided that when $Ar^2$ is arylene or substituted arylene, then G is not alkenylene or substituted alkenylene.

In one embodiment, L is a bond.

In one embodiment, T is O or S.

In one embodiment, T is $-N-(Y)_q-R^3$.

In one embodiment, $R^3$ is selected from the group consisting of hydrogen, alkyl, substituted alkyl, and aryl. In other embodiments, q is zero and $R^3$ is selected from the group consisting of hydrogen, methyl, (pyrrolidin-1-yl)methyl, (2-pyrrolidin-1-yl)eth-1-yl, (2-piperidin-1-yl)eth-1-yl, 2-(morpholin-4-yl)eth-1-yl, and benzyl. In another embodiment, q is zero and $R^3$ is hydrogen.

In one embodiment, q is one, Y is $-S(O)_2-$, and $R^3$ is phenyl.

In another embodiment, q is one, Y is $-(O)-$, and $-Y-R^3$ together form an acyl group.

In one embodiment, n is zero. In another embodiment, n is one or two.

In one embodiment, $R^4$ is selected from the group consisting of alkyl, substituted alkyl, alkoxy, substituted alkoxy, amino, substituted amino, nitro, heterocyclic, substituted heterocyclic, aryl, substituted aryl, heteroaryl, substituted heteroaryl, and halo.

In another embodiment $R^4$ is selected from the group consisting of methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl, 4-(morpholin-4-yl)methyl)phenyl, 3-(pyrrolidin-1-ylmethyl)phenyl, 4-(pyrrolidin-1-ylmethyl)phenyl, 3-pyridyl, 5-pyrimidinyl, 4-acetamidophenyl, 3-(N,N-dimethylaminomethyl)phenyl, 3-(piperidin-1-ylmethyl)phenyl, 3-(thiomorpholin-4-ylmethyl)phenyl, 4-(thiomorpholin-4-ylmethyl)phenyl, 3-(piperazin-1-ylmethyl)phenyl, 3-(4-methylsulfonylpiperazin-1-ylmethyl)phenyl, 3-(4-acetylpiperazin-1-ylmethyl)phenyl, 3-hydroxymethylphenyl, 4-methoxyphenyl, 4-methylphenyl, 3-(pyrrolidin-1-ylcarbonyl)phenyl, 4-hydroxymethylphenyl, 3-aminophenyl, 3-fluorophenyl, 4-fluorophenyl, 3-furyl, 3-(N-methanesulfonamidomethyl)phenyl, 3-(N-acetamidomethyl)phenyl, 3-methylthiophenyl, 3-methylsulfinylphenyl, 4-N,N-dimethylaminophenyl, 3-(1H-tetrazol-5-yl)phenyl, 5-(4-methylpiperazin-1-ylmethyl)-2-furyl, 5-(morpholin-4-ylmethyl)-2-furyl, 5-(4-methylpiperazin-1-ylmethyl)-2-thienyl, 1H-2-pyrrolyl, 2-thienyl and the like.

In one embodiment, W and $W^1$ are optionally substituted methylene. In one embodiment, W is optionally substituted methylene and $W^1$ is optionally substituted ethylene. In one embodiment, W is optionally substituted ethylene and $W^1$ is optionally substituted methylene. In one embodiment, W and $W^1$ are optionally substituted ethylene. As used herein, "optionally substituted methylene" refers to $-CR^1R^2-$ and "optionally substituted ethylene" refers to $-CR^1R^2CR^1R^2-$ where $R^1$ and $R^2$ are as defined above. In one preferred embodiment, W is methylene and $W^1$ is ethylene. In another preferred embodiment, W is ethylene and $W^1$ is methylene. In another preferred embodiment, W and $W^1$ are ethylene.

In one embodiment, $W^2$ is a bond. In one embodiment, $W^2$ is optionally substituted alkylene of the formula $[-C(R^1)(R^2)-]_p$. Preferably, $W^2$ either is a bond or is methylene.

In one embodiment, $Ar^2$ is heteroarylene or substituted heteroarylene. Examples of $-Ar^2-G-C(O)NHOH$ groups include, for example, 5-[-G-C(O)NHOH]-pyrimid-2-ylene, 5-[-G-C(O)NHOH]-thiazol-2-ylene, 5-[-G-C(O)NHOH]-pyrid-2-ylene, and 5-[-G-C(O)NHOH]-thien-2-ylene wherein attachment to $W^2$ is in all cases at the 2-position as shown in the following diagram.

| Structure | Name |
|---|---|
| 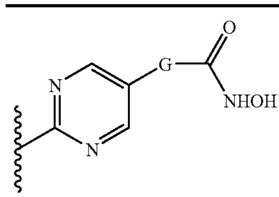 | 5-[-G-C(O)NHOH]-pyrimid-2-ylene |
| 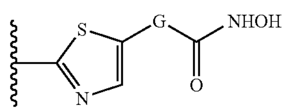 | 5-[-G-C(O)NHOH]-thiazol-2-ylene |
| 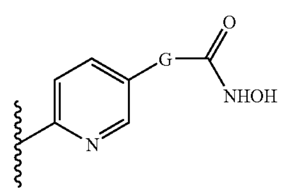 | 5-[-G-C(O)NHOH]-pyrid-2-ylene |
| 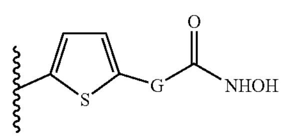 | 5-[-G-C(O)NHOH]-thien-2-ylene |

In one embodiment, $Ar^2$ is arylene or substituted arylene. An example of an arylene group is 4-phenylene.

In one embodiment $-Ar^2-G-C(O)NHOH$ groups include 5-[-G-C(O)NHOH]-pyrimid-2-ylene and 5-[-G-C(O)NHOH]-pyrid-2-ylene (and the N-oxide thereof). In another embodiment $-Ar^2-G-C(O)NHOH$ group is 5-[-G-C(O)NHOH]-pyrimid-2-ylene.

In one embodiment, G is a bond. In one embodiment, G is optionally substituted alkylene. In one embodiment, G is optionally substituted alkenylene; examples of which include, for instance, E-vinylene and Z-vinylene. In one embodiment, G is optionally substituted alkynylene.

In still another of its compound aspects, this invention is directed to a compound of formulae V(A) or V(B):

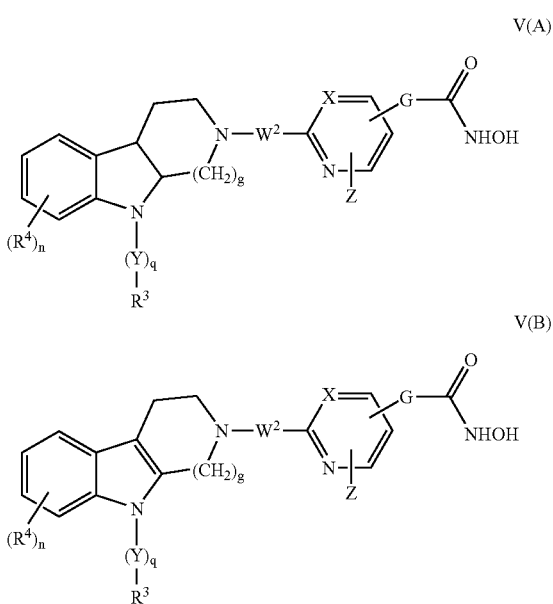

wherein $W^2$, g, X, Z and G are as defined above;

$R^3$ is selected from the group consisting of hydrogen, alkyl, substituted alkyl, aryl, substituted aryl, heteroaryl, substituted heteroaryl, heterocyclic and substituted heterocyclic;

$R^4$ is selected from the group consisting of acyl, acylamino, alkyl, substituted alkyl, alkoxy, substituted alkoxy, amino, substituted amino, aminoacyl, aminocarbonyloxy, oxycarbonylamino, aryl, substituted aryl, carboxyl, carboxyl ester, cyano, halo, heteroaryl, substituted heteroaryl, heterocyclic, substituted heterocyclic, hydroxyl, nitro, thiol, thioalkyl and substituted thioalkyl;

Y is selected from the group consisting of —(O)— and —S(O)$_2$—;

n is equal to 0, 1, 2 or 3;

q is equal to 0 or 1;

or a stereoisomer, tautomer, prodrug, or pharmaceutically acceptable salt thereof.

In one embodiment, when q is other than zero, Y is carbonyl. In another embodiment, when q is other than zero, Y is —SO$_2$—. In still another embodiment, q is zero.

In one embodiment, g is one. In another embodiment, g is two.

In one embodiment, $R^3$ is selected from the group consisting of hydrogen, alkyl, substituted alkyl and aryl. Examples of $R^3$ when q is zero include hydrogen, methyl, (pyrrolidin-1-yl)methyl, (2-pyrrolidin-1-yl)eth-1-yl, (2-piperidin-1-yl)eth-1-yl, 2-(morpholin-4-yl)eth-1-yl, benzyl, and the like. Preferably, $R^3$ is hydrogen. Examples of $R^3$—Y— when q is one include phenylsulfonyl and acyl.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-yl)phenyl, 3-(4-methylpiperazin-1-ylmethyl)phenyl, 2-(4-methylpiperazin-1-ylmethyl)phenyl, 3-(morpholin-4-yl)methyl)phenyl, 4-(morpholin-4-yl)methyl)phenyl, 3-(pyrrolidin-1-ylmethyl) phenyl, 4-(pyrrolidin-1-ylmethyl)phenyl, 3-pyridyl, 5-pyrimidinyl, 4-acetamidophenyl, 3-(N,N-dimethylaminomethyl)phenyl, 3-(piperidin-1-ylmethyl)phenyl, 3-(thiomorpholin-4-ylmethyl)phenyl, 4-(thiomorpholin-4-ylmethyl)phenyl, 3-(piperazin-1-ylmethyl)phenyl, 3-(4-methylsulfonylpiperazin-1-ylmethyl)phenyl, 3-(4-acetylpiperazin-1-ylmethyl)phenyl, 3-hydroxymethylphenyl, 4-methoxyphenyl, 4-methylphenyl, 3-(pyrrolidin-1-ylcarbonyl)phenyl, 4-hydroxymethylphenyl, 3-aminophenyl, 3-fluorophenyl, 4-fluorophenyl, 3-furyl, 3-(N-methanesulfonamidomethyl)phenyl, 3-(N-acetamidomethyl)phenyl, 3-methylthiophenyl, 3-methylsulfinylphenyl, 4-N,N-dimethylaminophenyl, 3-(1H-tetrazol-5-yl)phenyl, 5-(4-methylpiperazin-1-ylmethyl)-2-furyl, 5-(morpholin-4-ylmethyl)-2-furyl, 5-(4-methylpiperrazin-1-ylmethyl)-2-thienyl, 1H-2-pyrrolyl, 2-thienyl and the like In one embodiment, $W^2$ is a bond. In one embodiment, $W^2$ is optionally substituted alkylene of the formula [—C($R^1$)($R^2$)—]$_p$. Preferably, $W^2$ either is a bond or is methylene.

In one embodiment, X is CH (i.e., pyridyl). Preferred pyridyl groups include the 5-[-G-C(O)NHOH]-pyrid-2-yl and the N-oxide thereof. In another embodiment, X is nitrogen (i.e., pyrimidinyl). Particularly preferred pyrimidinyl groups include 5-[-G-C(O)NHOH]-pyrimidin-2-yl.

In one embodiment, Z is absent. In another embodiment, Z is halogen, alkyl or substituted alkyl (e.g., trifluoromethyl).

In one embodiment, G is a bond. In one embodiment, G is optionally substituted alkylene. In one embodiment, G is optionally substituted alkenylene; examples of which include E-vinylene and Z-vinylene. In one embodiment, G is optionally substituted alkynylene.

In still another of its compound aspects, this invention is directed to a compound of formula VI(A) and VI(B) or a stereoisomer, tautomer, prodrug, or pharmaceutically acceptable salt thereof:

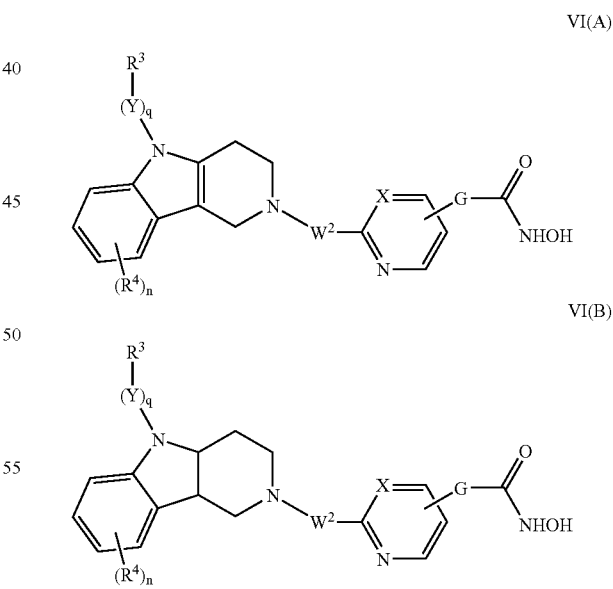

wherein $R^3$, $R^4$, $W^2$, X, Y and G are as defined above.

In one embodiment, when q is other than zero, Y is carbonyl. In another embodiment, when q is other than zero, Y is —SO$_2$—. In still another embodiment, q is zero.

In one embodiment, $R^3$ is selected from the group consisting of hydrogen, alkyl, substituted alkyl and aryl. Examples of $R^3$ when q is zero include hydrogen, methyl, (pyrrolidin-1-yl)methyl, (2-pyrrolidin-1-yl)eth-1-yl, (2-piperidin-1-yl)eth-1-yl, 2-(morpholin-4-yl)eth-1-yl, benzyl, and the like. Preferably, $R^3$ is hydrogen. Examples of $R^3$—Y— when q is one include phenylsulfonyl and acyl.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl, 4-(morpholin-4-yl)methyl)phenyl, 3-(pyrrolidin-1-ylmethyl)phenyl, 4-(pyrrolidin-1-ylmethyl)phenyl, 3-pyridyl, 5-pyrimidinyl, 4-acetamidophenyl, 3-(NAN-dimethylaminomethyl)phenyl, 3-(piperidin-1-ylmethyl)phenyl, 3-(thiomorpholin-4-ylmethyl)phenyl, 4-(thiomorpholin-4-ylmethyl)phenyl, 3-(piperazin-1-ylmethyl)phenyl, 3-(4-methylsulfonylpiperazin-1-ylmethyl)phenyl, 3-(4-acetylpiperazin-1-ylmethyl)phenyl, 3-hydroxymethylphenyl, 4-methoxyphenyl, 4-methylphenyl, 3-(pyrrolidin-1-ylcarbonyl)phenyl, 4-hydroxymethylphenyl, 3-aminophenyl, 3-fluorophenyl, 4-fluorophenyl, 3-furyl, 3-(N-methanesulfonamidomethyl)phenyl, 3-(N-acetamidomethyl)phenyl, 3-methylthiophenyl, 3-methylsulfinylphenyl, 4-N,N-dimethylaminophenyl, 3-(1H-tetrazol-5-yl)phenyl, 5-(4-methylpiperazin-1-ylmethyl)-2-furyl, 5-(morpholin-4-ylmethyl)-2-furyl, 5-(4-methylpiperrazin-1-ylmethyl)-2-thienyl, 1H-2-pyrrolyl, 2-thienyl and the like.

In one embodiment, $W^2$ is a bond. In one embodiment, $W^2$ is optionally substituted alkylene of the formula [—C($R^1$)($R^2$)—]$_p$. Preferably, $W^2$ either is a bond or is methylene.

In one embodiment, X is CH (i.e., pyridyl). Preferred pyridyl groups include the 5-[-G-C(O)NHOH]-pyrid-2-yl and the N-oxide thereof. In another embodiment, X is nitrogen (i.e., pyrimidinyl). Particularly preferred pyrimidinyl groups include 5-[-G-C(O)NHOH]-pyrimidin-2-yl.

In one embodiment, Z is absent. In another embodiment, Z is halogen, alkyl or substituted alkyl (e.g., trifluoromethyl).

In one embodiment, G is a bond. In one embodiment, G is optionally substituted alkylene. In one embodiment, G is optionally substituted alkenylene; examples of which include E-vinylene and Z-vinylene. In one embodiment, G is optionally substituted alkynylene.

In still another of its compound aspects, this invention is directed to a compound of formula VII or a stereoisomer, tautomer, prodrug, or pharmaceutically acceptable salt thereof:

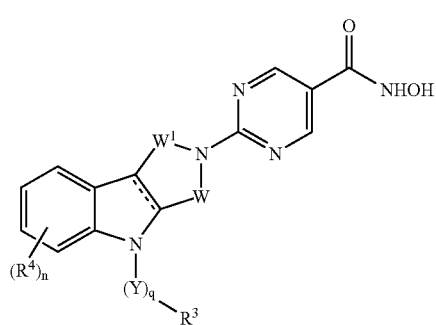

VII wherein the dashed line ----, W, $W^1$, $R^3$, $R^4$, Y, n and q are as defined above.

In still another of its compound aspects, this invention is directed to a compound of formula VII(A) and VII(B) or a stereoisomer, tautomer, prodrug, or pharmaceutically acceptable salt thereof:

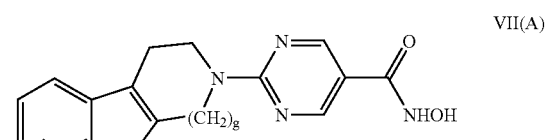

VII(A)

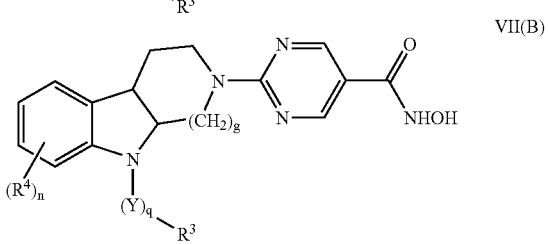

VII(B)

wherein $R^3$, $R^4$, Y, g, n and q are as defined above.

In one embodiment, when q is other than zero, Y is carbonyl. In another embodiment, when q is other than zero, Y is —SO$_2$—. In still another embodiment, q is zero.

In one embodiment, $R^3$ is selected from the group consisting of hydrogen, alkyl, substituted alkyl and aryl. Examples of $R^3$ when q is zero include hydrogen, methyl, (pyrrolidin-1-yl)methyl, (2-pyrrolidin-1-yl)eth-1-yl, (2-piperidin-1-yl)eth-1-yl, 2-(morpholin-4-yl)eth-1-yl, benzyl, and the like. Preferably, $R^3$ is hydrogen. Examples of $R^3$—Y— when q is one include phenylsulfonyl and acyl.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl, 4-(morpholin-4-yl)methyl)phenyl, 3-(pyrrolidin-1-ylmethyl)phenyl, 4-(pyrrolidin-1-ylmethyl)phenyl, 3-pyridyl, 5-pyrimidinyl, 4-acetamidophenyl, 3-(N,N-dimethylaminomethyl)phenyl, 3-(piperidin-1-ylmethyl)phenyl, 3-(thiomorpholin-4-ylmethyl)phenyl, 4-(thiomorpholin-4-ylmethyl)phenyl, 3-(piperazin-1-ylmethyl)phenyl, 3-(4-methylsulfonylpiperazin-1-ylmethyl)phenyl, 3-(4-acetylpiperazin-1-ylmethyl)phenyl, 3-hydroxymethylphenyl, 4-methoxyphenyl, 4-methylphenyl, 3-(pyrrolidin-1-ylcarbonyl)phenyl, 4-hydroxymethylphenyl, 3-aminophenyl, 3-fluorophenyl, 4-fluorophenyl, 3-furyl, 3-(N-methanesulfonamidomethyl)phenyl, 3-(N-acetamidomethyl)phenyl, 3-methylthiophenyl, 3-methylsulfinylphenyl, 4-N,N-dimethylaminophenyl, 3-(1H-tetrazol-5-yl)phenyl, 5-(4-methylpiperazin-1-ylmethyl)-2-furyl, 5-(morpholin-4-ylmethyl)-2-furyl, 5-(4-methylpiperrazin-1-ylmethyl)-2-thienyl, 1H-2-pyrrolyl, 2-thienyl and the like In one embodiment g is one. In another embodiment g is two.

In still another of its compound aspects, this invention is directed to a compound of formula VIII(A) and VIII(B) or a stereoisomer, tautomer, prodrug, or pharmaceutically acceptable salt thereof:

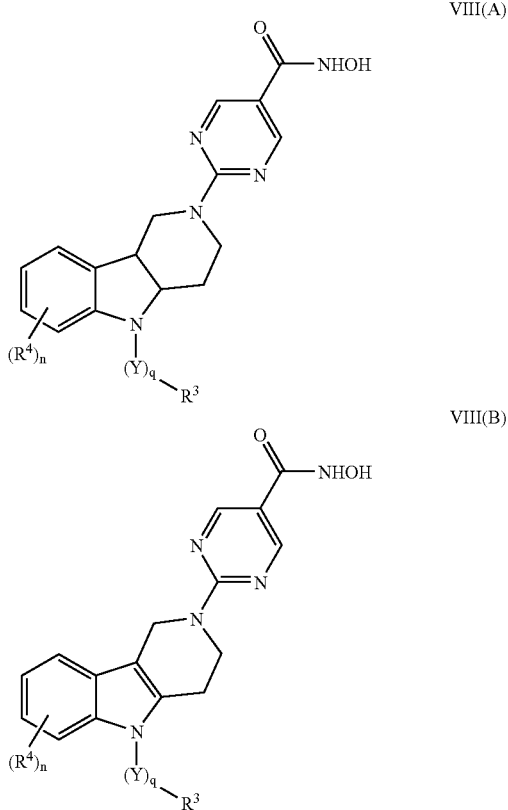

wherein $R^3$, $R^4$, Y, n and q are as defined above.

In one embodiment, when q is other than zero, Y is carbonyl. In another embodiment, when q is other than zero, Y is —SO$_2$—. In still another embodiment, q is zero.

In one embodiment, $R^3$ is selected from the group consisting of hydrogen, alkyl, substituted alkyl and aryl. Examples of $R^3$ when q is zero include hydrogen, methyl, (pyrrolidin-1-yl)methyl, (2-pyrrolidin-1-yl)eth-1-yl, (2-piperidin-1-yl)eth-1-yl, 2-(morpholin-4-yl)eth-1-yl, benzyl, and the like. Preferably, $R^3$ is hydrogen. Example of $R^3$—Y— when q is one include phenylsulfonyl and acyl.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl, 4-(morpholin-4-yl)methyl)phenyl, 3-(pyrrolidin-1-ylmethyl)phenyl, 4-(pyrrolidin-1-ylmethyl)phenyl, 3-pyridyl, 5-pyrimidinyl, 4-acetamidophenyl, 3-(N,N-dimethylaminomethyl)phenyl, 3-(piperidin-1-ylmethyl)phenyl, 3-(thiomorpholin-4-ylmethyl)phenyl, 4-(thiomorpholin-4-ylmethyl)phenyl, 3-(piperazin-1-ylmethyl)phenyl, 3-(4-methylsulfonylpiperazin-1-ylmethyl)phenyl, 3-(4-acetylpiperazin-1-ylmethyl)phenyl, 3-hydroxymethylphenyl, 4-methoxyphenyl, 4-methylphenyl, 3-(pyrrolidin-1-ylcarbonyl)phenyl, 4-hydroxymethylphenyl, 3-aminophenyl, 3-fluorophenyl, 4-fluorophenyl, 3-furyl, 3-(N-methanesulfonamidomethyl)phenyl, 3-(N-acetamidomethyl)phenyl, 3-methylthiophenyl, 3-methylsulfinylphenyl, 4-N,N-dimethylaminophenyl, 3-(1H-tetrazol-5-yl)phenyl, 5-(4-methylpiperazin-1-ylmethyl)-2-furyl, 5-(morpholin-4-ylmethyl)-2-furyl, 5-(4-methylpiperrazin-1-ylmethyl)-2-thienyl, 1H-2-pyrrolyl, 2-thienyl and the like.

In still another of its compound aspects, this invention is directed to a compound of formulae IX(A) or IX(B) or a stereoisomer, tautomer, prodrug, or pharmaceutically acceptable salt thereof:

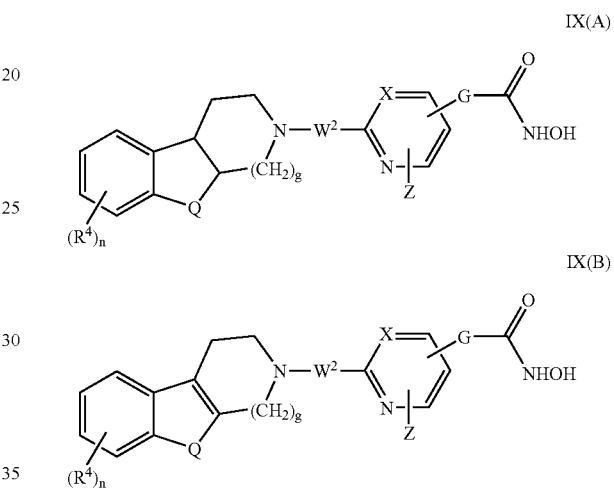

wherein $W^2$, g, X, Z and G are as defined above;

Q is O or S;

$R^4$ is selected from the group consisting of acyl, acylamino, alkyl, substituted alkyl, alkoxy, substituted alkoxy, amino, substituted amino, aminoacyl, aminocarbonyloxy, oxycarbonylamino, aryl, substituted aryl, carboxyl, carboxyl ester, cyano, halo, heteroaryl, substituted heteroaryl, heterocyclic, substituted heterocyclic, hydroxyl, nitro, thiol, thioalkyl and substituted thioalkyl n is equal to 0, 1, 2 or 3.

In one embodiment, g is one. In another embodiment, g is two.

In one embodiment, Q is oxygen. In another embodiment, Q is sulfur.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl and the like.

In one embodiment, $W^2$ is a bond. In one embodiment, $W^2$ is optionally substituted alkylene of the formula [—C($R^1$)($R^2$)—]$_p$. Preferably, $W^2$ either is a bond or is methylene.

In one embodiment, X is carbon (i.e., pyridyl). Preferred pyridyl groups include the 5-[-G-C(O)NHOH]-pyrid-2-yl and the N-oxide thereof. In another embodiment, X is nitrogen (i.e., pyrimidinyl). Particularly preferred pyrimidinyl groups include 5-[-G-C(O)NHOH]-pyrimidin-2-yl.

In one embodiment, Z is absent. In another embodiment, Z is halogen, alkyl or substituted alkyl (e.g., trifluoromethyl).

In one embodiment, G is a bond. In one embodiment, G is optionally substituted alkylene. In one embodiment, G is optionally substituted alkenylene; examples of which include E-vinylene and Z-vinylene. In one embodiment, G is optionally substituted alkynylene.

In still another of its compound aspects, this invention is directed to a compound of formula X(A) and X(B) or a stereoisomer, tautomer, prodrug, or pharmaceutically acceptable salt thereof:

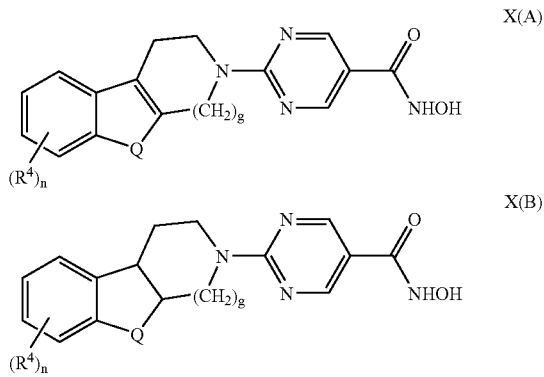

wherein $R^4$, Q, g, and n are as defined above.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl and the like.

In one embodiment g is one. In another embodiment g is two.

In one embodiment, Q is oxygen. In another embodiment, Q is sulfur.

In still another of its compound aspects, this invention is directed to a compound of formula XI(A) and XI(B) or a stereoisomer, tautomer, prodrug, or pharmaceutically acceptable salt thereof:

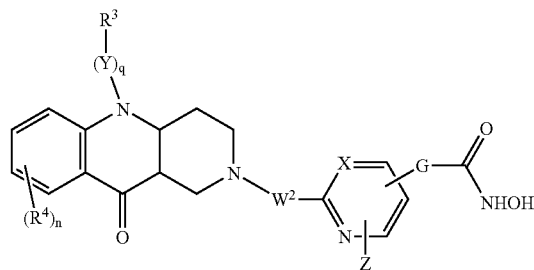

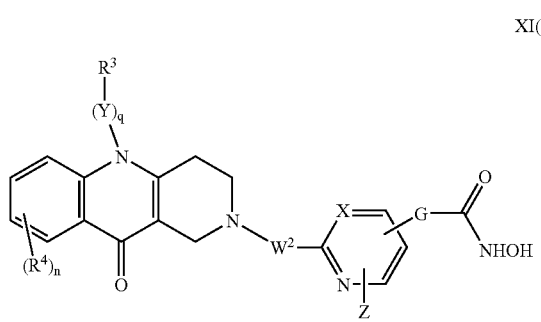

wherein $R^3$, $R^4$, $W^2$, X, Y, Z, G, n, and q are as defined above.

In one embodiment, when q is other than zero, Y is carbonyl. In another embodiment, when q is other than zero, Y is —SO$_2$—. In still another embodiment, q is zero.

In one embodiment, $R^3$ is selected from the group consisting of hydrogen, alkyl, substituted alkyl and aryl. Examples of $R^3$ when q is zero include hydrogen, methyl, (pyrrolidin-1-yl)methyl, (2-pyrrolidin-1-yl)eth-1-yl, (2-piperidin-1-yl)eth-1-yl, 2-(morpholin-4-yl)eth-1-yl, benzyl, and the like. Preferably, $R^3$ is hydrogen. Examples of $R^3$—Y— when q is one include phenylsulfonyl and acyl.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl, 4-(morpholin-4-yl)methyl)phenyl, 3-(pyrrolidin-1-ylmethyl)phenyl, 4-(pyrrolidin-1-ylmethyl)phenyl, 3-pyridyl, 5-pyrimidinyl, 4-acetamidophenyl, 3-(N,N-dimethylaminomethyl)phenyl, 3-(piperidin-1-ylmethyl)phenyl, 3-(thiomorpholin-4-ylmethyl)phenyl, 4-(thiomorpholin-4-ylmethyl)phenyl, 3-(piperazin-1-ylmethyl)phenyl, 3-(4-methylsulfonylpiperazin-1-ylmethyl)phenyl, 3-(4-acetylpiperazin-1-ylmethyl)phenyl, 3-hydroxymethylphenyl, 4-methoxyphenyl, 4-methylphenyl, 3-(pyrrolidin-1-ylcarbonyl)phenyl, 4-hydroxymethylphenyl, 3-aminophenyl, 3-fluorophenyl, 4-fluorophenyl, 3-furyl, 3-(N-methanesulfonamidomethyl)phenyl, 3-(N-acetamidomethyl)phenyl, 3-methylthiophenyl, 3-methylsulfinylphenyl, 4-N,N-dimethylaminophenyl, 3-(1H-tetrazol-5-yl)phenyl, 5-(4-methylpiperazin-1-ylmethyl)-2-furyl, 5-(morpholin-4-ylmethyl)-2-furyl, 5-(4-methylpiperrazin-1-ylmethyl)-2-thienyl, 1H-2-pyrrolyl, 2-thienyl and the like.

In one embodiment, $W^2$ is a bond. In one embodiment, $W^2$ is optionally substituted alkylene of the formula [—C($R^1$)($R^2$)—]$_p$. Preferably, $W^2$ either is a bond or is methylene.

In one embodiment, X is carbon (i.e., pyridyl). Preferred pyridyl groups include the 5-[-G-C(O)NHOH]-pyrid-2-yl and the N-oxide thereof. In another embodiment, X is nitrogen (i.e., pyrimidinyl). Particularly preferred pyrimidinyl groups include 5-[-G-C(O)NHOH]-pyrimidin-2-yl.

In one embodiment, Z is absent. In another embodiment, Z is halogen, alkyl or substituted alkyl (e.g., trifluoromethyl).

In one embodiment, G is a bond. In one embodiment, G is optionally substituted alkylene. In one embodiment, G is optionally substituted alkenylene; examples of which include E-vinylene and Z-vinylene. In one embodiment, G is optionally substituted alkynylene.

In still another of its compound aspects, this invention is directed to a compound of formula XII(A) and XII(B) or a stereoisomer, tautomer, prodrug, or pharmaceutically acceptable salt thereof:

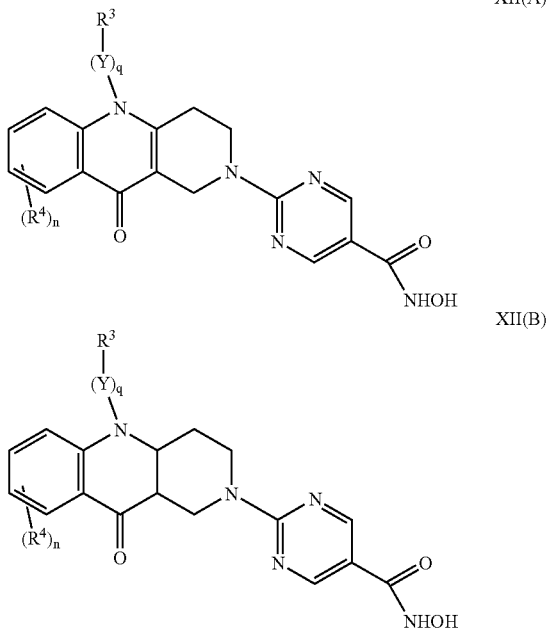

wherein $R^3$, $R^4$, Y, n and q are as defined above.

In one embodiment, when q is other than zero, Y is carbonyl. In another embodiment, when q is other than zero, Y is —$SO_2$—. In still another embodiment, q is zero.

In one embodiment, $R^3$ is selected from the group consisting of hydrogen, alkyl, substituted alkyl and aryl. Examples of $R^3$ when q is zero include hydrogen, methyl, (pyrrolidin-1-yl)methyl, (2-pyrrolidin-1-yl)eth-1-yl, (2-piperidin-1-yl)eth-1-yl, 2-(morpholin-4-yl)eth-1-yl, benzyl, and the like. Preferably, $R^3$ is hydrogen. Example of $R^3$—Y— when q is one include phenylsulfonyl and acyl.

In one embodiment, n is zero. In another embodiment, n is one, two or three, and is preferably one or two.

When n is other than zero, $R^4$ is preferably selected from the group consisting of alkyl, substituted alkyl, alkoxy, substituted alkoxy, heterocyclic, substituted heterocyclic, aryl, substituted aryl, heteroaryl, substituted heteroaryl and halo. Particularly preferred $R^4$ groups include methyl, methoxy, bromo, chloro, fluoro, trifluoromethyl, trifluoromethoxy, phenyl, 4-(4-methylpiperazin-1-ylmethyl)phenyl, 3-(4-methylpiperazin-1-ylmethyl)phenyl, 2-(4-methylpiperazin-1-ylmethyl)phenyl, 3-(morpholin-4-yl)methyl)phenyl, 4-(morpholin-4-yl)methyl)phenyl, 3-(pyrrolidin-1-ylmethyl)phenyl, 4-(pyrrolidin-1-ylmethyl)phenyl, 3-pyridyl, 5-pyrimidinyl, 4-acetamidophenyl, 3-(N,N-dimethylaminomethyl)phenyl, 3-(piperidin-1-ylmethyl)phenyl, 3-(thiomorpholin-4-ylmethyl)phenyl, 4-(thiomorpholin-4-ylmethyl)phenyl, 3-(piperazin-1-ylmethyl)phenyl, 3-(4-methylsulfonylpiperazin-1-ylmethyl)phenyl, 3-(4-acetylpiperazin-1-ylmethyl)phenyl, 3-hydroxymethylphenyl, 4-methoxyphenyl, 4-methylphenyl, 3-(pyrrolidin-1-ylcarbonyl)phenyl, 4-hydroxymethylphenyl, 3-aminophenyl, 3-fluorophenyl, 4-fluorophenyl, 3-furyl, 3-(N-methanesulfonamidomethyl)phenyl, 3-(N-acetamidomethyl)phenyl, 3-methylthiophenyl, 3-methylsulfinylphenyl, 4-N)N-dimethylaminophenyl, 3-(1H-tetrazol-5-yl)phenyl, 5-(4-methylpiperazin-1-ylmethyl)-2-furyl, 5-(morpholin-4-ylmethyl)-2-furyl, 5-(4-methylpiperrazin-1-ylmethyl)-2-thienyl, 1H-2-pyrrolyl, 2-thienyl and the like.

In one of its pharmaceutical composition aspect, this invention is directed to a pharmaceutical composition comprising an effective amount of one or more compounds according to formula I, II, III, III(A), IV, V(A), V(B) VI(A), VI(B), VII, VII(A), VII(B), VIII(A), VIII(B), IX(A), IX(B), X(A), X(B), XI(A), XI(B), XII(A) and/or XII(B) and a pharmaceutically inert carrier.

In another of its pharmaceutical aspects, this invention is directed to pharmaceutical compositions comprising an effective amount of one or more compounds according to formula I, II, III, III(A), IV, V(A), V(B) VI(A), VI(B), VII, VII(A), VII(B), VIII(A), VIII(B), IX(A), IX(B), X(A), X(B), XI(A), XI(B), XII(A) and/or XII(B) and an effective amount of at least one anti-cancer agent, and a pharmaceutically inert carrier.

In another of its pharmaceutical aspects, this invention is directed to use of a compound according to formula I, II, III, III(A), IV, V(A), V(B) VI(A), VI(B), VII, VII(A), VII(B), VIII(A), VIII(B), IX(A), IX(B), X(A), X(B), XI(A), XI(B), XII(A) and/or XII(B) for the manufacture of a medicament for treating the conditions disclosed herein.

Deacetylases are found in transcriptional repression pathways. In addition, histone deacetylases (HDAC) play an important role in cell proliferation and differentiation. Inhibition of histone deacetylation results in cell cycle arrest, cellular differentiation, apoptosis and reversal of the transformed phenotype. Therefore, HDAC inhibitors are useful in the treatment and/or amelioration of cell proliferative diseases or conditions, such as cancers. Other diseases in which said HDAC inhibitors are useful are hematological disorders, e.g., hemoglobinopathies (thalassemias, sickle cell anemias); autosomal dominant disorders, e.g., spinal muscular atrophy and Huntington's disease; genetic related metabolic disorder, e.g., cystic fibrosis and adrenoleukodystrophy (US2004/0029903 A1, U.S. Pat. No. 6,124,495); psoriasis (McLaughlin, F.; La Thangue, N. B., Current Drug Targets-Inflammation, 2004, 3, 213-219); fibrosis, e.g., liver fibrosis, cirrhosis and fibrotic skin diseases, e.g., hypertrophic scars, keloid and Dupuytren's contracture (U.S. Pat. No. 5,993,845); autoimmune diseases, e.g., systemic lupus erythematosus (US2003/0082666 A1); acute or chronic degenerative conditions or diseases of the eye, e.g., glaucoma, dry age-related macular degeneration, retinitis pigmentosa and other forms of heredodegenerative retinal disease, retinal detachment and tears; macular pucker, ischemia affecting the outer retina, cellular damage associated with diabetic retinopathy and retinal ischemia, damage associated with laser therapy (grid, focal, and panretinal) including photodynamic therapy, trauma, surgical (retinal translocation, subretinal surgery, or vitrectomy) or light-induced iatrogenic retinopathy, and preservation of retinal transplants (US2004/0092431 A1); ocular neovascular or edematous diseases and disorders, e.g., diabetic retinopathy, rubeosis iritis, uveitis, Fuch's heterochromatic iridocyclitis, neovascular glaucoma, corneal neovascularization, neovasculariztion resulting from combined vitrectomy and lensectomy, retinal ischemia, choroidal vascular insufficiency, choroidal thrombosis, carotid artery ischemia, contusive ocular injury, retinopathy of prematurity, retinal vein occlusion, proliferative vitreoretinopathy, corneal angiogenesis, retinal microvasculopathy, or retinal edema (US 2004/0092558 A1); connective tissue disease, e.g., rheumatoid arthritis, progressive systemic sclerosis, sjorgren's syndrome, dermatomyositis or mixed connective tissue disease (US 2003/0206946 A1); cardiac hypertrophy and heart failure (U.S. Pat. No. 6,706,686 B2); insulin resistance (US 2004/0058868 A1); amyotrophic lateral sclerosis (US 2004/0077591 A1); multiple sclerosis (US 2004/0077591 A1); Alzheimer's disease (US 2004/0077591 A1); neurodegenerative diseases (US 2004/0087657 A1); and lung diseases, e.g., cystic fibrosis, chronic obstructive pulmonary disease, asthma or acute and chronic bronchitis (US 2004/0167184 A1). Each of the above references is incorporated herein by reference in their entirety.

In one of its method aspects, this invention is directed to a method for inhibiting a proliferative disorder in a mammalian patient which method comprises administering to said patient a pharmaceutical composition comprising a pharmaceutically acceptable carrier and a therapeutically effective amount of one or more compounds of formula I, II, III, III(A), IV, V(A), V(B) VI(A), VI(B), VII, VII(A), VII(B), VIII(A), VIII(B), IX(A), IX(B), X(A), X(B), XI(A), XI(B), XII(A) and/or XII(B). In another of its method aspects, this invention is directed to a method for inhibiting a proliferative disorder in a mammalian patient which method comprises administering to said patient a pharmaceutical composition comprising a pharmaceutically acceptable carrier, an effective amount of at least one anti-cancer agent, and a therapeutically effective amount of one or more compounds of formula I, II, III, III(A), IV, V(A), V(B) VI(A), VI(B), VII, VII(A), VII(B), VIII(A), VIII(B), Ix(A), IX(B), X(A), X(B), XI(A), XI(B), XII(A) and/or XII(B). In yet another of its method aspects, this invention is directed to a method for inhibiting a proliferative disorder in a mammalian patient which method comprises administering to said patient a pharmaceutical composition comprising a pharmaceutically acceptable carrier and a therapeutically effective amount of one or more compounds of formula I, II, III, III(A), IV, V(A), V(B) VI(A), VI(B), VII, VII(A), VII(B), VIII(A), VIII(B), IX(A), IX(B), X(A), X(B), XI(A), XI(B), XII(A) and/or XII(B) in combination with at least one anti-cancer agent.

For the treatment of the above conditions, the compounds of the invention may be advantageously employed in combination with one or more other medicinal agents, more particularly, with other anti-cancer agents. Examples of anti-cancer agents are: platinum coordination compounds, for example, cisplatin, carboplatin or oxalyplatin; taxane compounds, for example, paclitaxel or docetaxel; topoisomerase I inhibitors such as camptothecin compounds, for example, irinotecan or topotecan; topoisomerase II inhibitors such as anti-tumour podophyllotoxin derivatives, for example, etoposide or teniposide; anti-tumour vinca alkaloids, for example, vinblastine, vincristine or vinorelbine; anti-tumor nucleoside derivatives, for example, 5-fluorouracil, gemcitabine or capecitabine; alkylating agents such as nitrogen mustard or nitrosourea, for example, cyclophosphamide, chlorambucil, carmustine or lomustine; anti-tumour anthracycline derivatives, for example, daunorubicin, doxorubicin, idarubicin or mitoxantrone; HER2 antibodies, for example, trastuzumab; estrogen receptor antagonists or selective estrogen receptor modulators, for example, tamoxifen, toremifene, droloxifene, faslodex or raloxifene; aromatase inhibitors such as exemestane, anastrozole, letrazole and vorozole; differentiating agents such as retinoids, vitamin D and retinoic acid metabolism blocking agents (RAMBA), for example, accutane; DNA methyl transferase inhibitors, for example, azacytidine; kinase inhibitors, for example, flavoperidol, imatinib mesylate or gefitinib; farnesyltransferase inhibitors; or other HDAC inhibitors.

In another of its method aspects, this invention is directed to a method for treating a mammalian patient with one or more diseases or disorders including hematological disorders, e.g., hemoglobinopathies (thalassemias, sickle cell anemias); autosomal dominant disorders, e.g., spinal muscular atrophy and Huntington's disease; genetic related metabolic disorders, e.g., cystic fibrosis and adrenoleukodystrophy; psoriasis; fibrosis, e.g., liver fibrosis, cirrhosis and fibrotic skin diseases, e.g., hypertrophic scars, keloid and Dupuytren's contracture; autoimmune diseases, e.g., systemic lupus ery-thematosus; acute or chronic degenerative conditions/diseases of the eye, e.g, glaucoma, dry age-related macular degeneration, retinitis pigmentosa and other forms of heredodegenerative retinal disease, retinal detachment and tears; macular pucker, ischemia affecting the outer retina, cellular damage associated with diabetic retinopathy and retinal ischemia, damage associated with laser therapy (grid, focal, and panretinal) including photodynamic therapy, trauma, surgical (retinal translocation, subretinal surgery, or vitrectomy) or light-induced iatrogenic retinopathy, and preservation of retinal transplants; ocular neovascular or edematous diseases and disorders, e.g., diabetic retinopathy, rubeosis iritis, uveitis, Fuch's heterochromatic iridocyclitis, neovascular glaucoma, corneal neovascularization, neovascularization resulting from combined vitrectomy and lensectomy, retinal ischemia, choroidal vascular insufficiency, choroidal thrombosis, carotid artery ischemia, contusive ocular injury, retinopathy of permaturity, retinal vein occlusion, proliferative vitreoretinopathy, corneal angiogenesis, retinal microvasculopathy, or retinal edema; connective tissue disease, e.g., rheumatoid arthritis, progressive systemic sclerosis, sjorgren's syndrome, dermatomyositis or mixed connective tissue disease; cardiac hypertrophy and heart failure; insulin resistance; amyotrophic lateral sclerosis; multiple sclerosis; Alzheimer's disease; neurodegenerative diseases; preneoplastic conditions, e.g. colon polyps; and lung diseases, e.g., cystic fibrosis, chronic obstructive pulmonary disease, asthma or acute and chronic bronchitis. Such methods comprise administering to said patient a pharmaceutical composition comprising a pharmaceutically acceptable carrier and a therapeutically effective amount of one or more compounds of formula I, II, III, III(A), IV, V(A), V(B) VI(A), VI(B), VII, VII(A), VII(B), VIII(A), VIII(B), IX(A), IX(B), X(A), X(B), XI(A), XI(B), XII(A) and/or XII(B).

Compounds of this invention include those in the Tables 1A, 1B, 2A, 2B, 3A, 3B, 4A, 4B, 5, 6, and 7 below (including and tautomers, isomers, prodrugs and pharmaceutically acceptable salts thereof).

TABLE 1A

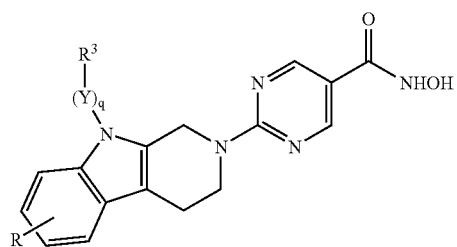

| Name | R | q | R³ | Ex. No. |
|---|---|---|---|---|
| N-hydroxy-2-(1,3,4,9-tetrahydro-2H-b-carbolin-2-yl)pyrimidine-5-carbox-amide | H | zero | H | 9 |

TABLE 1A-continued

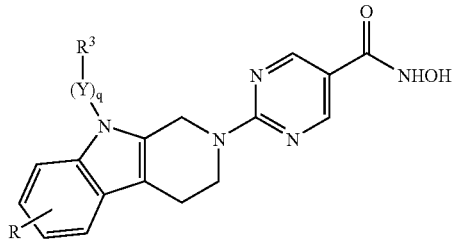
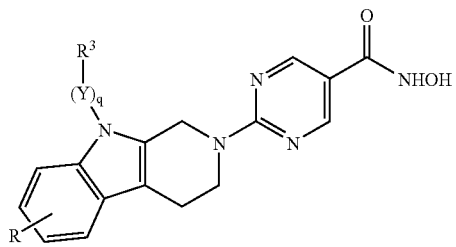

| Name | R | q | R³ | Ex. No. |
|---|---|---|---|---|
| N-hydroxy-2-(6-methoxy-1,3,4,9-tetrahydro-2H-b-carbolin-2-yl)pyrimidine-5-carboxamide | 6-OCH₃ | zero | H | 10 |
| N-hydroxy-2-(8-methyl-1,3,4,9-tetrahydro-2H-b-carbolin-2-yl)pyrimidine-5-carboxamide | 8-Me | zero | H | 61 |
| N-hydroxy-2-(7-fluoro-1,3,4,9-tetrahydro-2H-b-carbolin-2-yl)pyrimidine-5-carboxamide | 7-F | zero | H | 62 |
| N-hydroxy-2-(6-fluoro-1,3,4,9-tetrahydro-2H-b-carbolin-2-yl)pyrimidine-5-carboxamide | 6-F | zero | H | 63 |
| N-hydroxy-2-(6-methyl-1,3,4,9-tetrahydro-2H-b-carbolin-2-yl)pyrimidine-5-carboxamide | 6-Me | zero | H | 68 |
| N-hydroxy-2-(7-methyl-1,3,4,9-tetrahydro-2H-b-carbolin-2-yl)pyrimidine-5-carboxamide | 7-Me | zero | H | 65 |
| N-hydroxy-2-(6-benzyloxy-1,3,4,9-tetrahydro-2H-b-carbolin-2-yl)pyrimidine-5-carboxamide | 6-benzyloxy | zero | H | 64 |
| N-hydroxy-2-{6-[3-(morpholin-4-ylmethyl)phenyl]-1,3,4,9-tetrahydro-2H-b-carbolin-2-yl}pyrimidine-5-carboxamide | 6-[3-(morpholin-4-ylmethyl)-phenyl] | zero | H | 70 |
| N-hydroxy-2-{6-[3-((4-methylpiperazin-1-yl)methyl)phenyl]-1,3,4,9-tetrahydro-2H-b-carbolin-2-yl}pyrimidine-5-carboxamide | 6-[3-((4-methyl-piperazin-1-yl)methyl)-phenyl] | zero | H | 71 |
| N-hydroxy-2-{6-[4-((4-methylpiperazin-1-yl)methyl)phenyl]-1,3,4,9-tetrahydro-2H-b-carbolin-2-yl}pyrimidine-5-carboxamide | 6-[4-((4-methyl-piperazin-1-yl)methyl)-phenyl] | zero | H | 72 |
| N-hydroxy-2-{6-[2-((4-methylpiperazin-1-yl)methyl)phenyl]-1,3,4,9-tetrahydro-2H-b-carbolin-2-yl}pyrimidine-5-carboxamide | 6-[2-((4-methyl-piperazin-1-yl)methyl)-phenyl] | zero | H | 73 |
| N-hydroxy-2-{9-[2-pyrro-lidin-1-ylethyl]-1,3,4,9-tetrahydro-2H-b-carbolin-2-yl}pyrimidine-5-carboxamide | H | zero | 2-(pyrrolidin-1-yl)eth-1-yl | 23 |
| N-hydroxy-2-(9-methyl-1,3,4,9-tetrahydro-2H-b-carbolin-2-yl)pyrimidine-5-carboxamide | H | zero | CH₃ | 27 |
| N-hydroxy-2-{9-[2-pyrrolidin-1-ylmethyl]-1,3,4,9-tetrahydro-2H-b-carbolin-2-yl}pyrimidine-5-carboxamide | H | zero | pyrrolidin-1-yl-meth-1-yl | 30 |
| N-hydroxy-2-[9-(phenylsulfonyl)-1,3,4,9-tetrahydro-2H-b-carbolin-2-yl]pyrimidine-5-carboxamide | H | 1 Y = —SO₂— | phenyl | 26 |
| N-hydroxy-2-[9-(benzyl)-1,3,4,9-tetrahydro-2H-b-carbolin-2-yl)pyrimidine-5-carboxamide | H | zero | benzyl | 28 |
| N-hydroxy-2-[9-(2-piperidin-1-ylethyl)-1,3,4,9-tetrahydro-2H-b-carbolin-2-yl]pyrimidine-5-carboxamide | H | zero | 2-(piperidin-1-yl)eth-1-yl | 24 |
| N-hydroxy-2-(9-acetyl-1,3,4,9-tetrahydro-2H-b-carbolin-2-yl)pyrimidine-5-carboxamide | H | 1 Y = —C(O)— | —CH₃ | 29 |
| N-hydroxy-2-[9-(2-morpholin-4-ylethyl)-1,3,4,9-tetrahydro-2H-b-carbolin-2-yl]pyrimidine-5-carboxamide | H | zero | 2-(morpholin-4-yl)eth-1-yl | 25 |
| N-hydroxy-2-[9-(2-hydroxyethyl)-1,3,4,9-tetrahydro-2H-b-carbolin-2-yl]pyrimidine-5-carboxamide | H | zero | 2-hydroxyeth-1-yl | 58 |

TABLE 1A-continued

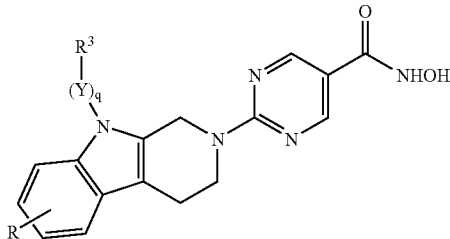

| Name | R | q | R³ | Ex. No. |
|---|---|---|---|---|
| N-hydroxy-2-[9-(1-methylpiperidin-3-yl)-1,3,4,9-tetrahydro-2H-b-carbolin-2-yl]pyrimidine-5-carboxamide | H | zero | 1-methylpiperidin-3-yl | 59 |

TABLE 1B

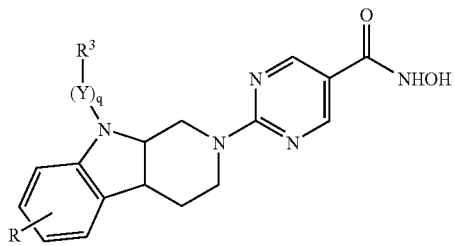

| Name | R | q | R³ | Ex. No. |
|---|---|---|---|---|
| N-hydroxy-2-(1,3,4,4a,9,9a-hexahydro-2H-b-carbolin-2-yl)pyrimidine-5-carboxamide | H | zero | H | |
| N-hydroxy-2-(6-methoxy-1,3,4,4a,9,9a-hexahydro-2H-b-carbolin-2-yl)pyrimidine-5-carboxamide | 6-OCH₃ | zero | H | |
| N-hydroxy-2-(6-methyl-1,3,4,4a,9,9a-hexahydro-2H-b-carbolin-2-yl)pyrimidine-5-carboxamide | 6-Me | zero | H | 67 |
| N-hydroxy-2-{9-[2-pyrrolid-in-1-ylethyl]-1,3,4,4a,9,9a-hexahydro-2H-b-carbolin-2-yl}pyrimidine-5-carboxamide | H | zero | 2-(pyrrolidin-1-yl)eth-1-yl | |
| N-hydroxy-2-(9-methyl-1,3,4,4a,9,9a-hexahydro-2H-b-carbolin-2-yl)pyrimidine-5-carboxamide | H | zero | CH₃ | |
| N-hydroxy-2-{9-[2-pyrrolidin-1-ylmethyl]-1,3,4,4a,9,9a-hexahydro-2H-b-carbolin-2-yl}pyrimidine-5-carboxamide | H | zero | pyrrolidin-1-yl-meth-1-yl | |

TABLE 1B-continued

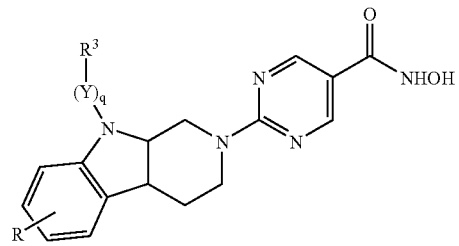

| Name | R | q | R³ | Ex. No. |
|---|---|---|---|---|
| N-hydroxy-2-[9-(phenylsulfonyl)-1,3,4,4a,9,9a-hexahydro-2H-b-carbolin-2-yl)pyrimidine-5-carboxamide | H | 1 Y = —SO₂— | Phenyl | |
| N-hydroxy-2-[9-(benzyl)-1,3,4,4a,9,9a-hexahydro-2H-b-carbolin-2-yl)pyrimidine-5-carboxamide | H | zero | benzyl | |
| N-hydroxy-2-[9-(2-piperidin-1-ylethyl)-1,3,4,4a,9,9a-hexahydro-2H-b-carbolin-2-yl]pyrimidine-5-carboxamide | H | zero | 2-(piperidin-1-yl)eth-1-yl | |
| N-hydroxy-2-(9-acetyl-1,3,4,4a,9,9a-hexahydro-2H-b-carbolin-2-yl)pyrimidine-5-carboxamide | H | 1 Y = —C(O)— | —CH₃ | |
| N-hydroxy-2-[9-(2-morpholin-4-ylethyl)-1,3,4,4a,9,9a-hexahydro-2H-b-carbolin-2-yl]pyrimidine-5-carboxamide | H | zero | 2-(morpholin-4-yl)eth-1-yl | |

TABLE 2A

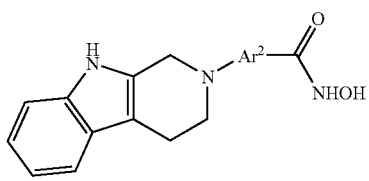

| Name | Ar² | Ex. No. |
|---|---|---|
| N-hydroxy-2-(1,3,4,9-tetrahydro-2H-b-carbolin-2-yl)-1,3-thiazole-5-carboxamide | thiazole (2,5-linked) | 19 |
| N-hydroxy-4-(1,3,4,9-tetrahydro-2H-b-carbolin-2-yl)benzamide | phenyl | 18 |
| N-hydroxy-6-(1,3,4,9-tetrahydro-2H-b-carbolin-2-yl)nicotinamide | pyridine (2,5-linked) | 4 |

TABLE 2B

Structure: hexahydro-b-carboline connected to Ar²–C(O)NHOH

| Name | Ar² | Ex. No. |
|---|---|---|
| N-hydroxy-2-(1,3,4,4a,9,9a-hexahydro-2H-b-carbolin-2-yl)-1,3-thiazole-5-carboxamide | (2,5-thiazolyl) | |

TABLE 2B-continued

| Name | Ar² | Ex. No. |
|---|---|---|
| N-hydroxy-4-(1,3,4,4a,9,9a-hexahydro-2H-b-carbolin-2-yl)benzamide | phenyl | |
| N-hydroxy-6-(1,3,4,4a,9,9a-hexahydro-2H-b-carbolin-2-yl)nicotinamide | (2,5-pyridyl) | |

TABLE 3A

Structure: R-substituted tetrahydro-pyrido[4,3-b]indole with N-(Y)q-R³, connected to pyrimidine-5-C(O)NHOH

| Name | R | q | R³ | Ex. No. |
|---|---|---|---|---|
| N-hydroxy-2-(1,3,4,5-tetrahydro-2H-pyrido[4,3-b]indol-2-yl)pyrimidine-5carboxamide | H | zero | H | 12 |
| N-hydroxy-2-(8-chloro-1,3,4,5-tetrahydro-2H-pyrido[4,3-b]indol-2-yl)pyrimidine-5-carboxamide | 8-Cl | zero | H | 14 |
| N-hydroxy-2-(8-methyl-1,3,4,5-tetrahydro-2H-pyrido[4,3-b]indol-2-yl)pyrimidine-5-carboxamide | 8-$CH_3$ | zero | H | 13 |
| N-hydroxy-2-(8-bromo-1,3,4,5-tetrahydro-2H-pyrido[4,3-b]indol-2-yl)pyrimidine-5-carboxamide | 8-Br | zero | H | 15 |
| N-hydroxy-2-(8-trifluoromethoxy-1,3,4,5-tetrahydro-2H-pyrido[4,3-b]indol-2-yl)pyrimidine-5-carboxamide | 8-$OCF_3$ | zero | H | 16 |
| N-hydroxy-2-(8-phenyl-1,3,4,5-tetrahydro-2H-pyrido[4,3-b]indol-2-yl)pyrimidine-5-carboxamide | 8-phenyl | zero | H | 17 |
| N-hydroxy-2-(8-fluoro-1,3,4,5-tetrahydro-2H-pyrido[4,3-b]indol-2-yl)pyrimidine-5-carboxamide | 8-fluoro | zero | H | 111 |
| N-hydroxy-2-(8-methoxy-1,3,4,5-tetrahydro-2H-pyrido[4,3-b]indol-2-yl)pyrimidine-5-carboxamide | 8-methoxy | zero | H | 57 |

TABLE 3A-continued

| Name | R | q | R³ | Ex. No. |
|---|---|---|---|---|
| N-hydroxy-2-(7-fluoro-1,3,4,5-tetrahydro-2H-pyrido[4,3-b]indol-2-yl)pyrimidine-5-carboxamide | 7-fluoro | zero | H | 35 |
| N-hydroxy-2-(7-methyl-1,3,4,5-tetrahydro-2H-pyrido[4,3-b]indol-2-yl)pyrimidine-5-carboxamide | 7-methyl | zero | H | 36 |
| N-hydroxy-2-(7,8-dimethyl-1,3,4,5-tetrahydro-2H-pyrido[4,3-b]indol-2-yl)pyrimidine-5-carboxamide | 7,8-dimethyl | zero | H | 56 |
| N-hydroxy-2-{8-[3-(pyrrolidin-1-ylmethyl)phenyl]-1,3,4,5-tetrahydro-2H-pyrido[4,3-b]indol-2-yl}pyrimidine-5-carboxamide | 8-[3-(pyrrolidin-1-ylmethyl)phenyl] | zero | H | 97 |
| N-hydroxy-2-{8-(pyridin-3-yl)-1,3,4,5-tetrahydro-2H-pyrido[4,3-b]indol-2-yl}pyrimidine-5-carboxamide | 8-pyridin-3-yl | zero | H | 47 |
| N-hydroxy-2-(7-chloro-8-methyl-1,3,4,5-tetrahydro-2H-pyrido[4,3-b]indol-2-yl)pyrimidine-5-carboxamide | 7-chloro-8-methyl | zero | H | 34 |
| N-hydroxy-2-(7-bromo-1,3,4,5-tetrahydro-2H-pyrido[4,3-b]indol-2-yl)pyrimidine-5-carboxamide | 7-bromo | zero | H | 112 |
| N-hydroxy-2-(8-trifluoromethyl-1,3,4,5-tetrahydro-2H-pyrido[4,3-b]indol-2-yl)pyrimidine-5-carboxamide | 8-trifluoromethyl | zero | H | 55 |
| N-hydroxy-2-{8-[4-(pyrrolidin-1-ylmethyl)phenyl]-1,3,4,5-tetrahydro-2H-pyrido[4,3-b]indol-2-yl}pyrimidine-5-carboxamide | 8-[4-(pyrrolidin-1-ylmethyl)phenyl] | zero | H | 103 |
| N-hydroxy-2-{8-(pyrimidin-5-yl)-1,3,4,5-tetrahydro-2H-pyrido[4,3-b]indol-2-yl}pyrimidine-5-carboxamide | 8-(pyrimidin-5-yl) | zero | H | 51 |
| N-hydroxy-2-{8-[3-(morpholin-4-ylmethyl)phenyl]-1,3,4,5-tetrahydro-2H-pyrido[4,3-b]indol-2-yl}pyrimidine-5-carboxamide | 8-[3-(morpholin-4-ylmethyl)phenyl] | zero | H | 90 |
| N-hydroxy-2-{8-[3-(piperidin-1-ylmethyl)phenyl]-1,3,4,5-tetrahydro-2H-pyrido[4,3-b]indol-2-yl}pyrimidine-5-carboxamide | 8-[3-(piperidin-1-ylmethyl)phenyl] | zero | H | 91 |

TABLE 3A-continued

| Name | R | q | R³ | Ex. No. |
|---|---|---|---|---|
| N-hydroxy-2-{8-[3-(N,N-dimethylaminomethyl)phenyl]-1,3,4,5-tetrahydro-2H-pyrido[4,3-b]indol-2-yl}pyrimidine-5-carboxamide | 8-[3-(N,N-dimethylaminomethyl)-phenyl] | zero | H | 92 |
| N-hydroxy-2-{8-[4-(N-acetamido)phenyl]-1,3,4,5-tetrahydro-2H-pyrido[4,3-b]indol-2-yl}pyrimidine-5-carboxamide | 8-[4-(N-acetamido)phenyl] | zero | H | 50 |
| N-hydroxy-2-(9-chloro-8-methyl-1,3,4,5-tetrahydro-2H-pyrido[4,3-b]indol-2-yl)pyrimidine-5-carboxamide | 9-chloro-8-methyl | zero | H | 54 |
| N-hydroxy-2-(8-nitro-1,3,4,5-tetrahydro-2H-pyrido[4,3-b]indol-2-yl)pyrimidine-5-carboxamide | 8-nitro | zero | H | 37 |
| N-hydroxy-2-{8-[3-(thiomorpholin-4-ylmethyl)phenyl]-1,3,4,5-tetrahydro-2H-pyrido[4,3-b]indol-2-yl}pyrimidine-5-carboxamide | 8-[3-(thiomorpholin-4-ylmethyl)phenyl] | zero | H | 94 |
| N-hydroxy-2-{8-[3-((4-hydroxymethylpiperidin-1-yl)methyl)phenyl]-1,3,4,5-tetrahydro-2H-pyrido[4,3-b]indol-2-yl}pyrimidine-5-carboxamide | 8-[3-((4-hydroxymethyl-piperidin-1-yl)methyl)phenyl] | zero | H | 93 |
| N-hydroxy-2-{8-(fur-2-yl)-1,3,4,5-tetrahydro-2H-pyrido[4,3-b]indol-2-yl}pyrimidine-5-carboxamide | 8-(fur-2-yl) | zero | H | 46 |
| N-hydroxy-2-(8-(N-acetamido)-1,3,4,5-tetrahydro-2H-pyrido[4,3-b]indol-2-yl)pyrimidine-5-carboxamide | 8-(N-acetamido) | zero | H | 77 |
| N-hydroxy-2-(8-(N-methylsulfonamido)-1,3,4,5-tetrahydro-2H-pyrido[4,3-b]indol-2-yl)pyrimidine-5-carboxamide | 8-(N-methylsulfonamido) | zero | H | 78 |
| N-hydroxy-2-{8-[3-(piperazin-1-ylmethyl)phenyl]-1,3,4,5-tetrahydro-2H-pyrido[4,3-b]indol-2-yl}pyrimidine-5-carboxamide | 8-[3-(piperazin-1-ylmethyl)phenyl] | zero | H | 99 |
| N-hydroxy-2-{8-[3-(N,N-di(2-hydroxyethyl)aminomethyl)-phenyl]-1,3,4,5-tetrahydro-2H-pyrido[4,3-b]indol-2-yl}pyrimidine-5-carboxamide | 8-[3-(N,N-di(2-hydroxyethyl)amino-methyl)phenyl] | zero | H | 95 |

TABLE 3A-continued

| Name | R | q | R³ | Ex. No. |
|---|---|---|---|---|
| N-hydroxy-2-(8-amino-1,3,4,5-tetrahydro-2H-pyrido[4,3-b]indol-2-yl)pyrimidine-5-carboxamide | 8-amino | zero | H | 76 |
| N-hydroxy-2-{8-[3-((4-methylpiperazin-1-yl)methyl)phenyl]-1,3,4,5-tetrahydro-2H-pyrido[4,3-b]indol-2-yl}pyrimidine-5-carboxamide | 8-[3-((4-methylpiperazin-1-yl)methyl)phenyl] | zero | H | 96 |
| N-hydroxy-2-{8-[3-((4-(methylsulfonyl)piperazin-1-yl)methyl)phenyl]-1,3,4,5-tetrahydro-2H-pyrido[4,3-b]indol-2-yl}pyrimidine-5-carboxamide | 8-[3-((4-(methylsulfonyl)-piperazin-1-yl)methyl)phenyl] | zero | H | 100 |
| N-hydroxy-2-{8-[3-((4-acetylpiperazin-1-yl)methyl)phenyl]-1,3,4,5-tetrahydro-2H-pyrido[4,3-b]indol-2-yl}pyrimidine-5-carboxamide | 8-[3-((4-acetylpiperazin-1-yl)methyl)phenyl] | zero | H | 101 |
| N-hydroxy-2-{8-[4-(morpholin-4-ylmethyl)phenyl]-1,3,4,5-tetrahydro-2H-pyrido[4,3-b]indol-2-yl}pyrimidine-5-carboxamide | 8-[4-(morpholin-4-ylmethyl)phenyl] | zero | H | 104 |
| N-hydroxy-2-{8-[4-(thiomorpholin-4-ylmethyl)phenyl]-1,3,4,5-tetrahydro-2H-pyrido[4,3-b]indol-2-yl}pyrimidine-5-carboxamide | 8-[4-(thiomorpholin-4-ylmethyl)phenyl] | zero | H | 105 |
| N-hydroxy-2-{8-[3-(hydroxymethyl)phenyl]-1,3,4,5-tetrahydro-2H-pyrido[4,3-b]indol-2-yl}pyrimidine-5-carboxamide | 8-[3-(hydroxymethyl)-phenyl] | zero | H | 43 |
| N-hydroxy-2-{8-[4-methoxyphenyl]-1,3,4,5-tetrahydro-2H-pyrido[4,3-b]indol-2-yl}pyrimidine-5-carboxamide | 8-[4-methoxyphenyl] | zero | H | 40 |
| N-hydroxy-2-{8-[4-methylphenyl]-1,3,4,5-tetrahydro-2H-pyrido[4,3-b]indol-2-yl}pyrimidine-5-carboxamide | 8-[4-methylphenyl] | zero | H | 41 |
| N-hydroxy-2-{8-[4-((4-methylpiperazin-1-yl)methyl)phenyl]-1,3,4,5-tetrahydro-2H-pyrido[4,3-b]indol-2-yl}pyrimidine-5-carboxamide | 8-[4-((4-methylpiperazin-1-yl)methyl)phenyl] | zero | H | 106 |
| N-hydroxy-2-{8-isopropyl-1,3,4,5-tetrahydro-2H-pyrido[4,3-b]indol-2-yl}pyrimidine-5-carboxamide | 8-isopropyl | zero | H | 38 |

TABLE 3A-continued

| Name | R | q | R³ | Ex. No. |
|---|---|---|---|---|
| N-hydroxy-2-{8-tert-butyl-1,3,4,5-tetrahydro-2H-pyrido[4,3-b]indol-2-yl}pyrimidine-5-carboxamide | 8-tert-butyl | zero | H | 39 |
| N-hydroxy-2-{8-[3-(pyrrolidin-1-ylcarbonyl)phenyl]-1,3,4,5-tetrahydro-2H-pyrido[4,3-b]indol-2-yl}pyrimidine-5-carboxamide | 8-[3-(pyrrolidin-1-ylcarbonyl)phenyl] | zero | H | 42 |
| N-hydroxy-2-{7-[3-(pyrrolidin-1-ylmethyl)phenyl]-1,3,4,5-tetrahydro-2H-pyrido[4,3-b]indol-2-yl}pyrimidine-5-carboxamide | 7-[3-(pyrrolidin-1-ylmethyl)phenyl] | zero | H | 121 |
| N-hydroxy-2-{7-phenyl-1,3,4,5-tetrahydro-2H-pyrido[4,3-b]indol-2-yl}pyrimidine-5-carboxamide | 7-phenyl | zero | H | 120 |
| N-hydroxy-2-{8-[4-(hydroxymethyl)phenyl]-1,3,4,5-tetrahydro-2H-pyrido[4,3-b]indol-2-yl}pyrimidine-5-carboxamide | 8-[4-(hydroxymethyl)phenyl] | zero | H | 107 |
| N-hydroxy-2-{8-[3-aminophenyl]-1,3,4,5-tetrahydro-2H-pyrido[4,3-b]indol-2-yl}pyrimidine-5-carboxamide | 8-[3-aminophenyl] | zero | H | 86 |
| N-hydroxy-2-{8-[3-fluorophenyl]-1,3,4,5-tetrahydro-2H-pyrido[4,3-b]indol-2-yl}pyrimidine-5-carboxamide | 8-[3-fluorophenyl] | zero | H | 44 |
| N-hydroxy-2-{8-[4-fluorophenyl]-1,3,4,5-tetrahydro-2H-pyrido[4,3-b]indol-2-yl}pyrimidine-5-carboxamide | 8-[4-fluorophenyl] | zero | H | 45 |
| N-hydroxy-2-{8-[fur-3-yl]-1,3,4,5-tetrahydro-2H-pyrido[4,3-b]indol-2-yl}pyrimidine-5-carboxamide | 8-[fur-3-yl] | zero | H | 52 |
| N-hydroxy-2-{8-[3-(N-acetamido)phenyl]-1,3,4,5-tetrahydro-2H-pyrido[4,3-b]indol-2-yl}pyrimidine-5-carboxamide | 8-[3-(N-acetamido)phenyl] | zero | H | 87 |
| N-hydroxy-2-{8-[3-(N-methylsulfonamido)phenyl]-1,3,4,5-tetrahydro-2H-pyrido[4,3-b]indol-2-yl}pyrimidine-5-carboxamide | 8-[3-(N-methylsulfonamido)phenyl] | zero | H | 88 |

TABLE 3A-continued

| Name | R | q | R³ | Ex. No. |
|---|---|---|---|---|
| N-hydroxy-2-{8-[3-(N-acetamidomethyl)phenyl]-1,3,4,5-tetrahydro-2H-pyrido[4,3-b]indol-2-yl}pyrimidine-5-carboxamide | 8-[3-(N-acetamidomethyl)phenyl] | zero | H | 82 |
| N-hydroxy-2-{8-[3-(N-methylsulfonamidomethyl)phenyl]-1,3,4,5-tetrahydro-2H-pyrido[4,3-b]indol-2-yl}pyrimidine-5-carboxamide | 8-[3-(N-methylsulfonamidomethyl)phenyl] | zero | H | 83 |
| N-hydroxy-2-{8-[3-(methylthio)phenyl]-1,3,4,5-tetrahydro-2H-pyrido[4,3-b]indol-2-yl}pyrimidine-5-carboxamide | 8-[3-methylthio)phenyl] | zero | H | 49 |
| N-hydroxy-2-{8-[3-(methylsulfinyl)phenyl]-1,3,4,5-tetrahydro-2H-pyrido[4,3-b]indol-2-yl}pyrimidine-5-carboxamide | 8-[3-(methylsulfonyl)phenyl] | zero | H | 79 |
| N-hydroxy-2-{8-[4-dimethylaminophenyl]-1,3,4,5-tetrahydro-2H-pyrido[4,3-b]indol-2-yl}pyrimidine-5-carboxamide | 8-[4-dimethylaminophenyl] | zero | H | 48 |
| N-hydroxy-2-{8-[3-(1H-tetrazol-5-yl)phenyl]-1,3,4,5-tetrahydro-2H-pyrido[4,3-b]indol-2-yl}pyrimidine-5-carboxamide | 8-[3-(1H-tetrazol-5-yl)phenyl] | zero | H | 84 |
| N-hydroxy-2-{8-[5-((4-methylpiperazin-1-yl)methyl)-2-furyl]-1,3,4,5-tetrahydro-2H-pyrido[4,3-b]indol-2-yl}pyrimidine-5-carboxamide | 8-[5-((4-methylpiperazin-1-yl)methyl)-2-furyl] | zero | H | 108 |
| N-hydroxy-2-{8-[5-(morpholin-4-yl)methyl-2-furyl]-1,3,4,5-tetrahydro-2H-pyrido[4,3-b]indol-2-yl}pyrimidine-5-carboxamide | 8-[5-morpholin-4-yl)methyl-2-furyl] | zero | H | 109 |
| N-hydroxy-2-{8-[5-((4-methylpiperazin-1-yl)methyl)-thien-2-yl]-1,3,4,5-tetrahydro-2H-pyrido[4,3-b]indol-2-yl}pyrimidine-5-carboxamide | 8-[5-((4-methylpiperazin-1-yl)methyl)-thien-2-yl] | zero | H | 110 |
| N-hydroxy-2-{8-[1H-pyrrol-2-yl]-1,3,4,5-tetrahydro-2H-pyrido[4,3-b]indol-2-yl}pyrimidine-5-carboxamide | 8-[1H-pyrrol-2-yl] | zero | H | 53 |
| N-hydroxy-2-{8-[thien-2-yl]-1,3,4,5-tetrahydro-2H-pyrido[4,3-b]indol-2-yl}pyrimidine-5-carboxamide | 8-[thien-2-yl] | zero | H | 60 |

TABLE 3A-continued

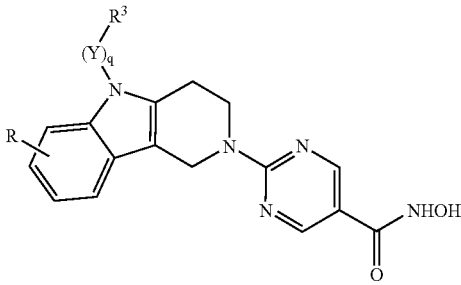

| Name | R | q | R³ | Ex. No. |
|---|---|---|---|---|
| N-hydroxy-2-{8-[(4-methylpiperazin-1-yl)methyl]-1,3,4,5-tetrahydro-2H-pyrido[4,3-b]indol-2-yl}pyrimidine-5-carboxamide | 8-[(4-methylpiperazin-1-yl)methyl] | zero | H | 123 |
| N-hydroxy-2-{5-acetyl-8-methyl-1,3,4,5-tetrahydro-2H-pyrido[4,3-b]indol-2-yl}pyrimidine-5-carboxamide | methyl | 1 Y = —C(O)— | CH₃ | 74 |

TABLE 3B

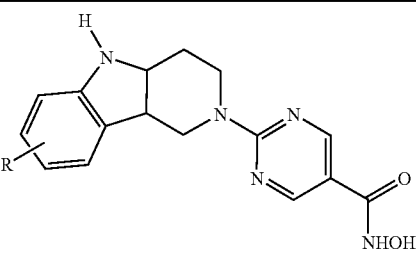

| Name | R | Ex. No. |
|---|---|---|
| N-hydroxy-2-(1,1a,3,4,4a,5-hexahydro-2H-pyrido[4,3-b]indol-2-yl)pyrimidine-5carboxamide | H | |
| N-hydroxy-2-(8-chloro-1,1a,3,4,4a,5-hexahydro-2H-pyrido[4,3-b]indol-2-yl)pyrimidine-5-carboxamide | 8-Cl | |
| N-hydroxy-2-(8-methyl-1,3,4,4a,5,9b-hexahydro-2H-pyrido[4,3-b]indol-2-yl)pyrimidine-5-carboxamide | 8-CH₃ | 75 |

TABLE 3B-continued

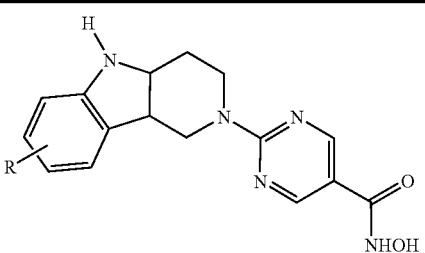

| Name | R | Ex. No. |
|---|---|---|
| N-hydroxy-2-(8-bromo-1,1a,3,4,4a,5-hexahydro-2H-pyrido[4,3-b]indol-2-yl)pyrimidine-5-carboxamide | 8-Br | |
| N-hydroxy-2-(8-trifluoromethoxy-1,1a,3,4,4a,5-hexahydro-2H-pyrido[4,3-b]indol-2-yl)pyrimidine-5-carboxamide | 8-OCF₃ | |

TABLE 4A

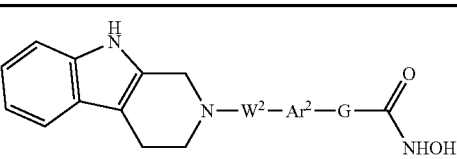

| Name | W² | Ar² | G | Ex. No. |
|---|---|---|---|---|
| (2E)-N-hydroxy-3-[2-(1,3,4,9-tetrahydro-2H-b-carbolin-2-yl)pyrimidin-5-yl]acrylamide | bond | 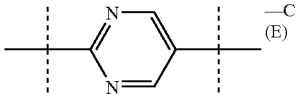 | —CH=CH— (E) | 20 |

TABLE 4A-continued

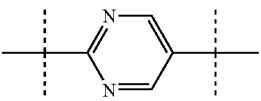

| Name | W² | Ar² | G | Ex. No. |
|---|---|---|---|---|
| N-hydroxy-3-[2-(1,3,4,9-tetrahydro-2H-b-carbolin-2-yl)pyrimidin-5-yl]propionamide | bond | pyrimidine (2,5) | —CH₂CH₂— | 21 |
| (2E)-N-hydroxy-3-[5-(1,3,4,9-tetrahydro-2H-b-carbolin-2-ylmethyl)-thien-2-yl]acrylamide | —CH₂— | thiophene (2,5) | —CH=CH— (E) | 3 |

TABLE 4B

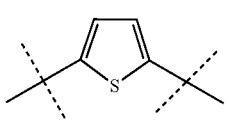

| Name | W² | Ar² | G | Ex. No. |
|---|---|---|---|---|
| (2E)-N-hydroxy-3-[2-(1,3,4,4a,9,9a-hexahydro-2H-b-carbolin-2-yl)pyrimidin-5-yl]acrylamide | bond | pyrimidine (2,5) | —CH=CH— (E) | |
| N-hydroxy-3-[2-(1,3,4,4a,9,9a-hexahydro-2H-b-carbolin-2-yl)pyrimidin-5-yl]propionamide | bond | pyrimidine (2,5) | —CH₂CH₂— | |
| (2E)-N-hydroxy-3-[5-(1,3,4,4a,9,9a-hexahydro-2H-b-carbolin-2-ylmethyl)-thien-2-yl]acrylamide | —CH₂— | thiophene (2,5) | —CH=CH— (E) | |

TABLE 5

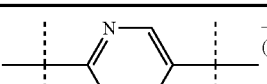

| Name | X | Ex. No. |
|---|---|---|
| N-hydroxy-6-(6,7-dimethoxy-3,4-dihydroisoquinolin-2(1H)-yl)nicotinamide | 6,7-dimethoxy | CH | 5 |
| N-hydroxy-2-(6,7-dimethoxy-3,4-dihydroisoquinolin-2(1H)-yl)pyrimidine-5-carboxamide | 6,7-dimethoxy | N | 11 |

TABLE 5-continued

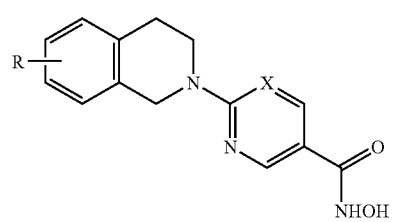

| Name | X | Ex. No. |
|---|---|---|
| N-hydroxy-2-(7-dimethoxy-3,4-dihydroisoquinolin-2(1H)-yl)pyrimidine-5-carboxamide | 7-dimethoxy | N | 31 |

TABLE 6

[Structure: tetrahydroazepino[4,5-b]indole connected to pyrimidine-5-carboxamide with NHOH, with R substituent on benzene ring]

| Name | R | Ex. No. |
|---|---|---|
| N-hydroxy-2-(1,4,5,6-tetrahydroazepino[4,5-b]indol-3(2H)-1-yl)pyrimidine-5-carboxamide | H | 114 |
| N-hydroxy-2-(9-methoxy-1,4,5,6-tetrahydroazepino[4,5-b]indol-3(2H)-1-yl)pyrimidine-5-carboxamide | 9-methoxy | 113 |
| N-hydroxy-2-(9-fluoro-1,4,5,6-tetrahydroazepino[4,5-b]indol-3(2H)-1-yl)pyrimidine-5-carboxamide | 9-fluoro | 115 |
| N-hydroxy-2-(9-[3-(morpholin-4-ylmethy)phenyl]-1,4,5,6-tetrahydroazepino[4,5-b]indol-3(2H)-1-yl)pyrimidine-5-carboxamide | 9-[3-morpholin-4-ylmethy)phenyl] | 116 |
| N-hydroxy-2-(9-[3-((4-methylpiperazin-1-yl)methy)phenyl]-1,4,5,6-tetrahydroazepino[4,5-b]indol-3(2H)-1-yl)pyrimidine-5-carboxamide | 9-[3-((4-methylpiperazin-1-yl)methy)phenyl] | 117 |

TABLE 7

| Structure | Name | Example Number |
|---|---|---|
| [benzothieno-pyridine fused with pyrimidine carboxamide NHOH] | 2-(3,4-dihydro[1]benzothieno[2,3-c]pyridin-2(1H)-yl)-N-hydroxypyrimidine-5-carboxamide | 118 |
| [benzofuro-pyridine fused with pyrimidine carboxamide NHOH] | 2-(3,4-dihydro[1]benzofuro[2,3-c]pyridin-2(1H)-yl)-N-hydroxypyrimidine-5-carboxamide | 119 |
| [benzo[de]isoquinoline with pyrimidine carboxamide NHOH] | 2-(1H-benzo[de]isoquinolin-2(3H)-yl)-N-hydroxypyrimidine-5-carboxamide | 32 |
| [tetrahydrobenzo-naphthyridinone with pyrimidine carboxamide NHOH] | N-hydroxy-2-(10-oxo-3,4,5,10-tetrahydrobenzo[b]-1,6-naphthyridin-2(1H)-yl)pyrimidine-5-carboxamide | 122 |

DEFINITIONS

Unless otherwise limited by a specific recitation herein, the following terms have the following meanings;

"Alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Alkylene" refers to divalent alkylene groups having from 1 to 10 carbon atoms, preferably Ito 5 carbon atoms and more preferably 1 to 3 carbon atoms. This term is exemplified by groups such as methylene, 1,2-ethylene, 1,3-propylene, 1,2-propylene, 1,4-butylene, 1,5-pentylene and the like.

"Substituted alkyl" refers to a monovalent alkyl group having from 1 to 3, and preferably 1 to 2, substituents selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, thiol, and thioalkyl.

"Substituted alkylene" refers to divalent alkylene group having from 1 to 3, and preferably 1 to 2, substituents selected from the group consisting of those recited for substituted alkyl.

"Alkoxy" refers to the group "alkyl-O-" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Alkylsulfinyl" refers to the group —S(O)alkyl.

"Arylsulfinyl" refers to the group —S(O)aryl.

"Alkylsulfonyl" refers to the group —S(O)$_2$alkyl.

"Arylsulfonyl" refers to the group —S(O)$_2$aryl.

"Aminoacyl" refers to the group —C(O)NR$^{10}$R$^{10}$ where each R$^{10}$ is independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where each R$^{10}$ is joined to form together with the nitrogen atom a heterocyclic or substituted heterocyclic ring.

"Alkenyl" refers to a monovalent alkenyl group having from 2 to 10 carbon atoms and preferably 2 to 6 carbon atoms and having at least 1 and preferably from 1-2 sites of vinyl (double bond) unsaturation. The term "alkenyl" encompasses any and all combinations of cis and trans isomers arising from the presence of unsaturation.

"Alkenylene" refers to divalent alkenylene groups having from 2 to 10 carbon atoms and preferably 2 to 6 carbon atoms and having at least 1 and preferably from 1-2 sites of vinyl (double bond) unsaturation. The term "alkenylene" encompasses any and all combinations of cis and trans isomers arising from the presence of unsaturation.

"Substituted alkenyl" refers to alkenyl groups having from 1 to 3 substituents, and preferably 1 to 2 substituents, selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on a vinyl carbon atom.

"Substituted alkenylene" refers to divalent alkenylene group having from 1 to 3, and preferably 1 to 2, substituents selected from the group consisting of those recited for substituted alkenyl.

"Alkynyl" refers to a monovalent alkynyl, group having from 2 to 10 carbon atoms and preferably 2 to 6 carbon atoms and having at least 1 and preferably from 1-2 sites of acetylene (triple bond) unsaturation.

"Alkynylene" refers to divalent alkynylene groups having from 2 to 10 carbon atoms and preferably 2 to 6 carbon atoms and having at least 1 and preferably from 1-2 sites of acetylene (triple bond) unsaturation.

"Substituted alkynyl" refers to alkynyl groups having from 1 to 3 substituents, and preferably 1 to 2 substituents, selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on an acetylenic carbon atom.

"Substituted alkynylene" refers to divalent alkynylene group having from 1 to 3, and preferably 1 to 2, substituents selected from the group consisting of those recited for substituted alkynyl.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocylic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. Also included within the term substituted amino are sulfoamido groups represented by the formula —NR'SO$_2$R'" where R' is as defined above and R'" is selected from the group consisting of alkyl, substituted alkyl, aryl, substituted aryl, cycloalkyl, substituted cycloalkyl, heterocyclic, substituted heterocyclic, heteroaryl and substituted heteroaryl.

"Aminocarbonyloxy" refers to the group NH$_2$—C(O)—O—.

"Oxycarbonylamino" refers to the group alkoxy-C(O)—NH$_2$— or ayloxy-C(O)—NH$_2$—.

"Acylamino" refers to the groups —NR$^{11}$C(O)alkyl, —NR$^{11}$C(O)substituted alkyl, —NR$^{11}$C(O)cycloalkyl, —NR$^{11}$C(O)substituted cycloalkyl, —NR$^{11}$C(O)alkenyl, —NR$^{11}$C(O)substituted alkenyl, —NR$^{11}$C(O)aryl, —NR$^{11}$C(O)substituted aryl, —NR$^{11}$C(O)heteroaryl, —NR$^{11}$C(O)substituted heteroaryl, —NR$^{11}$C(O)heterocyclic, and —NR$^{11}$C(O)substituted heterocyclic where R$^{11}$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is to an aromatic ring atom. Preferred aryls include phenyl and naphthyl, e.g, 2-naphthyl.

"Substituted aryl" refers to aryl groups which are substituted with from 1 to 3 substituents, and preferably 1 to 2 substituents, selected from the group consisting of hydroxy, acyl, acylamino, alkyl, substituted alkyl, alkoxy, substituted alkoxy, alkenyl, substituted alkenyl, amino, substituted amino, aminoacyl, aryl, substituted aryl, aryloxy, substituted aryloxy, cycloalkoxy, substituted cycloalkoxy, carboxyl, carboxyl esters, cyano, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, alkylsulfinyl, arylsulfinyl, alkylsulfonyl, arylsulfonyl, thiol, and thioalkyl.

"Arylene" refers to a divalent aryl group of from 6 to 14 carbon atoms having a single ring (e.g., phenylene) or multiple condensed rings (e.g., naphthylene or anthrylene) which condensed rings may or may not be aromatic (e.g., 2-benzoxazolinone, 2H-1,4-benzoxazin-3(4H)-one-7-yl, and the like) provided that the points of attachment are to an aromatic ring atom. Preferred arylenes include phenylene (e.g. 1,4-phenylene) and naphthylene (e.g, 1,2-naphthylene).

"Substituted arylene" refers to arylene groups which are substituted with from 1 to 3 substituents, and preferably 1 to 2 substituents, selected from the group consisting of hydroxy, acyl, acylamino, alkyl, substituted alkyl, alkoxy, substituted alkoxy, alkenyl, substituted alkenyl, amino, substituted amino, aminoacyl, aryl, substituted aryl, aryloxy, substituted aryloxy, cycloalkoxy, substituted cycloalkoxy, carboxyl, carboxyl esters, cyano, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, alkylsulfinyl, arylsulfinyl, alkylsulfonyl, arylsulfonyl, thiol, and thioalkyl.

"Heteroarylene" refers to a divalent heteroaryl group of from 1 to 15 carbon atoms, preferably from 1 to 10 carbon atoms, and 1 to 4 heteroatoms selected from the group consisting of oxygen, nitrogen, and sulfur within the ring. Optionally, either or both of any nitrogen and/or sulfur atoms within the ring can be oxidized. Such heteroaryl groups can have a single ring (e.g., pyridyl or furyl) or multiple condensed rings (e.g., indolizinyl or benzothienyl) provided that the point of attachment is through a heteroaryl ring atom. Preferred heteroaryls include pyridyl, pyrrolyl, indolyl, thiophenyl, and furyl.

"Substituted heteroarylene" refers to heteroarylene groups which are substituted with from 1 to 3 substituents, and preferably 1 to 2 substituents, selected from the group consisting of hydroxy, acyl, acylamino, alkyl, substituted alkyl, alkoxy, substituted alkoxy, alkenyl, substituted alkenyl, amino, substituted amino, aminoacyl, aryl, substituted aryl, aryloxy, substituted aryloxy, cycloalkoxy, substituted cycloalkoxy, carboxyl, carboxyl esters, cyano, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, alkylsulfinyl, arylsulfinyl, alkylsulfonyl, arylsulfonyl, thiol, and thioalkyl.

"1,2-fused aryl" refers to an aryl group that is fused to an optionally substituted cycloalkyl or an optionally substituted heterocyclic group at positions alpha/beta on the aryl ring. Accordingly, such groups are construed as fused 1,2-aryl groups regardless of the numbering system of the aryl moiety provided that fusion is alpha/beta. For example, napthalene fused at the 2,3-positions thereof with piperidine as shown below would be construed as a fused 1,2-aryl group as the napthyl group is fused at positions alpha/beta on the naphthyl ring to the 3,4-positions of the piperidinyl group:

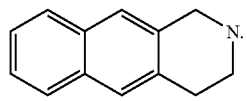

"Substituted 1,2-fused aryl" refers to fused 1,2-aryl groups substituted with 1 to 3 substituents as defined above for substituted aryl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or pharmaceutically acceptable salts thereof.

"Carboxyl esters" refers to the groups —C(O)O-alkyl, —C(O)O-substituted alkyl, —C(O)Oaryl, and —(O)O-substituted aryl wherein alkyl, substituted alkyl, aryl and substituted aryl are as defined herein.

"Cycloalkyl" refers to monovalent cyclic alkyl groups of from 3 to 10 carbon atoms having single or multiple condensed rings which condensed rings may or may not be cycloalkyl provided that the point of attachment is to a cycloalkyl ring atom. Examples of cycloalkyl groups include, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to a monovalent aromatic group of from 1 to 15 carbon atoms, preferably from 1 to 10 carbon atoms, and 1 to 4 heteroatoms selected from the group consisting of oxygen, nitrogen, and sulfur within the ring. Optionally, either or both of any nitrogen and/or sulfur atoms within the ring can be oxidized. Such heteroaryl groups can have a single ring (e.g., pyridyl or furyl) or multiple condensed rings (e.g., indolizinyl or benzothienyl) provided that the point of attachment is through a heteroaryl ring atom. Preferred heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"1,2-fused heteroaryl" refers to a heteroaryl group that is fused to an optionally substituted cycloalkyl or an optionally substituted heterocyclic group at positions alpha/beta on the heteroaryl ring. Accordingly, such groups are construed as fused 1,2-heteroaryl groups regardless of the numbering system of the heteroaryl moiety provided that fusion is alpha/beta. For example, quinoline fused at the 2,3-positions thereof with piperidine as shown below would be construed as a fused 1,2-heteroaryl group as the quinoline group is fused at positions alpha/beta on the ring to the 3,4-positions of the piperidinyl group:

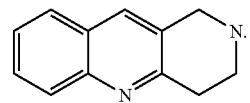

"Substituted 1,2-fused heteroaryl" refers to fused 1,2-heteroaryl groups substituted with 1 to 3 substituents as defined above for substituted heteroaryl.

"Heteroaryloxy" refers to the group —O-heteroaryl and "substituted heteroaryloxy" refers to the group —O-substituted heteroaryl.

"Heterocycle" or "heterocyclic" refers to a monovalent saturated or unsaturated group having a single ring or multiple condensed rings, from 1 to 10 carbon atoms and from 1 to 4 hetero atoms selected from the group consisting of nitrogen, sulfur and oxygen within the ring wherein, in fused ring systems, one or more the rings can be aryl or heteroaryl provided that the point of attachment is to a heterocyclic (non-aromatic) ring atom. Optionally, either or both of any nitrogen and/or sulfur atoms within the ring can be oxidized.

"Substituted heterocyclic" refers to heterocyclic groups that are substituted with from 1 to 3 of the same substituents as defined for substituted cycloalkyl.

"1,2-fused heterocyclic" refers to a first heterocyclic group that is fused to an optionally substituted cycloalkyl or an optionally substituted second heterocyclic group at positions alpha/beta on the first heterocyclic ring. Accordingly, such groups are construed as fused 1,2-heterocyclic groups regardless of the numbering system of the heterocyclic moiety provided that fusion is alpha/beta. For example, indoline fused at the 2,3-positions thereof with piperidine as shown below would be construed as a fused 1,2-heterocyclic group as the indoline group is fused at positions alpha/beta on the ring to the 3,4-positions of the piperidinyl group:

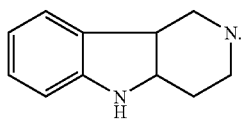

"Substituted 1,2-fused heterocyclic" refers to fused 1,2-heterocyclic groups substituted with 1 to 3 substituents as defined above for substituted heterocyclic.

Examples of heterocycles and heteroaryls include, but are not limited to, azetidine, benzofuran, 2,3-dihydrobenzofuran, pyrrole, imidazole, pyrazole, pyridine, pyrazine, pyrimidine, pyridazine, indolizine, isoindole, indole, indoline, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydro-benzo[b]thiophene, thiazole, thiazolidine, thiophene, benzo[b]thiophene, 2,3-dihydrobenzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

"Thiol" refers to the group —SH.

"Thioalkyl" refers to the group —S-alkyl.

"Substituted thioalkyl" refers to the group —S-substituted alkyl.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

"Pharmaceutically acceptable salt" refers to pharmaceutically acceptable salts of any of the compounds of formula I, II, III, III(A), IV, V(A), V(B) VI(A), VI(B), VII, VII(A), VII(B), VIII(A), VIII(B), IX(A), IX(B), X(A), X(B), XI(A), XI(B), XII(A) and/or XII(A) which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutical acceptable salt thereof" also refers to the salts of the tautomers, stereoisomers, or prodrugs of I, II, III, III(A), IV, V(A), V(B) VI(A), VI(B), VII, VII(A), VII(B), VIII(A), VIII (B), IX(A), IX(B), X(A), X(B), XI(A), XI(B), XII(A) and/or XII(B).

"Mammals" include human and non-human animals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

"Prodrug" refers to any derivative of a compound of this invention that is capable of directly or indirectly providing a compound of this invention or an active metabolite or residue thereof when administered to a subject. Particularly favored derivatives and prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "platinum coordination compound" is used herein to denote any tumor cell growth inhibiting platinum coordination compound which provides platinum in the form of an ion.

The term "taxane compounds" indicates a class of compounds having the taxane ring system and related to or derived form extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has similar mechanism of action which involves the introduction of DNA strand breaks of the formation of free radicals.

The term "camptothecin compounds" is used to indicate compounds that are related to or derived from the parent camptothecin compound which is water-insoluble alkaloid derived from the Chinese tree *Camptothecin acuminate* and the Indian tree *Nothapodytes foetida*.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus* var. *caesius* and their derivatives, characterized by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is highly purified recombinant DNA-derived humanized monoclonal IgG1 kappa antibody that binds with high affinity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, inhibiting its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promoters of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "comprises" or "comprising" and grammatical variations thereof when used in this specification are to be taken to specify the presence of stated features, integers, steps or components or groups thereof, but do not preclude the presence or addition of one or more other features, integers, steps, components or groups thereof.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

The following U.S. patents are incorporated by reference in their entirety to the extent that they describe the synthesis of 1,2,3,4,5,6-hexahydroazepino[4,5-b]indoles: U.S. Pat. No. 3,676,558; U.S. Pat. No. 3,839,357; and U.S. Pat. No. 6,407,092.

The following U.S. patents are incorporated by reference in their entirety to the extent that they describe the synthesis of 1,2,3,4-tetrahydro-9H-pyrido[3,4-b]indoles: U.S. Pat. No. 6,090,945 and U.S. Pat. No. 6,861,410.

U.S. Pat. No. 4,001,263 is hereby incorporated by reference in its entirety to the extent that it describes the preparation of 2,3,4,5-tetrahydro-1H-pyrido[4,3-b]indoles.

U.S. Pat. No. 4,006,164 is hereby incorporated by reference to the extent that it describes the preparation of 1,2,3,4-tetrahydropyrrolo[3,4-b]indoles.

As to the synthesis of compounds of this invention, Scheme 1 below illustrates a general method for synthesis of compounds of this invention wherein $W^2$ and G are bonds and

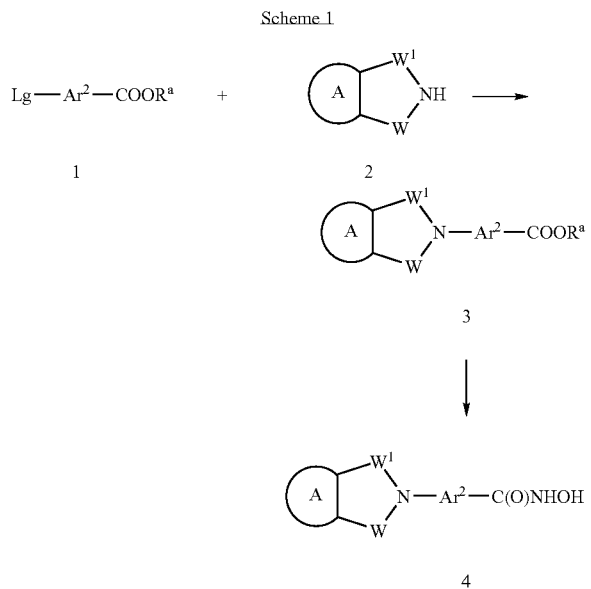

Scheme 1 wherein A, $Ar^2$, W, and $W^1$ are as defined above, Lg is a suitable leaving group such as halogen, mesylate, tosylate, sulfone, triflate and the like and $R^a$ is alkyl or substituted alkyl and preferably is methyl or ethyl.

Specifically, in Scheme 1, carboxylic acid ester 1 having a suitable leaving group (LG) is combined with from about one to five equivalents of cyclic amine 2 in a suitable inert diluent. The reaction is typically conducted at an elevated temperature of from about 25° to about 180° C. in a suitable solvent in the presence of a base to scavenge any acid generated during the reaction (particularly when Lg is halo). The reaction is continued for about one to 72 hours to produce an intermediate ester 3. Suitable solvents include, for example, acetonitrile, tetrahydrofuran (THF), dioxane, dimethylformamide (DMF) or N,N-dimethylacetamide. Suitable bases include alkali metal carbonates such sodium carbonate, potassium carbonate and cesium carbonate or organic bases such as triethylamine (TEA) and diisopropylethylamine (DIEA). Upon reaction completion, compound 3 is recovered by conventional methods including neutralization, evaporation, extraction, precipitation, chromatography, filtration, and the like, or, alternatively, is used in the next reaction without purification and/or isolation.

Hydroxamic acids 4 are produced by treating ester 3 with an excess, typically from greater than one to about 20 equivalents of 10 to 50% hydroxylamine in a suitable solvent such as water, methanol, or ethanol. The reaction is conducted in the presence of an excess of alkali metal hydroxide, typically from greater than one to about 20 equivalents of an alkali metal hydroxide. The reaction is typically conducted at from about 0 to 60° C. and is continued until substantially complete which typically occurs within about one to 72 hours. Upon reaction completion, the compound 4 is recovered by conventional methods including neutralization, evaporation, extraction, precipitation, chromatography, filtration, and the like.

Scheme 2 below illustrates a general method for synthesis of compounds of this invention wherein $W^2$ is methylene and G is or is not a bond and further wherein A, $Ar^2$, W, $W^1$ and $R^a$ are as defined above.

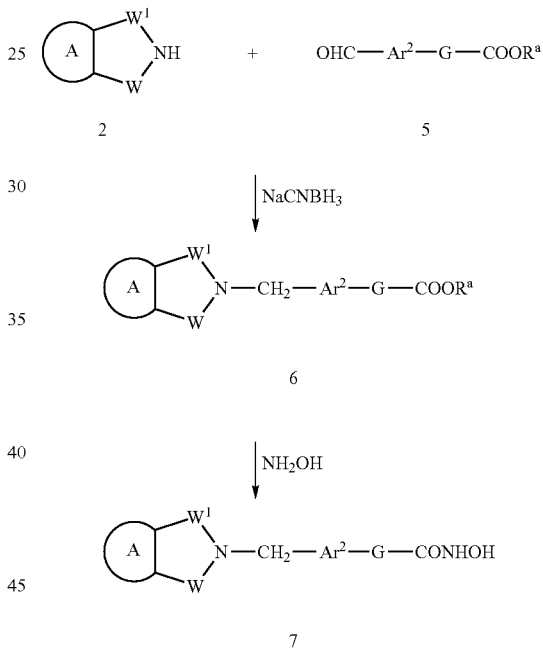

Scheme 2

Specifically, in Scheme 2, reductive amination of aromatic aldehyde 5 in the presence of amine 2 provides for compound 6. Reductive amination proceeds by combining approximately stoichiometric equivalents of amine 2 with aldehyde 5 in a suitable solvent such as methanol, ethanol, tetrahydrofuran, trimethylorthoformate, dioxane, and the like to provide for intermediate imine (not shown). The imine is reduced to the amine, compound 6, in situ by the presence an excess, preferably from greater than one to about ten equivalents of a borohydride reducing agent, such as sodium cyanoborohydride ($NaCNBH_3$), sodium borohydride, sodium triacetoxyborohydride and the like. The reaction is typically conducted at a temperature of from about 0 to 60° C. and continued until the reaction is substantially complete which typically occurs in about 15 minutes to 48 hours. Upon reaction completion, compound 6 is recovered by conventional methods including neutralization, evaporation, extraction, precipitation, chromatography, filtration, and the like, or, alternatively, is used in the next reaction without purification and/or isolation.

Variants of this reaction are possible and are well known in the art including the addition of acids such as, but not limited to, acetic acid or trifluoroacetic acid (TFA) and the addition of drying agents such as anhydrous magnesium or sodium sulfate. Catalytic hydrogenation of the imine can also be used but is less preferred. Such hydrogenation typically uses platinum or palladium catalysts, preferably 5% palladium on carbon, and one to five atmospheres of hydrogen at 20 to 80° C. for 15 minutes to 48 hours. Suitable solvents include those recited above and preferred $R^a$ groups include methyl and ethyl.

Hydroxamic acids 7 are produced by treating ester 6 with an excess, typically from greater than one to about 20 equivalents of 10 to 50% hydroxylamine in a suitable solvent such as water, methanol, or ethanol. The reaction is conducted in the presence of an excess of alkali metal hydroxide, typically from greater than one to about 20 equivalents of an alkali metal hydroxide. The reaction is typically conducted at from about 0 to 60° C. and is continued until substantially complete which typically occurs within about one to 72 hours. Upon reaction completion, the compound 4 is recovered by conventional methods including neutralization, evaporation, extraction, precipitation, chromatography, filtration, and the like.

In Scheme 2, it is understood that further elaboration of the $W^2$ group (other than methylene) is well within the skill of the art. For example, alkylene aldehydes attached to the $Ar^2$ can be employed rather than direct aldehyde attachment. Still further, an ω-haloalkylene-$Ar^2$-G-$CO_2R^a$ or substituted alkylene compound can be used to provide for alkylene or substituted $W^2$ linkage as depicted in Scheme 1.

Scheme 3 below illustrates a further general method for synthesis of compounds of this invention wherein $W^2$ is methylene and G is or is not a bond and further wherein A, $Ar^2$, W, $W^1$ and $R^a$ are as defined above.

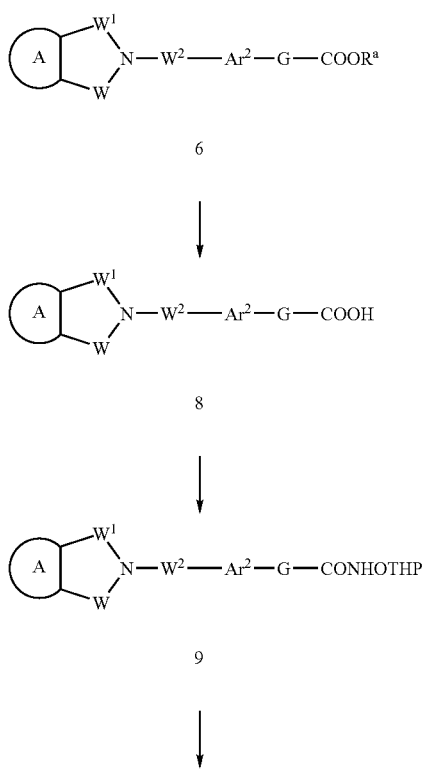

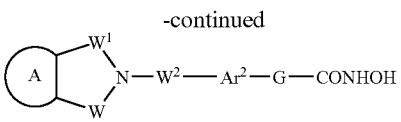

Specifically, in Scheme 3, ester 6 is hydrolyzed under conventional conditions to provide for acid 8. In one embodiment, hydrolysis proceeds by addition of an excess and preferably from greater than one to about 10 equivalents of a base such as an alkaline earth hydroxide including, for example, lithium hydroxide, sodium hydroxide, potassium hydroxide and the like. The reaction is conducted in a suitable solvent such as mixtures of water with ethanol, methanol and tetrahydrofuran. The reaction is typically conducted at from about 20 to 100° C. and is continued until it is substantial complete which typically occurs in about 15 minutes to 24 hours. Upon reaction completion, compound 8 is recovered by conventional methods including neutralization, evaporation, extraction, precipitation, chromatography, filtration, and the like, or, alternatively, is used in the next reaction without purification and/or isolation.

Alternatively, if the $R^a$ group of compound 6 is a tertiary alkyl group, such as tertiary-butyl, hydrolysis of this ester is accomplished by contact with about one to 50 equivalents of a strong acid such as hydrochloric acid or trifluoroacetic acid in a suitable solvent such as dichloromethane or dichloroethane. The reaction is typically conducted at from about 0 to 50° C. and is continued until it is substantial complete which typically occurs in about 15 minutes to 24 hours. Upon reaction completion, compound 8 is recovered by conventional methods including neutralization, evaporation, extraction, precipitation, chromatography, filtration, and the like, or, alternatively, is used in the next reaction without purification and/or isolation.

Carboxylic acid 8 is converted to tetrahydropyranyl protected hydroxamates 9 by contact with $NH_2OTHP$ in the presence of any of a number of well known peptide coupling reagents and a base. In one preferred embodiment, carboxylic acid 8 is contacted with a peptide-coupling reagent (e.g., EDCI) and about one to five equivalents of an organic base such as triethylamine or diisopropylethylamine, about one to five equivalents of HOBT, and about one to three equivalents of $NH_2OTHP$ in a suitable solvent such as dichloromethane, acetonitrile, tetrahydofuran, dimethylformamide and the like. The reaction is typically conducted at from about 0 to 80° C. and is continued until it is substantial complete which typically occurs in about 1 to 72 hours. Upon reaction completion, compound 9 is recovered by conventional methods including neutralization, evaporation, extraction, precipitation, chromatography, filtration, and the like, or, alternatively, is used in the next reaction without purification and/or isolation.

The protecting group of tetrahydropyranyl protected hydroxamate 9 is then cleaved to provide for the corresponding hydroxamic acid 7. Cleavage occurs by treatment with an excess and preferably from greater than one to about 50 equivalents of a strong acid such as hydrochloric acid or tetrahydrofuran in a suitable solvent such as dichloromethane, dichloroethane tetrahydrofuran and the like. The reaction is typically conducted at from about 0 to 50° C. and is continued until it is substantial complete which typically occurs in about 0.25 to 24 hours. Upon reaction completion, compound 7 is recovered by conventional methods including neutralization, evaporation, extraction, precipitation, chromatography, filtration, and the like.

Scheme 4 below illustrates a general method for synthesis of compounds of this invention wherein G is alkylene or alkenylene and further wherein A, Ar², W, W¹ and R$^a$ are as defined above.

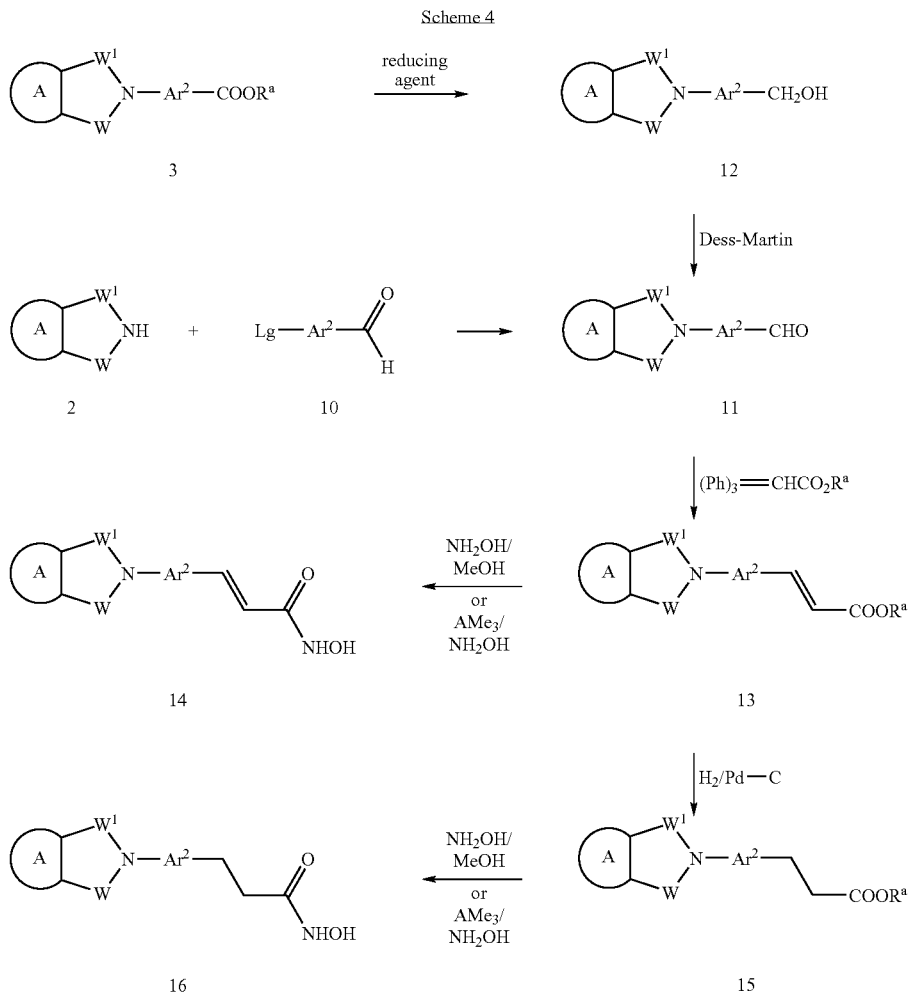

Scheme 4

Specifically, in Scheme 4, carboxylic acid ester 3 is reduced under conventional conditions to provide for alcohol 12 which is converted to aldehyde 11 under conventional Dess-Martin conditions. Preferably, reduction of carboxylic acid ester 3 proceeds in the presence of an excess of reducing agent, typically from greater than 1 to about 5 equivalents, in a suitable solvent. Suitable reducing agents include, for example, diisobutylaluminum hydride, lithium aluminum hydride, and lithium borohydride. Suitable solvents include, for example, diethylether, tetrahydrofuran, dichloromethane and dioxane. The reaction is typically conducted at from about −30 to 80° C. and is continued until it is substantial complete which typically occurs in about 15 minutes to 24 hours. Upon reaction completion, compound 12 is recovered by conventional methods including neutralization, evaporation, extraction, precipitation, chromatography, and the like; or, alternatively, used in the next step without purification and/or isolation.

The alcohol group of compound 12 is oxidized to the aldehyde group in compound 11 by contact with about one to five equivalents of oxidizing agents in a suitable solvent. Suitable oxidizing agents include, for example, manganese dioxide, nickel oxide, and, preferably, 1,1,1-triacetoxy-1,1-dihydro-1,2-benziodoxol-3(1H)-one. Suitable solvents include, for example, dichloromethane, tetrahydrofuran, dichloroethane, and the like. The reaction is typically conducted at from about 0 to 60° C. and is continued until it is substantial complete which typically occurs in about 30 minutes to 24 hours. Upon reaction completion, compound 11 is recovered by conventional methods including neutralization, evaporation, extraction, precipitation, chromatography, and the like; or, alternatively, used in the next step without purification and/or isolation.

Alternatively, compound 11 can be prepared by contacting aldehyde 10 bearing a leaving group Lg with an excess and preferably from greater than one to about five equivalents of amine 2 in a suitable solvent in the presence of a suitable base. Suitable leaving groups (Lg) include, for example, halogens, sulphones, and triflates. Suitable solvents include, for example, acetonitrile, tetrahydrofuran, dioxane, dimethylformamide or N,N-dimethylacetamide. Suitable bases include alkali metal carbonates such as sodium carbonate, potassium carbonate and cesium carbonate or organic bases such as triethylamine or diisopropylethylamine. The reaction is typically conducted at from about 25 to 180° C. and is continued until it is substantial complete which typically occurs in about 1 to 72 hours. Upon reaction completion, compound 11 is recovered by conventional methods including neutralization, evaporation, extraction, precipitation, chromatography, and the like; or, alternatively, used in the next step without purification and/or isolation.

The aldehyde group of compound 11 is a functionality suitable for use in a Wittig-Homer reaction to form vinyl compound 13. Specifically, aldehyde 11 is contacted with from about one to five equivalents of triphenylphosphoranylidene acetate, such as the methyl or ethyl ester, in a suitable solvent such as tetrahydrofuran, dichloromethane, dioxane and the like. The reaction is typically conducted at from about 0 to 80° C. and is continued until it is substantial complete which typically occurs in about 1 to 48 hours. Upon reaction completion, compound 13 is recovered by conventional methods including neutralization, evaporation, extraction, precipitation, chromatography, and the like; or, alternatively, used in the next step without purification and/or isolation.

Conversion of carboxylic acid ester of compound 13 to the corresponding hydroxamic acid 14 proceeds as described above. Alternatively, compound 13 can be treated with a mixture of about five to 20 equivalents of dry hydroxylamine hydrochloride and about 10 to 40 equivalents of trimethylaluminum in a suitable solvent at about 0 to 60° C. for about one to 48 hours to provide for compound 14. Suitable solvents include dichloromethane, dichloroethane, and toluene. Upon reaction completion, compound 11 is recovered by conventional methods including neutralization, evaporation, extraction, precipitation, chromatography, and the like; or, alternatively, used in the next step without purification and/or isolation.

Optionally, the vinylene group of compound 14 can be saturated under conventional conditions to provide for the ethylene group of compound 15. Preferably, hydrogenation occurs in a suitable solvent under about one to five atmospheres of hydrogen gas using about five to 200% weight of a catalyst at about 20 to 65° C. in about 1 to 72 hours. Suitable solvents include but are not limited to methanol, ethanol, tetrahydrofuran, ethyl acetate and the like. Suitable catalysts include, for example, palladium hydroxide, palladium on carbon, platinum hydroxide and the like. Upon reaction completion, compound 15 is recovered by conventional methods including neutralization, evaporation, extraction, precipitation, chromatography, and the like; or, alternatively, used in the next step without purification and/or isolation.

Carboxylic acid ester 15 is converted to the corresponding hydroxamic acid by any of the methods described above to provide for compound 16 which is recovered by conventional methods including neutralization, evaporation, extraction, precipitation, chromatography, and the like.

Preferred $Ar^1/Ar^3$ groups of this invention are indolyl groups fused to the nitrogen heterocycle represented by W, NH and $W^1$ at the 2,3 positions of the indolyl ring. Scheme 5 below illustrates methods for substitution at the nitrogen ring atom of such preferred indolyl groups.

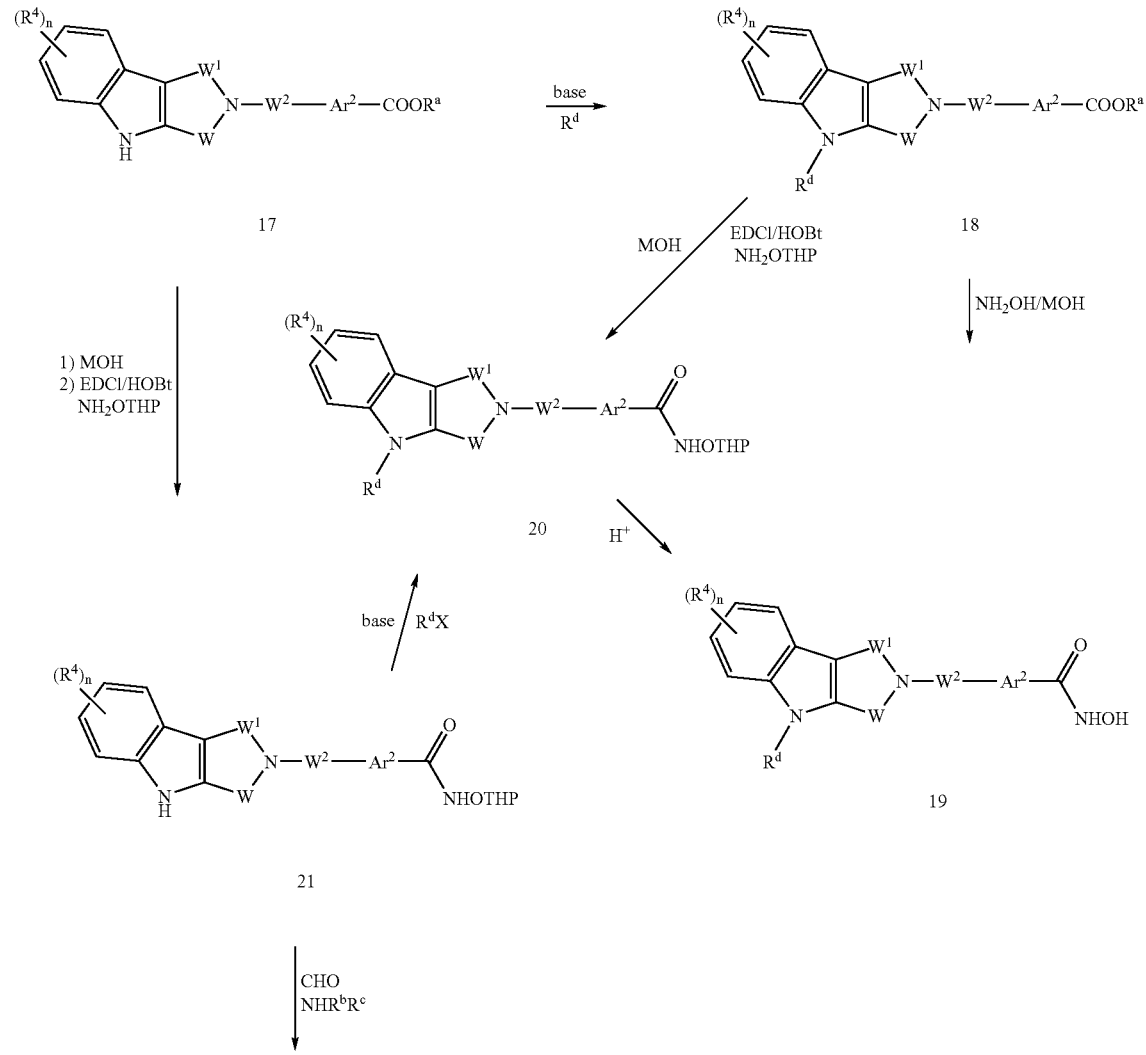

Scheme 5

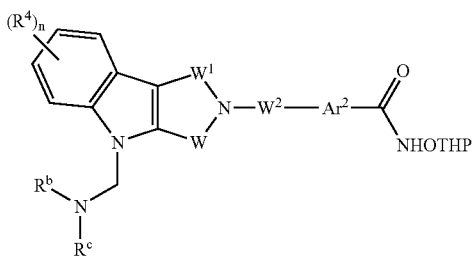

22

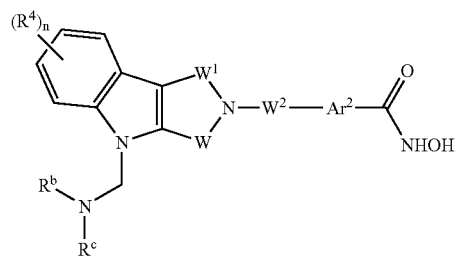

23 wherein $R^4$, W, $W^1$, $W^2$, $Ar^2$, THP and n are as defined above; $R^b$ and $R^c$ are independently, hydrogen, alkyl, substituted alkyl, aryl, substituted aryl, heteroaryl, substituted heteroaryl, heterocyclic or substituted heterocyclic, or $R^b$ and $R^c$ are joined together with the nitrogen atom pendent thereto to form a heterocyclic or substituted heterocyclic ring; $R^d$ is —$(Y)_q R^3$ where $R^3$ is as defined above, X is a leaving group such as a halogen and M is a metal salt such as sodium, potassium, lithium and the like.

Specifically, compound 17, prepared in the manner described in Scheme 1 above, is treated with a suitable base in an inert solvent at from about 0 to 60° C. followed by addition of at least a stoichiometric equivalent of an alkylating (q is zero and $R^3$ is alkyl or substituted alkyl), acylating (q is one, Y is carbonyl), benzoylating (q is one, Y is carbonyl and $R^3$ is aryl or substituted aryl) or sulfonylating reagent (q is one, Y is —$SO_2$—). Suitable bases include, for example, powdered sodium hydroxide, sodium hydride, potassium tertiary butoxide, potassium hydride and the like. Suitable inert solvents include but are not limited to toluene, dimethylformamide, tetrahydrofuran, and the like. The reaction is typically conducted at from about 20 to 110° C. and is continued until it is substantial complete which typically occurs in about 0.5 to 72 hours. Upon reaction completion, compound 18 is recovered by conventional methods including neutralization, evaporation, extraction, precipitation, chromatography, and the like; or, alternatively, used in the next step without purification and/or isolation.

Hydroxamic acid 19 is produced from the corresponding carboxylic acid ester 18 by any of the methods described in any of Schemes 1-4 above. Alternatively, carboxylic acid ester 18 is hydrolyzed and converted to the corresponding tetrahydropyranyl protected hydroxamate 20 by the methods described in any of Schemes 1-4 above. Hydrolysis of the tetrahydropyranyl group of 20 is accomplished by the methods described in any of Schemes 1-4 to give hydroxamic acids 19.

In still another alternative embodiment, carboxylic acid ester 17 is hydrolyzed and converted to the corresponding tetrahydropyranyl protected hydroxamate 21 by methods described in any of Schemes 1-4 above. Subsequent alkylation (q is zero and $R^3$ is alkyl or substituted alkyl), acylation (q is one, Y is carbonyl), benzoylation (q is one, Y is carbonyl and $R^3$ is aryl or substituted aryl), or sulfonylation (q is one, Y is —$SO_2$—) by the methods described for the synthesis of compound 18 provides for compound 20. Hydrolysis of the tetrahydropyranyl group of compound 20 by any of the methods described in Schemes 1-4 provides for hydroxamic acid 19.

In another embodiment, treatment of tetrahydropyranyl protected hydroxamic acid 21 with an excess and preferably from greater than one to about five equivalents of 37% aqueous formaldehyde and an excess and preferably from greater than one to about five equivalents of an amine provides for aminomethylene intermediate 22. The reaction is typically conducted in a suitable solvent such ethanol, methanol, tetrahydrofuran, and the like at from about 20 to 100° C. and is continued until it is substantial complete which typically occurs in about 1 to 48 hours. Upon reaction completion, compound 22 is recovered by conventional methods including neutralization, evaporation, extraction, precipitation, chromatography, and the like; or, alternatively, used in the next step without purification and/or isolation. Subsequent hydrolysis of the tetrahydropyranyl group of compound 22 by any of the methods described in Schemes 1-4 provides the aminomethylene hydroxamic acid, compound 23.

In another embodiment of this invention, aryl and heteroaryl substituted indoles 31 are produced as shown in Scheme 5B wherein $R^4$, $R^d$, $W^1$, W, $W^2$, $Ar^2$, $R^a$ and n are defined as above and $Ar^4$ is an optionally substituted aryl or an optionally substituted heteroaryl group. Typically, a bromo or iodo substituted indole 28 is treated with about one to three equivalents of a boronic acid 29 and about 0.01 to one equivalents of a suitable palladium catalyst in the presence of about one to three equivalents of a base such as an alkali metal carbonate in a suitable solvent for about one to 72 hours at about 20 to 150° C. to give the aryl and heteroaryl substituted indole esters 30. A preferred $R^d$ is hydrogen. Examples of suitable solvents include, but are not limited to, dimethylformamide, dimethylacetamide, dioxane, and tetrahydrofuran. Examples of palladium catalysts include, but are not limited to, diacetoxybis(triphenylphospine)-palladium, dichlorobis(triphenylphospine)-palladium, and tetrakis(triphenylphosphine)-palladium. Examples of suitable alkali metal carbonates include, but are not limited to, sodium, potassium or cesium carbonate. Subsequent conversion of the esters 30 to the hydroxamic acids 31 are accomplished by any one of the means described in Scheme 1 to 5.

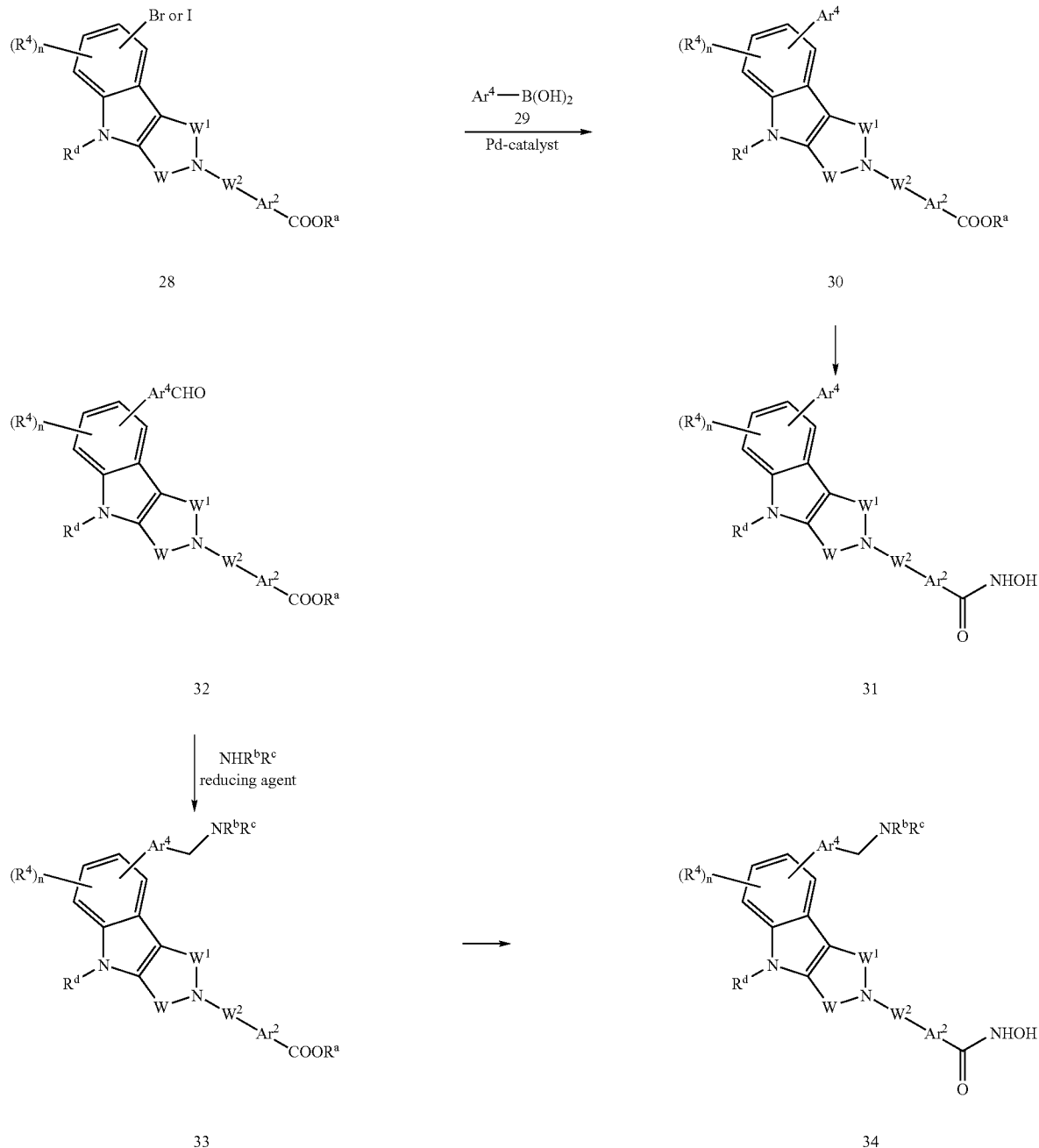

Scheme 5B

In another embodiment of this invention, aryl and heteroaryl substituted indoles 34 with appended aminomethyl groups are produced as shown in Scheme 5B wherein all variables are defined as above. Typically, an aryl or heteroaryl substituted indole ester 32 bearing an aldehyde is produced as shown and described for Scheme 5B. Said ester 32, is reductively aminated with one to 50 equivalents of an amine, NHR-$^b$R$^c$, in a suitable solvent at from about 0° to 80° C. for about one to 72 hours in the presence of about one to ten equivalents of a suitable borohydride reducing agent. Alternatively, the suitable borohydride reducing agent can be replaced by about 0.05 to 1 equivalents of a suitable palladium catalyst and about one to ten atmospheres of hydrogen. Suitable solvents include, but or not limited to, methylene chloride, tetrahydrofuran, dioxane, ethanol, trimethylorthoformate, tetramethylorthoformate, ether, dichloroethane, or ethylacetate. Suitable borohydride reducing reagents include, but are not limited to, sodium borohydride, sodium cyanoborohydride, and sodium triacetoxyborohydride. Suitable palladium catalysts include, but are not limited to, palladium on carbon, palladium on alumina, palladium on barium carbonate, or palladium oxide. Subsequent conversion of the ester 33 to a hydroxamic acid is accomplished by any of the means described in Scheme 1 to 5.

The 2,3 double bond of indolyl groups fused to the nitrogen heterocycle represented by W, NH and $W^1$ at the 2,3 positions of the indolyl ring are particularly susceptible to hydrogenation which is depicted in Scheme 6 below.
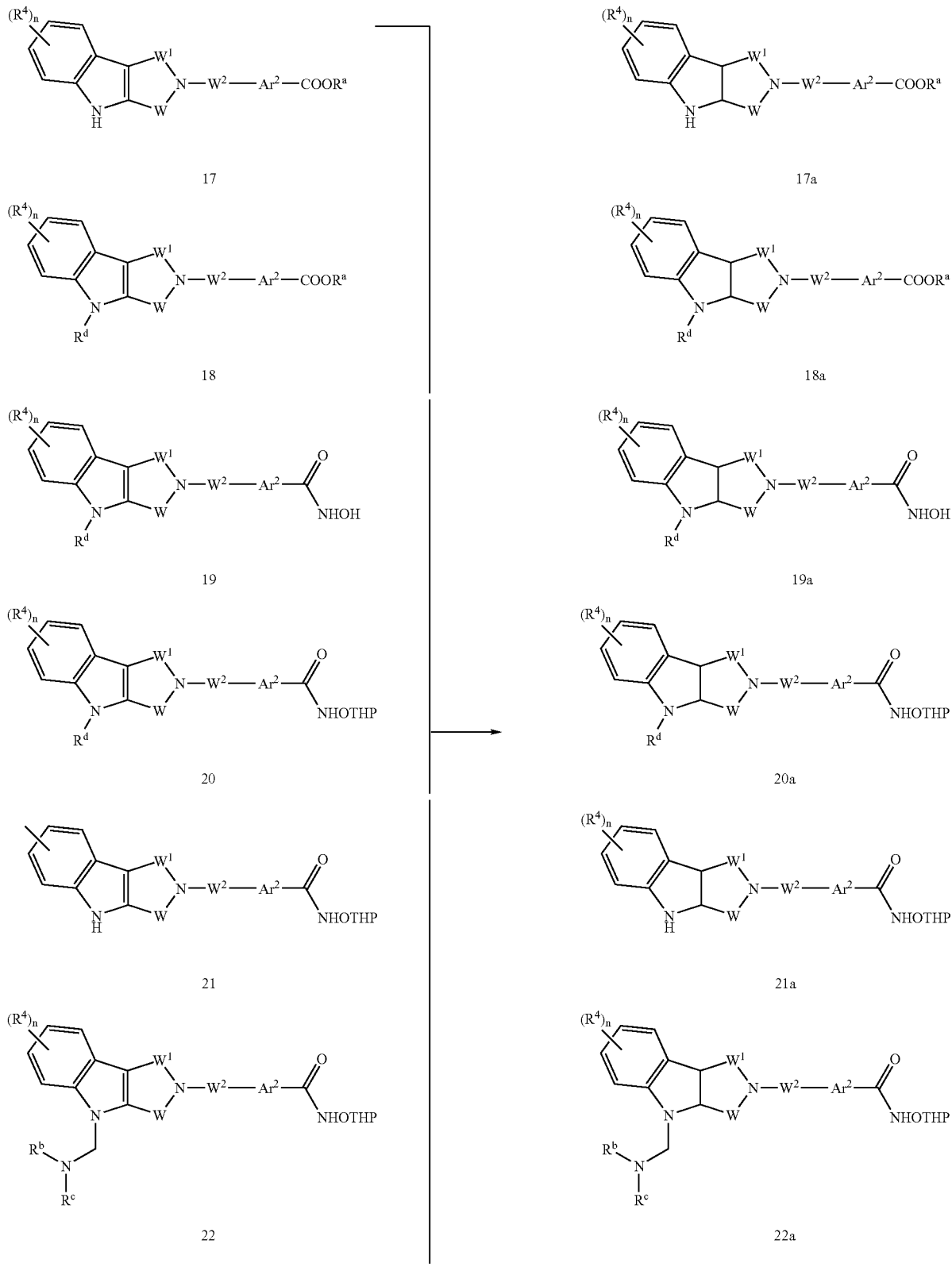

-continued

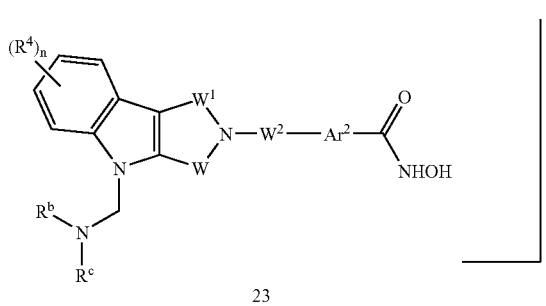

23

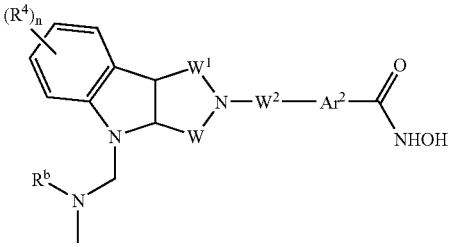

23a

Specifically, in Scheme 6, the 2,3-double bond for each of compounds 17-23 can be hydrogenated by in a suitable solvent with about one to 20 fold weight to volume ratio of trifluoroacetic acid and about one to five equivalents of a hydride reducing agent to provide for the corresponding 2,3-dihydroindole derivatives, compounds 17a-23a. Suitable solvents include but are not limited to pure trifluoroacetic acid, dichloromethane, dichloroethane, tetrahydrofuran, and the like. Suitable hydride reducing agents include but are not limited to triethylsilane, sodium borohydride, and sodium cyanoborohydride. The reaction is typically conducted at from about −30 to 50° C. and is continued until it is substantial complete which typically occurs in about 0.5 to 72 hours.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of this invention associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh. Alternatively, poorly water soluble compounds can be prepared in the form of nanoparticles to enhance their solubility. See, for example, International Patent Application Publication No. WO 03/024424 for "Stabilization of Active Agents by Formulation into Nanoparticulate Form" which is incorporated herein by reference in its entirety.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The compounds of the present invention maybe administered to patients either alone or in combination with other known anti-tumor agents. When administered alone about 0.005 to about 100 mg/kg, more preferably about 0.005 to about 10 mg/kg, are administered to the patient. Higher and lower dosages may be used. Administration may occur once a day, or several times in a day. In addition the treatment may be repeated every 7, 14, 21 or 28 days.

When administered in combination with other anti-cancer agents, the compounds of the present invention may be prepared in a formulation that includes both one or more of the compounds of this invention and one or more other anti-cancer agents. Alternatively the other anti-cancer agents may be administered in a separate formulation which may be administered before, after or simultaneously with the compounds of this invention. When administered in combination with at least one other anti-cancer agent, about 0.005 to about 100 mg/kg, more preferably about 0.5 to about 10 mg/kg, of one or more compounds of this invention are administered to the patient. Higher and lower dosages may be used. The dosages of the other anti-cancer agents are known in the art. Administration may occur once a day, or several times in a day. In addition the treatment may be repeated every 7, 14, 21 or 28 days.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Lactose | 5 |
| Active Ingredient | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository-mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 mL |

FORMULATION EXAMPLE 10

A topical formulation may be prepared as follows:

| Ingredient | Quantity |
| --- | --- |
| Active Ingredient | 1-40 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Bm = | broad multiplet |
| Bs = | broad singlet |
| Bt = | broad triplet |
| Boc = | N-tert-butoxycarbonyl |
| d = | doublet |
| dd = | doublet of doublets |
| DCM = | Dichloromethane |
| DIEA = | diisopropylethylamine |
| DMEM = | Delbaco's minimum eagle's medium |
| DMF = | N,N-dimethylformamide |
| DMSO = | Dimethylsulfoxide |
| EDC = | 1-[3-(dimethylaminopropyl]-1-ethylcarbodiimide |
| EtOAc = | ethyl acetate |
| g or gm = | grams |
| h = | hour |
| HOBt = | N-hydroxybenzotriazole |
| HPLC = | high performance liquid chromatography |
| HPLC % = | Percent purity |
| L = | Liter |
| LCMS or LC/MS = | Liquid chromatography/mass spectrum |
| m = | multiplet |
| M = | molar |
| M + 1 = | molecular weight + 1 |
| Me = | methyl |
| MeOH = | methanol |
| min = | minutes |
| mg = | milligram |
| mL = | milliliter |
| mm = | millimeter |
| mM = | millimolar |
| mmol = | millimol |
| MHz = | Megahertz |
| N = | normal |
| nm = | nanometers |
| NMR = | nuclear magnetic resonance |
| NH$_2$OTHP = | O-(tetrahydro-2H-pyran-2-yl)hydroxylamine |
| m/e or m/z = | mass to charge ratio in mass spectrum |
| q = | quartet |
| q.s. = | means adding a quantity sufficient to achieve a certain state |
| RPHPLC = | reverse phase high performance liquid chromatography |
| rt = | room temperature |
| Rt = | retention time |
| s = | singlet |
| sec = | seconds |
| t = | triplet |
| TFA = | Trifluoroacetic acid |

| | |
|---|---|
| THF = | tetrahydrofuran |
| TLC or tlc = | thin layer chromatography |
| w/v = | weight to volume |
| v/v = | volume to volume |
| μL = | Microliter |
| μM = | Micromolar |
| μm = | Micron |

All the chemicals starting materials were obtained from commercial suppliers and used without further purification.

Flash column chromatography was performed with silica (60-120 mesh). Analytical RPHPLC was done using Shimadzu HPLC equipped with a PDA detector using the following columns and systems: a Thermo Hypersil BDS, 4.6×150 mm, 5 μm particle size, C-18 column, isocratic using acetonitrile:0.1% TFA in water (60:40), flow rate=0.5 mL/min (System-1); Thermo Hypersil BDS, 4.6×250 mm, 5 μm particle size, C-18 column, linear gradient A-acetonitrile: B-0.1% TFA in water; 0.01 min A(10%):B(90%); 5.00 min A(10%):B(90%); 15.00 min A(90%):B(10%); 20.00 min A(90%):B(10%); 25.00 min A(10%):B(90%); 30.00 min A(10%):B(90%); 30.00 min Stop; flow rate=1.5 mL/min (System-2).

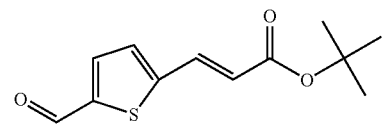

Example 1 tert-butyl(2E)-3-(5-formylthien-2-yl)acrylate

A mixture of 5-bromothiophene-2-carboxaldehyde (2.41 g, 12.6 mmol), DMF (40 mL), potassium carbonate (1.75 g, 12.6 mmol), tert-butyl acrylate (8 mL, 56.5 mmol), and CombiPhos-Pd6 (200 mg, CombiPhos Catalysts, Inc., P.O. Box 220, Princeton, N.J. 08542) was heated in a 135 to 140° C. oil bath overnight. The solvent was evaporated, the residue stirred in DCM, and the mixture filtered through a pad of diatomaceous earth. The solvent was evaporated and the residue purified by flash chromatography on silica gel eluting with 20% EtOAc/hexane to give an orange solid (1.68 g), m/e=239 (M+1). $^1$H NMR (CDCl$_3$) ppm: 1.54 (9H, s), 6.36 (1H, d), 7.28 (1H, d), 7.64 (1H, d), 7.68 (1H, d), 9.9 (1H, s).

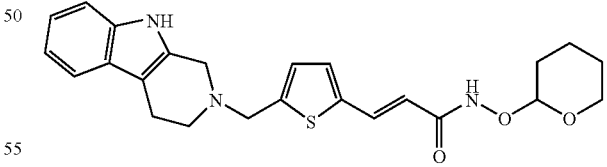

Example 2

(2E)-3-[5-(1,3,4,9-tetrahydro-2H-b-carbolin-2-ylmethyl)thien-2-yl]-N-(tetrahydro-2H-pyran-2-yloxy)acrylamide A solution of 1,2,3,4-tetrahydro-9H-pyrido[3,4-b]indole (160 mg) in THF was treated with Example 1 (200 mg). The solution was then treated with sodium triacetoxyborohydride (260 mg) and stirred four hours. The reaction was then heated in a 50 to 60° C. oil bath for 2 hours. Additional sodium triacetoxyborohydride (50 mg) was added and the heating continued overnight. Additional 1,2,3,4-tetrahydro-9H-pyrido[3,4-b]indole (60 mg) and sodium triacetoxyborohydride (40 mg) was added and heating continued for eight hours. The reaction was quenched with aqueous potassium carbonate and extracted with EtOAc. The organics-were washed with water, dried and the solvent was evaporated. The residue was purified by flash chromatography on silica gel eluting with 40% EtOAc/hexane to give tert-butyl(2E)-3-[5-(1,3,4,9-tetrahydro-2H-b-carbolin-2-ylmethyl)thien-2-yl]acrylate as an orange glass (45 mg), m/e=395 (M+1).

A solution of tert-butyl(2E)-3-[5-(1,3,4,9-tetrahydro-2H-b-carbolin-2-ylmethyl)thien-2-yl]acrylate (45 mg) in DCM (1 mL) was treated with TFA (0.4 mL). After two hours, the solvent was thoroughly evaporated and the residue treated with ether to precipitate (2E)-3-[5-(1,3,4,9-tetrahydro-2H-b-carbolin-2-ylmethyl)thien-2-yl]acrylic acid as a tan solid, m/e=339 (M+1).

A solution of (2E)-3-[5-(1,3,4,9-tetrahydro-2H-b-carbolin-2-ylmethyl)thien-2-yl]acrylic acid in DCM (2 mL) and DIEA (0.11 mL) was sequentially treated with HOBT (32 mg), EDCI (64 mg) and NH$_2$OTHP (40 mg). After three hours, the solvent was evaporated and the residue purified by flash chromatography on silica gel eluting with EtOAc. (2E)-3-[5-(1,3,4,9-Tetrahydro-2H-b-carbolin-2-ylmethyl)thien-2-yl]-N-(tetrahydro-2H-pyran-2-yloxy)acrylamide was obtained as a yellow oil (37 mg), m/e=438 (M+1).

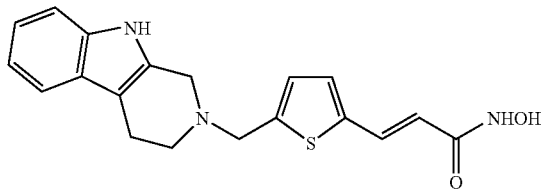

Example 3

(2E)-N-hydroxy-3-[5-(1,3,4,9-tetrahydro-2H-b-carbolin-2-ylmethyl)thien-2-yl]acrylamide A solution of Example 2 (37 mg) in DCM (0.6 mL) was treated with TFA (0.4 mL). After four hours, the solvent was evaporated and the residue purified by preparative hplc using a linear gradient of water and acetonitrile (0 to 100% acetonitrile). Freeze drying of the pure samples gave a flocculant yellow solid (2.1 mg), m/e=354 (M+1). $^1$H NMR (DMSOd$_6$) ppm: 3.05 (2H, bs), 3.8 (2H, bs), 4.45 (2H, bs), 4.75 (2H, bs), 6.23 (1H, d), 7.01 (1H, t), 7.1 (1H, t) 7.26-7.5 (5H, m), 7.59 (1H, d), 10.75 (1H, bs), 10.95 (1H, bs).

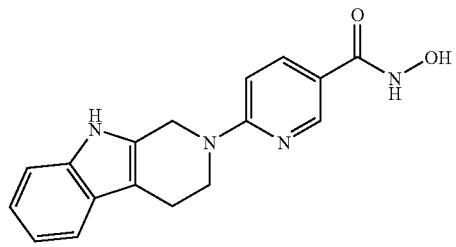

Example 4

N-hydroxy-6-(1,3,4,9-tetrahydro-2H-b-carbolin-2-yl)nicotinamide

A mixture of methyl-6-chloronicotinate (170 mg), 1,2,3,4-tetrahydro-9H-pyrido[3,4-b]indole (170 mg), potassium carbonate (150 mg) and dioxane (6 mL) was heated in a 100° C. oil bath overnight. Another aliquote of 1,2,3,4-tetrahydro-9H-pyrido[3,4-b]indole (170 mg) was added and the heating was continue for five hours. The reaction was cooled and partitioned between water and EtOAc. The organics were washed with water, dried, and the solvent evaporated. The residue was purified by filtration through silica gel eluting with EtOAc to give methyl 6-(1,3,4,9-tetrahydro-2H-b-carbolin-2-yl)nicotinate as a brown solid (75 mg), m/e=308 (M+1).

A solution of 6-(1,3,4,9-tetrahydro-2H-b-carbolin-2-yl)nicotinate (12 mg) in dioxane (1.5 mL) was treated with 50% aqueous hydroxylamine (0.2 mL). After 15 minutes, 1N sodium hydroxide (0.06 mL) was added and the reaction was stirred for 72 hours. The reaction was quenched with 1N hydrochloric acid (0.06 mL) and the solvent evaporated. The residue was purified by preparative hplc and the pure samples freeze dried to give N-hydroxy-6-(1,3,4,9-tetrahydro-2H-b-carbolin-2-yl)nicotinamide as a yellow solid (4 mg), m/e=308 (M+1). $^1$H NMR (DMSOd$_6$) ppm: 2.8 (2H, m), 4.05 (2H, m), 4.85 (2H, s), 6.9-7.08 (3H, m), 7.29 (1H, d), 7.39 (1H, d), 7.87-7.91 (1H, m), 8.5 (1H m), 10.9 (1H, s), 11.05 (1H, bs).

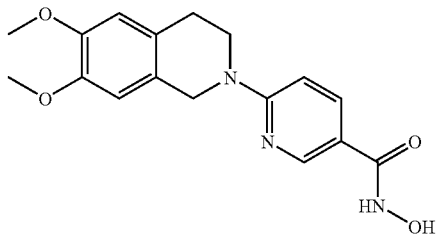

Example 5

6-(6,7-dimethoxy-3,4-dihydroisoquinolin-2(1H)-yl)-N-hydroxynicotinamide

A mixture of methyl-6-chloronicotinate (170 mg), 6,7-dimethoxy-1,2,3,4-tetrahydroisoquinoline (205 mg), potassium carbonate (150 mg) and dioxane (5 mL) was heated in a 100° C. oil bath overnight. An additional aliquote of 6,7-dimethoxy-1,2,3,4-tetrahydroisoquinoline (100 mg) was added and heating was continued for five hours. The reaction was partitioned between water and EtOAc. The organics were washed with water, dried, and the solvent evaporated. The residue was purified by flash chromatography eluting with EtOAc to give methyl 6-(6,7-dimethoxy-3,4-dihydroisoquinolin-2(1H)-yl)nicotinate as a white solid (180 mg), m/e=329 (M+1).

A solution of 6-(6,7-dimethoxy-3,4-dihydroisoquinolin-2 (1H)-yl)nicotinate (12 mg) in dioxane (0.8 mL) was treated with 50% aqueous hydroxylamine (0.2 mL). After 10 minutes the reaction was treated with 1N sodium hydroxide (0.06 mL) and the solution stirred for 72 hours. The reaction was quenched with 1N hydrochloric acid (0.06 mL) and the solvent was evaporated. The residue was purified by preparative hplc and the pure samples freeze dried to give 6-(6,7-dimethoxy-3,4-dihydroisoquinolin-2(1H)-yl)-N-hydroxynicotinamide as a yellow solid (7.9 mg), m/e=330 (M+1). $^1$H NMR (DMSOd$_6$) ppm: 2.8 (2H, m), 3.72 (6H, s) 3.9 (2H, m), 4.7 (2H, s), 6.76 (1H, s), 6.83 (1H, s), 6.9 (1H, d), 7.9 (1H, m), 8.55 (1H, s), 11 (1H, bs).

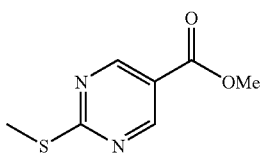

Example 6 methyl 2-(methylthio)pyrimidine-5-carboxylate

To a three necked round-bottom flask equipped with a magnetic stirrer and a reflux condenser under nitrogen, methyl 3,3-dimethoxy propionate (5.00 g, 33.2 mmol), anhydrous 1,2-dimethoxyethane (25 ml), anhydrous methyl formate (5 ml) and 60% NaH (1.70 g, 42.5 mmol) was added. After warming the reaction mixture at 50° C. until the evolution of hydrogen gas was ceased, it was cooled in an ice/water bath and slowly allowed to reach ambient temperature over night with stirring. Anhydrous diethyl ether (25 mL) was added, and the resulting suspension was filtered under nitrogen, washed with anhydrous diethyl ether (10 mL), and dried under vacuum for two hours to give 5 g of sodium 3,3-dimethoxy-2-carbomethoxy-prop-1-en-1-oxide as a hydroscopic white powder.

To a solution of S-methyl-iso-uronium sulphate (5.0 g, 19.1 mmol) in anhydrous DMF (10 mL) was added sodium 3,3-dimethoxy-2-carbomethoxyprop-1-en-1-oxide (4.5 g, 22.7 mmol) and the reaction mixture was heated at 100° C. under nitrogen atmosphere for one hour. The reaction mixture was brought to room temperature and water (25 mL) was added. A white solid precipitated was then collected by filtration, washed with water (10 mL) and dried under vacuum for two hours to give 1.25 g of Example 6. HPLC: (RT=3.88 min.); $^1$H NMR (CDCl$_3$, 200 MHz) ppm: 9.03 (2H, s), 3.96 (3H, s), 2.65 (3H, s).

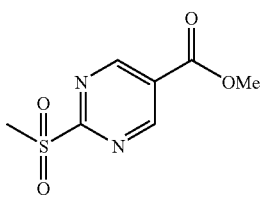

Example 7

Methyl-2-(methylsulfonyl)pyrimidine-5-carboxylate

To a cooled solution of Example 6 (3.0 g, 16.3 mmol) in DCM (15 mL) was added m-chloroperbenzoic acid (7.01 g, 40.7 mmol) and the reaction mixture was stirred at room temperature. After six hours, saturated solution of NaHCO3 (15 mL) were added to the reaction mixture and stirred for 15 min. The organic layer was separated, washed with saturated solution of sodium bicarbonate (15 mL), dried over sodium sulfate, filtered and concentrated to give the crude Example 7 (1.6 g), which was carried to the next reaction without purification. $^1$H NMR (CDCl$_3$, 200 MHz) ppm: 9.44 (2H, s), 4.05 (3H, s), 3.41 (3H, s).

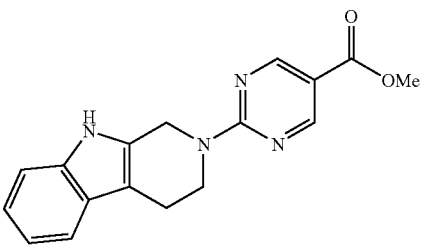

Example 8

Methyl 2-(1,3,4,9-tetrahydro-2H-b-carbolin-2-yl)pyrimidine-5-carboxylate

To Example 7 (0.2 g, 0.869 mmol) in acetonitrile (20 mL), 1,2,3,4-tetrahydro-9H-pyrido[3,4-b]indole (0.175 g, 0.869 mmol) and potassium carbonate (0.220 g, 1.6 mmol) was added and refluxed at 80° C. for 12 hours. After filtering the potassium carbonate, the solvent was removed to obtain the crude ester that was purified by column chromatography using EtOAc in hexanes (50%). Rf=0.3. $^1$H NMR (DMSO-d$_6$, 400 MHz) ppm: 8.9 (s, 2H, 2Ar—H), 7.88 (brs, 1H, NH), 7.53 (d, 1H, J=8 Hz, 1Ar—H), 7.37 (d, 1H, J=8 Hz, 1Ar—H), 7.21-7.12 (m, 2H, 2Ar—H), 5.11 (s, 2H, CH$_2$), 4.35 (t, 2H, J=4 Hz, CH2), 3.91 (s, 3H, OMe), 2.94 (t, 2H, J=4 Hz, CH$_2$), m/e=308 (M$^+$) (M, 308.335 Calcd. for C$_{17}$H$_{16}$N$_4$O$_2$).

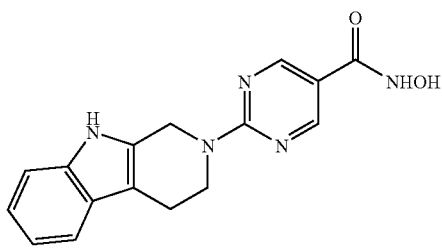

Example 9

N-hydroxy-2-(1,3,4,9-tetrahydro-2H-b-carbolin-2-yl)pyrimidine-5-carboxamide

To Example 8 (0.032 g, 0.09 mmol) in MeOH (5 mL) and DCM (2 mL), aq. hydroxylamine (50%, 1 mL) and aq. sodium hydroxide (100 mg in 0.5 mL of water) was added at 0° C. and then let it attain room temperature over 4 hours. The solvent was evaporated, water (2 mL) was added to the residue and then acidified with HCl in ether. The resulting white precipitate was filtered and dried under vacuum for 12 hours to obtain Example 9 (25 mg, 83% yield). $^1$H NMR (300 MHz, CD$_3$OD) ppm: 8.70 (s, 2H), 7.17 (d, J=8.7 Hz, 1H), 6.85 (s, 1H)-6.70 (m, 1H), 5.02 (m, 2H), 4.28 (m, 2H), 2.82 (m, 2H).

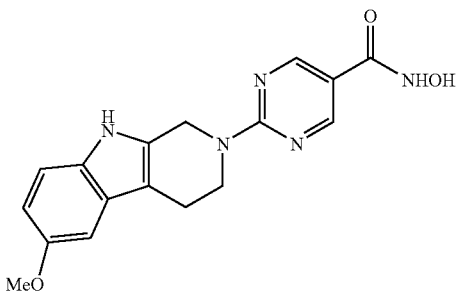

Example 10

N-hydroxy-2-(6-methoxy-1,3,4,9-tetrahydro-2H-b-carbolin-2-yl)pyrimidine-5-carboxamide To Example 7 (0.2 g, 0.869 mmol) in acetonitrile (20 mL), 6-methoxy-2,3,4,9-tetrahydro-1H-b-carboline (0.175 g, 0.869 mmol) and potassium carbonate (0.220 g, 1.6 mmol) was added and refluxed at 80° C. for 12 hours. After filtering the potassium carbonate, the solvent was removed to obtain the crude ester that was purified by column chromatography using EtOAc in hexanes (50%). To the purified ester (0.032 g, 0.09 mmol) in MeOH (5 mL) and DCM (2 mL), aq. hydroxylamine (50%, 1 mL) and aq. sodium hydroxide (100 mg in 0.5 mL of water) was added at 0° C. and then let it attain room temperature over 4 hours. The solvent was removed, water (2 mL) was added to the residue and then acidified with HCl in ether. The resulting white precipitate was filtered and dried under vacuum for 12 hours to obtain Example 10 (25 mg, 83%). $^1$H NMR (300 MHz, CD$_3$OD) ppm: 8.70 (s, 2H), 7.17 (d, J=8.7 Hz, 1H), 6.85 (s, 1H), 6.70 (m, 1H), 5.02 (m, 2H), 4.28 (m, 2H), 2.82 (m, 2H).

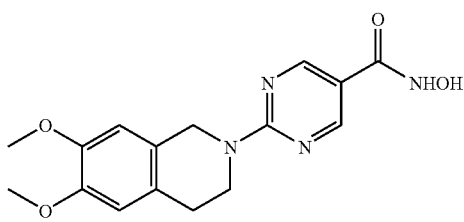

Example 11

2-(6,7-dimethoxy-3,4-dihydroisoquinolin-2(1H)-yl)-N-hydroxypyrimidine-5-carboxamide To Example 7 (0.2 g, 0.869 mmol) in acetonitrile (20 mL), 6,7-dimethoxy-1,2,3,4-tetrahydroisoquinoline (0.2 g, 0.869 mmol) and potassium carbonate (0.220 g, 1.6 mmol) was added and refluxed at 80° C. for 12 hours. After filtering the potassium carbonate, the solvent was removed to obtain the crude ester that was purified by column chromatography using EtOAc in hexanes (50%). To the purified ester (0.1 g, 0.30 mmol) in MeOH (5 mL) and DCM (2 mL), aq. hydroxylamine (50%, 1 mL) and aq. sodium hydroxide (100 mg in 0.5 mL of water) was added at 0° C. and then let it attain room temperature over 4 hours. The solvent was evaporated, water (2 mL) was added to the residue and then acidified with HCl in ether. The resulting white precipitate was filtered and kept under vacuum for 12 hours to obtain Example 11 (80 mg, 80%). $^1$H NMR (300 MHz, DMSO-d$_6$) ppm: 11.00 (s, 1H), 9.00 (s, 1H), 8.69 (s, 2H), 6.60 (s, 1H), 6.81 (s, 1), 4.82 (m, 2H), 4.00 (t, J=6 Hz, 2H), 3.72 (s, 3H), 3.71 (s, 3H), 3.33 (m, 2H), 2.78 (t, J=5.4 Hz).

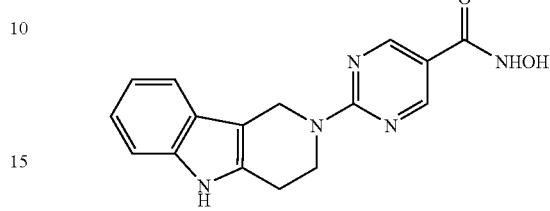

Example 12

N-hydroxy-2-(1,3,4,5-tetrahydro-2H-pyrido[4,3-b]indol-2-yl)pyrimidine-5-carboxamide To Example 7 (0.2 g, 0.869 mmol) in acetonitrile (20 mL), 2,3,4,5-tetrahydro-1H-pyrido[4,3-b]indole (0.149 g, 0.869 mmol) and potassium carbonate (0.220 g, 1.6 mmol) was added and refluxed at 80° C. for 12 hours. After filtering the potassium carbonate, the solvent was removed to obtain the crude ester that was purified on column chromatography using EtOAc in hexanes (50%). To the purified ester (0.1 g, 0.32 mmol) in MeOH (5 mL) and DCM (2 mL), aq. hydroxylamine (50%, 1 mL) and aq. sodium hydroxide (100 mg in 0.5 mL of water) was added at 0° C. and then let it attain room temperature over 4 hours. The solvent was evaporated, water (2 mL) was added to the residue and then acidified with HCl in ether. The resulting white precipitate was filtered and then purified by preparative HPLC to give Example 12 (80 mg, 80%) $^1$H NMR (300 MHz, CD$_3$OD) ppm: 8.60 (s, 2H), 7.37 (d, J=8.7 Hz, ifH), 7.15 (d, J=8.7 Hz, 1H), 6.90 (m, 2H), 4.92 (m, 2H), 4.22 (m, 2H), 2.82 (m, 2H).

Examples 13-16 were synthesized in the same manner as example 12 using the substituted 2,3,4,5-tetrahydro-1H-pyrido[4,3-b]indole specified for the specific example below.

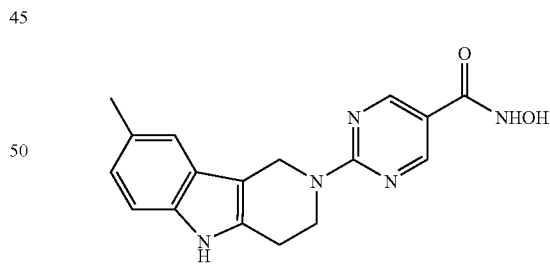

Example 13

N-hydroxy-2-(8-methyl-1,3,4,5-tetrahydro-2H-pyrido[4,3-b]indol-2-yl)pyrimidine-5-carboxamide From 8-methyl-2,3,4,5-tetrahydro-1H-pyrido[4,3-b]indole and Example 7 was obtained Example 13 using the method described in Example 12 (55 mg, 56% yield). HPLC: (RT=13.64 min). $^1$HNMR (CD$_3$OD) ppm: 8.73 (s, 2H), 7.23 (m, 2H), 6.94 (m, 1H), 5.00 (s, 2H), 4.34 (t, 2H, J=5.4 Hz), 2.92 (m, 2H), 2.42 (s, 3H); m/e=324(M+1).

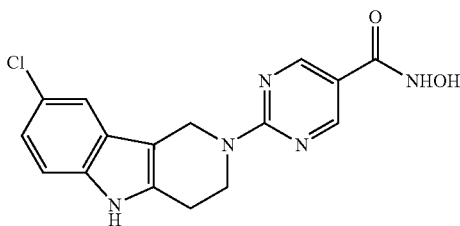

Example 14

2-(8-chloro-1,3,4,5-tetrahydro-2H-pyrido[4,3-b]indol-2-yl)-N-hydroxypyrimidine-5-carboxamide From 8-chloro-2,3,4,5-tetrahydro-1H-pyrido[4,3-b]indole and Example 7 was obtained Example 14 using the method described in Example 12 (200 mg, 96% yield). HPLC: (Rt=13.86 min). $^1$HNMR (CD$_3$OD) ppm: 8.75 (s, 2H), 8.49 (s, 1H), 7.42 (s, 1H), 7.52 (m, 1H), 7.02 (s, 1H), 5.00 (s, 2H), 4.34 (m, 2H), 2.94 (m, 2H); m/e=343.8 (M+1).

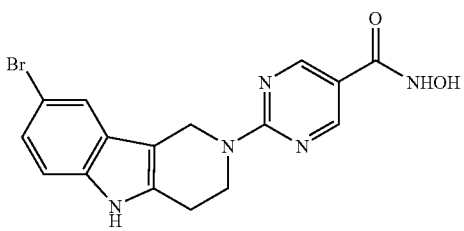

Example 15

2-(8-bromo-1,3,4,5-tetrahydro-2H-pyrido[4,3-b]indol-2-yl)-N-hydroxypyrimidine-5-carboxamide From methyl 2-(8-bromo-1,3,4,5-tetrahydro-2H-pyrido[4,3-b]indol-2-yl)pyrimidine-5-carboxylate (Example 33) was obtained Example 15 using the method described in Example 12 (35 mg, 44% yield). HPLC: (RT=13.97 min). $^1$HNMR (CD$_3$OD) ppm: 8.74 (s, 2H), 7.58 (m, 1H), 7.21 (m, 3H), 5.01 (s, 2H), 4.34 (m, 2H), 2.94 (m, 2H); m/e=389.9 (M+1).

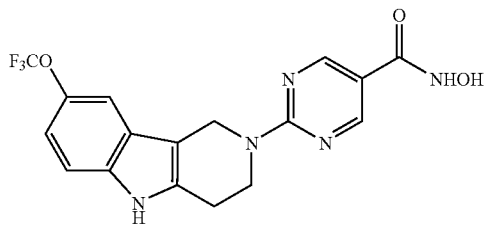

Example 16

N-hydroxy-2-[8-(trifluoromethoxy)-1,3,4,5-tetrahydro-2H-pyrido[4,3-b]indol-2-yl]pyrimidine-5-carboxamide From 8-(trifluoromethoxy)-2,3,4,5-tetrahydro-1H-pyrido[4,3-b]indole and Example 7 was obtained Example 16 using the method described in Example 12 (30 mg, 43% yield). HPLC: (RT=14.44 min). $^1$HNMR (CD$_3$OD) ppm: 8.74 (s, 2H), 7.33 (m, 2H), 7.01 (m, 1H), 5.03 (s, 2H), 4.35 (m, 2H), 2.95 (m, 2H); m/e=394(M+1).

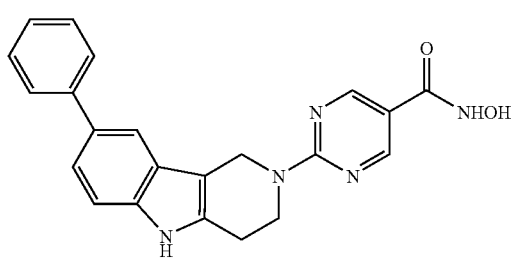

Example 17

N-hydroxy-2-(8-phenyl-1,3,4,5-tetrahydro-2H-pyrido[4,3-b]indol-2-yl)pyrimidine-5-carboxamide To a solution of methyl 2-(8-bromo-1,3,4,5-tetrahydro-2H-pyrido[4,3-b]indol-2-yl)pyrimidine-5-carboxylate (Example 33) (140 mg, 0.362 mmol) in anhydrous toluene and MeOH (5:1 mL) were added tetrakistriphenylphosphine palladium (210 mg, 0.181 mmol), phenylboronic acid (55 mg, 0.430 mmol) and 2M aqueous sodium carbonate (500 mg in 3 ml water) at room temperature. The reaction mixture was stirred at 100° C. for 6 hours. After completion, the reaction mixture was diluted with water and the compound was extracted with EtOAc. The combined organic layers were dried over sodium sulfate, filtered and concentrated under reduced pressure. The residue obtained was purified by column chromatography to obtain 2-(8-phenyl-1,3,4,5-tetrahydro-2H-pyrido[4,3-b]indol-2-yl)pyrimidine-5-carboxylate (35 mg, 25% yield). $^1$H NMR (200 MHz, CDCl$_3$) ppm: 8.90 (s, 2H), 7.78 (bs, 1H), 7.68-7.12 (m, 8H), 5.10 (s, 2H), 4.37 (t, 2H, J=5.8 Hz), 3.88 (s, 3H), 2.96 (m, 2H); m/e=384.8 (M+1).

To a stirred solution of 2-(8-phenyl-1,3,4,5-tetrahydro-2H-pyrido[4,3-b]indol-2-yl)pyrimidine-5-carboxylate (25 mg, 0.065 mmol) in MeOH and DCM (15 mL: 10 mL) was added hydroxylamine hydrochloride (11.31 g, 162.1 mmol) at 0° C. and the mixture was stirred for 15 min. Sodium methoxide (10.53 g, 195.5 mmol) was added at 0-5° C. under nitrogen atmosphere and the mixture was stirred at room temperature for 2 hours. After completion of the reaction, the mixture was partitioned between DCM and water. It was then neutralized with 1N hydrochloric acid and the organic layer was separated. The aqueous layer was extracted with DCM and the combined DCM layers were dried and concentrated to Example 17 (13 mg, 60%), HPLC (RT=14.75 min). $^1$HNMR (CD$_3$OD) ppm: 8.75 (s, 2H), 7.68-7.28 (m, 8H), 5.09 (s, 2H), 4.36 (m, 2H), 2.96 (m, 2H); m/e=385.9 (M+1).

Example 40-53 were prepared in the same manner as Example 17 by substituting the appropriate aryl or heteroaryl boronic acid for phenylboronic acid.

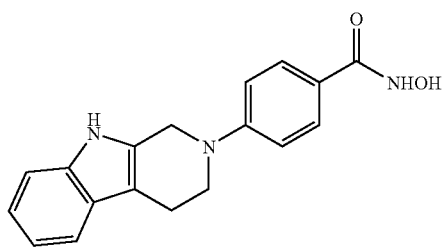

Example 18

N-hydroxy-4-(1,3,4,9-tetrahydro-2H-b-carbolin-2-yl)benzamide

To a solution of compound 1,2,3,4-tetrahydro-9H-pyrido[3,4-b]indole (400 mg, 2.32 mmol) in anhydrous DMF (20 mL) was added methyl-4-fluorobenzoate (390 mg, 2.32 mmol), potassium carbonate (640 mg, 4.64 mmol) and cesium carbonate (1.51 g, 4.64 mmol) at room temperature. The reaction mixture was then stirred at 100° C. for 12 hours. After completion of the reaction, it was filtered and the solvent was removed under reduced pressure. The residue obtained was purified by column chromatography to obtain an intermediate ester (55 mg, 8% yield), HPLC: (RT=17.43 min). $^1$H NMR (200 MHz, CDCl$_3$) ppm: 7.98 (d, 2H, J=9.2 Hz), 7.82 (bs, 1H), 7.53 (d, 1H, J=6.4 Hz), 7.36-6.93 (m, 5H), 4.55 (s, 2H), 4.35 (q, 2H, J=6.8 Hz), 3.87 (m, 2H), 2.94 (t, 2H, J=5.6 Hz), 1.37 (t, 3H, 7.2 Hz); m/e=321 (M+1).

To the purified ester (0.1 g, 0.32 mmol) in MeOH (5 mL) and DCM (2 mL), aq. hydroxylamine (50%, 1 mL) and aq. sodium hydroxide (100 mg in 0.5 mL of water) was added at 0° C. and then let it attain room temperature over 4 hours. The solvent was removed, water (2 mL) was added to the residue and then acidified with HCl in ether. The resulting white precipitate was filtered and dried under vacuum to obtain Example 18 (80 mg, 80%). $^1$H NMR (300 MHz, CD$_3$OD) ppm: 7.68 (d, J=8.7 Hz, 2H), 7.37 (dd, J=32.4, 8.1 Hz, 2H), 7.05 (m, 4H), 4.52 (m, 2H), 3.79 (m, 2H), 2.89 (m, 2H).

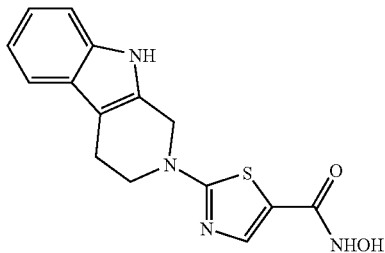

Example 19

N-hydroxy-2-(1,3,4,9-tetrahydro-2H-b-carbolin-2-yl)-1,3-thiazole-5-carboxamide To methyl 2-bromo-1,3-thiazole-5-carboxylate (500 mg, 2.25 mmol) in acetonitrile (10 mL), 1,2,3,4-tetrahydro-9H-pyrido[3,4-b]indole (387 mg, 2.25 mmol) and potassium carbonate (621 mg, 4.50 mmol) was added and refluxed at 80° C. for 4 hours. After filtering the potassium carbonate, the solvent was removed and the solid obtained was washed with EtOAc and then taken as such for the next reaction (365 mg, 52%). To the (80 mg, 0.25 mmol) in MeOH (5 mL) and DCM (2 mL), aq. hydroxylamine (50%, 1 mL) and aq. sodium hydroxide (100 mg in 0.5 mL of water) was added at 0° C. and then let it attain room temperature over 4 hours. The solvent was evaporated, water (2 mL) was added to the residue and then acidified with HCl in ether. The resulting white precipitate was filtered and then dried under vacuum for 12 hours to obtain Example 19 (25 mg, 23% yield), m/e=315 (M+1).

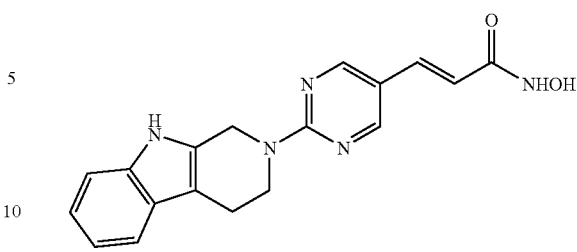

Example 20

(2E)-N-hydroxy-3-[2-(1,3,4,9-tetrahydro-2H-b-carbolin-2-yl)pyrimidin-5-yl]acrylamide To a stirred solution of Example 8 (2.7 g, 0.0088 moles) in dry acetonitrile (30 ml) was added 4-dimethylaminopyridine (0.11 g, 0.00088 moles) and Boc-anhydride (2.2 ml, 0.0096 moles) at 0° C. The temperature was slowly allowed to come to room temperature and stirring was continued for >12 hours. After completion of the reaction, acetonitrile was removed in vacuum. The residue was dissolved in DCM (30 ml). The organic layer was washed with water (20 ml), brine (20 ml), dried (Na$_2$SO$_4$) and concentrated. The crude residue was washed with hexane (20 ml) to give tert-butyl 2-[5-(methoxycarbonyl)pyrimidin-2-yl]-1,2,3,4-tetrahydro-9H-b-carboline-9-carboxylate (3.1 g, 87%). Rf=0.2. $^1$H NMR (DMSO-d$_6$, 400 MHz) ppm: 8.8 (s, 2H, 2Ar—H), 8.06 (d, 1H, J=8 Hz, 1Ar—H), 7.51 (d, 1H, J=8 Hz, 1Ar—H), 7.33-7.24 (m, 2H, 2Ar—H), 5.2 (s, 2H, CH$_2$), 4.24 (t, 2H, CH$_2$), 3.45 (s, 3H, OMe), 2.0 (brs, 2H, CH$_2$), 1.68 (s, 9H, 3CH$_3$). M/e=409 (M+1) (M, 408.451 Calcd. for C$_{22}$H$_{24}$N$_4$O$_4$).

To a stirred solution of tert-butyl 2-[5-(methoxycarbonyl)pyrimidin-2-yl]-1,2,3,4-tetrahydro-9H-b-carboline-9-carboxylate (3.0 g, 0.0073 moles) in dry DCM (30 mL) was added diisobutyl aluminum hydride (14.7 mL, 0.022 moles, 1.5N in DCM) at −78° C. The temperature was slowly allowed to rise to −25° C. and continued the stirring for further 6.0 hours. After completion of the reaction, MeOH (20 mL) and water (20 mL) was added to the reaction and allowed to come to room temperature. The reaction mixture was then extracted using DCM. The combined organic layer was washed with water (20 mL), brine (20 ml), dried (Na$_2$SO$_4$) and concentrated. The compound was purified by recrystallization using mixture of diethyl ether and hexane to give pure tert-butyl 2-[5-(hydroxymethyl)pyrimidin-2-yl]-1,2,3,4-tetrahydro-9H-b-carboline-9-carboxylate (2.1 g, 75% yield). Rf=0.3. $^1$H NMR (DMSO-d$_6$, 400 MHz) ppm: 8.38 (s, 2H, 2Ar—H), 8.05 (d, 1H, J=8 Hz, 1—H), 7.49 (d, 1H, J=8 Hz, 1Ar—H), 7.31-7.22 (m, 2H, 2Ar—H), 5.15 (s, 2H, CH$_2$), 5.10 (t, 1H, J=8 Hz, OH), 4.34 (d, 2H, J=8 Hz, CH$_2$), 4.11 (t, 2H, CH$_2$), 2.75 (brs, 2H, CH$_2$), 1.68 (s, 9H, 3CH$_3$). M/e=381 (M+1) (M, 380.440 Calcd. for C$_{21}$H$_{24}$N$_4$O$_3$).

To a stirred solution of tert-butyl 2-[5-(hydroxymethyl)pyrimidin-2-yl]-1,2,3,4-tetrahydro-9H-b-carboline-9-carboxylate (2.0 g, 0.0053 moles) in dry DCM (20 mL) was added 1,1,1-triacetoxy-1,1-dihydro-1,2-benziodoxol-3(1H)-one (2.68 g, 0.0063 moles). After stirring for 5.0 hours, Na$_2$S$_2$O$_3$ (1.0 g), NaHCO$_3$ (1.0 g) in water (15 mL) was added. The two layers were separated. The organic layer was washed with water (20 mL), dried (Na$_2$SO$_4$) and concentrated. The crude product was crystallized using mixture of diethyl ether-hexane to give pure tert-butyl 2-[5-(formyl)pyrimidin-2-yl]-1,2,3,4-tetrahydro-9H-b-carboline-9-carboxylate (1.4 g, 74% yield). Rf=0.4. $^1$H NMR (DMSO-d$_6$, 400 MHz) ppm: 9.8 (s, 1H, CHO), 8.8 (s, 2H, 2Ar—H), 8.06 (d, 1H, J=8 Hz, 1Ar—H), 7.52 (d, 1H, J=8 Hz, 1Ar—H), 7.33-7.24 (m, 2H, 2Ar—H), 5.32 (s, 2H, CH$_2$), 4.28 (t, 2H, J=8 Hz, CH$_2$), 2.82 (t, 2H, J=8 Hz, CH$_2$), 1.69 (s, 3H, 3CH$_3$); m/e=379 (M+1) (M, 378.425 Calcd. for C$_{21}$H$_{22}$N$_4$O$_3$).

To a stirred solution methyl(triphenylphosphoranylidene) acetate (2.39 g, 0.0071 moles) in dry DCM (20 mL) was added tert-butyl 2-[5-(formyl)pyrimidin-2-yl]-1,2,3,4-tetrahydro-9H-b-carboline-9-carboxylate (1.35 g, 0.0036 moles) at 0° C. in dry DCM (10 mL). After stirring for >12 hours, the reaction mixture was washed with 10% NaHCO$_3$ solution (20 mL), brine (20 mL), dried (Na$_2$SO$_4$) and concentrated. The compound was purified through silica gel column chromatography using 15% EtOAc in hexane to give tert-butyl 2-{5-[(1E)-3-methoxy-3-oxoprop-1-enyl]pyrimidin-2-yl}-1,2,3,4-tetrahydro-9H-b-carboline-9-carboxylate (1.22 g, 78% yield). $^1$H NMR (DMSO-d$_6$, 400 MHz) ppm: 8.81 (s, 2H, 2Ar—H), 8.06 (d, 1H, J=8 Hz, 1Ar—H), 7.54 (d, 1H, J=16 Hz, =CH), 7.50 (d, 1H, J=8 Hz, 1Ar—H), 7.32-7.23 (m, 2H, 2Ar—H), 6.60 (d, 1H, J=16 Hz, —CH), 5.23 (s, 2H, CH$_2$), 4.19 (t, 2H, CH$_2$), 3.7 (s, 3H, OMe), 2.78 (brs, 2H, CH$_2$), 1.68 (s, 9H, 3CH$_3$). M/e=435 (M+1) (M, 434.488 Calcd. for C$_{24}$H$_{26}$N$_4$O$_4$).

Freshly dried hydroxylamine hydrochloride (0.14 g, 0.002 moles) was suspended in dry DCM (10 mL) at 0° C. To this was added 2 M Me$_3$Al in toluene (2.1 mL, 0.0041 moles) at 0 IC. The temperature of the clear reaction mixture was slowly taken to room temperature and tert-butyl 2-{5-[(1E)-3-methoxy-3-oxoprop-1-enyl]pyrimidin-2-yl}-1,2,3,4-tetrahydro-9H-b-carboline-9-carboxylate (0.15 g) was added. After stirring overnight, the reaction was cooled to 0° C. and saturated solution of sodium potassium tartarate (10 mL) was added. The solid formed was filtered and purified by hplc to give Example 20 (50 mg, 43% yield). $^1$H NMR (DMSO-d$_6$, 400 MHz) ppm: 10.93 (s, 1H, NH or OH), 10.70 (brs, 1H, NH or OH), 8.6 (s, 2H, 2Ar—H), 7.41-7.31 (m, 3H, 2Ar—H and =CH), 7.04 (t, 1H, J=8 Hz, 1Ar—H), 6.95 (t, 1H, J=8 Hz, 1Ar—H), 6.37 (d, 1H, J=16 Hz, =CH), 4.99 (s, 2H, CH$_2$), 4.20 (brs, 2H, CH$_2$), 2.79 (brs, 2H, CH$_2$). M/e=336 (M+1) (M, 335.360 Calcd. for C$_{18}$H$_{17}$N$_5$O$_2$).

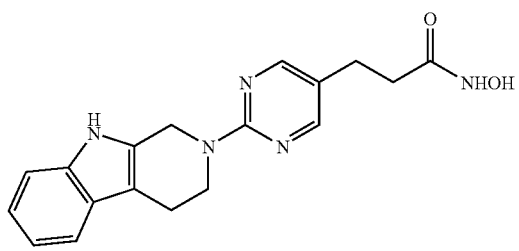

Example 21

N-hydroxy-3-[2-(1,3,4,9-tetrahydro-2H-b-carbolin-2-yl)pyrimidin-5-yl]propanamide To a stirred solution of tert-butyl 2-{5-[(1E)-3-methoxy-3-oxoprop-1-enyl]pyrimidin-2-yl}-1,2,3,4-tetrahydro-9H-b-carboline-9-carboxylate (0.25 g, 0.0005 moles) (See Example 20) in 10 mL of dry THF was added 1:1 mixture of Pd (OH)$_2$ (50 mg) & Pd/C (50 mg) and stirred in the hydrogen atmosphere using balloon. After stirring for >12 hours, the reaction was filtered through a celite pad. The filtrate was concentrated and the crude residue was purified through silica column using 30% EtOAc in hexane to give methyl 3-{2-[9-(tert-butyloxycarbonyl)-1,3,4,9-tetrahydro-2H-b-carbolin-2-yl]pyrimidin-5-yl}propanoate (0.16 g, 63% yield). $^1$H NMR (DMSO-d$_6$, 400 MHz) ppm: 8.33 (s, 2H, 2Ar—H), 8.06 (d, 1H, J=8 Hz, 1Ar—H), 7.49 (d, 1H, J=8 Hz, 1Ar—H), 7.31-7.22 (m, 2H, 2Ar—H), 5.12 (s, 2H, CH$_2$), 4.09 (t, 2H, J=8 Hz, CH$_2$), 3.57 (s, 3H, OMe), 2.74 (brs, 2H, CH$_2$), 2.7 (t, 2H, CH$_2$), 2.67 (t, 2H, CH$_2$), 1.68 (s, 9H, 3CH$_3$). M/e=437 (M+1) (M, 436.504 Calcd. for C$_{24}$H$_{28}$N$_4$O$_4$).

Freshly dried hydroxylamine hydrochloride (0.14 g, 0.002 moles) was suspended in dry DCM (10 mL) at 0° C. To this was added 2 M Me$_3$Al in toluene (2.1 mL, 0.0041 moles) at 0° C. The temperature of the clear reaction mixture was slowly taken to room temperature and methyl 3-{2-[9-(tert-butyloxycarbonyl)-1,3,4,9-tetrahydro-2H-b-carbolin-2-yl]pyrimidin-5-yl}propanoate (0.15 g) was added. After stirring overnight, the reaction was cooled to 0° C. and saturated solution of sodium potassium tartarate (10 mL) was added. The solid formed was filtered and purified through HPLC to give Example 21 (40 mg, 34% yield). $^1$H NMR (DMSO-d$_6$, 400 MHz) ppm: 10.9 (s, 1H, NH or OH), 10.35 (s, 1H, NH or OH), 8.27 (s, 2H, 2Ar—H), 7.38 (d, 1H, J=4 Hz, 1Ar—H), 7.31 (d, 1H, J=8 Hz, 1Ar—H), 7.05-6.94 (m, 2H, 2Ar—H), 4.89 (s, 2H, CH$_2$), 4.11 (t, 2H, J=8 Hz, CH$_2$), 4.75 (brs, 2H, CH$_2$), 2.66 (t, 2H, J=8 Hz, CH$_2$), 2.21 (t, 2H, J=8 Hz, CH$_2$); m/e=338 (M+1) (M, 337.376 Calcd. for C$_{18}$H$_{19}$N$_5$O$_2$).

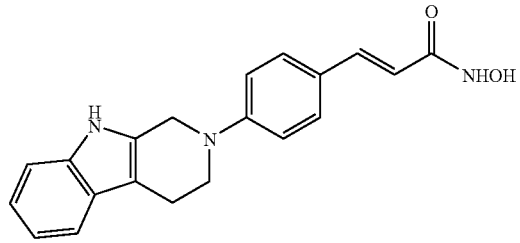

Example 22

(2E)-N-hydroxy-3-[4-(1,3,4,9-tetrahydro-2H-b-carbolin-2-yl)phenyl]acrylamide

To a solution of 1,2,3,4-tetrahydro-9H-pyrido[3,4-b]indole (250 mg, 1.460 mmol) in dry DMF (10 mL) were added 4-fluorobenzaldehyde (181 mg, 1.460 mmol) and CsF (266 mg, 1.752 mmol) and the reaction mixture was stirred at 65° C. for 5 hours. After completion, the reaction mixture was diluted with water (25 mL) and EtOAc (25 mL). The organic layer was separated and the aqueous layer was washed twice with EtOAc. The combined organic layers were dried over anhydrous sodium sulphate and concentrated under vacuum to provide the crude compound. It was then purified by column chromatography using silica gel to obtain 4-(1,3,4,9-tetrahydro-2H-b-carbolin-2-yl)benzaldehyde (125 mg). $^1$H NMR (CDCl$_3$+DMSO-D$_6$, 200 MHz) ppm: 9.93 (1H, bs), 9.74 (1H, s), 7.99 (1H, s), 7.76 (2H, d, J=8.8 Hz), 7.44 (1H, m), 7.32 (1H, m), 7.13-6.97 (3H, m), 4.61 (2H, s), 3.86 (2H, t, J=5.6 Hz), 2.93 (2H, m); m/e=277 (M+1).

To a solution of compound 4-(1,3,4,9-tetrahydro-2H-b-carbolin-2-yl)benzaldehyde (125 mg, 0.453 mmol) in dry acetonitrile (15 ml) was added (triphenylphosphoranylidene) acetate (166 mg, 0.489 mmol) and the reaction mixture was stirred at 65° C. for 3 hours. After completion, the solvent was evaporated and the mixture was diluted with water (25 mL) and EtOAc (25 mL). The organic layer was separated and the aqueous layer was washed with EtOAc (25 mL). The combined organic layers were dried over anhydrous sodium sulfate and concentrated under vacuum to provide the crude compound. It was then purified by column chromatography using silica gel to obtain methyl(2E)-3-[4-(1,3,4,9-tetrahydro-2H-b-carbolin-2-yl)phenyl]acrylate (55 mg). HPLC: (RT=17.11 min); $^1$H NMR (CDCl$_3$, 200 MHz) ppm: 7.84 (1H, s), 7.65 (1H, d, J=15.8 Hz), 7.49-7.08 (6H, m), 6.91 (2H, d, J=9.2 Hz), 6.28 (1H, d, J=15.8 Hz), 4.50 (2H, s), 3.79-3.73 (5H, m), 2.93 (2H, t, J=5.8 Hz); m/e=333 (M+1).

To the purified ester methyl(2E)-3-[4-(1,3,4,9-tetrahydro-2H-b-carbolin-2-yl)phenyl]acrylate (0.1 g, 0.32 mmol) in MeOH (5 mL) and DCM (2 mL), aq. hydroxylamine (50%, 1 mL) and aq. sodium hydroxide (100 mg in 0.5 mL of water) was added at 0° C. and then let it attain room temperature over 4 hours. The solvent was removed, water (2 mL) was added to the residue and then acidified with HCl in ether. The resulting white precipitate was filtered and dried under vacuum to obtain Example 22 (80 mg, 80% yield). $^1$H NMR (300 MHz, CD$_3$OD) ppm: 7.43-7.28 (m, 6H), 7.04-6.91 (m, 5H), 6.22 (d, J=15.9 Hz, 1H), 4.52 (m, 2H), 3.79 (m, 2H), 2.80 (m, 2H).

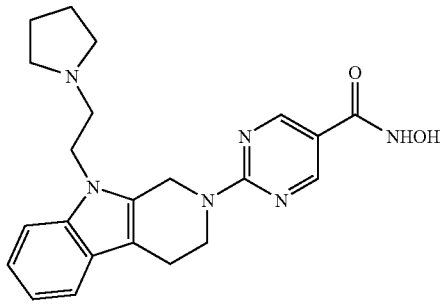

Example 23

N-hydroxy-2-{9-[2-pyrrolidin-1-ylethyl]-1,3,4,9-tetrahydro-2H-b-carbolin-2-yl}pyrimidine-5-carboxamide To Example 8 (200 mg, 0.649 mmol) in toluene (20 mL) chloro-2-(pyrrolidin-1-yl)ethane (166 mg, 0.973 mmol) and powdered sodium hydroxide (51 mg, 1.29 mmol) was added and heated at 110° C. for 12 hours. It was then poured into water and extracted with EtOAc. The residue obtained on removal of solvent was taken as such for next hydroxamate reaction. To the crude ester (50 mg, 0.12 mmol) in MeOH, aq. hydroxylamine (50%, 1 mL) and aq. sodium hydroxide (100 mg in 0.5 mL of water) was added at 0° C. and then let it attain room temperature over 4 hours. The solvent was removed, water (2 mL) was added to the residue and then acidified with HCl in ether. The resulting white precipitate was filtered and then purified by hplc to obtain Example 23 (10 mg, 20%) $^1$H NMR (300 MHz, CD$_3$OD) ppm: 8.70 (s, 2H), 7.47 (m, 2H), 7.25 (m, 1H), 7.10 (m, 1H), 6.90 (m, 1H), 5.02 (m, 2H), 4.62 (m, 2H), 4.26 (m, 2H), 3.60-3.80 (m, 4H), 3.20 (m, 2H), 2.82 (m, 2H), 2.02-2.30 (m, 4H).

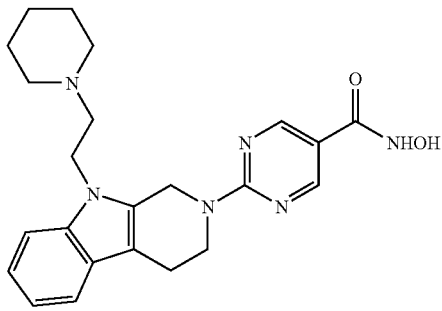

Example 24

N-hydroxy-2-[9-(2-piperidin-1-ylethyl)-1,3,4,9-tetrahydro-2H-b-carbolin-2-yl]pyrimidine-5-carboxamide To sodium hydride (38 mg, 1.62 mmol) in anhydrous DMF (10 mL) was added Example 8 (200 mg, 0.6 mmol, in 5 mL DMF) with stirring at room temperature. After stirring the reaction mixture for 1 hour, chloro-2-(piperidin-1-yl)ethane (149 mg, 1.62 mmol) in 3 mL DMF was added and the reaction mixture was stirred for a further 16 hours. The solvent was removed under reduced pressure, water (10 mL) was added and the pH was adjusted to 2 using 2 N HCl and then extracted with EtOAc. The organic layer was dried over anhydrous sodium sulfate, filtered and concentrated under reduced pressure to give the 2-[9-(2-piperidin-1-ylethyl)-1,3,4,9-tetrahydro-2H-b-carbolin-2-yl]pyrimidine-5-carboxylic acid (200 mg, 78% yield), m/e=420 (M+1).

To a solution of the acid 2-[9-(2-piperidin-1-ylethyl)-1,3,4,9-tetrahydro-2H-b-carbolin-2-yl]pyrimidine-5-carboxylic acid (200 mg, 0.49 mmol) in DCM (20 mL) was added EDCI (140 mg, 0.73 mmol), HOBT (99 mg, 0.73 mmol), DIEA (183 mg, 1.46 mmol) and NH$_2$OTHP (57 mg, 0.48 mmol) under nitrogen atmosphere. The reaction mixture was stirred at room temperature for 16 hours. The reaction mixture was concentrated under reduced pressure and the residue obtained was purified by column chromatography using EtOAc in hexanes (50%) to obtain N-(tetrahydro-2H-pyran-2-yloxy)-2-[9-(2-piperidin-1-ylethyl)-1,3,4,9-tetrahydro-2H-b-carbolin-2-yl]pyrimidine-5-carboxamide (80 mg). $^1$H NMR (200 MHz, CDCl$_3$) ppm: 8.75 (s, 2H), 7.50 (d, 1H, J=7.0 Hz), 7.30 (m, 1H), 7.16 (m, 2H), 5.13 (s, 2H), 5.04 (s, 1H), 4.24 (m, 4H), 4.00 (m, 1H), 2.91 (m, 2H), 2.70 (m, 2H), 2.49 (m, 4H), 1.85-1.45 (m, 11H); m/e=504 (M+1).

To a solution N-(tetrahydro-2H-pyran-2-yloxy)-2-[9-(2-piperidin-1-ylethyl)-1,3,4,9-tetrahydro-2H-b-carbolin-2-yl]pyrimidine-5-carboxamide (75 mg) in MeOH (1 mL) was added 18% HCl in ether (5 mL) at 0° C. The reaction mixture was stirred at 0° C. for 15 min. Solvent was removed under reduced pressure. To the crude product, ether was added and the precipitated solid was filtered and dried to give Example 24 (15 mg). $^1$H NMR (CD$_3$OD, 200 MHz) ppm: 8.83 (s, 2H), 7.54 (m, 2H), 7.25 (m, 1H), 7.16 (m, 2H), 5.21 (s, 2H), 4.60 (m, 2H), 4.33 (m, 2H), 3.67 (m, 4H), 3.52-2.93 (m, 6H), 2.93 (m, 2H), 1.98 (m, 6H); m/e=421 (M+1). HPLC: (RT: 12.81 min).

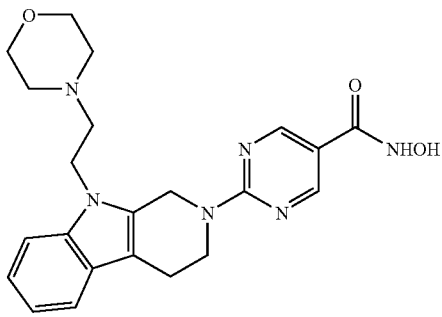

Example 25

N-hydroxy-2-[9-(2-morpholin-4-ylethyl)-1,3,4,9-tetrahydro-2H-b-carbolin-2-yl]pyrimidine-5-carboxamide To sodium hydride (140 mg, 5.83 mmol) in anhydrous DMF (10 mL) was added Example 8 (200 mg, 0.6 mmol, in 10 mL DMF) with stirring at room temperature. After stirring the reaction mixture for 1 houor, 4-(2-chloroethyl)morpholine (172 mg, 1.62 mmol) in 3 mL DMF was added to it and the reaction mixture was stirred for further 16 hours. The solvent was removed under reduced pressure, water (10 mL) was added and the pH was adjusted to 2 using 2 N HCl and then extracted with EtOAc. The organic layer was dried over anhydrous sodium sulphate, filtered and concentrated under reduced pressure to give the N-hydroxy-2-[9-(2-morpholin-4-ylethyl)-1,3,4,9-tetrahydro-2H-b-carbolin-2-yl]pyrimidine-5-carboxylic acid (160 mg, 68% yield), m/e=407 (M+1).

To a solution of 2-[9-(2-morpholin-4-ylethyl)-1,3,4,9-tetrahydro-2H-b-carbolin-2-yl]pyrimidine-5-carboxylic acid (160 mg, 0.39 mmol) in DCM (20 mL) were added EDCI (170 mg, 0.88 mmol), HOBT (90 mg, 0.66 mmol), DIEA (152 mg, 1.17 mmol) and NH$_2$OTHP (47 mg, 0.4 mmol) under nitrogen atmosphere. The reaction mixture was stirred at room temperature for 16 hours. The reaction mixture was concentrated under reduced pressure and the residue obtained was purified by column chromatography using EtOAc in hexanes (50%) to obtain N-(tetrahydro-2H-pyran-2-yloxy)-2-[9-(2-morpholin-4-ylethyl)-1,3,4,9-tetrahydro-2H-b-carbolin-2-yl]pyrimidine-5-carboxamide (46 mg, 23% yield). $^1$H NMR (200 MHz, CDCl$_3$) ppm: 8.75 (s, 2H), 7.50 (d, 1H, J=7.0 Hz), 7.30 (m, 1H), 7.16 (m, 2H), 5.13 (s, 2H), 5.04 (s, 1H), 4.24 (m, 4H), 4.00 (m, 1H), 3.69 (m, 4H), 2.91 (m, 2H), 2.70 (m, 2H), 2.49 (m, 4H), 1.85 (m, 2H), 1.47 (m, 5H); m/e=506 (M+1).

To a solution of N-(tetrahydro-2H-pyran-2-yloxy)-2-[9-(2-morpholin-4-ylethyl)-1,3,4,9-tetrahydro-2H-b-carbolin-2-yl]pyrimidine-5-carboxamide (46 mg) in MeOH (1 mL) was added 18% HCl in ether (4 mL) at 0° C. The reaction mixture was stirred at 0° C. for 15 min. The solvent was removed under reduced pressure. To the crude residue obtained, ether was added and the precipitated solid was filtered and dried to give Example 25 (24 mg, 63% yield). $^1$H NMR (CD$_3$OD, 200 MHz) ppm: 8.85 (s, 2H), 7.54 (m, 1H), 7.25 (m, 1H), 7.14 (m, 2H), 5.24 (s, 2H), 4.99 (m, 2H), 4.70 (m, 2H), 4.36 (m, 2H), 4.12 (m, 2H), 3.95 (m, 2H), 3.63 (m, 4H), 2.94 (m, 2H); m/e=422 (M+1). HPLC: (RT: 12.94 min).

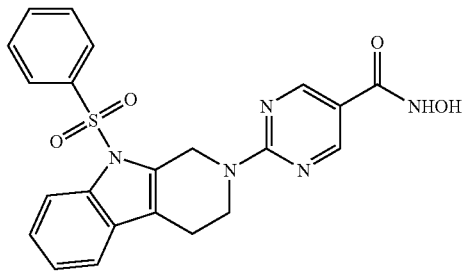

Example 26

N-hydroxy-2-[9-(phenylsulfonyl)-1,3,4,9-tetrahydro-2H-b-carbolin-2-yl]pyrimidine-5-carboxamide To a stirred solution of Example 8 (150 mg, 0.487 mmol) in THF (15 mL) was added potassium t-butoxide (81 mg, 0.720 mmol) and 18-crown-6 (2 mg) at 0° C. The suspension was stirred for 10-15 min at 0° C. and then benzenesulfonyl chlorde (0.86 mg, 0.486 mmol) was added. The reaction mixture was further stirred at 0° C. for 30 min. and then stirred at room temperature for 3 hours. The reaction mixture was diluted with EtOAc and water. The organic layer was washed with saturated sodium bicarbonate, dried over sodium sulfate and concentrated under vacuum. The crude product was purified by column chromatography using EtOAc in hexanes (50%) to obtain methyl 2-[9-(phenylsulfonyl)-1,3,4,9-tetrahydro-2H-b-carbolin-2-yl]pyrimidine-5-carboxylate (60 mg). $^1$HNMR (200 MHz, DMSO-d$_6$) ppm: 8.8 (s, 2H), 8.14-7.25 (m, 9H), 5.42 (s, 2H), 4.26 (t, 2H, J=5.4 Hz), 3.91 (s, 3H), 2.81 (2H, t, J=5.4 Hz); m/e=449 (M+1).

To a stirred solution of methyl 2-[9-(phenylsulfonyl)-1,3,4,9-tetrahydro-2H-b-carbolin-2-yl]pyrimidine-5-carboxylate (50 mg) in MeOH and DCM (5 mL, 3:2) was added hydroxylamine hydrochloride (6.42 g, mmol) at room temperature. After 15 min, sodium methoxide (4.45 g, mmol) was added at 0-5° C. under nitrogen atmosphere and the reaction mixture was stirred at room temperature for 3 hours. Water was added (5 mL) and neutralized with 1N hydrochloric acid and the organic layer was separated. The aqueous layer was extracted once with DCM (50 mL) and the combined organic layer was dried and concentrated to obtain Example 26 (25 mg). $^1$HNMR (DMSO-d$_6$) ppm: 8.78 (s, 2H), 8.13 (m, 1H), 7.94 (m, 1H), 7.61-7.26 (m, 7H), 5.43 (s, 2H), 4.27 (t, 2H, J=5.3 Hz), 2.79 (2H, t, J=5.3 Hz); m/e=449.9 (M+1); HPLC: (RT=15.33 min).

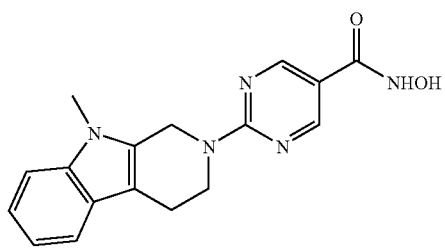

Example 27

N-hydroxy-2-(9-methyl-1,3,4,9-tetrahydro-2H-b-carbolin-2-yl)pyrimidine-5-carboxamide To a stirred solution of Example 8 (200 mg, mmol) in DMF (5 mL) was added potassium t-butoxide (145 mg) at 0° C. After stirring the suspension for 10-15 min at 0° C., methyl iodide (0.11 g, mmol) was added. The mixture was stirred at 0° C. for 30 min. and then stirred at room temperature for 3 hours. After completion, the reaction mixture was diluted with EtOAc. The organic layer was separated, washed with saturated sodium bicarbonate, dried over sodium sulfate and concentrated under vacuum. The crude product obtained was purified by column chromatography using EtOAc in hexanes (50%) to obtain methyl 2-(9-methyl-1,3,4,9-tetrahydro-2H-b-carbolin-2-yl)pyrimidine-5-carboxylate (160 mg, 76.5% yield). $^1$HNMR (DMSO-d$_6$) ppm: 2.8 (t, 2H, CH$_2$); 3.65 (s, 3H, N—CH$_3$); 3.8 (s, 3H, OCH$_3$); 4.2 (t, 2H, CH$_2$); 5.15 (s, 2H, CH$_2$); 7.0-7.2 (m, 2H); 7.4 (d, 2H); 8.8 (s, 2H); m/e=323 (M+1).

To a stirred solution of methyl 2-(9-methyl-1,3,4,9-tetrahydro-2H-b-carbolin-2-yl)pyrimidine-5-carboxylate (160 mg, mmol) in MeOH and DCM (5 mL, 3:2) was added hydroxylamine hydrochloride (10.3 g, mmol) at room temperature and stirred for 15 min. Sodium methoxide (5.3 g, mmol) was added at 0-5° C. under nitrogen atmosphere and the mixture was stirred at room temperature for 3 hours. After completion of the reaction, the mixture was partitioned between DCM and water, neutralized with 1N hydrochloric acid and the organic layer was separated. The aqueous layer was extracted with DCM (50 mL) and the combined organic layers were dried and concentrated to obtain Example 27 (60 mg, 37.5% yield). $^1$HNMR (200 MHz, DMSO-d$_6$) ppm: 2.8 (t, 2H); 3.65 (s, 3H, N—CH$_3$); 4.2 (t, 2H); 5.00 (s, 2H); 6.95-7.2 (m, 2H); 7.4 (d, 2H); 8.7 (s, 2H); m/e=323.9 (M+1).

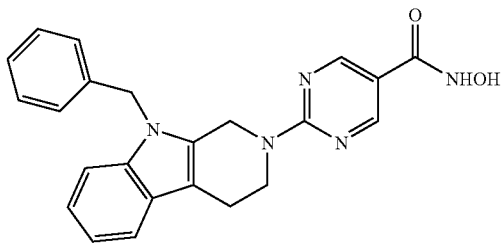

Example 28

N-hydroxy-2-(9-benzyl-1,3,4,9-tetrahydro-2H-b-carbolin-2-yl)pyrimidine-5-carboxamide To a stirred solution of Example 8 (200 mg, mmol) in DMF (mL) was added potassium t-butoxide (150 mg) at 0° C. After stirring at 0° C. for 15 min., benzyl bromide (0.1 mL, mmol) was added slowly. After completion of addition, the reaction mixture was allowed to attain room temperature and stirred for a further 3 hours. After completion of reaction, the reaction mixture was diluted with EtOAc. The organic layer was separated and washed with saturated sodium bicarbonate and water. After drying the organic layer using sodium sulfate, it was concentrated to obtain a crude product that was then purified by column chromatography to obtain methyl 2-(9-benzyl-1,3,4,9-tetrahydro-2H-b-carbolin-2-yl)pyrimidine-5-carboxylate (200 mg, 77.0% yield), m/e=398.9 (M+1).

To a stirred solution of methyl 2-(9-benzyl-1,3,4,9-tetrahydro-2H-b-carbolin-2-yl)pyrimidine-5-carboxylate (100 mg) in THF and water (5 mL each) was added lithium hydroxide (23 mg, mmol) at room temperature. The mixture was stirred for 3 hours at room temperature and after which it was acidified with 1N hydrochloric acid. It was then extracted with ethyl acetate and concentrated to obtain the 2-(9-benzyl-1,3,4,9-tetrahydro-2H-b-carbolin-2-yl)pyrimidine-5-carboxylic acid (80 mg, 83% yield), m/e=382.9 (M−1).

To a stirred solution of 2-(9-benzyl-1,3,4,9-tetrahydro-2H-b-carbolin-2-yl)pyrimidine-5-carboxylic acid (90 mg) in DCM (5 mL) was added EDCI (74 mg) at 0° C. and the reaction mixture was stirred for 20 min. NH$_2$OTHP (30 mg) was added and the temperature was allowed to attain room temperature. After stirring at room temperature overnight, it was diluted with DCM. The organic layer was washed with water and then concentrated under vacuum. The residue obtained was purified by column chromatography to obtain N-(tetrahydro-2H-pyran-2-yloxy)-2-[9-benzyl-1,3,4,9-tetrahydro-2H-b-carbolin-2-yl]pyrimidine-5-carboxamide (60 mg, 53% yield), m/e=484 (M+1).

A solution of N-(tetrahydro-2H-pyran-2-yloxy)-2-[9-benzyl-1,3,4,9-tetrahydro-2H-b-carbolin-2-yl]pyrimidine-5-carboxamide (60 mg, mmol) was stirred with hydrogen chloride in ether (5 mL) at 0-5° C. for 30 min. The product that separated out was filtered and washed with ether to obtain Example 28 (19 mg, 38%). $^1$H NMR (200 MHz, DMSO-d$_6$) ppm: 2.8 (t, 2H); 4.2 (t, 2H); 5.0 (s, 2H); 5.4 (s, 2H); 7.0-7.6 (m, 9H); 8.7 (s, 2H); m/e=400.0 (M+1).

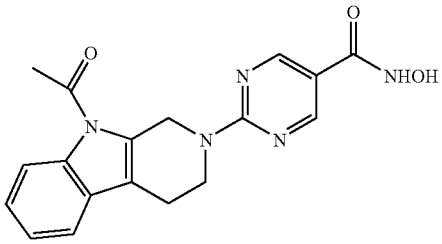

Example 29

2-(9-acetyl-1,3,4,9-tetrahydro-2H-b-carbolin-2-yl)-N-hydroxypyrimidine-5-carboxamide To a stirred solution of Example 8 (500 mg, mmol) in THF and water (10 mL, 1:1) was added lithium hydroxide (205 mg, mmol) at room temperature and the mixture was stirred for 4-5 hours. After completion, the reaction mixture was acidified using 1N hydrochloric acid. The mixture was extracted with EtOAc, washed with brine, the organics dried over sodium sulfate and concentrated to give 2-(1,3,4,9-tetrahydro-2H-b-carbolin-2-yl)pyrimidine-5-carboxylic acid (400 mg, 83% yield).

To a stirred solution of 2-(1,3,4,9-tetrahydro-2H-b-carbolin-2-yl)pyrimidine-5-carboxylic acid (400 mg) in DCM (10 mL) was added EDCI (390 mg, mmol) at 0° C. After stirring the reaction mixture at 0° C. for 15 min. NH$_2$OTHP (160 mg, mmol) was added. After stirring overnight, the reaction was diluted with DCM (30 mL). The organic layer was washed with saturated sodium bicarbonate and water. The crude product obtained on removal of solvent was purified by column chromatography using EtOAc in hexanes (50%) to obtain N-(tetrahydro-2H-pyran-2-yloxy)-2-[1,3,4,9-tetrahydro-2H-b-carbolin-2-yl]pyrimidine-5-carboxamide (250 mg, 46.8% yield), m/e=394 (M+1).

To a stirred solution of N-(tetrahydro-2H-pyran-2-yloxy)-2-[1,3,4,9-tetrahydro-2H-b-carbolin-2-yl]pyrimidine-5-carboxamide (120 mg, mmol) in DMF (5 mL) was added sodium hydride (22 mg) at 0° C. and the mixture was stirred for 20 min. Acetyl chloride (30 mg, mmol) was added and the reaction was allowed to attain room temperature and stirred 3 hours. After completion, the reaction mixture was partitioned between EtOAc and water. The organic layer was separated and washed with water, saturated sodium bicarbonate and concentrated. Pure N-(tetrahydro-2H-pyran-2-yloxy)-2-[9-acetyl-1,3,4,9-tetrahydro-2H-b-carbolin-2-yl]pyrimidine-5-carboxamide (80 mg, 60% yield) was obtained by column chromatography m/e=436 (M+1).

A solution of N-(tetrahydro-2H-pyran-2-yloxy)-2-[9-acetyl-1,3,4,9-tetrahydro-2H-b-carbolin-2-yl]pyrimidine-5-carboxamide (80 mg, mmol) was stirred in hydrogen chloride in ether (5 mL) for 25-30 min at 0° C. and the solid that separated out was filtered. The product was washed with ether and dried under vacuum to obtain Example 29 (30 mg, 46.8% yield). $^1$HNMR (200 MHz, CD$_3$OD) ppm: 2.8 (s, 3H, CH3); 2.9 (t, 2H, CH2); 4.3 (t, 2H); 5.4 (s, 2H); 7.2-7.4 (m, 2H); 7.5 (m, 1H); 7.9 (d, 1H); 8.8 (s, 2H); m/e=352 (M$^+$+1).

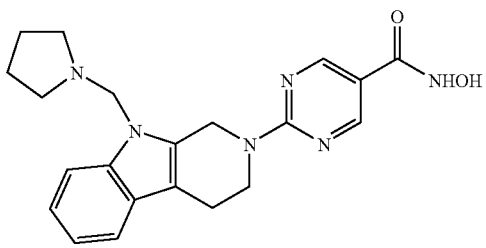

Example 30

N-hydroxy-2-{9-[2-pyrrolidin-1-ylmethyl]-1,3,4,9-tetrahydro-2H-b-carbolin-2-yl}pyrimidine-5-carboxamide A solution of N-(tetrahydro-2H-pyran-2-yloxy)-2-[1,3,4,9-tetrahydro-2H-b-carbolin-2-yl]pyrimidine-5-carboxamide (See intermediate in Example 29) (100 mg, 0.26 mmol) in EtOH (0.6 mL) was treated 37% aqueous formaldehyde (0.025 mL) and pyrrolidine (22 mg) and heated to reflux overnight. The reaction mixture was cooled, diluted with water, and extracted with EtOAc. The extracts were washed with water, dried and the solvent evaporated to give N-(tetrahydro-2H-pyran-2-yloxy)-2-[9-[2-pyrrolidin-1-ylmethyl] 1,3,4,9-tetrahydro-2H-b-carbolin-2-yl]pyrimidine-5-carboxamide (60 mg), m/e=477 (M+1).

A solution of N-(tetrahydro-2H-pyran-2-yloxy)-2-[9-[2-pyrrolidin-1-ylmethyl]1,3,4,9-tetrahydro-2H-b-carbolin-2-yl]pyrimidine-5-carboxamide (60 mg) was stirred in hydrogen chloride in ether (5 mL) for 25-30 min at 0° C. and the solid that separated out was filtered. The product was washed with ether and dried under vacuum to obtain Example 30 (40 mg), m/e=393 (M+1).

Examples 31 and 32 were prepared in the same manner as Example 11 by substituting the appropriate tetrahydroisoquinoline for 6,7-dimethoxy-1,2,3,4-tetrahydroisoquinoline.

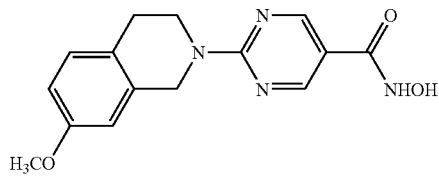

Example 31

2-(7-methoxy-3,4,dihydroisoquinolin-2(1H)-yl)-N-hydroxypyrimidine-5-carboxamide

From 7-methoxy-1,2,3,4-tetrahydroisoquinoline and Example 7 was obtained the trifluoroacetic acid salt of Example 31 as a floculant white solid after hplc purification. $^1$H NMR (300 MHz, DMSO-d$_6$) ppm: 2.82 (m, 2H), 3.73 (s, 3H), 4.00 (m, 2H), 4.89 (s, 2H), 6.75 (m, 1H), 6.86 (m, 1H), 7.08 (m, 1H), 8.75 (s, 2H), 11.1 (bs, 1H); m/e=301 (M+1).

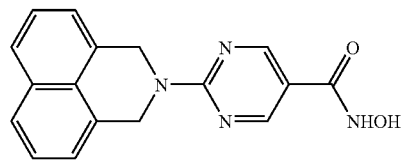

Example 32

2-(1H-benzo[de]isoquinolin-2(3H)-yl)-N-hydroxy-pyrimidine-5-carboxamide

From 2,3-dihydro-1H-benzo[de]isoquinoline and Example 7 was obtained Example 32. $^1$H NMR (300 MHz, DMSO-D$_6$): 5.34 (s, 4H), 7.47 (m, 4H), 7.79 (m, 2H), 8.69 (s, 2H), 8.70 (S, 2H), m/e=307 (M+1).

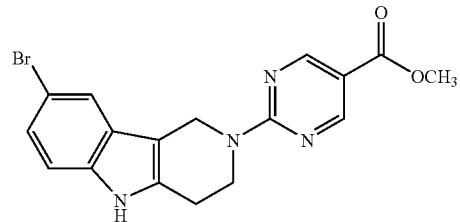

Example 33 methyl 2-(8-bromo-1,3,4,5-tetrahydro-2H-pyrido[4,3-b]indol-2-yl)pyrimidine-5-carboxylate To a stirred solution of 4-bromophenylhydrazine hydrochloride (5.0 g, 22.36 mmol) in ethanol (100 mL), piperidin-4-one hydrochloride (1.316 g, 8.5984 mmol) was added and the mixture was heated to reflux. The reflux was maintained for 4 hours, then cooled to room temperature and dry hydrogen chloride gas was passed for 1 hour through the reaction mixture. The mixture was then again heated to reflux and maintained for 2 h. After completion of reaction, ethanol was distilled off under vacuum and the residue was dissolved in water. The aqueous layer was neutralized with 2N sodium hydroxide solution and was extracted in dichloromethane (2×100 mL). The pH of the aqueous layer was then adjusted to 12.0 with 2N sodium hydroxide solution and the product was extracted with ethyl acetate. The ethyl acetate layer was dried over anhydrous sodium sulfate and concentrated under vacuum. The crude solid was washed with diethyl ether (50 mL) to obtain 8-bromo-2,3,4,5-tetrahydro-1H-pyrido[4,3-b]indole (2.2 g, 39.3%) with purity 98.82% by HPLC. $^1$HNMR (200 MHz, DMSO-d$_6$) δ: 2.7 (t, 2H, CH$_2$), 3.0 (t, 2H, CH$_2$), 3.8 (d, 2H, CH$_2$), 7.05 (d, 1H, Ar—H), 7.2 (d, 1H, Ar—H), 7.45 (s, 1H, Ar—H), 10.97 (bs, 1H, NH). m/e=251 (M$^+$+1).

To a solution of 8-bromo-2,3,4,5-tetrahydro-1H-pyrido[4,3-b]indole (250 mg, 0.991 mmol) in anhydrous DMF (10 mL) was added Example 7 (258 mg, 1.194 mmol) and potassium carbonate (204 mg, 1.401 mmol) at room temperature. The reaction mixture was stirred at 100° C. for 6 hours. After completion, the reaction mixture was diluted with water and the compound was extracted with EtOAc. The combined organic layers were dried over sodium sulfate, filtered and concentrated under reduced pressure. The residue obtained was purified by column chromatography to obtain Example 33 (80 mg, 21%). HPLC: (RT=17.39 min). $^1$H NMR (200 MHz, CDCl$_3$) ppm: 8.88 (s, 2H), 7.95 (bs, 1H), 7.65-7.15 (m, 3H), 5.05 (s, 2H), 4.35 (m, 2H), 3.88 (s, 3H), 2.93 (t, 2H, J=5.4 Hz); m/e=387 (M+1).

Examples 34 to 39 were prepared in the same manner as Example 15 by substituting the appropriate phenylhydrazine for the 4-bromophenylhydrazine used in making Example 33 and processing the resulting ester to the hydroxamic acid as described for Example 12.

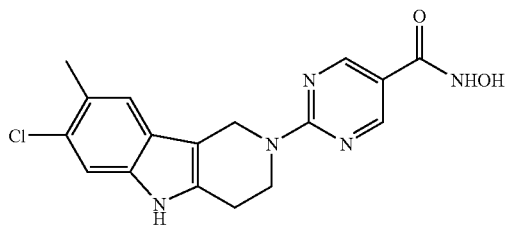

Example 34

N-hydroxy-2-(7-chloro-8-methyl-1,3,4,5-tetrahydro-2H-pyrido[4,3-b]indol-2-yl)pyrimidine-5-carboxamide Example 34 was obtained by substituting 3-chloro-4-methylphenyl hydrazine for 4-bromophenylhydrazine. A white solid (0.12 g, 60%) of 94.6% purity by HPLC; $^1$HNMR (200 MHz, DMSO-D$_6$) δ: 2.39 (s, 3H, CH$_3$), 2.9 (t, 2H, CH$_2$), 4.2 (t, 2H, CH$_2$), 5.0 (s, 2H, CH$_2$), 7.3 (s, 1H, Ar), 7.4 (s, 1H, Ar), 8.78 (s, 2H, Pyrimidine), 9.05 (bs, 1H, NH), 10.95 (s, 1H, NH), 11.1 (bs, 1H, OH).

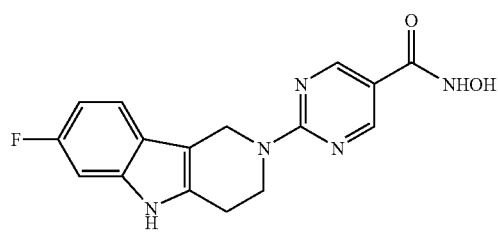

Example 35

N-hydroxy-2-(7-fluoro-1,3,4,5-tetrahydro-2H-pyrido[4,3-b]indol-2-yl)pyrimidine-5-carboxamide Example 35 was obtained by substituting 3-fluorophenyl hydrazine for 4-bromophenylhydrazine. A solid (40 mg, 71.8%) with HPLC purity 94.97%; $^1$HNMR (200 MHz, DMSO-D$_6$) δ: 2.9 (t, 2H, CH$_2$); 4.2 (t, 2H, CH$_2$); 4.9 (s, 2H, CH$_2$); 6.8 (m, 1H, Ar); 7.07 (dd, 1H, Ar); 7.4 (m, 1H, Ar); 8.7 (s, 2H, pyrimidine); 11.03 (s, 1H, NH); m/e=328 (M+1).

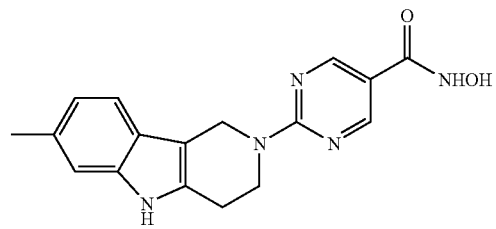

Example 36

N-hydroxy-2-(7-methyl-1,3,4,5-tetrahydro-2H-pyrido[4,3-b]indol-2-yl)pyrimidine-5-carboxamide Example 36 was obtained by substituting 3-methylphenyl hydrazine for 4-bromophenylhydrazine. A solid; $^1$HNMR (200 MHz, DMSO-D$_6$) δ: 2.81 (t, 2H, CH$_2$); 4.2 (t, 2H, CH$_2$); 4.9 (s, 2H, CH$_2$); 6.8 (d, 1H, Ar); 7.15 (s, 1H, Ar); 7.3 (d, 1H, Ar); 8.7 (s, 2H, pyrimidine); 10.78 (s, 1H, NH); m/e=324 (M+1).

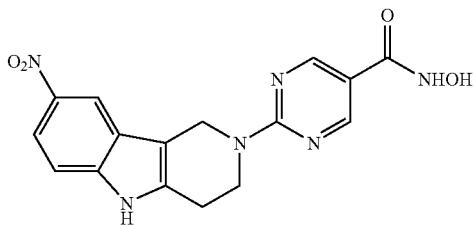

Example 37

N-hydroxy-2-(8-nitro-1,3,4,5-tetrahydro-2H-pyrido[4,3-b]indol-2-yl)pyrimidine-5-carboxamide Example 37 was obtained by substituting 4-nitrophenyl hydrazine for 4-bromophenylhydrazine. A greenish yellow colored solid (0.1 g, 86.02%); $^1$HNMR (200 MHz, DMSO-d$_6$) δ: 2.9 (t, 2H, CH$_2$), 4.2 (t, 2H, CH$_2$), 5.1 (s, 2H, CH$_2$), 7.45 (d, 1H, Ar—H), 8.0 (d, 1H, Ar—H), 8.45 (s, 1H, Ar—H), 8.7 (s, 2H, Pyrimidine); m/e=355.1 (M+1).

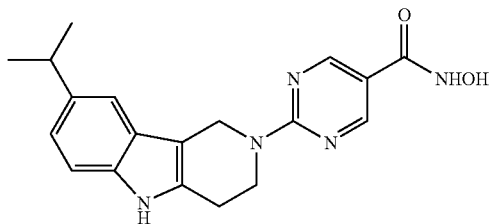

Example 38

N-hydroxy-2-{8-isopropyl-1,3,4,5-tetrahydro-2H-pyrido[4,3-b]indol-2-yl}pyrimidine-5-carboxamide Example 38 was obtained by substituting 4-isopropylphenyl hydrazine for 4-bromophenylhydrazine. A solid (0.045 g, 56.25%), m/e=352 (M+1).

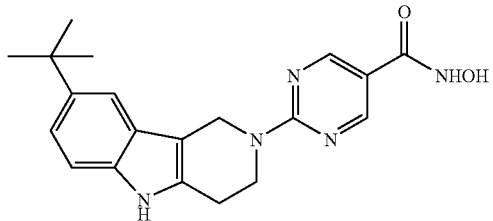

Example 39

N-hydroxy-2-{8-tert-butyl-1,3,4,5-tetrahydro-2H-pyrido[4,3-b]indol-2-yl}pyrimidine-5-carboxamide Example 39 was obtained by substituting 4-tert-butylphenyl hydrazine for 4-bromophenylhydrazine. A solid (0.2 g, 86.9%), m/e=366 (M+1).

Examples 111 and 112 were prepared in the same manner as Example 15 by substituting the appropriate phenylhydrazine for the 4-bromophenylhydrazine used in making Example 33 and processing the resulting ester to the hydroxamic acid as described for Example 12.

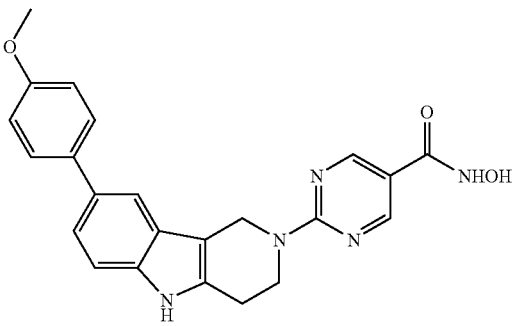

Example 40

N-hydroxy-2-{8-[4-methoxyphenyl]-1,3,4,5-tetrahydro-2H-pyrido[4,3-b]indol-2-yl}pyrimidine-5-carboxamide Example 40 was obtained by substituting 4-methoxyphenylboronic acid for phenylboronic acid. White solid (0.07 g, 53.7%) of 94.45% purity by HPLC; $^1$HNMR (200 MHz, DMSO-D$_6$) δ: 2.99 (t, 2H, CH$_2$), 3.8 (s, 3H, OCH$_3$), 4.22 (t, 2H, CH$_2$), 5.0 (s, 2H, CH$_2$), 7.0 (d, 2H, Ar—H), 7.35 (d, 2H, Ar—H), 7.65 (d, 2H, Ar—H), 7.7 (s, 1H, Ar—), 8.7 (s, 2H, Pyrimidine-H), 9.0 (s, 1H, NH), 10.9 (s, 1H, NH), 11.11 (bs, 1H, OH); m/e=416 (M+1).

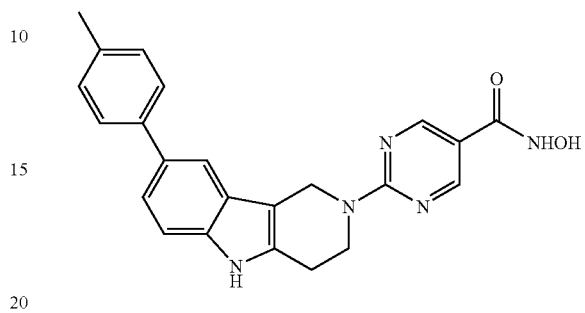

Example 41

N-hydroxy-2-{8-[4-methylphenyl]-1,3,4,5-tetrahydro-2H-pyrido[4,3-b]indol-2-yl}pyrimidine-5-carboxamide Example 41 was obtained by substituting 4-methylphenylboronic acid for phenylboronic acid. A white solid (17 mg, 33.9%) with 95.45% purity (by HPLC) $^1$HNMR (200 MHz, DMSO-D$_6$) δ: 2.3 (s, 3H, CH$_3$), 2.85 (t, 2H, CH$_2$), 4.24 (t, 2H, CH$_2$), 5.0 (s, 2H, CH$_2$), 7.2 (d, 2H, Ar—H), 7.35 (d, 2H, Ar—H), 7.6 (d, 2H, Ar—H), 7.7 (s, 1H, Ar—H), 8.75 (s, 2H, Pyrimidine-H), 9.0 (bs, 1H, NH), 10.9 (s, 1H, NH); m/e=400.0 (M+1).

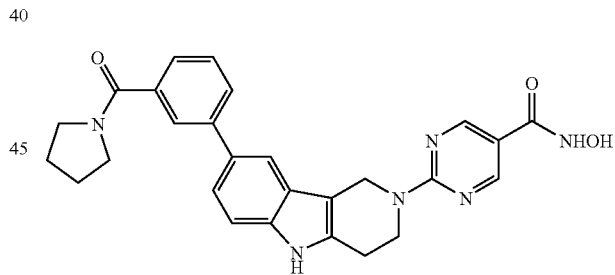

Example 42

N-hydroxy-2-{8-[3-(pyrrolidin-1-ylcarbonyl)phenyl]-1,3,4,5-tetrahydro-2H-pyrido[4,3-b]indol-2-yl}pyrimidine-5-carboxamide Example 42 was obtained by substituting 3-(pyrrolidin-1-ylcarbonyl)phenylboronic acid for phenylboronic acid. A white solid 85 mg (56.6%) of 97.25% pure by HPLC; $^1$HNMR (200 MHz, CD$_3$OD) δ: 2.0 (m, 4H, 2×CH$_2$), 2.99 (t, 2H, CH$_2$), 3.5-3.7 (m, 4H, 2×CH$_2$), 4.4 (t, 2H, CH$_2$), 5.1 (s, 2H, CH$_2$), 7.4-7.85 (m, 7H, Ar—H), 8.7 (s, 2H, Pyrimidine-H); m/e=484 (M+1).

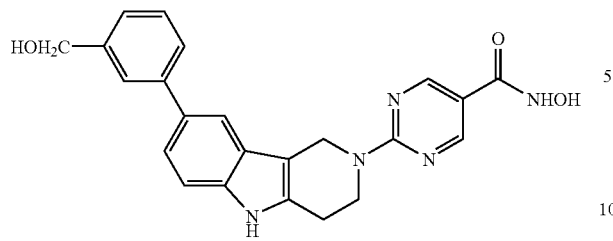

Example 43

N-hydroxy-2-{8-[3-(hydroxymethyl)phenyl]-1,3,4,5-tetrahydro-2H-pyrido[4,3-b]indol-2-yl}pyrimidine-5-carboxamide Example 43 was obtained by substituting 3-(hydroxymethyl)phenylboronic acid for phenylboronic acid. A white solid (0.025 g, 41.66%) of 91.09% purity by HPLC; $^1$HNMR (200 MHz, CD$_3$OD) □: 2.99 (t, 2H, CH$_2$), 4.4 (t, 2H, CH$_2$), 4.7 (s, 2H, CH$_2$), 5.18 (s, 2H, CH$_2$), 7.2-7.75 (m, 7H, Ar—H), 8.88 (s, 2H, Pyrimidine-H); m/e=416 (M+1).

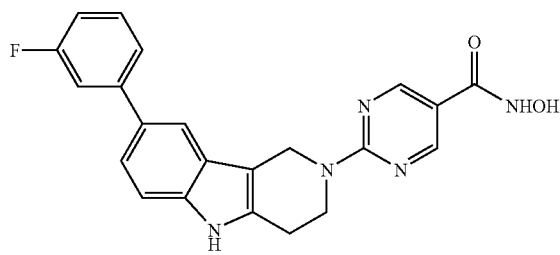

Example 44

N-hydroxy-2-{8-[3-fluorophenyl]-1,3,4,5-tetrahydro-2H-pyrido[4,3-b]indol-2-yl}pyrimidine-5-carboxamide Example 44 was obtained by substituting 3-fluorophenylboronic acid for phenylboronic acid. A pale yellow colored solid (0.013 g, 21.6%) of 94.45% purity by HPLC; $^1$HNMR (200 MHz, DMSO-d$_6$) δ: 2.9 (t, 2H, CH$_2$), 4.25 (t, 2H, CH$_2$), 5.0 (s, 2H, CH$_2$), 7.0 (t, 1H, Ar—H), 7.2-7.6 (m, 5H, Ar—H), 7.8 (s, 1H, Ar—H), 8.7 (s, 2H, Pyrimidine), 9.0 (bs, 1H, NH); m/e=404 (M+1).

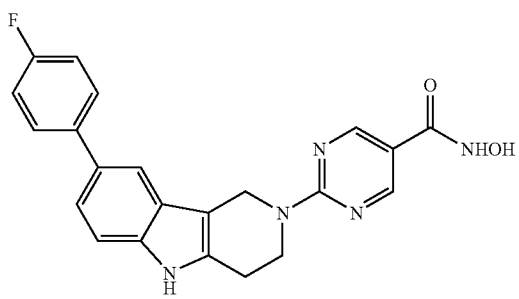

Example 45

N-hydroxy-2-{8-[4-fluorophenyl]-1,3,4,5-tetrahydro-2H-pyrido[4,3-b]indol-2-yl}pyrimidine-5-carboxamide Example 45 was obtained by substituting 4-fluorophenylboronic acid for phenylboronic acid. A pale yellow colored solid (0.01 g, 25%) of 99.23% purity by HPLC; $^1$HNMR (200 MHz, CD$_3$OD) δ: 2.9 (t, 2H, CH$_2$), 4.25 (t, 2H, CH$_2$), 5.1 (s, 2H, CH$_2$), 7.0-7.2 (t, 2H, Ar—H), 7.35 (t, 2H, Ar—H), 7.6 (m, 3H, Ar—H), 8.7 (s, 2H, Pyrimidine); m/e=404 (M+1).

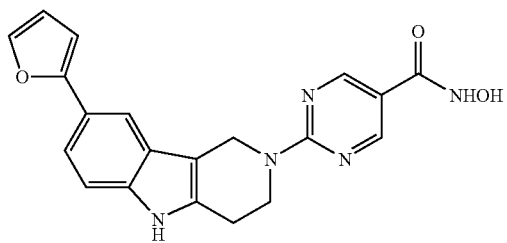

Example 46

N-hydroxy-2-{8-(fur-2-yl)-1,3,4,5-tetrahydro-2H-pyrido[4,3-b]indol-2-yl}pyrimidine-5-carboxamide Example 46 was obtained by substituting fur-2-ylboronic acid for phenylboronic acid. A solid (1.08 g); HPLC:(RT-14.2); m/e=376 (M+1).

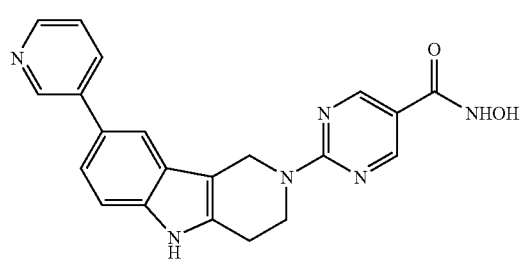

Example 47

N-hydroxy-2-{8-(pyridin-3-yl)-1,3,4,5-tetrahydro-2H-pyrido[4,3-b]indol-2-yl}pyrimidine-5-carboxamide Example 47 was obtained by substituting pyridin-3-ylboronic acid for phenylboronic acid. A solid (0.017 g, 23.93%); HPLC: 91.59% (RT=11.31); $^1$HNMR (CD$_3$OD, 200 MHz) δ: 8.72 (s, 2H), 8.82 (s, 1H), 8.41 (d, 1H), 8.06 (d, 1H), 7.412-7.77 (m, 5H), 5.09 (s, 2H), 4.24 (m, 2H), 2.84 (m, 2H); m/e=386 (M+1).

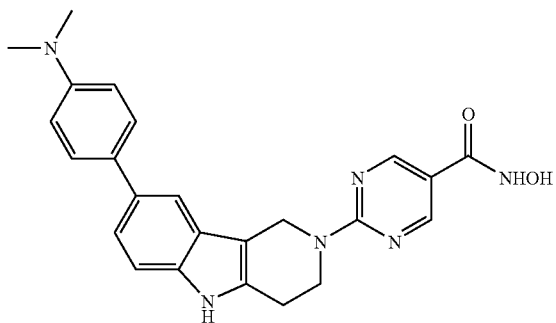

Example 48

N-hydroxy-2-{8-[4-dimethylaminophenyl]-1,3,4,5-tetrahydro-2H-pyrido[4,3-b]indol-2-yl}pyrimidine-5-carboxamide Example 48 was obtained by substituting 4-(dimethylamino)phenylboronic acid. A whtie solid (20 mg, 83%); $^1$H NMR (300 MHz, DMSO-d$_6$): 2.89 (m, 2H), 3.30 (s, 6H), 4.25 (m, 2H), 5.01 (s, 2H), 7.11 (m, 2H), 7.32 (s, 1H), 7.64-7.70 (m, 3H), 8.71 (s, 2H), 10.94 (s, 1H); m/e=429 (M+1).

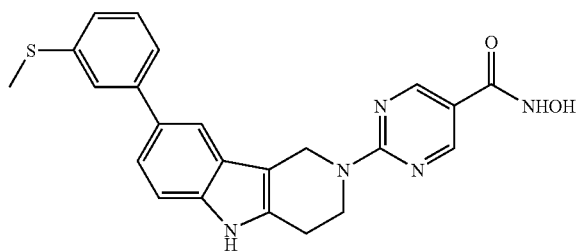

Example 49

N-hydroxy-2-{8-[3-(methylthio)phenyl]-1,3,4,5-tetrahydro-2H-pyrido[4,3-b]indol-2-yl}pyrimidine-5-carboxamide Example 49 was obtained by substituting 3-(methylthio)phenylboronic acid for phenylboronic. A solid (0.065 g, 86%); HPLC: 97.97% (RT-15.32); $^1$HNMR (DMSO-D$_6$, 200 MHz) δ: 11.01 (1H, s), 8.77 (2H, s), 7.80 (1H, s), 7.54-7.15 (Ar, 7H, m), 5.01 (2H, s), 4.23 (2H, m), 3.33 (3H, s), 2.88 (2H, m); m/e=432 (M+1).

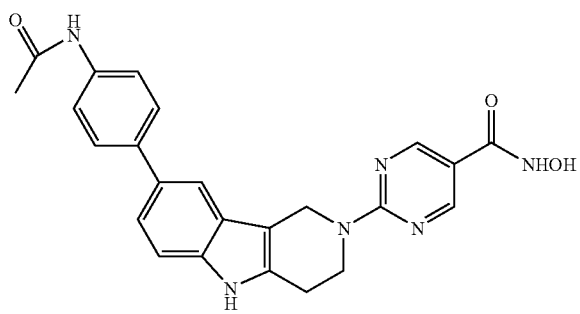

Example 50

N-hydroxy-2-{8-[4-(N-acetamido)phenyl]-1,3,4,5-tetrahydro-2H-pyrido[4,3-b]indol-2-yl}pyrimidine-5-carboxamide Example 50 was obtained by substituting 4-(N-acetamido)phenylboronic acid for phenylboronic acid. A solid (0.030 g, 35.2%); HPLC: 88.28% (RT-12.75); $^1$HNMR (DMSO-D$_6$, 200 MHz) δ: 10.97 (1H, s), 9.96 (1H, s), 8.72 (2H, s), 7.73-7.33 (Ar, 7H, m), 5.01 (2H, s), 4.24 (2H, m), 2.80 (2H, m), 2.05 (3H, s); m/e=443 (M+1).

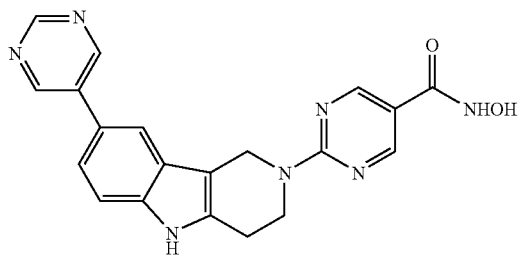

Example 51

N-hydroxy-2-{8-(pyrimidin-5-yl)-1,3,4,5-tetrahydro-2H-pyrido[4,3-b]indol-2-yl}pyrimidine-5-carboxamide Example 51 was obtained by substituting pyrimidin-5-ylboronic acid for phenylboronic acid. A solid (0.025 g, 35.61%); HPLC: 94.4128% (RT-11.98); $^1$HNMR (CD$_3$OD, 200 MHz) δ: 9.20 (1H, s), 9.15 (2H, s), 8.81 (2H, s), 7.96 (1H, s), 7.14 (2H, d), 5.18 (2H, s), 4.39 (2H, m), 2.82 (2H, m); m/e=388 (M+1).

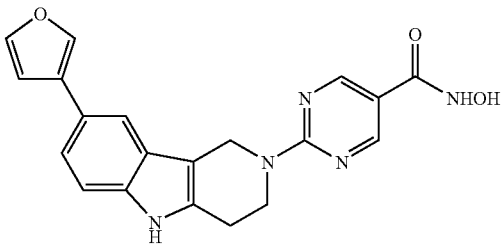

Example 52

N-hydroxy-2-{8-[fur-3-yl]-1,3,4,5-tetrahydro-2H-pyrido[4,3-b]indol-2-yl}pyrimidine-5-carboxamide Example 52 was obtained by substituting fur-3-ylboronic acid for phenylboronic acid. A solid; (0.116 g). $^1$HNMR (DMSO-D$_6$, 200 MHz) δ: 10.93 (1H, s), 8.75 (2H, s), 8.09 (1H, s), 7.60 (2H, d), 7.28 (2H, s), 7.00 (1H, s), 4.99 (2H, s), 4.24 (2H, m), 2.87 (2H, m); m/e=376

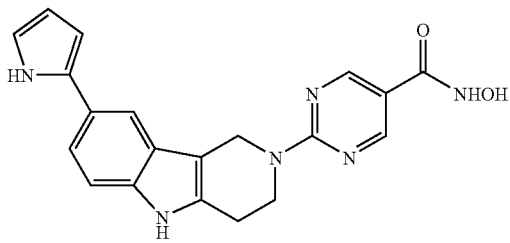

Example 53

N-hydroxy-2-{8-[1H-pyrrol-2-yl]-1,3,4,5-tetrahydro-2H-pyrido[4,3-b]indol-2-yl}pyrimidine-5-carboxamide Example 53 was obtained by substituting 1H-pyrrol-2-ylboronic acid for phenylboronic acid. A solid (0.015 g, 35%); $^1$H NMR (200 MHz, CD$_3$OD): δ 2.89 (m, 2H), 4.40 (m, 2H), 5.15 (m, 2H), 6.1 (m, 2H), 6.8 (s, 1H), 7.20 (s, 1H), 7.40 (m, 2H), 8.66 (s, 2H); MS: 375 (M+1).

Examples 54 to 57 were prepared in the same manner as Example 15 by substituting the appropriate phenylhydrazine for the 4-bromophenylhydrazine used in making Example 33 and processing the resulting ester to the hydroxamic acid as described for Example 12.

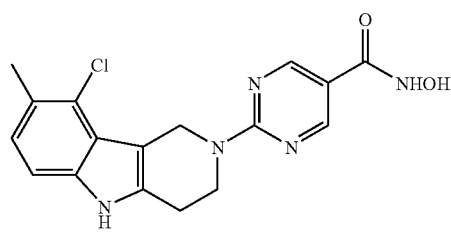

Example 54

N-hydroxy-2-(9-chloro-8-methyl-1,3,4,5-tetrahydro-2H-pyrido[4,3-b]indol-2-yl)pyrimidine-5-carboxamide Example 54, an isomer of Example 34, was also obtained by substituting 3-chloro-4-methylphenyl hydrazine for 4-bromophenylhydrazine. A white solid (0.03 g, 60%); $^1$H NMR (200 MHz, CD$_3$OD): δ 2.35 (s, 3H), 2.89 (m, 2H), 4.40 (m, 2H), 5.15 (m, 2H), 7.40 (m, 2H), 8.66 (s, 2H); m/e=358 (M+1).

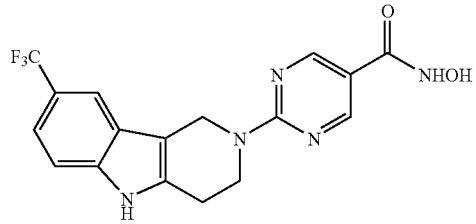

Example 55

N-hydroxy-2-(8-trifluoromethyl-1,3,4,5-tetrahydro-2H-pyrido[4,3-b]indol-2-yl)pyrimidine-5-carboxamide Example 55 was obtained by substituting 4-(trifluoromethyl)phenyl hydrazine for 4-bromophenylhydrazine. A solid (0.07 g, 70%); $^1$H NMR (200 MHz, CD$_3$OD): δ 2.89 (m, 2H), 4.40 (m, 2H), 5.15 (m, 2H), 7.40 (m, 2H), 7.80 (s, 1H), 8.66 (s, 2H); m/e=378 (M+1).

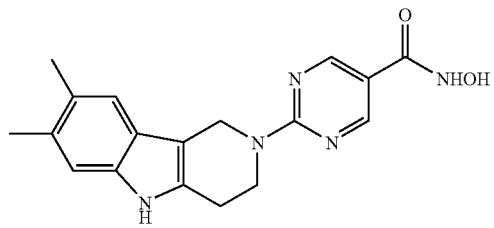

Example 56

N-hydroxy-2-(7,8-dimethyl-1,3,4,5-tetrahydro-2H-pyrido[4,3-b]indol-2-yl)pyrimidine-5-carboxamide Example 56 was obtained by substituting 3,4-dimethylphenyl hydrazine for 4-bromophenylhydrazine. A solid, (0.071 gm), m/e=338 (M+1).

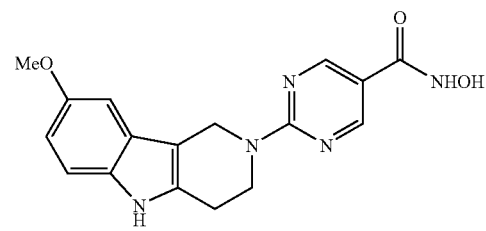

Example 57

N-hydroxy-2-(8-methoxy-1,3,4,5-tetrahydro-2H-pyrido[4,3-b]indol-2-yl)pyrimidine-5-carboxamide Example 57 was obtained by substituting 4-methoxyphenyl hydrazine for 4-bromophenylhydrazine in the reaction sequence. A white solid; $^1$H NMR (300 MHz, DMSO-D$_6$) δ: 2.83 (m, 2H), 3.74 (s, 3H), 4.21 (m, 2H), 4.92 (s, 2H), 8.65 (m, 1), 6.97 (d, J=2.4, 1H), 7.14 (d, J=8.7, 1H), 8.70 (S, 2H), 10.23 (s, 2H), 10.74 (s, 1H); m/e=340 (M+1).

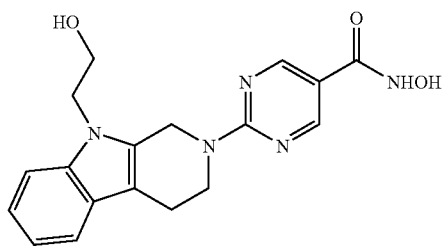

Example 58

N-hydroxy-2-[9-(2-hydroxyethyl)-1,3,4,9-tetrahydro-2H-b-carbolin-2-yl]pyrimidine-5-carboxamide To a stirred solution of Example 8 (0.1 gm, 0.32 mmoles) in DMF at 0° C. under nitrogen atmosphere was added NaH (0.025 gm, 1.04 mmol) and stirred for 30 minutes. To the reaction mixture was added O-(tert-butyl-dimethylsilyl)-2-bromoethanol (0.077 gm, 0.32 mmol), the cooling was removed and the reaction stirred for 3 hr. The progress of the reaction was monitored by tlc. Upon completion of the reaction, the reaction mixture was partitioned between ethyl acetate and water. The organic layer was separated and dried over sodium sulphate, filtered and the solvent was removed under reduced pressure to provide an intermediate acid (0.07 gm).

To a stirred solution of the acid (0.07 gm, 0.15 mmol) in DCM (15 mL) at 0-5° C. was added HOBt (013 gm, 0.23 mmol), EDC (0.043 gm, 0.23 mmol), DIEA (0.065 gm, 0.53 mmol) and NH$_2$OTHP (0.017 gm, 0.15 mmol) and the reaction was stirred over night, The progress of the reaction was monitored by TLC and upon completion of the reaction, the reaction mixture was partitioned between DCM and water. The organic layer was separated, dried over sodium sulphate, filtered and the solvent was removed under reduced pressure to provide the protected hydroxamic acid (0.025 gm).

To a stirred solution of the protected hydroxamic acid at 0° C. (0.025 gm, 0.04 mmol) in methanol (3 mL) was added ether-HCl (5 mL). After 15 minutes, the progress of the reaction was monitored by tlc and upon completion of the reaction, the solvent was removed under reduced pressure at 40° C. and the residue purified by ether washings to obtain Example 58 (0.011 gm). $^1$HNMR (CD$_3$OD, 200 MHz) δ: 8.75 (2H, s), 7.63-7.02 (5H, m), 5.01 (2H, s), 4.31 (4H, m), 3.87 (4H, m), 2.88 (2H, m); m/e=354 (M+1).

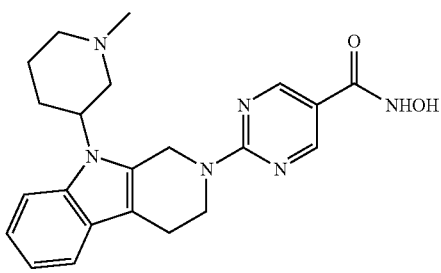

Example 59

N-hydroxy-2-[9-(1-methylpiperidin-3-yl)-1,3,4,9-tetrahydro-2H-b-carbolin-2-yl]pyrimidine-5-carboxamide To a stirred solution of Example 8 (500 mg, 1.62 mmol) in THF (5 mL) and water (5 mL) was added lithium hydroxide (205 mg, 8.54 mmol) at room temperature and the mixture was stirred for 4-5 h. The reaction was monitored by TLC and after completion, the reaction mixture was acidified using 1N hydrochloric acid. The mixture was extracted with ethyl acetate, washed with brine, dried over sodium sulfate and concentrated to obtain the carboxylic acid (400 mg, 83%).

To a stirred solution of the carboxylic acid (400 mg, 1.36 mmol) in DCM was added EDCI (390 mg, 2.0 mmol) at 0° C. The mixture was stirred at 0° C. for 15 min and then NH$_2$OTHP (160 mg, 1.36 mmol) was added. The reaction mixture stirred overnight. After completion of the reaction it was diluted with DCM. The DCM layer was separated, washed with saturated sodium bicarbonate, water and concentrated. The crude product obtained was purified by silica gel column chromatography to obtain the protected hydroxamic acid (250 mg, 46.8%), m/e=394 (M$^+$+1)

To a stirred solution of the protected hydroxamic acid (262 mg, 0.66 mmol) in DMF (5 mL) was added sodium hydride (60 mg, 2.5 mmol) and the mixture was stirred at room temperature for 20 min. 3-Bromo-N-methylpiperadine (600 mg, 3.3 mmol) was added and the reaction mixture was allowed to stir at room temperature for 12 h. After removing DMF, water was added and the mixture extracted with DCM. The pure alkylated product (35 mg, 9%) was obtained by purifying through silica gel column chromatography using 20% methanol in DCM (100 mg, 31%); m/e=477 (M+1)

The alkylated product (30 mg, 0.06 mmol) was stirred in 30% TFA in DCM (10 mL) for 25-30 min at room temperature. After removing the solvents the solid that separated out was filtered, washed with ether and dried under vacuum to get Example 59 (20 mg, 83%) as a white solid; m/e=407 (M+1).

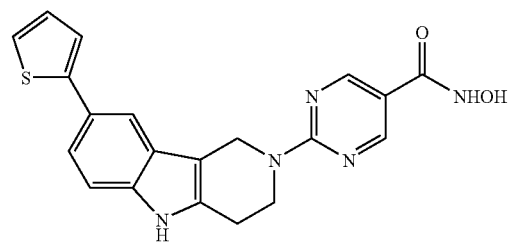

Example 60

N-hydroxy-2-{8-[thien-2-yl]-1,3,4,5-tetrahydro-2H-pyrido[4,3-b]indol-2-yl}pyrimidine-5-carboxamide To a solution of Example 33 (0.25 g, 0.64 mmol) in dimethylacetamide (5 mL) were added thiophene (0.5 mL) and potassium acetate (0.126 g, 1.28 mmol) and the reaction mixture was thoroughly degassed and freshly prepared tetrakistriphenylphosphine palladium(0) (0.06 g, 0.052 mmoles) was added under nitrogen atmosphere at room temperature. The reaction mixture temperature was raised to 80° C. and continued stirring for 12 hr in a sealed tube. The progress of the reaction was monitored by TLC and upon completion of the reaction the solvent was evaporated under reduced pressure. The mixture was partitioned between ethyl acetate (100 mL) and water (15 mL) and the organic layer was separated, dried over Na$_2$SO$_4$ filtered and the solvent was removed under reduced pressure to give crude residue. Purification by column chromatography using silica gel provided an intermediate ester (0.048 g, 19.06%). HPLC: 76.71 (Rt 16.35 min).

To a 0° C. solution of the intermediate ester (0.04 g, 0.10 mmol) in methanol:DCM (5:2 mL) was added 50% aqueous NH20H solution (1 mL) and to the mixture was added solution of NaOH (0.040 g) in water (0.2 mL). The reaction mixture was stirred at room temperature for 1 hr and the progress of the reaction was monitored by TLC. Upon completion of the reaction the solvent was removed under reduced pressure. The pH of the mixture was adjusted to 7.5 using 1N hydrochloric acid and the obtained solid was filtered and washed with water followed by diethyl ether. Drying under vacuum gave Example 60 (0.008 g, 20%). HPLC: 85.67% (Rt-13.09); $^1$HNMR (DMSO-D$_6$, 200 MHz) δ: 10.90 (1H, s), 8.71 (2H, s), 6.95 (2H, m), 7.46-7.02 (Ar, 6H, m), 4.99 (2H, s), 4.23 (m, 2H), 2.86 (2H, m); m/e=392 (M+1).

Examples 61-65 were prepared in the same manner as Example 10 by substituting the appropriate 2,3,4,9-tetrahydro-1H-b-carboline for 6-methoxy-2,3,4,9-tetrahydro-1H-b-carboline.

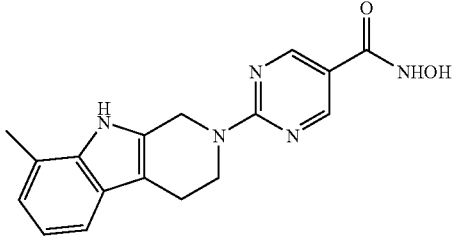

Example 61

N-hydroxy-2-(8-methyl-1,3,4,9-tetrahydro-2H-b-carbolin-2-yl)pyrimidine-5-carboxamide Example 61 was obtained by substituting 8-methyl-2,3,4,9-tetrahydro-1H-b-carboline for 6-methoxy-2,3,4,9-tetrahydro-1H-b-carboline. A solid (0.008 gm); $^1$HNMR (CD$_3$OD, 200 MHz) δ: 8.73 (2H, s), 7.24 (1H, d), 6.86 (2H, m), 4.90 (2H, s), 4.30 (2H, m) 2.85 (2H, m), 2.48 (3H, s); m/e=324 (M+1).

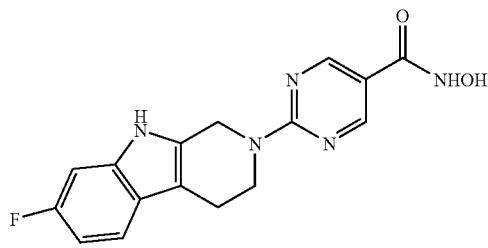

Example 62

N-hydroxy-2-(7-fluoro-1,3,4,9-tetrahydro-2H-b-carbolin-2-yl)pyrimidine-5-carboxamide Example 62 was obtained by substituting 7-fluoro-2,3,4,9-tetrahydro-1H-b-carboline for 6-methoxy-2,3,4,9-tetrahydro-1H-b-carboline. A solid (0.027 g, 67%); $^1$H NMR (200 MHz, CD$_3$OD): δ 2.89 (m, 2H), 4.40 (m, 2H), 5.15 (m, 2H), 6.57 (s, 1H), 7.36 (m, 2H), 8.66 (s, 2H); m/e=328 (M+1).

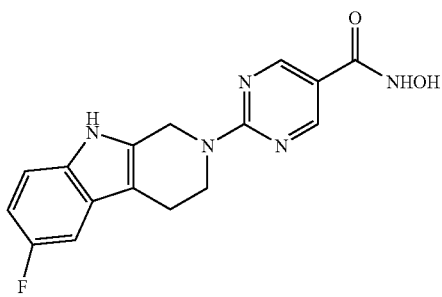

Example 63

N-hydroxy-2-(6-fluoro-1,3,4,9-tetrahydro-2H-b-carbolin-2-yl)pyrimidine-5-carboxamide Example 63 was obtained by substituting 6-fluoro-2,3,4,9-tetrahydro-1H-b-carboline for 6-methoxy-2,3,4,9-tetrahydro-1H-b-carboline. A solid (25 mg); $^1$HNMR (200 MHz, CD$_3$OD) δ: 2.93 (t, 2H, CH$_2$), 4.28 (t, 2H, CH$_2$), 5.1 (s, 2H, CH$_2$), 6.89 (t, 1H, Ar—H), 7.1 (d, 1H, Ar—H), 7.3 (m, 1H, Ar—H), 8.82 (s, 2H, Pyrimidine ring-H); m/e=328 (M+1).

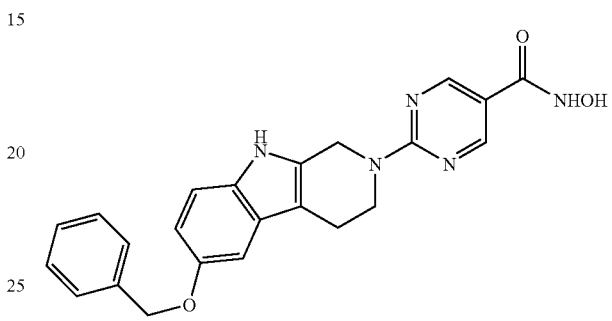

Example 64

N-hydroxy-2-(6-benzyloxy-1,3,4,9-tetrahydro-2H-b-carbolin-2-yl)pyrimidine-5-carboxamide Example 64 was obtained by substituting 6-benzyloxy-2,3,4,9-tetrahydro-1H-b-carboline for 6-methoxy-2,3,4,9-tetrahydro-1H-b-carboline. A solid (0.075 gm); $^1$HNMR (CD$_3$OD, 200 MHz) δ: 8.82 (2H, s), 7.35-6.90 (Ar, 8H, m), 5.20 (2H, s), 5.01 (2H, s), 4.24 (2H, m), 2.80 (2H, m); m/e=416 (M+1).

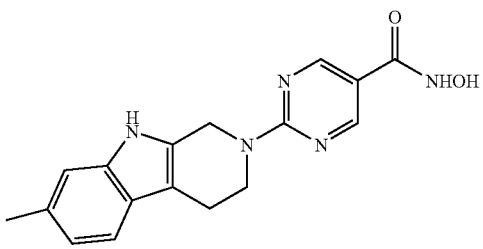

Example 65

N-hydroxy-2-(7-methyl-1,3,4,9-tetrahydro-2H-b-carbolin-2-yl)pyrimidine-5-carboxamide Example 65 was obtained by substituting 7-methyl-2,3,4,9-tetrahydro-1H-b-carboline for 6-methoxy-2,3,4,9-tetrahydro-1H-b-carboline. A solid (0.02 g, 22.13%); HPLC: 80.03% (Rt-14.11). $^1$HNMR (CD$_3$OD, 200 MHz) δ: 8.73 (2H, s), 6.82-7.38 (Ar-3H, m), 5.2 (2H, s), 4.30 (2H, t), 2.80 (2H, m), 2.42 (3H,s); m/e=324 (M+1).

111

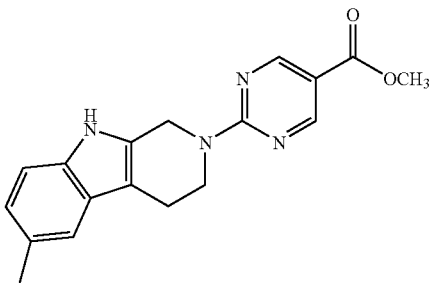

Example 66

Methyl 2-(6-methyl-1,3,4,9-tetrahydro-2H-b-carbolin-2-yl)pyrimidine-5-carboxylate To a stirred solution of 2-(5-methyl-1H-indol-3-yl)ethanamine (0.54 g, 2.56 mmol) in water was added (5 mL) glyoxalic acid (228 mg, 3.08 mmol) and the reaction stirred for 10 min. A potassium hydroxide solution (140 mg in 5 mL) was added and stirred at room temperature for 1 h. The progress of the reaction was monitored by TLC and after completion, the solid material obtained was filtered. The wet cake was suspended in water (5 mL), conc. hydrochloric acid (1 mL) was added and the mixture heated to 60-70° C. for 0.5 h. Additional conc. HCl (1 mL) was added and the solvent evaporated by heating on a hot plate. The dry solid was suspended in water (10 mL) and heated to 45-55° C. and the pH was adjusted to 12 with 20% KOH solution. The solid product obtained was filtered and dried to give the tetrahydrocarboline (200 mg, 37%). $^1$HNMR (200 MHz, CDCl$_3$) δ: 2.45 (s, 3H, CH$_3$), 2.75 (t, 2H, CH$_2$), 3.2 (t, 2H, CH$_2$), 4.1 (s, 2H, CH$_2$), 6.99 (d, 1H, Ar—H), 7.1 (s, 1H, Ar—H), 7.2 (d, 1H, Ar—H).

To a stirred solution of the tetrahydrocarboline (0.15 g, 0.80 mmol) in DMF (10 mL) were added Example 7 (0.226 g, 1.0462 mmol) and potassium carbonate (0.278 g, 2.01 mmol) The mixture was heated to 80-90° C. for 2-3 h. The progress of the reaction was followed by TLC and after completion DMF was distilled off under vacuum. The residue was partitioned between ethyl acetate (100 mL) and water and the two layers were separated. The aqueous layer was extracted with ethyl acetate (100 mL) and both the organic layers were combined. The ethyl acetate layer was dried over anhydrous sodium sulfate, concentrated under vacuum and the residue was purified by washing with diethyl ether (100 mL) to give Example 66 (100 mg, 38.5%). $^1$HNMR (200 MHz, CDCl$_3$) δ: 2.4 (s, 3H, CH$_3$), 2.8 (t, 2H, CH$_2$), 3.8 (s, 3H, CH$_3$), 4.3 (t, 2H, CH$_2$), 5.1 (s, 2H, CH$_2$), 7.0 (d, 1H, Ar—H), 7.18 (s, 1H, Ar—H), 7.2 (d, 1H, Ar—H), 7.79 (bs, 1H, NH), 8.8 (s, 2H, CH$_2$).

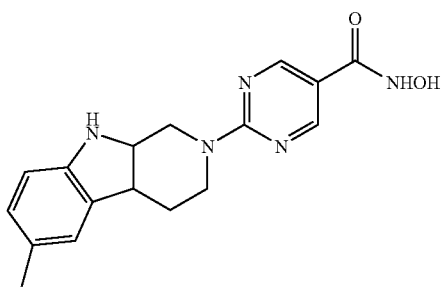

112

Example 67

N-hydroxy-2-(6-methyl-1,3,4,4a,9,9a-hexahydro-2H-b-carbolin-2-yl)pyrimidine-5-carboxamide To a stirred solution of Example 66 (150 mg, 0.46 mmol) in dry DCM was added TFA (8.88 g, 77.89 mmol) and the mixture stirred for 30 min. Triethylsilane (4.368 g, 37.56 mmol) was added at room temperature and stirred for 2 h. The progress of the reaction mass was monitored by TLC and after completion, the reaction was diluted with DCM (20 mL) and washed with saturated solution of sodium bicarbonate (20 mL), then with water. The organic layer was dried over sodium sulfate and concentrated. The residue was purified by column chromatography to give the reduced tetrahydrocarboline (55 mg, 36%); m/e=325 (M+1).

To a stirred solution of the reduced tetrahydrocarboline (50 mg, 0.15 mmol) in methanol (3 mL) and DCM (2 mL) was added 50% aqueous hydroxylamine hydrochloride (1 mL) and sodium hydroxide solution (40 mg mmol) in 0.25 mL of water at 0° C. and the mixture was stirred at 0° C. for 10 min. The reaction was then allowed to come to room temperature and maintained at room temperature for 1 h. The progress of the reaction was monitored by TLC and after completion, the solvents were removed under vacuum. The mixture was diluted with water (10 mL) and neutralized with 2N hydrochloric acid (pH 6.5-7.0). The white solid that separated out was filtered and dried to give Example 67 (32 mg, 63.8%) with HPLC purity of 98.5%. $^1$HNMR (200 MHz, DMSO-d$_6$) δ: 1.8 (m, 1H), 2.0 (m, 1H), 2.2 (s, 3H, CH$_3$), 3.45-4.0 (m, 6H), 5.4 (s, 1H), 6.4 (d, 1H, Ar—H), 6.7 (d, 1H, Ar—H), 6.9 (s, 1H, Ar—H), 8.65 (s, 2H, Pyrimidine), 9.0 (bs, 1H, NH), 11.0 (bs, 1H, NH); m/e=326 (M+1).

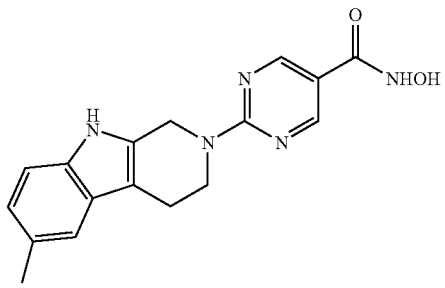

Example 68

N-hydroxy-2-(6-methyl-1,3,4,9-tetrahydro-2H-b-carbolin-2-yl)pyrimidine-5-carboxamide To a stirred solution of Example 66 (70 mg, 0.21 mmol) in methanol (5 mL) and DCM (3 mL), 50% aqueous hydroxylamine hydrochloride (1.5 mL) and sodium hydroxide solution (60 mg 1.5 mmol) in 0.5 mL of water were added at 0° C. and the mixture was stirred at 0° C. for 10 min. The reaction was then allowed to come to room temperature and maintained at room temperature for 1 h. The progress of the reaction was monitored by TLC and after completion; the solvents were removed under vacuum. The mixture was diluted with water (10 mL) and neutralized with 2N hydrochloric acid (pH 6.5-7.0). The white product separated out, was filtered and dried to give Example 68 (50 mg, 71.4%) with HPLC purity of 96.91%. $^1$HNMR (200 MHz, DMSO-d$_6$) δ: 2.4 (s, 3H, CH$_3$), 2.78 (t, 2H, CH$_2$), 4.2 (t, 2H, CH$_2$), 5.0 (s, 2H, CH$_2$), 6.82 (d, 1H, Ar—H), 7.18 (s, 1H, Ar—H), 7.2 (d, 1H, Ar—H), 8.75 (s, 2H, Pyrimidine-H), 10.78 (bs, 1H, NH); m/e=324 (M+1).

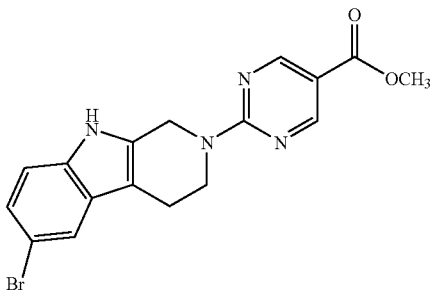

Example 69

Methyl 2-(6-bromo-1,3,4,9-tetrahydro-2H-b-carbo-lin-2-yl)pyrimidine-5-carboxylate

To a stirred solution of 2-(5-bromo-1H-indol-3-yl)etha-namine (1.0 g, 3.64 mmol) in methanol:toluene (1:1, 20 mL) was added paraformaldehyde (200 mg, 20%). The reaction mass was refluxed for 24 h. The progress of the reaction was monitored by TLC and after completion, the reaction mass was concentrated and the crude was washed with ethyl acetate. The aqueous layer was adjusted to pH=12 with 20% KOH solution. The precipitated solid was extracted with ethyl acetate and the organic layer washed with brine solution and concentrated to give the tetrahydrocarboline (350 mg, 38.39%). $^1$HNMR (200 MHz, DMSO-d$_6$) δ: 2.65 (t, 2H, CH$_2$), 3.0 (t, 2H, CH$_2$), 3.92 (s, 2H, CH$_2$), 7.1 (d, 1H, Ar—H), 7.21 (d, 1H, Ar—H), 7.45 (s, 1H, Ar—H), 10.95 (s, 1H, NH); m/e=251 (M+1).

To a stirred solution of the tetrahydrocarboline (350 mg, 1.4 mmol) in DMF (20 mL) were added Example 7 (453 mg, 2.09 mmol) and potassium carbonate (580 mg, 4.20 mmol) and the mixture was heated to 80-90° C. for 2-3 h. The progress of the reaction was followed by TLC and after completion DMF was distilled off under vacuum. The residue was partitioned between ethyl acetate (150 mL) and water and the two layers were separated. The aqueous layer was extracted with ethyl acetate (150 mL) and both the organic layers were combined. The ethyl acetate layer was dried over anhydrous sodium sulfate, concentrated under vacuum and the residue was purified by washing with diethyl ether (100 mL) to give Example 69 (250 mg, 46.31%). $^1$HNMR (200 MHz, DMSO-d$_6$) δ: 2.93 (t, 2H, CH$_2$), 3.8 (s, 3H, OCH$_3$), 4.28 (t, 2H, CH$_2$), 5.0 (s, 2H, CH$_2$), 7.18 (d, 1H, Ar—H), 7.22 (d, 1H, Ar—H), 7.7 (s, 1H, Ar—H), 8.82 (s, 2H, Pyrimidine-H), 11.2 (s, 1H N—H); m/e=387(M+1).

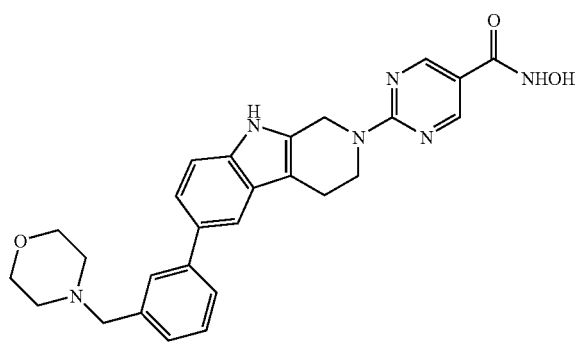

Example 70

N-hydroxy-2-{6-[3-(morpholin-4-ylmethyl)phenyl]-1,3,4,9-tetrahydro-2H-b-carbolin-2-yl}pyrimidine-5-carboxamide

To a stirred solution of Example 69 (420 mg, 1.08 mmol) and 3-formylphenyl boronic acid (320 mg, 2.172 mmol) in THF/water (1:1, 20 mL) was added tetrakistriphenylphos-phinepalladium(0) (126 mg, 0.10 mmol) and potassium carbonate (900 mg, 6.32 mmol) and the resulting mixture was heated to reflux for 5-6 h. The progress of the reaction was monitored by TLC and after completion the reaction was cooled to room temperature. The mixture was diluted with ethyl acetate (100 mL) and the two layers were separated. The organic layer was washed with water, dried over anhydrous sodium sulfate and concentrated in vacuum. The residue was purified by column chromatography using silica gel to give the coupling product (200 mg, 44.64%). $^1$HNMR (200 MHz, CD$_3$OD) δ: 3.0 (t, 2H, CH$_2$), 3.9 (s, 3H, OCH$_3$), 4.42 (t, 2H, CH$_2$), 5.25 (s, 2H, CH$_2$), 7.42 (s, 1H, Ar—H), 7.5-7.8 (m, 6H, Ar—H), 8.21 (bs, 1H, N—H), 8.9 (s, 2H, Pyrimidine-H), 10.1 (s, 1H, CHO); m/e=413 (M+1).

To a stirred solution of the coupling product (200 mg, 0.48 mmol) in dry DCM (10 mL) were added morpholine (423 mg, 4.85 mmol) and sodium triacetoxyborohydride (512 mg, 2.42 mmol) at room temperature and the mixture was stirred at the same temperature overnight. After completion, the reaction was diluted with DCM (40 mL) and washed with saturated sodium bicarbonate solution and water. The organic layer was dried over anhydrous sodium sulfate and concentrated in vacuum. The residue was purified by column chromatography to give the reductive alkylation product (160 mg, 68.37%). $^1$HNMR (200 MHz, CDCl$_3$) δ: 2.58 (t, 4H, 2×CH$_2$), 3.0 (t, 2H, CH$_2$), 3.62 (s, 2H, CH$_2$), 3.75 (t, 4H, 2×CH$_2$), 3.9 (s, 3H, OCH$_3$), 4.41 (t, 2H, CH$_2$), 5.18 (s, 2H, CH$_2$), 7.2-7.5 (m, 3H, Ar—H), 7.5-7.7 (m 2H, Ar—H), 7.8 (s, 1H, Ar—H), 7.92 (s, 1H, Ar—H), 8.95 (s, 2H, pyrimidine-H); m/e=484 (M+1).

To a stirred solution of the reductive alkylation product (150 mg, 0.31 mmol) in methanol (8 mL) and DCM (4 mL), 50% aqueous hydroxylamine hydrochloride (5 mL, 35.97 mmol) and sodium hydroxide solution (120 mg 3.0 mmol in 0.5 mL of water) were added at 0° C. and the mixture was stirred at 0° C. for 10 min. The reaction was then allowed to come to room temperature and maintained at room temperature for 1 h. The progress of the reaction was monitored by TLC and after completion the solvents were removed under vacuum. The mixture was diluted with water (10 mL) and neutralized with 2N hydrochloric acid (pH 6.5-7.0). The white product separated out, was filtered and dried to give Example 70 (100 mg, 88.95%) of 94.5% purity by HPLC. $^1$HNMR (200 MHz, CD$_3$OD) δ: 2.6 (t, 4H, CH$_2$), 2.9 (t, 2H, CH$_2$), 3.61 (s, 2H, CH$_2$), 3.75 (t, 4H, 2×CH$_2$), 4.25 (t, 2H, CH$_2$), 5.10 (s, 2H, CH$_2$), 7.21 (d, 1H, Ar—H), 7.32-7.65 (m, 6H, Ar—H), 8.78 (s, 2H, Pyrimidine-H); m/e=485 (M+1).

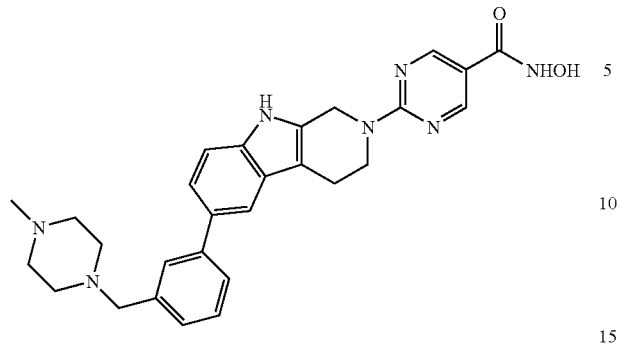

Example 71

N-hydroxy-2-{6-[3-((4-methylpiperazin-1-yl)me-thyl)phenyl]-1,3,4,9-tetrahydro-2H-b-carbolin-2-yl}pyrimidine-5-carboxamide Example 71 was prepared in the same manner as Example 70 by substituting 1-methylpiperazine for morpholine in the reductive alkylation reaction. A white solid (0.05 g, 50%) of 98.2% purity by HPLC; $^1$HNMR (200 MHz, CD$_3$OD) δ: 2.3 (s, 3H, CH$_3$), (m, 8H, 4×CH$_2$), 2.95 (t, 2H, CH$_2$), 3.65 (s, 2H, CH$_2$), 4.36 (t, 2H, CH$_2$), 5.15 (s, 2H, CH$_2$), 7.2-7.8 (m, 7H, Ar—H), 8.8 (s, 2H, Pyrimidine); m/e=497.8 (M+1).

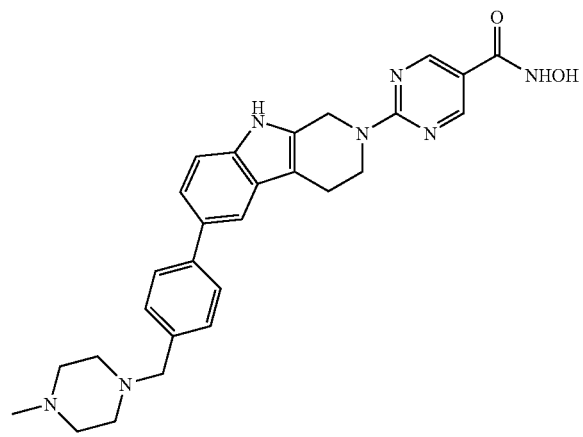

Example 72

N-hydroxy-2-{6-[4-((4-methylpiperazin-1-yl)me-thyl)phenyl]-1,3,4,9-tetrahydro-2H-b-carbolin-2-yl}pyrimidine-5-carboxamide Example 72 was prepared in the same manner as Example 71 by substituting 4-formylphenyl boronic acid for 3-formylphenyl boronic acid in the palladium catalyzed coupling reaction with Example 69. A white solid (0.110 g, 73%) of 96.5% purity by HPLC. $^1$HNMR (200 MHz, CD$_3$OD) δ: 2.35 (s, 3H, CH$_3$), 2.6 (m, 8H, 4×CH$_2$), 2.97 (t, 2H, CH$_2$), 3.60 (s, 2H, CH$_2$), 4.35 (t, 2H, CH$_2$), 5.05 (s, 2H, CH$_2$), 7.32-7.8 (m, 7H, Ar—H), 8.78 (s, 2H, Pyrimidine-H); m/e 498 (M+1).

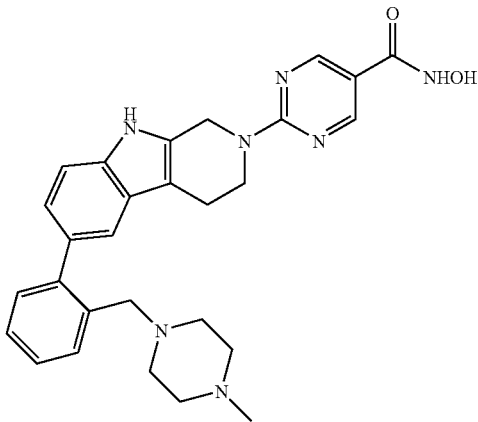

Example 73

N-hydroxy-2-{6-[2-((4-methylpiperazin-1-yl)me-thyl)phenyl]-1,3,4,9-tetrahydro-2H-b-carbolin-2-yl}pyrimidine-5-carboxamide Example 73 was prepared in the same manner as Example 71 by substituting 2-formylphenyl boronic acid for 3-formylphenyl boronic acid in the palladium catalyzed coupling reaction with Example 69. A white solid (92 mg, 45%) of 96.1% purity by HPLC. $^1$HNMR (200 MHz, CD$_3$OD) δ: 2.28 (s, 3H, CH$_3$), 2.45 (m, 8H, 4×CH$_2$) 2.92 (t, 2H, CH$_2$), 3.55 (s, 2H, CH$_2$), 4.38 (t, 2H, CH$_2$), 5.09 (s, 2H, CH$_2$), 7.05 (d, 1H, Ar—H), 7.25-7.65 (m, 6H, Ar—H), 8.78 (s, 2H, Pyrimidine-H); m/e=498 (M+1).

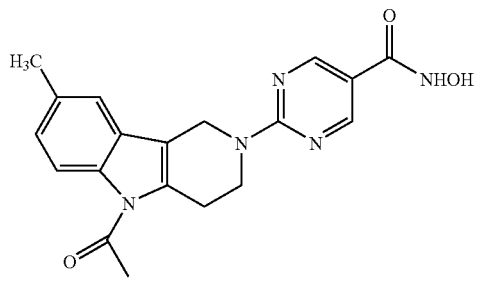

Example 74

N-hydroxy-2-{5-acetyl-8-methyl-1,3,4,5-tetrahydro-2H-pyrido[4,3-b]indol-2-yl}pyrimidine-5-carboxamide From 8-methyl-2,3,4,5-tetrahydro-1H-pyrido[4,3-b]indole and Example 7 was obtained methyl-2-(8-methyl-1,3,4,5-tetrahydro-2H-pyrido[4,3-b]indol-2-yl)pyrimidine-5-carboxylate using the method described in Example 12. To a solution of methyl-2-(8-methyl-1,3,4,5-tetrahydro-2H-pyrido[4,3-b]indol-2-yl)pyrimidine-5-carboxylate (110 mg) in DMF (5 mL) was added sodium hydride (22 mg) at 0° C. and the mixtue was stirred for 20 min. Acetyl chloride (30 mg) was added and the reaction was allowed to attain room temperature and stirred another 3 hours. The reaction mixtue was partitioned between ethyl acetate and water. The organic layer was separated and washed with water and saturated aqueous sodium bicarbonate. The solvent was dried and evaporated and the residue purified by chromatography to give methyl-2-(5-acetyl-8-methyl-1,3,4,5-tetrahydro-2H-pyrido[4,3-b]indol-2-yl)pyrimidine-5-carboxylate.

To a cooled solution of hydroxylamine hydrochloride (0.043 g, 0.618 mmol) in DCM (3 mL) was added trimethylaluminium (0.135 g, 1.87 mmol) at 0° C. The reaction mixture was warmed to Rt for 1 h and methyl-2-(5-acetyl-8-methyl-1,3,4,5-tetrahydro-2H-pyrido[4,3-b]indol-2-yl)pyrimidine-5-carboxylate (0.050 g, 0.13 mmol) was added to it and stirred for another 4 h. The reaction mixture was quenched with 6N HCl and the reaction mixture was extracted with ethyl acetate (2×25 mL), the organic layer was dried over anhydrous sodium sulphate, filtered and concentrated under vacuum to afford Example 74 (0.020 g, 40%). $^1$H NMR (200 MHz, CD$_3$OD): δ 2.20 (s, 3H), 2.35 (s, 3H), 2.89 (m, 2H), 3.33 (m, 2H), 4.20 (m, 2H), 6.51 (s, 1H), 7.20 (m, 2H), 8.66 (s, 2H); m/e=366 (M+1).

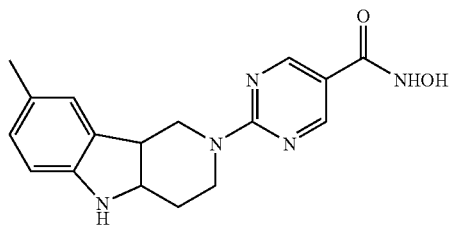

Example 75

N-hydroxy-2-(8-methyl-1,3,4,4a,5,9b-hexahydro-2H-pyrido[4,3-b]indol-2-yl)pyrimidine-5-carboxamide Methyl 2-(8-methyl-1,3,4,5-tetrahydro-2H-pyrido[4,3-b]indol-2-yl)pyrimidine-5-carboxylate was obtained from Example 7 and 8-methyl-2,3,4,5-tetrahydro-1H-pyrido[4,3-b]indole using the method described in Example 12. To a stirred solution of methyl 2-(8-methyl-1,3,4,5-tetrahydro-2H-pyrido[4,3-b]indol-2-yl)pyrimidine-5-carboxylate (0.250 g, 0.776 mmol) in dry DCM, TFA (2.5 ml, 129.81 mmol) was added and stirred for 30 min. Then triethylsilane (2.5 ml, 62.6 mmol) was added at room temperature and stirred for 2 h. The progress of the reaction was monitored by TLC and after completion, the reaction mixture was diluted with DCM and washed with saturated solution of sodium bicarbonate and the organic layer was washed with brine, dried over anhydrous Na$_2$SO$_4$, filtered and concentrated under reduced pressure. The residue was purified by silica gel column chromatography to furnish methyl 2-(8-methyl-1,3,4,4a,5,9b-hexahydro-2H-pyrido[4,3-b]indol-2-yl)pyrimidine-5-carboxylate (69 mg, 27.5%). $^1$H NMR (200 MHz, CDCl$_3$): δ 1.69 (m, 2H), 2.35 (s, 3H), 2.7 (m; 2H), 3.01 (m, 4H), 3.90 (s, 3H), 6.23 (m, 1H), 6.80 (2H, m), 8.91 (s, 2H); m/e=325 (M+1).

To a cooled (0° C.) solution of methyl 2-(8-methyl-1,3,4,4a,5,9b-hexahydro-2H-pyrido[4,3-b]indol-2-yl)pyrimidine-5-carboxylate (0.050 g, 0.15 mmol) in MeOH:DCM (6 mL, 2:1) was added aqueous 50% NH$_2$OH solution (1 mL) and NaOH (0.04 g, 1.0 mmol) dissolved in water (0.25 mL). The reaction mixture was stirred for 3 h at room temperature and then concentrated under reduced pressure to give a crude residue. The residue was neutralized with 2N HCl, the precipitated solid was filtered and dried to give pure Example 75 (0.015 g, 30%). $^1$H NMR (200 MHz, CD$_3$OD): δ 1.69 (m, 2H), 2.35 (s, 3H), 2.7 (m, 2H), 3.01 (in, 4H), 6.23 (m, 1H), 6.80 (2H, m), 8.65 (s, 2H); m/e=326 (M+1).

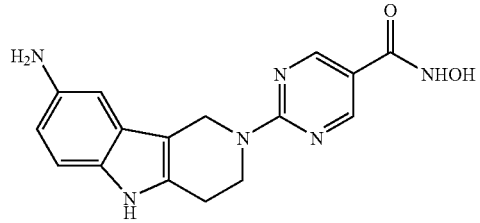

Example 76

N-hydroxy-2-(8-amino-1,3,4,5-tetrahydro-2H-pyrido[4,3-b]indol-2-yl)pyrimidine-5-carboxamide To a solution of 4-nitrophenylhydrazine hydrochloride (3.0 g, 15.8 mmol) in acetic acid (30 mL) were added 4-piperidone.HCl (1.1 g, 111.3 mmol) and sodium acetate (1.29 g, 15.7 mmol). The reaction mixture temperature was raised to 80° C. and continued stirring for 1 hr. The progress of the reaction was monitored by TLC and upon completion of the reaction the mixture was cooled to rt and 3 mL of concenctrated sulfuric acid was added. The reaction mixture temperature was raised to 90° C. and continued stirring for 3 hr. The acetic acid was removed under reduced pressure and the pH of the reaction mixture was adjusted to 8.0 with solid K$_2$CO$_3$. The mixture was partitioned between ethyl acetate (100 ml) and water (35 mL). The organic layer was separated, dried over Na$_2$SO$_4$ filtered and the solvent was removed under reduced pressure to give a crude residue, which was purified by ether washings to provide compound nitro tetrahydrocarboline (1.2 g); m/e=217 (M+1); HPLC: 94.9% (Rt=11.62).

To a solution of the nitro tetrahydrocarboline (1.1 g, 5.0 mmol) in DMF (25 mL) at rt was added Example 7 (1.642 g, 7.6 mmol) and K$_2$CO$_3$ (1.4 g, 10.02 mmol). The reaction mixture temperature was raised to 100° C. and continued stirring for 12 hr. The progress of the reaction was monitored by tlc analysis and upon completion of the reaction the DMF was removed under reduced pressure. The reaction was partitioned between ethyl acetate (100 mL) and water (80 mL) and the organic layer was separated, dried over sodium sulfate, filtered and the solvent was removed under reduced pressure to give a crude residue which was purified by ether washings to provide methyl-2-(8-nitro-1,3,4,5-tetrahydro-2H-pyrido[4,3-b]indol-2-yl)pyrimidine-5-carboxylate (0.6 g, 33.33%).

To a solution of methyl-2-(8-nitro-1,3,4,5-tetrahydro-2H-pyrido[4,3-b]indol-2-yl)pyrimidine-5-carboxylate (0.5 g, 1.41 mmol) in methanol (50 mL) was added Raney Nickel (0.3 g). The reaction mixture was evacuated and stirred at rt under hydrogen atmosphere over night. The progress of the reaction was monitored by TLC and upon completion of the reaction, the mixture was filtered through celite under nitrogen atmosphere and washed with methanol (2×30 mL). The methanol was removed under reduced pressure to give crude residue which was purified by column chromatography to give the methyl-2-(8-amino-1,3,4,5-tetrahydro-2H-pyrido[4,3-b]indol-2-yl)pyrimidine-5-carboxylate (0.2 g, 43.9%); (Rt=12.46).

To a 0° C. solution of methyl-2-(8-amino-1,3,4,5-tetrahydro-2H-pyrido[4,3-b]indol-2-yl)pyrimidine-5-carboxylate (0.09 g, 0.27 mmol) in methanol:DCM (5:2 mL) was added 50% aquesou NH2OH solution (2 mL) and to the mixture was added a solution of NaOH (0.08 g) in water (0.5 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the solid produced was filtered and washed with water followed by diethyl ether and dried under vacuum to obtain Example 76 (0.05 g, 55.5%); m/e=325 (M+1).

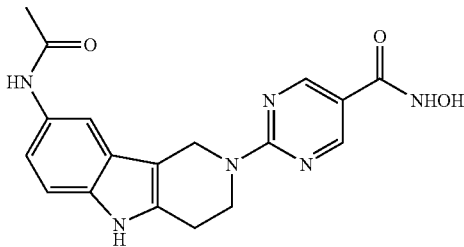

Example 77

N-hydroxy-2-(8-(N-acetamido)-1,3,4,5-tetrahydro-2H-pyrido[4,3-b]indol-2-yl)pyrimidine-5-carboxamide To a solution of methyl-2-(8-amino-1,3,4,5-tetrahydro-2H-pyrido[4,3-b]indol-2-yl)pyrimidine-5-carboxylate (See Example 76) (0.12 g, 0.37 mmoles) in DCM (20 mL) was added 4-dimethylaminopyridine (0.133 g, 0.92 mmol) and acetic anhydride (0.056 g, 0.55 mmol) and the mixture stirred for 10 hr. The progress of the reaction was monitored by TLC and upon completion of the reaction the mixture was partitioned between DCM (50 mL) and water (30 mL) and the organic layer was separated, dried over Na2SO4 filtered and the solvent was removed under reduced pressure to give crude residue which was purified by column chromatography using basified silica gel to provide methyl-2-(8-(N-acetamido)-1,3,4,5-tetrahydro-2H-pyrido[4,3-b]indol-2-yl)pyrimidine-5-carboxylate (0.040 g, 29.4%) (Rt=13.43).

To a 0° C. solution of methyl-2-(8-(N-acetamido)-1,3,4,5-tetrahydro-2H-pyrido[4,3-b]indol-2-yl)pyrimidine-5-carboxylate (0.04 g, 0.11 mmol) in methanol:DCM (5:2 mL) was added 50% aqueous NH2OH solution (1.0 mL) and to the mixture was added solution of NaOH (0.03 g) in water (0.3 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the solid produced was filtered and washed with water followed by diethyl ether and dried under vacuum to obtain Example 77 (0.014 g, 27%). MS: 366 (M+1).

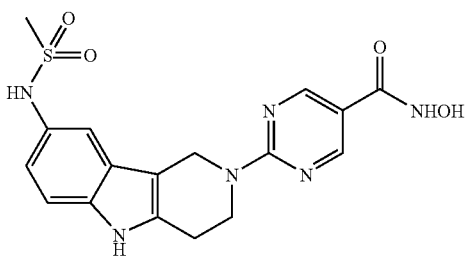

Example 78

N-hydroxy-2-(8-(N-methylsulfonamido)-1,3,4,5-tetrahydro-2H-pyrido[4,3-b]indol-2-yl)pyrimidine-5-carboxamide To a solution of methyl-2-(8-amino-1,3,4,5-tetrahydro-2H-pyrido[4,3-b]indol-2-yl)pyrimidine-5-carboxylate (0.1 g, 0.31 mmol) in DCM (20 mL) was added 4-dimethylaminopyridine (0.094 g, 0.77 mmol) and methanesulfonyl chloride (0.053 g, 0.46 mmol) under nitrogen atmosphere and the mixture stirred for 10 hr. The progress of the reaction was monitored by TLC and upon completion of the reaction the mixture was partitioned between DCM (50 mL) and water (30 mL). The organic layer was separated, dried over Na2SO4 filtered and the solvent was removed under reduced pressure to give crude residue which was purified by column chromatography using basified silica gel to provide methyl-2-(8-(N-methylsulfonamido)-1,3,4,5-tetrahydro-2H-pyrido[4,3-b]indol-2-yl)pyrimidine-5-carboxylate (0.08 g, 64.5%) (Rt=13.95).

To a 0° C. solution of the methyl-2-(8-(N-methylsulfonamido)-1,3,4,5-tetrahydro-2H-pyrido[4,3-b]indol-2-yl)pyrimidine-5-carboxylate (0.07 g, 0.17 mmol) in methanol:DCM (5:2 mL) was added 50% aqueous ammonium hydroxide solution (1.5 mL) and to the mixture was added a solution of NaOH (0.05 g) in water (0.3 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the solid produced was filtered and washed with water followed by diethyl ether and was dried under vacuum to obtain Example 78 (0.03 g, 42%); m/e=403 (M+1).

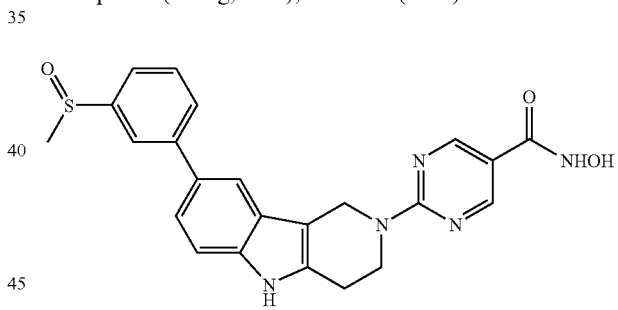

Example 79

N-hydroxy-2-{8-[3-(methylsulfinyl)phenyl]-1,3,4,5-tetrahydro-2H-pyrido[4,3-b]indol-2-yl}pyrimidine-5-carboxamide To a 0° C. solution of methyl-2-{8-[3-(methylthio)phenyl]-1,3,4,5-tetrahydro-2H-pyrido[4,3-b]indol-2-yl}pyrimidine-5-carboxylate (See Example 49) (0.1 g, 0.23 mmol) in DCM (20 mL) was added 3-chloro-peroxybenzoic acid (0.04 g, 0.23 mmol) and stirred for 1 hr under nitrogen atmosphere. The progress of the reaction was monitored by TLC and upon completion, the reaction the mixture was partitioned between DCM (50 mL) and saturated sodium bicarbonate solution (25 mL) and the organic layer was separated, washed with water (2×25 mL), dried over sodium sulphate filtered and the solvent was removed under reduced pressure. The residue was purified by column chromatography using silica gel to provide compound methyl-2-{8-[3-(methylsulfinyl)phenyl]-1,3,4,5-tetrahydro-2H-pyrido[4,3-b]indol-2-yl}pyrimidine-5-carboxylate (0.08 g, 77.6%).

To a 0° C. solution of the methyl-2-{8-[3-(methylsulfinyl)phenyl]-1,3,4,5-tetrahydro-2H-pyrido[4,3-b]indol-2-yl}pyrimidine-5-carboxylate (0.080 g, 0.18 mmol) in methanol:DCM (5:2 mL) was added 50% aqueous hydroxylamine solution (1.6 mL) and to the mixture was added solution of NaOH (0.065 g) in water (0.3 mL). The reaction mixture was stirred at room temperature for 1 hr and the progress of the reaction was monitored by TLC. Upon completion, the solvent was removed under reduced pressure. The pH of the mixture was adjusted to 7.5 using 1N HCl and the solid produced was filtered and washed with water followed by diethyl ether and the solid was dried under vacuum to obtain Example 79 (0.048 g, 60%). $^1$HNMR (DMSO-D$_6$, 200 MHz) δ: 11.06 (1H, s), 8.72 (2H, s), 7.81-7.40 (Ar, 7H, m), 5.03 (2H, s), 4.25 (2H, m), 2.89 (2H, m), 2.82 (3H, s); m/e=448 (M+1).

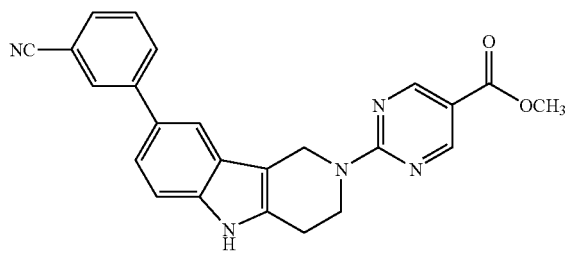

Example 80

Methyl-2-{8-[3-cyanophenyl]-1,3,4,5-tetrahydro-2H-pyrido[4,3-b]indol-2-yl}pyrimidine-5-carboxylate To a stirred solution of Example 33 (1 g, 2.59 mmol) and 3-cyanophenyl boronic acid (0.761 g, 5.18 mmol) in THF/water (1:1, 30 mL), tetrakis(triphenyl phosphine)palladium (0) (0.3 g, 0.25 mmol), potassium carbonate (2.145 g, 15.54 mmol) were added at room temperature and the resulting mixture was heated to reflux for 5-6 h. The progress of the reaction was monitored by TLC and after completion; the reaction was cooled to room temperature. The mixture was diluted with ethyl acetate (150 mL) and the two layers were separated. The organic layer was washed with water, dried over anhydrous sodium sulfate and concentrated in vacuum. The residue was purified by column chromatography using silica gel to give Example 80 (400 mg, 37.7%). $^1$HNMR (200 MHz, DMSO-d$_6$) δ: 3.0 (t, 2H, CH$_2$), 3.9 (s, 3H, OCH$_3$), 4.35 (t, 2H, CH$_2$), 5.16 (s, 2H, CH$_2$), 7.3-8.1 (m, 7H, Ar—H), 8.95 (s, 2H, pyrimidine-H); m/e=410 (M+1).

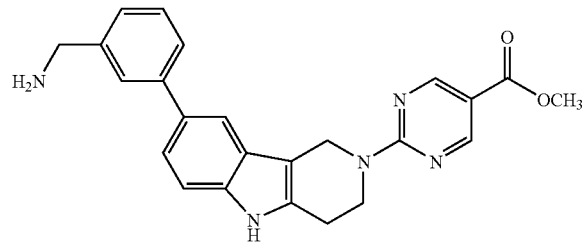

Example 81

Methyl-2-{8-[3-(aminomethyl)phenyl]-1,3,4,5-tetrahydro-2H-pyrido[4,3-b]indol-2-yl}pyrimidine-5-carboxylate To a stirred solution of Example 80 (320 mg, 0.78 mmol) in ethanol (50 mL), Raney Ni (48 mg) was added carefully. Then the reaction mass was maintained under hydrogen atmosphere overnight at room temperature. The progress of the reaction was monitored by TLC, and after completion, the reaction mass was filtered over a celite bed and the filtrate was concentrated to give Example 81 (300 mg, 92.87%). $^1$HNMR (200 MHz, DMSO-D$_6$) δ: 2.98 (t, 2H, CH$_2$), 3.92 (s, 3H, OCH$_3$), 4.1 (s, 2H, CH$_2$), 4.35 (t, 2H, CH$_2$), 5.17 (s, 2H, CH$_2$), 7.3-8.0 (m, 7H, Ar—H), 8.85 (s, 2H, pyrimidine-H); 11.1 (bs, 1H, NH); m/e=415 (M+1).

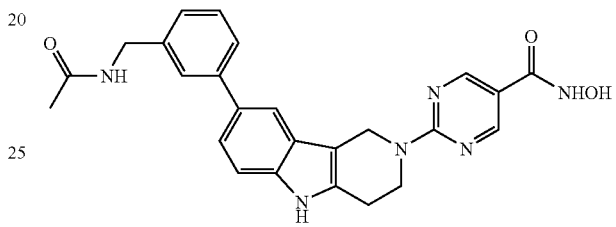

Example 82

N-hydroxy-2-{8-[3-(N-acetamidomethyl)phenyl]-1,3,4,5-tetrahydro-2H-pyrido[4,3-b]indol-2-yl}pyrimidine-5-carboxamide To a stirred solution of Example 81 (100 mg, 0.24 mmol) in dry DCM (10 mL), 4-dimethylaminopyridine (147 mg, 1.21 mmol) was added, then acetic anhydride (0.023 mL, 0.24 mmol) was added at 0° C. and stirred for 5 min. The reaction mass was maintained at room temperature and stirred for 1 h. The progress of the reaction was monitored by TLC, and after completion, the reaction mass was extracted with DCM and water. The DCM layer was dried over sodium sulfate and concentrated. The crude was purified by column chromatography to give methyl-2-{8-[3-(N-acetamidomethyl)phenyl]-1,3,4,5-tetrahydro-2H-pyrido[4,3-b]indol-2-yl}pyrimidine-5-carboxylate (50 mg, 45.45%) with HPLC purity of 98.32%; m/e=456 (M+1).

To a stirred solution of methyl-2-{8-[3-(N-acetamidomethyl)phenyl]-1,3,4,5-tetrahydro-2H-pyrido[4,3-b]indol-2-yl}pyrimidine-5-carboxylate (50 mg, 0.10 mmol) in methanol (5 mL) and DCM (2 mL), 50% aqueous hydroxylamine hydrochloride (1 mL, 7.19 mmol) and sodium hydroxide solution (40 mg 1.0 mmol) in 0.25 mL of water were added at 0° C. and the mixture was stirred at 0° C. for 10 min. The reaction was then allowed to come to room temperature and maintained at room temperature for 1 h. The progress of the reaction was monitored by TLC and after completion the solvents were removed under vacuum. The mixture was diluted with water (10 mL) and neutralized with 2N hydrochloric acid (pH 6.5-7.0). The white solid that separated out was filtered and dried to give Example 82 (20 mg, 40%) of 97.64% pure by HPLC. $^1$HNMR (200 MHz, DMSO-d$_6$) δ: 1.9 (s, 3H, CH$_3$), 2.9 (t, 2H, CH$_2$), 4.2 (t, 2H, CH$_2$), 4.3 (d, 2H, CH$_2$), 5.0 (s, 2H, CH$_2$), 7.1-7.8 (m, 7H, Ar—H), 8.4 (bs, 1H, NH), 8.79 (s, 2H, Pyrimidine-H); m/e=457 (M+1).

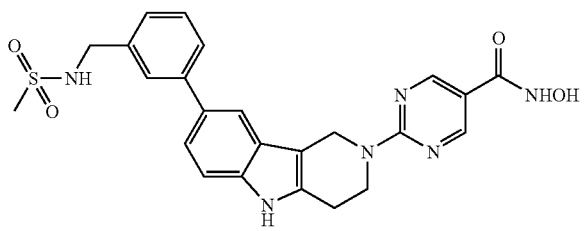

Example 83

N-hydroxy-2-{8-[3-(N-methylsulfonamidomethyl)phenyl]-1,3,4,5-tetrahydro-2H-pyrido[4,3-b]indol-2-yl}pyrimidine-5-carboxamide To a stirred solution of Example 81 (150 mg, 0.36 mmol) in dry DCM (20 mL), 4-dimethylaminopyridine (221 mg, 1.81 mmol) was added, and then methanesulfonyl chloride (0.029 mL, 0.36 mmol) was added at 0° C. and stirred for 10 min. The reaction mass was maintained at room temperature and stirred for 1 hr. The progress of the reaction was monitored by TLC, and after completion, the reaction mass was extracted with DCM and water. The DCM layer dried over sodium sulfate and concentrated. The crude was purified by column chromatography to give methyl-2-{8-[3-(N-methylsulfonamidomethyl)phenyl]-1,3,4,5-tetrahydro-2H-pyrido[4,3-b]indol-2-yl}pyrimidine-5-carboxylate (75 mg, 30.6%) with HPLC purity (91.85%); m/e=492 (M+1).

To a stirred solution of methyl-2-{8-[3-(N-methylsulfonamidomethyl)phenyl]-1,3,4,5-tetrahydro-2H-pyrido[4,3-b]indol-2-yl}pyrimidine-5-carboxylate (70 mg, 0.14 mmol) in methanol (6 mL) and DCM (3 mL), 50% aqueous hydroxylamine hydrochloride (2 mL, 14.38 mmol) and sodium hydroxide solution (80 mg 2.0 mmol) in 0.5 mL of water were added at 0° C. and the mixture was stirred at 0° C. for 10 min. The reaction was then allowed to come to room temperature and maintained at room temperature for 1 h. TLC monitored the progress of the reaction and after completion the solvents were removed under vacuum. The mixture diluted with water (10 mL) and neutralized with 2N hydrochloric acid (pH 6.5-7.0). The white solid that separated out was filtered and dried to give Example 83 (0.05 g, 71.4%) of 95.05% purity by HPLC. $^{1}$HNMR (200 MHz, DMSO-d$_6$) δ: 2.8 (s, 3H, CH$_3$), 2.9 (t, 2H, CH$_2$), 4.2 (s, 2H, CH$_2$), 4.25 (t, 2H, CH$_2$), 5.0 (s, 2H, CH$_2$), 7.2-7.8 (m, 7H, Ar—H), 8.78 (s, 2H, Pyrimidine-H), 10.9 (bs, 1H, NH); m/e=493 (M+1).

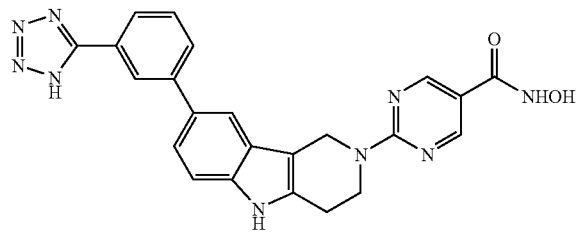

Example 84

N-hydroxy-2-{8-[3-(1H-tetrazol-5-yl)phenyl]-1,3,4,5-tetrahydro-2H-pyrido[4,3-b]indol-2-yl}pyrimidine-5-carboxamide To a solution of Example 80 (150 mg, 0.366 mmoles) in 2-methoxyethanol (20 mL) were added NaN$_3$ (24 mg, 0.36 mmol) and LiCl (24 g, 0.52 mmol) under nitrogen atmosphere. The reaction mixture was thoroughly degassed and the temperature was raised to 120° C. and continued stirring for 4 hr. The progress of the reaction was monitored by TLC and upon completion, the reaction was quenched with cold water (5 ml) and the pH was adjusted to 2 using 4N HCl. The precipitate obtained was filtered and washed with chilled acetone and the crude residue was purified by column chromatography using silica gel to provide methyl-2-{8-[3-(1H-tetrazol-5-yl)phenyl]-1,3,4,5-tetrahydro-2H-pyrido[4,3-b]indol-2-yl}pyrimidine-5-carboxylate (75 mg, yield 45.4%); m/e=452 (M+1).

To a 0° C. solution of methyl-2-{8-[3-(1H-tetrazol-5-yl)phenyl]-1,3,4,5-tetrahydro-2H-pyrido[4,3-b]indol-2-yl}pyrimidine-5-carboxylate (0.060 g, 0.13 mmol) in methanol:DCM (5:2 mL) was added 50% aqueous hydroxylamine solution (1.2 mL) and to the mixture was added a solution of NaOH (0.050 g) in water (0.3 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the obtained solid was filtered and washed with water followed by diethyl ether and the solid was dried under vacuum to obtain Example 84 (0.018 gm). $^{1}$HNMR: DMSO-D$_6$, 200 MHz) δ: 11.11 (1H, s), 8.73 (2H, s), 8.05-7.43 (Ar, 7H, m), 5.03 (2H, m), 2.99 (2H, m); m/e=454 (M+1).

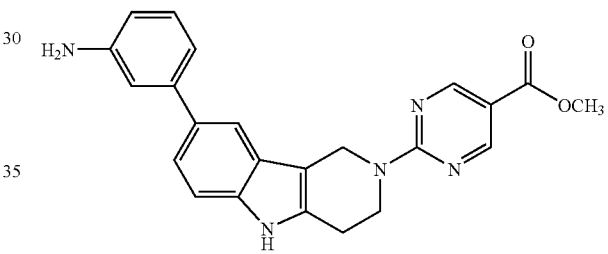

Example 85

Methyl-2-{8-[3-aminophenyl]-1,3,4,5-tetrahydro-2H-pyrido[4,3-b]indol-2-yl}pyrimidine-5-carboxylate To a stirred solution of Example 33 (200 mg, 0.51 mmol) and 3-(tert-butoxylcarbonylaminophenylboronic acid (246 mg, 1.03 mmol) in THF/water (1:1, 20 mL) was added tetrakis(triphenylphosphine)palladium(0) (59 mg, 0.05 mmol) and potassium carbonate (214 mg, 1.55 mmol) and the resulting mixture was heated to reflux for 5-6 h. The progress of the reaction was monitored by TLC and after completion the reaction was cooled to room temperature. The mixture was diluted with ethyl acetate (100 mL) and the two layers were separated. The organic layer was washed with water, dried over anhydrous sodium sulfate and concentrated in vacuum. The residue was purified by column chromatography using silica gel to give methyl-2-{8-[3-(tert-butyloxycarbonylamino)phenyl]-1,3,4,5-tetrahydro-2H-pyrido[4,3-b]indol-2-yl}pyrimidine-5-carboxylate (160 mg, 62.0%; m/e=500 (M+1)

To a stirred solution of methyl-2-{8-[3-(tert-butyloxycarbonylamino)phenyl]-1,3,4,5-tetrahydro-2H-pyrido[4,3-b]indol-2-yl}pyrimidine-5-carboxylate (160 mg, 0.320 mmol) in dry DCM (10 mL), TFA (0.247 mL, 3.20 mmol) was added under nitrogen atmosphere at 0° C. The reaction was maintained at room temperature for 1 h. The progress of the reaction was monitored by TLC and after the completion the volatiles were removed by evaporation. The crude was washed with hexane to give Example 85 (120 mg, 93.75%). ¹HNMR (200 MHz, CD₃OD) δ: 3.0 (t, 2H, CH₂), 3.9 (s, 3H, OCH₃), 4.42 (t, 2H, CH₂), 5.25 (s, 2H, CH₂), 7.3-7.9 (m, 7H, Ar—H), 8.9 (s, 2H, pyrimidine-H).

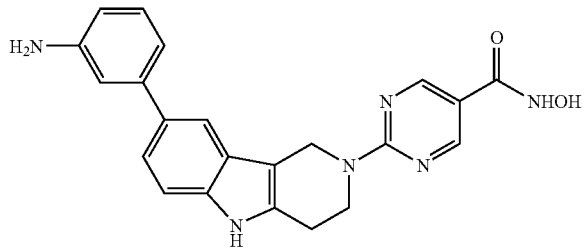

Example 86

N-hydroxy-2-{8-[3-aminophenyl]-1,3,4,5-tetrahydro-2H-pyrido[4,3-b]indol-2-yl}pyrimidine-5-carboxamide To a stirred solution of Example 85 (120 mg, 0.30 mmol) in methanol (5 mL) and DCM (3 mL), 50% aqueous hydroxylamine hydrochloride (2.5 mL, 17.97 mmol) and sodium hydroxide solution (100 mg 2.5 mmol) in 0.7 mL of water were added at 0° C. and the mixture was stirred at 0° C. for 10 min. The reaction was then allowed to come to room temperature and maintained at room temperature for 1 h. The progress of the reaction was monitored by TLC and after completion the solvents were removed under vacuum. The mixture diluted with water (10 mL) and neutralized with 2N hydrochloric acid (pH 6.5-7.0). The white solid that separated out was filtered and dried to give Example 86 (0.05 g) of 98.6% purity by HPLC. ¹HNMR (200 MHz, CD₃OD) δ: 3.0 (t, 2H, CH₂), 4.4 (t, 2H, CH₂), 5.16 (s, 2H, CH₂), 7.3-7.9 (m, 7H, Ar—H), 8.79 (s, 2H, Pyrimidine-H); m/e=401 (M+1).

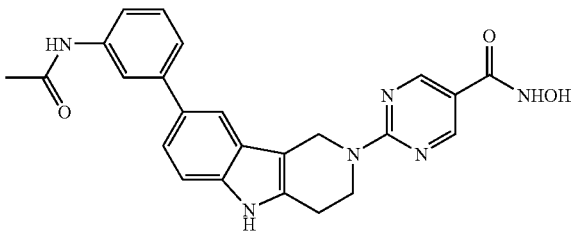

Example 87

N-hydroxy-2-{8-[3-(N-acetamido)phenyl]-1,3,4,5-tetrahydro-2H-pyrido[4,3-b]indol-2-yl}pyrimidine-5-carboxamide To a stirred solution of Example 86 (100 mg, 0.25 mmol) in dry DCM (10 mL), 4-dimethylaminopyridine (153 mg, 1.25 mmol) was added, then acetic anhydride (0.035 mL, 0.37 mmol) was added at 0° C. and the mixture was stirred for 5 min. The reaction mass was maintained at room temperature and stirred for 1 h. The progress of the reaction was monitored by TLC and after completion, the reaction mass was extracted with DCM. The DCM layer was dried over sodium sulfate and concentrated. The residue was purified by column chromatography to give methyl-2-{8-[3-(N-acetamido)phenyl]-1,3,4,5-tetrahydro-2H-pyrido[4,3-b]indol-2-yl}pyrimidine-5-carboxylate (60 mg, 54.54%). ¹HNMR (200 MHz, CDCl₃) δ: 2.21 (s, 3H, CH₃); 3.0 (t, 2H, CH₂), 3.9 (s, 3H, OCH₃), 4.42 (t, 2H, CH₂), 5.16 (s, 2H, CH₂), 7.3-7.8 (m, 7H, Ar—H), 8.9 (s, 2H, pyrimidine-H); m/e=442 (M+1).

To a stirred solution of methyl-2-{8-[3-(N-acetamido)phenyl]-1,3,4,5-tetrahydro-2H-pyrido[4,3-b]indol-2-yl}pyrimidine-5-carboxylate (0.1 g, 0.22 mmol) in methanol (5 mL) and DCM (3 mL), 50% aqueous hydroxylamine hydrochloride (2 mL, 14.38 mmol) and sodium hydroxide solution (80 mg 2.0 mmol) in 0.5 mL of water were added at 0° C. and the mixture was stirred at 0° C. for 10 min. The reaction was then allowed to come to room temperature and maintained at room temperature for 1 h. The progress of the reaction was monitored by TLC and after completion the solvents were removed under vacuum. The mixture was diluted with water (10 mL) and neutralized with 2N hydrochloric acid (pH-6.5-7.0). The white solid that separated out was filtered and dried to give Example 87 (0.05 g, 50%) of 95.27% purity by HPLC. ¹HNMR (200 MHz, DMSO-d₆) δ: 2.5 (s, 3H, CH₃), 2.85 (s, 2H, CH₂), 4.25 (t, 2H, CH₂), 5.05 (s, 2H, CH₂), 7.2-7.85 (m, 7H, Ar—H), 8.75 (s, 2H, Pyrimidine), 9.0 (bs, 1H, NH), 10.0 (bs, 1H, NH—OH), 11.0 (bs, 1H, OH); m/e=443 (M+1).

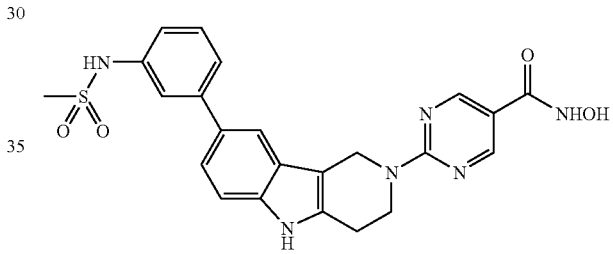

Example 88

N-hydroxy-2-{8-[3-(N-methylsulfonamido)phenyl]-1,3,4,5-tetrahydro-2H-pyrido[4,3-b]indol-2-yl}pyrimidine-5-carboxamide To a stirred solution of Example 86 (100 mg, 0.25 mmol) in dry DCM (10 mL), 4-dimethylaminopyridine (153 mg, 1.25 mmol) was added, then methanesulfonyl chloride (0.03 mL, 0.37 mmol) was added at 0° C. and stirred for 10 min. The reaction mass was maintained at room temperature and stirred for 1 h. The progress of the reaction was monitored by TLC, and after completion, the reaction mass was extracted with DCM and water. The DCM layer was dried over sodium sulfate and concentrated. The crude was purified by column chromatography to give methyl-2-{8-[3-(N-methylsulfonamido)phenyl]-1,3,4,5-tetrahydro-2H-pyrido[4,3-b]indol-2-yl}pyrimidine-5-carboxylate (45 mg, 37.8%). ¹HNMR (200 MHz, CDCl₃) δ: 2.98 (t, 2H, CH₂), 3.1 (s, 3H, CH₃), 3.9 (s, 3H, OCH₃), 4.42 (t, 2H, CH₂), 5.17 (s, 2H, CH₂), 7.3-7.8 (m, 7H, Ar—H), 7.98 (bs, 1H, NH), 8.9 (s, 2H, pyrimidine-H); m/e=443 (M+1)

To a stirred solution of methyl-2-{8-[3-(N-methylsulfonamido)phenyl]-1,3,4,5-tetrahydro-2H-pyrido[4,3-b]indol-2-yl}pyrimidine-5-carboxylate (45 mg, 0.09 mmol) in methanol (3 mL) and DCM (2 mL), 50% aqueous hydroxylamine hydrochloride (1 mL, 7.19 mmol) and sodium hydroxide solution (40 mg 1.0 mmol) in 0.25 mL of water were added at 0° C. and the mixture was stirred at 0° C. for 10 min. The reaction was then allowed to come to room temperature and maintained at room temperature for 1 h. The progress of the reaction was monitored by TLC and, after completion, the solvents were removed under vacuum. The residue was diluted with water (10 mL) and neutralized with 2N hydrochloric acid (pH 6.5-7.0). The white product that separated out was filtered and dried to give Example 88 (20 mg, 44.45%) of 95.27% purity by HPLC. $^1$HNMR (200 MHz, CD$_3$OD) δ: 2.98 (t, 2H, CH$_2$), 3.1 (s, 3H, CH$_3$), 4.2 (t, 2H, CH$_2$), 5.12 (s, 2H, CH$_2$), 7.18-7.75 (m, 7H, Ar—H), 8.78 (s, 2H, Pyrimidine), 11.0 (bs, 1H, NH).

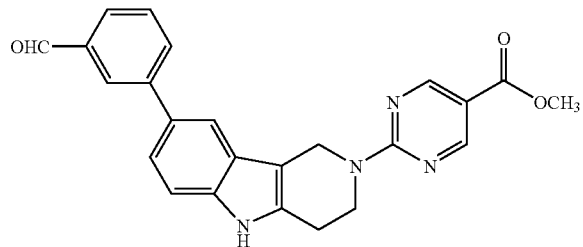

Example 89

Methyl-2-{8-[3-(formyl)phenyl]-1,3,4,5-tetrahydro-2H-pyrido[4,3-b]indol-2-yl}pyrimidine-5-carboxylate To a solution of Example 33 (0.650 g, 1.67 mmol) in THF:H$_2$O (4:1) was added K$_2$CO$_3$ (0.579 g, 4.19 mmol) and 3-formylphenylboronic acid (0.501 g, 3.36 mmol). The reaction mixture was thoroughly degassed and freshly prepared tetrakis(triphenylphosphine)palladium(0) (0.387 g, 0.33 mmol) was added under nitrogen atmosphere at room temperature. The reaction mixture temperature was raised to 80° C. and stirring continued for 12 hr. The progress of the reaction was monitored by TLC and upon completion of the reaction the THF was removed under reduced pressure. The mixture was partitioned between ethyl acetate (100 mL) and water (15 mL). The organic layer was separated, dried over Na$_2$SO$_4$ filtered and the solvent was removed under reduced pressure to give crude residue, which was purified by column chromatography using silica gel to provide Example 89 (0.35 g, 50.4%); $^1$HNMR (CDCl$_3$, 200 MHz) δ: 10.11 (s, 1H), 8.90 (s, 2H), 8.17 (s, 1H), 8.00-7.92 (m, 2H), 7.85-7.80 (m, 2H), 7.64, 7.38 (m, 4H), 5.15 (s, 2H), 4.39 (t, 2H, J=5.4 Hz), 3.88 (s, 3H), 2.98 (t, 2H, J=5.4 Hz); m/e=413 (M+1).

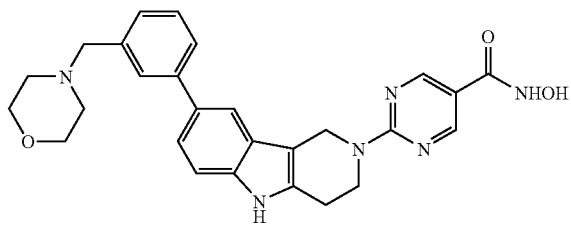

Example 90

N-hydroxy-2-{8-[3-(morpholin-4-ylmethyl)phenyl]-1,3,4,5-tetrahydro-2H-pyrido[4,3-b]indol-2-yl}pyrimidine-5-carboxamide To a stirred solution of Example 89 (0.110 mg, 0.26 mmol) in dry DCM (10 mL) were added morpholine (0.349 g, 4.00 mmol) and sodium triacetoxyborohydride (0.422 g, 2.00 mmol) at room temperature and the mixture was stirred at the same temperature overnight. After completion, the reaction was diluted with DCM (40 mL) and washed with saturated sodium bicarbonate solution and water. The organic layer was dried over anhydrous sodium sulfate and concentrated in vacuum. The residue was purified by column chromatography to give methyl-2-{8-[3-(morpholin-4-ylmethyl)phenyl]-1,3,4,5-tetrahydro-2H-pyrido[4,3-b]indol-2-yl}pyrimidine-5-carboxylate (0.08 g, 62%). $^1$HNMR (200 MHz, CDCl$_3$) δ: 2.58 (m, 4H, 2×CH$_2$), 3.0 (t, 2H, CH$_2$), 3.62 (m, 2H, CH$_2$), 3.75 (m, 4H, 2×CH$_2$), 3.9 (s, 3H, OCH$_3$), 4.41 (t, 2H, CH$_2$), 5.18 (s, 2H, CH$_2$), 7.38-7.5 (m, 3H, Ar—H), 7.5-7.7 (m, 2H, Ar—H), 7.8 (s, 1H, Ar—H), 7.92 (s, 1H, Ar—H), 8.95 (s, 2H, pyrimidine-H); m/e=484 (M+1).

To a stirred solution of methyl-2-{8-[3-(morpholin-4-ylmethyl)phenyl]-1,3,4,5-tetrahydro-2H-pyrido[4,3-b]indol-2-yl}pyrimidine-5-carboxylate (0.08 g, 0.16 mmol) in methanol (4 mL) and DCM (2 mL), 50% aqueous hydroxylamine hydrochloride (1.6 mL, 11.51 mmol) and sodium hydroxide solution (65 mg 1.62 mmol) in 0.5 mL of water were added at 0° C. and the mixture was stirred at 0° C. for 10 min. The reaction was then allowed to come to room temperature and maintained at room temperature for 1 h. The progress of the reaction was monitored by TLC and after completion the solvents were removed under vacuum. The mixture was diluted with water (10 mL) and neutralized with 2N hydrochloric acid (pH 6.5-7.0). The white product that separated out was filtered and dried to give Example 90 (0.05 g, 62.5%) of 94.5% purity by HPLC. $^1$HNMR (200 MHz, DMSO-d$_6$) δ: 2.4 (m, 4H, CH$_2$), 2.9 (t, 2H, CH$_2$), 3.46 (s, 2H, CH$_2$), 3.58 (m, 4H, 2×CH$_2$), 4.25 (t, 2H, CH$_2$), 5.0 (s, 2H, CH$_2$), 7.2 (d, 1H, Ar—H), 7.32-7.65 (m, 5H, Ar—H), 7.8 (s, 1H, Ar—H), 8.7 (s, 2H, Pyrimidine-H), 11.0 (bs, 1H, NH); m/e=485 (M+1).

Examples 91-97 were synthesized in the same manner as Example 90 by substituting the appropriate amine for morpholine in the reaction.

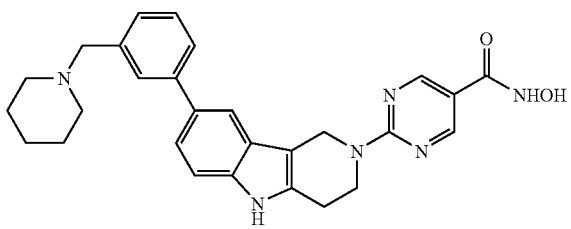

Example 91

N-hydroxy-2-{8-[3-(piperidin-1-ylmethyl)phenyl]-1,3,4,5-tetrahydro-2H-pyrido[4,3-b]indol-2-yl}pyrimidine-5-carboxamide Example 91 was obtained by substituting piperidine for morpholine in the reaction with Example 89. A white solid (0.05 g, 50%) of 95.27% purity by HPLC. $^1$HNMR (200

MHz, CD$_3$OD) δ: 1.5 (m, 2H, CH$_2$) 1.7 (m, 4H, 2×CH$_2$), 2.63 (m, 4H, 2×CH$_2$), 3.0 (t, 2H, CH$_2$), 3.79 (s, 2H, CH$_2$), 4.4 (t, 2H, CH$_2$), 5.18 (s, 2H, CH$_2$), 7.3 (d, 1H, Ar—H), 7.4-7.8 (m, 6H, Ar—H), 8.79 (s, 2H, Pyrimidine-H); m/e=483 (M+1).

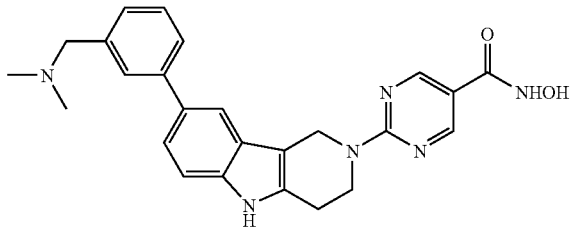

Example 92

N-hydroxy-2-{8-[3-(N,N-dimethylaminomethyl)phenyl]-1,3,4,5-tetrahydro-2H-pyrido[4,3-b]indol-2-yl}pyrimidine-5-carboxamide Example 92 was obtained by substituting dimethylamine for morpholine in the reaction with Example 89. A white solid (50 mg, 50%) of 93.98% purity by HPLC. $^1$HNMR (200 MHz, CD$_3$OD) δ: 2.8 (s, 6H, 2×CH$_3$), 2.99 (t, 2H, CH$_2$), 4.18 (s, 2H, CH$_2$,), 4.4 (t, 2H, CH$_2$), 5.18 (s, 2H, CH$_2$,), 7.3-7.75 (m, 7H, Ar—H), 8.7 (s, 2H, Pyrimidine-H); m/e=444 (M+1).

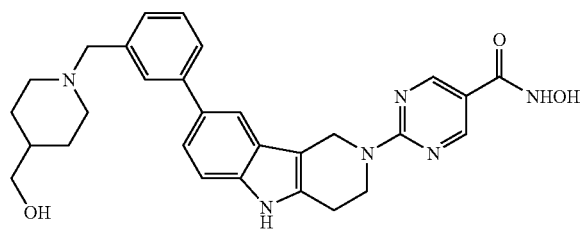

Example 93

N-hydroxy-2-{8-[3-((4-hydroxymethylpiperidin-1-yl)methyl)phenyl]-1,3,4,5-tetrahydro-2H-pyrido[4,3-b]indol-2-yl}pyrimidine-5-carboxamide Example 93 was obtained by substituting 4-hydroxymethylpiperidine for morpholine in the reaction with Example 89. A white solid (40 mg, 40%) of 97.6% purity by HPLC. $^1$HNMR (200 MHz, CD$_3$OD) δ: 1.3 (m, 3H, CH$_2$ CH), 1.8 (m, 2H, CH$_2$), 2.3 (t, 2H, CH$_2$), 2.99 (t, 2H, CH$_2$), 3.2 (m, 2H, CH$_2$), 3.43 (d, 2H, CH$_2$), 3.8 (s, 2H, CH$_2$), 4.4 (t, 2H, CH$_2$), 5.18 (s, 2H, CH$_2$), 7.2-7.8 (m, 7H, Ar—H), 8.8 (s, 2H, Pyrimidine-H); m/e=513 (M+1).

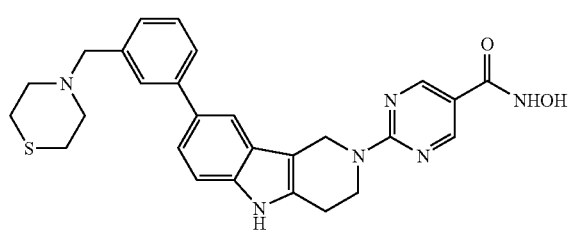

Example 94

N-hydroxy-2-{8-[3-(thiomorpholin-4-ylmethyl)phenyl]-1,3,4,5-tetrahydro-2H-pyrido[4,3-b]indol-2-yl}pyrimidine-5-carboxamide Example 94 was obtained by substituting thiomorpholine for morpholine in the reaction with Example 89. A white solid (70 mg, 70%) of 97.25% purity by HPLC. $^1$HNMR (200 MHz, CD$_3$OD) δ: 2.75 (t, 4H, 2×CH$_2$), 2.82 (t, 4H, 2×CH$_2$), 2.9 (t, 2H, CH$_2$), 3.7 (s, 2H, CH$_2$), 4.4 (t, 2H, CH$_2$), 516 (s, 2H, CH$_2$), 7.2-7.8 (m, 7H, Ar—H), 8.79 (s, 2H, Pyrimidine-H); m/e=501 (M+1).

Example 95

N-hydroxy-2-{8-[3-(N,N-di(2-hydroxyethyl)aminomethyl)phenyl]-1,3,4,5-tetrahydro-2H-pyrido[4,3-b]indol-2-yl}pyrimidine-5-carboxamide Example 95 was obtained by substituting N,N-di(2-hydroxyethyl)amine for morpholine in the reaction with Example 89. A white solid (27 mg, 64.2%) with 97.65% purity (by HPLC). $^1$HNMR (200 MHz, CD$_3$OD) δ: 2.8 (t, 4H, 2×CH$_2$), 2.99 (t, 2H, CH$_2$), 3.7 (t, 4H, 2×CH$_2$), 3.85 (s, 2H, CH$_2$), 4.4 (t, 2H, CH$_2$), 5.18 (s, 2H, CH$_2$), 7.2-7.8 (m, 7H, Ar—H), 8.8 (s, 2H, Pyrimidine-H); m/e=503 (M+1).

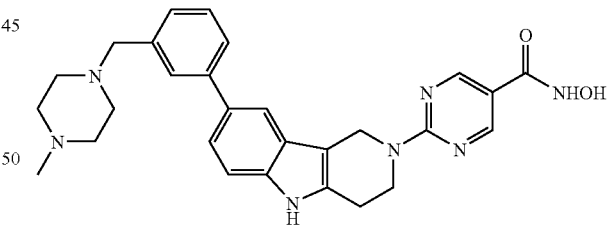

Example 96

N-hydroxy-2-{8-[3-((4-methylpiperazin-1-yl)methyl)phenyl]-1,3,4,5-tetrahydro-2H-pyrido[4,3-b]indol-2-yl}pyrimidine-5-carboxamide Example 96 was obtained by substituting 4-methylpiperazine for morpholine in the reaction with Example 89. A white solid (0.114 g). $^1$HNMR (DMSO-d$_6$) δ: 10.996 (s, 1H), 8.728 (s, 2H), 7.759 (s, 1H), 7.765 (d, 2H), 7.356 (m, 5H), 5.016 (s, 2H), 4.252 (m, 2H), 2.891 (m, 2H), 3.869 (s, 2H).

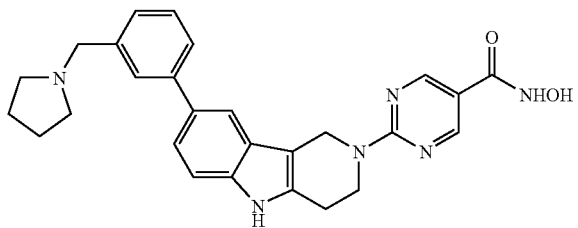

Example 97

N-hydroxy-2-{8-[3-(pyrrolidin-1-ylmethyl)phenyl]-1,3,4,5-tetrahydro-2H-pyrido[4,3-b]indol-2-yl}pyrimidine-5-carboxamide Example 97 was obtained by substituting pyrrolidine for morpholine in the reaction with Example 89. A white solid (0.46 g, 95.5%). HPLC (Rt=12.71); m/e=469 (M+1).

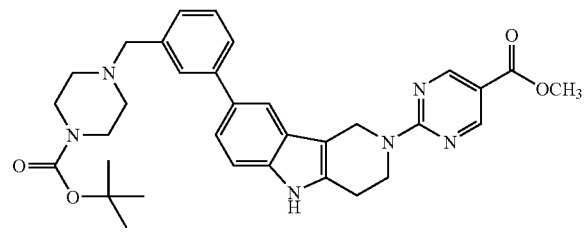

Example 98

Methyl-2-{8-[3-(N-tert-butylcarbonylpiperazin-1-ylmethyl)phenyl]-1,3,4,5-tetrahydro-2H-pyrido[4,3-b]indol-2-yl}pyrimidine-5-carboxylate To a stirred solution of Example 89 (1.0 g, 2.42 mmol) in dry DCM (100 mL) was added N-tert-butylcarbonylpiperazine (4.51 g, 24.24 mmol) and sodium triacetoxyborohydride (2.56 g, 12.13 mmol) at room temperature and the mixture was stirred at the same temperature overnight. After completion, the reaction was diluted with DCM (400 mL) and washed with saturated sodium bicarbonate solution and water. The organic layer was dried over anhydrous sodium sulfate and concentrated in vacuum. The residue was purified by column chromatography to give Example 98 (1.0 g, 70.82%). $^1$HNMR (200 MHz, CDCl$_3$) δ: 1.5 (s, 9H, 3×CH$_3$), 2.45 (t, 4H, 2×CH$_2$), 3.0 (t, 2H, CH$_2$), 3.42 (t, 4H, 2×CH$_2$), 3.6 (s, 2H, CH$_2$), 3.92 (s, 3H, OCH$_3$), 4.4 (t, 2H, CH$_2$), 5.18 (s, 2H, CH$_2$), 7.3-7.8 (m, 7H, Ar—H), 8.9 (s, 2H, Pyrimidine-H); m/e=583 (M+1).

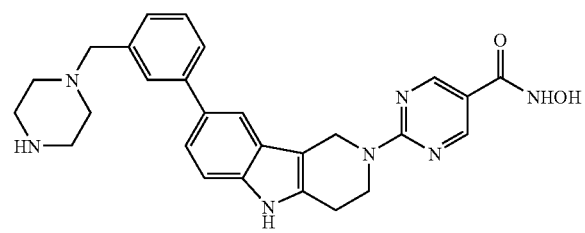

Example 99

N-hydroxy-2-{8-[3-(piperazin-1-ylmethyl)phenyl]-1,3,4,5-tetrahydro-2H-pyrido[4,3-b]indol-2-yl}pyrimidine-5-carboxamide To a 0° C. solution of Example 98 (0.180 g) in DCM (10 mL) was added ether/HCl (10 ml) and the mixture stirred for 30 min. The progress of the reaction was monitored by TLC and solvent was evaporated and washed with ether to give methyl-2-{8-[3-(piperazin-1-ylmethyl)phenyl]-1,3,4,5-tetrahydro-2H-pyrido[4,3-b]indol-2-yl}pyrimidine-5-carboxylate (0.16 g, 78.36%).

To a 0° C. solution of methyl-2-{8-[3-(piperazin-1-ylmethyl)phenyl]-1,3,4,5-tetrahydro-2H-pyrido[4,3-b]indol-2-yl}pyrimidine-5-carboxylate (0.16 g) in methanol:DCM (7.5:3.5) was added 50% aqueous hydroylamine solution (3.5 mL) and to the mixture was added a solution of NaOH (125 mg) in water (0.75 mL). The reaction mixture was stirred at room temperature for 1 hr and the progress of the reaction was monitored by TLC analysis and upon completion of the reaction the solvent was removed under reduced pressure. The pH of the mixture was adjusted to 7.5 using 1N hydrochloric acid and the obtained solid was filtered and washed with water followed by diethyl ether. The solid was dried under vacuum to obtain Example 99 (0.16 g, 99.78%); m/e=484 (M+1).

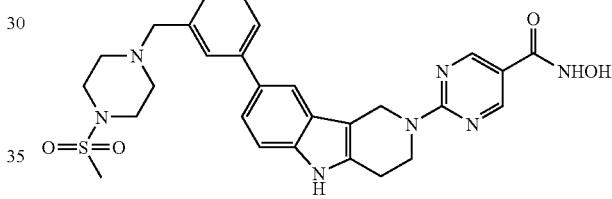

Example 100

N-hydroxy-2-{8-[3-((4-(methylsulfonyl)piperazin-1-yl)methyl)phenyl]-1,3,4,5-tetrahydro-2H-pyrido[4,3-b]indol-2-yl}pyrimidine-5-carboxamide To a stirred solution of Example 98 (10 g, 1.72 mmol) in dry DCM (100 mL) TFA (0.979 g, 8.58 mmol) was added under nitrogen atmosphere at 0° C. The reaction was maintained at room temperature for 1 h. The progress of the reaction was monitored by TLC and after the completion the volatiles were removed by evaporation. The crude was washed with hexane to give methyl-2-{8-[3-(piperazin-1-ylmethyl)phenyl]-1,3,4,5-tetrahydro-2H-pyrido[4,3-b]indol-2-yl}pyrimidine-5-carboxylate (800 mg, 96%).

To a stirred solution of methyl-2-{8-[3-(piperazin-1-ylmethyl)phenyl]-1,3,4,5-tetrahydro-2H-pyrido[4,3-b]indol-2-yl}pyrimidine-5-carboxylate (800 mg, 1.65 mmol) in dry DCM (50 mL) was added 4-dimethylaminopyridine (1.012 g, 8.29 mmol), then methanesulfonyl chloride (0.155 mL, 1.99 mmol) was added at 0° C. and stirred for 10 min. The reaction mass was maintained at room temperature and stirred for 1 h. The progress of the reaction was monitored by TLC and after completion the reaction mass was diluted with water and extracted with DCM. The DCM layer dried over sodium sulfate and concentrated. The residue was purified by column chromatography to give methyl-2-{8-[3-((4-(methylsulfonyl)piperazin-1-yl)methyl)phenyl]-1,3,4,5-tetrahydro-2H- pyrido[4,3-b]indol-2-yl}pyrimidine-5-carboxylate (900 mg, 95.40%) with HPLC purity 95.40%. ¹HNMR (200 MHz, CD₃OD) δ: 2.62 (t, 4H, 2×CH₂), 2.85 (s, 3H, CH₃) 3.0 (t, 2H, CH₂), 3.22 (t, 4H, 2×CH₂), 3.7 (s, 2H, CH₂) 3.95 (s, 3H, OCH₃), 4.4 (t, 2H, CH₂), 5.18 (s, 2H, CH₂), 7.2-7.8 (m, 7H, Ar—H), 8.9 (s, 2H, Pyrimidine-H); m/e=561 (M+1).

To a stirred solution of methyl-2-{8-[3-((4-(methylsulfonyl)piperazin-1-yl)methyl)phenyl]-1,3,4,5-tetrahydro-2H-pyrido[4,3-b]indol-2-yl}pyrimidine-5-carboxylate (0.90 g, 1.60 mmol) in methanol (50 mL) and DCM (25 mL), 50% aqueous hydroxylamine hydrochloride (20 mL, 143.88 mmol) and sodium hydroxide solution (800 mg 20 mmol) in 5 mL of water were added at 0° C. and the mixture was stirred at 0° C. for 10 min. The reaction was then allowed to come to room temperature and maintained at room temperature for 1 h. The progress of the reaction was monitored by TLC and after completion the solvents were removed under vacuum. The mixture diluted with water (10 mL) and neutralized with 2N hydrochloric acid (pH 6.5-7.0). A white solid separated out which and was filtered and dried to give Example 100 (900 mg, 93%) with HPLC purity 96.16%. ¹HNMR (200 MHz, CD₃OD) δ: 2.62 (t, 4H, 2×CH₂), 2.85 (s, 3H, CH₃) 3.0 (t, 2H, CH₂), 3.22 (t, 4H, 2×CH₂), 3.7 (s, 2H, CH₂) 4.4 (t, 2H, CH₂), 5.18 (s, 2H, CH₂), 7.2-7.8 (m, 7H, Ar—H), 8.9 (s, 2H, Pyrimidine-H); m/e=562 (M+1).

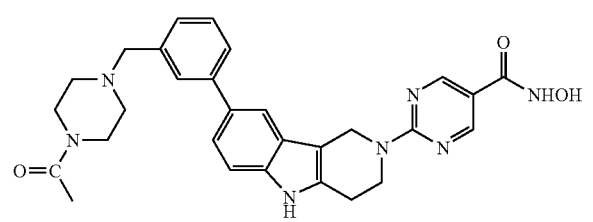

Example 101

N-hydroxy-2-{8-[3-((4-acetylpiperazin-1-yl)methyl)phenyl]-1,3,4,5-tetrahydro-2H-pyrido[4,3-b]indol-2-yl}pyrimidine-5-carboxamide To a stirred solution of methyl-2-{8-[3-(piperazin-1-ylmethyl)phenyl]-1,3,4,5-tetrahydro-2H-pyrido[4,3-b]indol-2-yl}pyrimidine-5-carboxylate (1.5 g, 3.11 mmol) in dry DCM (50 mL) was added 4-dimethylaminopyridine (1.9 g, 15.57 mmol) and then acetic anhydride (0.35 mL, 3.72 mmol) was added at 0° C. and stirred for 5 min. The reaction mass was maintained at room temperature and stirred for 1 h. The progress of the reaction was monitored by TLC, and after completion the reaction mass was diluted with water and extracted with DCM. The DCM layer dried over sodium sulfate and concentrated. The residue was purified by column chromatography to give methyl-2-{8-[3-((4-acetylpiperazin-1-yl)methyl)phenyl]-1,3,4,5-tetrahydro-2H-pyrido[4,3-b]indol-2-yl}pyrimidine-5-carboxylate (1.4 g, 85.88%) with HPLC purity 99.25%; m/e=525 (M⁺+1).

To a stirred solution of methyl-2-{8-[3-((4-acetylpiperazin-1-yl)methyl)phenyl]-1,3,4,5-tetrahydro-2H-pyrido[4,3-b]indol-2-yl}pyrimidine-5-carboxylate (1.4 g, 2.67 mmol) in methanol (50 mL) and DCM (25 mL), 50% aqueous hydroxylamine hydrochloride (28 m, 201.43 mmol) and sodium hydroxide solution (1.2 g 30 mmol in 12 mL of water) were added at 0° C. and the mixture was stirred at 0° C. for 10 min. The reaction was then allowed to come to room temperature and maintained at room temperature for 1 h. The progress of the reaction was monitored by TLC and after completion the solvents were removed under vacuum. The mixture diluted with water (50 mL) and neutralized with 2N hydrochloric acid (pH 6.5-7.0). A white product separated out and was filtered and dried to give Example 101 (1.1 g, 78.57%) of 94.95% purity by HPLC. ¹HNMR (200 MHz, CD₃OD) δ: 2.1 (s, 3H, CH₃), 2.2.58 (m, 4H, 2×CH2), 2.97 (t, 2H, CH₂), 3.6 (t, 4H, 2×CH₂), 3.62 (s, 2H, CH₂), 4.4 (t, 2H, CH₂), 5.18 (s, 2H, CH₂), 7.22-7.8 (m, 7H, Ar—H), 8.7 8 (s, 2H, Pyrimidine-H); m/e=525.8 (M+1).

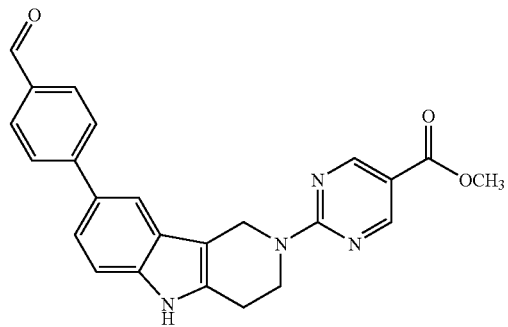

Example 102

Methyl-2-{8-[4-(formyl)phenyl]-1,3,4,5-tetrahydro-2H-pyrido[4,3-b]indol-2-yl}pyrimidine-5-carboxylate To a 0° C. solution of Example 33 (1.5 g, 3.37 mmol) in THF:H₂0 (4:1) were added Cs₂CO₃ (10.07 g, 30.99 mmol) and 4-formylphenylboronic acid (1.158 g, 7.75 mmol). The reaction mixture was thoroughly degassed and freshly prepared tetrakis(triphenylphosphine)palladium(0) (1.119 g, 0.96 mmol) was added under nitrogen atmosphere at room temperature. The reaction mixture temperature was raised to 80° C. and continued stirring for 12 hr. The progress of the reaction was monitored by TLC and upon completion of the reaction the THF was removed under reduced pressure. The mixture was partitioned between ethyl acetate (100 mL) and water (15 mL). The organic layer was separated, dried over Na₂SO₄ filtered and the solvent was removed under reduced pressure to give crude residue, which was purified by column chromatography using silica gel to provide Example 102 (1.0, 62.6%). ¹HNMR (CDCl₃, 200 MHz) δ: 10.11 (s, 1H), 8.90 (s, 2H), 8.17 (s, 1H), 8.00-7.92 (m, 2H), 7.85-7.80 (m, 2H), 7.64-7.38 (m, 4H), 5.15 (s, 2H), 4.39 (t, 2H, J=5.4 Hz), 3.88 (s, 3H), 2.98 (t, 2H, J=5.4 Hz); m/e=413(M+1).

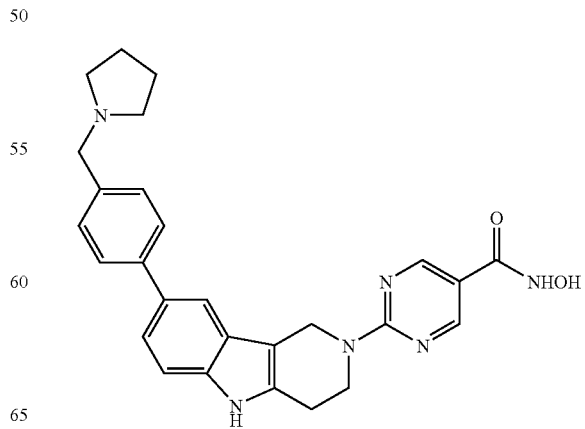

Example 103

N-hydroxy-2-{8-[4-(pyrrolidin-1-ylmethyl)phenyl]-1,3,4,5-tetrahydro-2H-pyrido[4,3-b]indol-2-yl}pyrimidine-5-carboxamide To a 0° C. solution of Example 102 (1.0 g, 2.42 mmol) in DCM (50 mL) was added Na(OAc)₃BH (1.028 g, 4.8 mmol) and stirred for 10 min. To the reaction mixture was added pyrrolidine (0.861 g, 12.13 mmol) under nitrogen atmosphere and the reaction mixture was continued stirring at room temperature for 4 hr. The progress of the reaction was monitored by TLC and upon completion of the reaction the mixture was partitioned between DCM (100 mL) and water (15 mL) and the organic layer was separated, washed with water (2×10 mL), dried over sodium sulfate filtered and the solvent was removed under reduced pressure to give crude residue, which was purified by column chromatography using silica gel to provide methyl-2-{8-[4-(pyrrolidin-1-ylmethyl)phenyl]-1,3,4,5-tetrahydro-2H-pyrido[4,3-b]indol-2-yl}pyrimidine-5-carboxylate (2 g, 95%).

To a 0° C. solution of methyl-2-{8-[4-(pyrrolidin-1-ylmethyl)phenyl]-1,3,4,5-tetrahydro-2H-pyrido[4,3-b]indol-2-yl}pyrimidine-5-carboxylate (1.23 g) in MeOH:DCM (30:12 mL) was added 50% aqueous hydroylamine solution (24 mL) and to the mixture was added solution of NaOH (960 mg) in water (7 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the obtained solid was filtered and washed with water followed by diethyl ether and dried under vacuum to give Example 103 (1.24 g). $^1$HNMR (CD₃OD, 200 MHz) δ: 8.74 (s, 2H), 7.70 (d, 4H), 7.39 (m, 5H), 5.08 (s, 2H), 4.36 (m, 2H), 3.87 (s, 2H), 2.95 (m, 2H), 2.81 (m, 4H), 1.92 (m, 4H); m/e=468 (M+1).

Examples 104 to 106 were prepared in the same manner as Example 103 by substituting the appropriate amine for pyrrolidine in the reaction with Example 33.

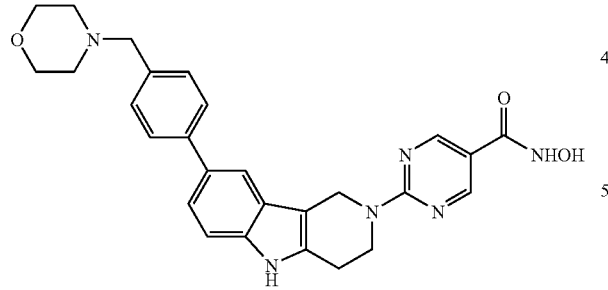

Example 104

N-hydroxy-2-{8-[4-(morpholin-4-ylmethyl)phenyl]-1,3,4,5-tetrahydro-2H-pyrido[4,3-b]indol-2-yl}pyrimidine-5-carboxamide Example 104 was obtained by substituting morpholine for pyrrolidine in the reaction with Example 33. A solid (0.023 g, 15.26%); $^1$HNMR (CD₃OD, 200 MHz) δ: 8.74 (2H, s), 7.67-7.37 (8H, m), 5.09 (2H, s), 4.37 (2H, m), 2.96 (2H, m), 3.76 (4H, m), 2.56 (4H, m), 3.59 (2H, s); m/e=485 (M+1).

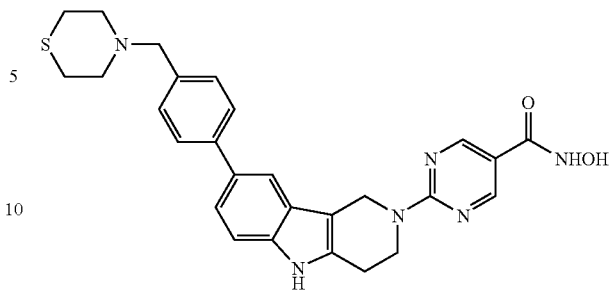

Example 105

N-hydroxy-2-{8-[4-(thiomorpholin-4-ylmethyl)phenyl]-1,3,4,5-tetrahydro-2H-pyrido[4,3-b]indol-2-yl}pyrimidine-5-carboxamide Example 105 was obtained by substituting thiomorpholine for pyrrolidine in the reaction with Example 33. A solid (0.035 g, 49.91%); $^1$HNMR (CD₃OD, 200 MHz) δ: 8.74 (s, 2H), 7.68 (d, 4H), 7.37 (d, 4H), 5.09 (s,2H), 4.34 (s, 2H), 3.68 (s, 2H), 2.84 (m, 2H), 2.84 (m, 4H), 2.72 (m, 4H); m/e=500 (M+1).

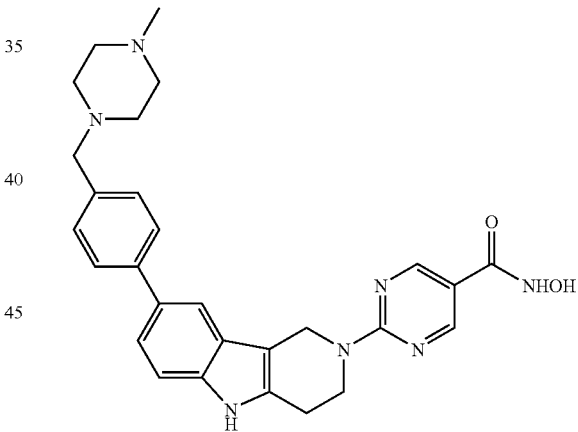

Example 106

N-hydroxy-2-{8-[4-((4-methylpiperazin-1-yl)methyl)phenyl]-1,3,4,5-tetrahydro-2H-pyrido[4,3-b]indol-2-yl}pyrimidine-5-carboxamide Example 106 was obtained by substituting N-methylpiperazine for pyrrolidine in the reaction with Example 33. A solid (0.005 g); HPLC (Rt-11.77 min). $^1$HNMR (DMSO-d₆) (200 MHz) δ: 10.99 (1H, s), 8.72 (2H, s), 7.75 (1H, s), 7.67 (2H, d), 7.35 (5H, m), 5.01 (s, 2H), 4.25 (2H, m), 2.89 (2H, m), 3.38 (2H, s), 2.49 (8H, m), 2.24 (3H, m); m/e=498 (M+1).

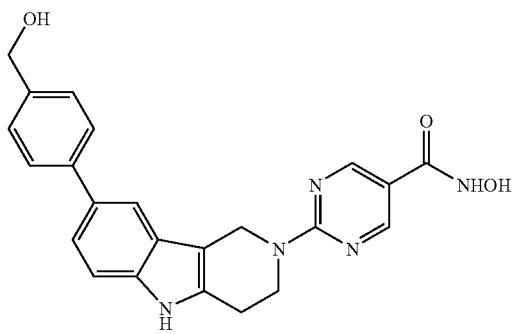

Example 107

N-hydroxy-2-{8-[4-(hydroxymethyl)phenyl]-1,3,4,5-tetrahydro-2H-pyrido[4,3-b]indol-2-yl}pyrimidine-5-carboxamide To a solution of Example 102 (0.150 g, 0.36 mmol) in DCM was added NaBH$_4$ (0.069 g, 1.81 mmol) under nitrogen atmosphere at 0° C. The reaction mixture temperature was raised to room temperature and continued stirring for 3 hr. The progress of the reaction was monitored by TLC and upon completion, the mixture was partitioned between DCM (25 mL) and water (15 mL) and the organic layer was separated, dried over Na$_2$SO$_4$ filtered and the solvent was removed under reduced pressure to give crude residue, which was purified by column chromatography using silica gel to provide methyl-2-{8-[4-(hydroxymethyl)phenyl]-1,3,4,5-tetrahydro-2H-pyrido[4,3-b]indol-2-yl}pyrimidine-5-carboxylate (0.050 g, 33.2%).

To a 0° C. solution of methyl-2-{8-[4-(hydroxymethyl)phenyl]-1,3,4,5-tetrahydro-2H-pyrido[4,3-b]indol-2-yl}pyrimidine-5-carboxylate (0.050 g) in methanol:DCM (5:2 mL) was added 50% aqueous hydroxylamine solution (1 mL) and to the mixture was added solution of NaOH (0.04 g) in water (0.2 mL). The reaction mixture was stirred at room temperature for 1 hr and the progress of the reaction was monitored by TLC and upon completion the solvent was removed under reduced pressure. The pH of the mixture was adjusted to 7.5 using 1N HCl and the obtained solid was filtered and washed with water followed by diethyl ether and dried under vacuum to give Example 107 (0.022 g, 44%). HPLC (Rt=12.84); $^1$HNMR (DMSO-D$_6$, 200 MHz) δ: 10.98 (2H, s), 8.80 (2H, s), 7.76-7.35 (Ar, 7H, m), 5.02 (2H, s), 4.53 (2H, s), 4.25 (2H, m), 2.89 (2H, m); m/e=416 (M+1).

5-formyl-2-furanboronic acid (0.180 g, 1.29 mmol). The reaction mixture was thoroughly degassed and freshly prepared tetrakis(triphenylphosphine)palladium(0) (0.186 g, 0.16 mmol) was added under nitrogen atmosphere at room temperature. The reaction mixture temperature was raised to 80° C. and continued stirring for 12 hr. The progress of the reaction was monitored by TLC analysis and upon completion of the reaction the THF was removed under reduced pressure. The mixture was partitioned between ethyl acetate (100 mL) and water (15 mL). The organic layer was separated, dried over Na$_2$SO$_4$ filtered and the solvent was removed under reduced pressure to give crude residue, which was purified by column chromatography using silica gel to give methyl-2-{8-[5-(formyl)-2-furyl]-1,3,4,5-tetrahydro-2H-pyrido[4,3-b]indol-2-yl}pyrimidine-5-carboxylate (0.12 g, 46.2%)

To a 0° C. solution of methyl-2-{8-[5-(formyl)-2-furyl]-1,3,4,5-tetrahydro-2H-pyrido[4,3-b]indol-2-yl}pyrimidine-5-carboxylate (0.12 g, 0.29 mmol) in DCM (20 mL) was added Na(OAc)$_3$BH (0.126 g, 0.59 mmol) and stirred for 10 min. To the reaction mixture was added N-methylpiperzine (0.149 g, 1.49 mmol) under nitrogen atmosphere and the reaction mixture was continued stirring at room temperature for 4 hr. The progress of the reaction was monitored by TLC and upon completion of the reaction the mixture was partitioned between DCM (50 mL) and water (25 mL) and the organic layer was separated, washed with water (2×25 mL), dried over sodium sulfate filtered and the solvent was removed under reduced pressure to give crude residue, which was purified by column chromatography using silica gel to provide methyl-2-{8-[5-((4-methylpiperazin-1-yl)methyl)-2-furyl]-1,3,4,5-tetrahydro-2H-pyrido[4,3-b]indol-2-yl}pyrimidine-5-carboxylate (0.1 g, 69.4%).

To a 0° C. solution of methyl-2-{8-[5-((4-methylpiperazin-1-yl)methyl)-2-furyl]-1,3,4,5-tetrahydro-2H-pyrido[4,3-b]indol-2-yl}pyrimidine-5-carboxylate (0.1 g) in methanol:DCM (5:2 mL) was added 50% aqueous hydroxylamine solution (2 mL) and to the mixture was added solution of NaOH (0.8 g) in water (0.5 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the obtained solid was filtered and washed with water followed by diethyl ether and dried under vacuum to give Example 108 (0.08, 64.87%). HPLC: (Rt=11.58); m/e=488 (M+1).

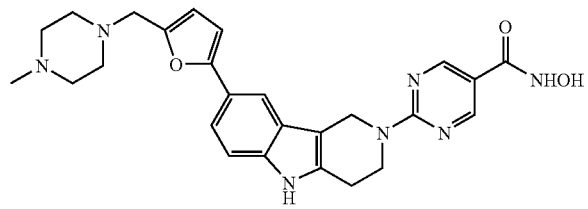

Example 108

N-hydroxy-2-{8-[5-((4-methylpiperazin-1-yl)methyl)-2-furyl]-1,3,4,5-tetrahydro-2H-pyrido[4,3-b]indol-2-yl}pyrimidine-5-carboxamide To a solution of Example 33 (0.25 g, 0.64 mmol) in THF:H$_2$O (4:1) were added Cs$_2$CO$_3$ (1.689 g, 5.16 mmol) and

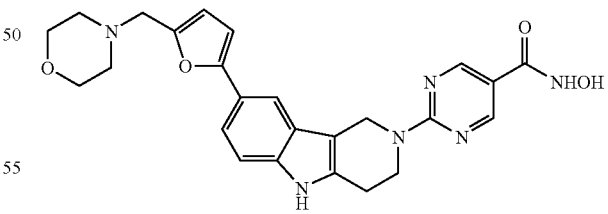

Example 109

N-hydroxy-2-{8-[5-(morpholin-4-yl)methyl-2-furyl]-1,3,4,5-tetrahydro-2H-pyrido[4,3-b]indol-2-yl}pyrimidine-5-carboxamide Example 109 was prepared in the same manner as Example 108 by substituting morpholine for N-methylpiperazine in the reaction sequence. A solid (0.075 g, 48.89%); HPLC: (Rt=12.01 min.); m/e=475 (M+1).

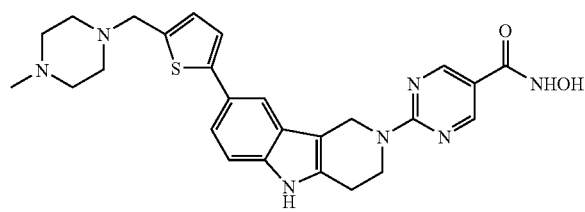

Example 110

N-hydroxy-2-{8-[5-((4-methylpiperazin-1-yl)methyl)-thien-2-yl]-1,3,4,5-tetrahydro-2H-pyrido[4,3-b]indol-2-yl}pyrimidine-5-carboxamide To a solution of Example 33 (0.5 g, 1.29 mmol) in THF:H$_2$O (4:1) were added Cs$_2$CO$_3$ (3.354 g, 10.32 mmol) and 5-formyl-2-thiopheneboronic acid (0.503 g, 3.22 mmol). The reaction mixture was thoroughly degassed and freshly prepared tetrakis(triphenylphosphine)palladium(0) (0.446 g, 0.38 mmol) was added under nitrogen atmosphere at room temperature. The reaction mixture temperature was raised to 80° C. and continued stirring for 12 hr. The progress of the reaction was monitored by TLC and upon completion of the reaction the THF was removed under reduced pressure. The mixture was partitioned between ethyl acetate (100 mL) and water (15 mL) and the organic layer was separated, dried over Na$_2$SO$_4$ filtered and the solvent was removed under reduced pressure to give crude residue, which was purified by column chromatography using silica gel to provide methyl-2-{8-[5-(formyl)-thien-2-yl]-1,3,4,5-tetrahydro-2H-pyrido[4,3-b]indol-2-yl}pyrimidine-5-carboxylate (0.1 g).

To a 0° C. solution of methyl-2-{8-[5-(formyl)-thien-2-yl]-1,3,4,5-tetrahydro-2H-pyrido[4,3-b]indol-2-yl}pyrimidine-5-carboxylate (0.09 g, 0.21 mmol) in DCM (50 mL) was added Na(OAc)$_3$BH (0.114 g, 0.53 mmol) and stirred for 10 min. To the reaction mixture was added N-methylpiperazine (0.107 g, 1.07 mmol) under nitrogen atmosphere and the reaction mixture was continued stirring at room temperature for 4 hr. The progress of the reaction was monitored by TLC and upon completion of the reaction the mixture was partitioned between DCM (100 mL) and water (15 mL) and the organic layer was separated, washed with water (2×10 mL), dried over sodium sulphate filtered and the solvent was removed under reduced pressure to give crude residue, which was purified by column chromatography using silica gel to provide methyl-2-{8-[5-((4-methylpiperazin-1-yl)methyl)-thien-2-yl]-1,3,4,5-tetrahydro-2H-pyrido[4,3-b]indol-2-yl}pyrimidine-5-carboxylate (0.08 g).

To a 0° C. solution of the methyl-2-{8-[5-((4-methylpiperazin-1-yl)methyl)-thien-2-yl]-1,3,4,5-tetrahydro-2H-pyrido[4,3-b]indol-2-yl}pyrimidine-5-carboxylate (0.08 g, 0.165 mmol) in methanol:DCM (5:2 mL) was added 50% aqueous hydroxylamine solution (1.5 mL) and to the mixture was added solution of NaOH (0.060 g) in water (0.3 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the obtained solid was filtered and washed with water followed by diethyl ether and the solid was dried under vacuum to give Example 110 (0.040 g). $^1$HNMR (DMSO-D$_6$, 200 MHz) δ: 11.01 (1H, s), 8.70 (2H, s), 7.70 (1H, s), 7.29 (2H, m), 7.21 (1H, s), 6.89 (1H, s), 4.95 (s, 2H), 4.20 (2H, m), 3.63 (2H, s), 2.85 (2H, m), 2.49-2.32 (8H, m), 2.14 (3H, s); m/e=504 (M$^+$).

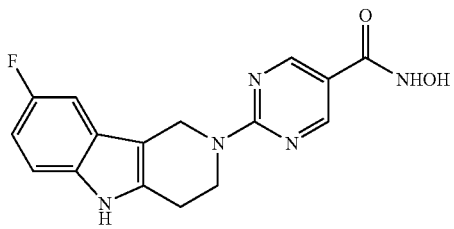

Example 111

N-hydroxy-2-(8-fluoro-1,3,4,5-tetrahydro-2H-pyrido[4,3-b]indol-2-yl)pyrimidine-5-carboxamide Example 111 was obtained by substituting 4-fluorophenylhydrazine for 4-bromophenylhydrazine in the reaction sequence. A solid; $^1$H NMR (DMSO-d$_6$, 300 MHz) δ: 2.82 (m, 2H), 4.23 (m, 2H), 4.90 (s, 2H), 6.85 (t, J=9 Hz, 1H), 7.27 (m, 2H), 8.70 (s, 2H), 11.02 (s, 1H), 11.08 (s, if H); m/e=316 (M+1).

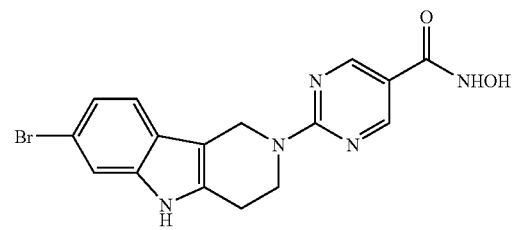

Example 112

N-hydroxy-2-(7-bromo-1,3,4,5-tetrahydro-2H-pyrido[4,3-b]indol-2-yl)pyrimidine-5-carboxamide Example 112 was obtained by substituting 3-bromophenylhydrazine for 4-bromophenylhydrazine in the reaction sequence. A white solid (12 mg); $^1$HNMR (200 MHz, DMSO-d$_6$) δ: 8.73 (2H, s), 7.46 (1H, s), 7.39 (2H, d, J=8.4 Hz), 7.15 (2H, d, J=8.4 Hz), 5.03 (2H, s), 4.34 (2H, t, J=5.6 Hz), 2.93 (2H, t, J=5.6 Hz); m/e=387.8 (M+1).

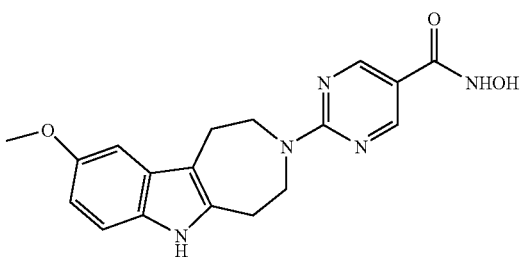

Example 113

N-hydroxy-2-(9-methoxy-1,4,5,6-tetrahydroazepino[4,5-b]indol-3(2H)-1-yl)pyrimidine-5-carboxamide To tert-butyl 4-oxoazepane-1-carboxylate (1 g, 4.68 mmol) and 4-methoxyphenylhydrazine (820 mg, 4.7 mmol) in absolute ethanol (50 mL), DIEA (1 g,) and acetic acid (0.5 mL) was added and the mixture refluxed for 1 h. After removing the solvent, the residue obtained was taken as such for the next step.

The crude product from the previous reaction was taken in formic acid (50 mL) and heated at 100° C. for one hour. After which it was poured into water and made basic by adding aqueous sodium hydroxide and then extracted with DCM. The crude 9-methoxy-1,2,3,4,5,6-hexahydroazepino[4,5-b]indole obtained was taken as such for the next step.

To Example 7 (1 g, 4.3 mmol) in acetonitrile (50 mL), crude 9-methoxy-1,2,3,4,5,6-hexahydroazepino[4,5-b]indole (1 g, 4.6 mmol) and potassium carbonate (1 g, 7.2 mmol) was added and the mixture refluxed for 4 h. The crude product obtained on removal of solvent was chromatographed on silica gel column by using 50% ethyl acetate in hexanes followed by re-crystallization from hexane and DCM (1:1) resulted in pure methyl-2-(9-methoxy-1,4,5,6-tetrahydroazepino[4,5-b]indol-3(2H)-1-yl)pyrimidine-5-carboxylate (200 mg, 13.3%); m/e=353 (M+1).

To the methyl-2-(9-methoxy-1,4,5,6-tetrahydroazepino[4,5-b]indol-3(2H)-1-yl)pyrimidine-5-carboxylate (200 mg, 0.56 mmol) in methanol (10 mL) and DCM (10 mL), 50% aqueous hydroxylamine (2 mL) and aqueous sodium hydroxide (160 mg, 4 mmol) was added and stirred at room temperature for 4 h. After removing the solvent, the residue was dissolved in water (10 mL) and acidified with concentrated hydrochloric acid. The white solid precipitated was filtered, washed with water (30 mL), ether (20 mL) and dried under vacuum to give Example 113 (180 mg, 90%). $^1$H NMR (300 MHz, DMSO-d$_6$) δ: 2.91-3.01 (m, 4H), 3.73 (s, 3H), 4.07 (m, 4H), 6.60 (m, 1H), 6.88 (s, 1H), 7.08 (m, 1H), 8.69 (m, 2H), 8.98 (s, 1H), 10.57 (s, 1H), 11.03 (s, 1H); m/e=354 (M+1).

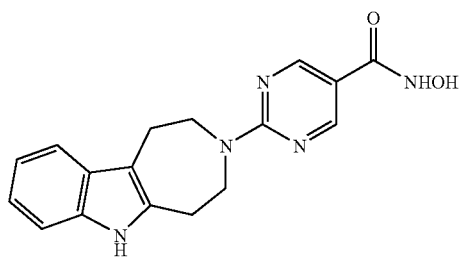

Example 114

N-hydroxy-2-(1,4,5,6-tetrahydroazepino[4,5-b]indol-3(2H)-1-yl)pyrimidine-5-carboxamide Example 114 was prepared in the same manner as Example 113 by substituting phenylhydrazine for 4-methoxyphenylhydrazine in the reaction sequence. A solid; $^1$H NMR (DMSO-d$_6$, 300 MHz) 6; 2.94-3.05 (m, 4H, 4.07 (m, 4H), 6.94 (m, 2H), 7.21 (d, J=7.8 Hz, 1H), 7.38 (d, J=7.5 Hz, 1H), 8.98 (bs, 1H), 10.74 (s, 1H), 11.03 (s, 1H); m/e=322 (M+1).

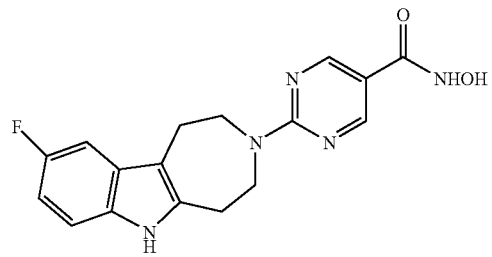

Example 115

N-hydroxy-2-(9-fluoro-1,4,5,6-tetrahydroazepino[4,5-b]indol-3(2H)-1-yl)pyrimidine-5-carboxamide Example 115 was prepared in the same manner as Example 113 by substituting 4-fluorophenylhydrazine for 4-methoxyphenylhydrazine in the reaction sequence. A solid; $^1$H NMR (DMSO-d$_6$, 300 MHz) 6; 2.90 (t, J=5 Hz, 2H), 3.03 (t, J=5 Hz, 2H), 4.06 (m, 4H), 6.79 (t, J=9 Hz, 1H), 7.16 (m, 2H), 8.69 (s, $^2$H), 8.98 (s, 1H), 10.86 (s, 1H), 11.03 (s, 1H); m/e=340 (M+1).

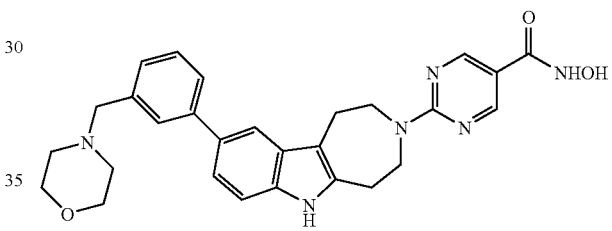

Example 116

N-hydroxy-2-(9-[3-(morpholin-4-ylmethy)phenyl]-1,4,5,6-tetrahydroazepino[4,5-b]indol-3(2H)-1-yl)pyrimidine-5-carboxamide Methyl-2-(9-bromo-1,4,5,6-tetrahydroazepino[4,5-b]indol-3(2H)-1-yl)pyrimidine-5-carboxylate was obtained by substituting 4-bromophenylhydrazine for 4-methoxyphenylhydrazine in the reaction sequence used to make methyl-2-(9-methoxy-1,4,5,6-tetrahydroazepino[4,5-b]indol-3(2H)-1-yl)pyrimidine-5-carboxylate in Example 113. To a solution of methyl-2-(9-bromo-1,4,5,6-tetrahydroazepino[4,5-b]indol-3(2H)-1-yl)pyrimidine-5-carboxylate (1.9 g, 4.73 mmol) in THF:H$_2$O (4:1) were added Cs$_2$CO$_3$ (12.33 g, 37.90 mmol) and 3-formylphenylboronic acid (1.41 g, 9.46 mmol). The reaction mixture was thoroughly degassed and freshly prepared tetrakis(triphenylphosphine)palladium(0) (1.36 g, 1.18 mmol) was added under nitrogen atmosphere at room temperature. The reaction mixture temperature was raised to 80° C. and continued stirring for 12 hr. The progress of the reaction was monitored by TLC and upon completion of the reaction the THF was removed under reduced pressure. The mixture was partitioned between ethyl acetate (100 mL) and water (15 mL). The organic layer was separated, dried over Na$_2$SO$_4$ filtered and the solvent was removed under reduced pressure to give crude residue, which was purified by column chromatography using silica gel to provide methyl-2-(9-[3-

(formyl)phenyl]-1,4,5,6-tetrahydroazepino[4,5-b]indol-3 (2H)-1-yl)pyrimidine-5-carboxylate (0.9 g, 44.7%)

To a 0° C. solution of methyl-2-(9-[3-(formyl)phenyl]-1,4,5,6-tetrahydroazepino[4,5-b]indol-3(2H)-1-yl)pyrimidine-5-carboxylate (0.15 g, 0.35 mmol) in DCM (20 mL) was added Na(OAc)$_3$BH (0.149 g, 0.70 mmol) and stirred for 10 min. To the reaction mixture was added morpholine (0.153 g, 1.76 mmol) under nitrogen atmosphere and the reaction mixture was continued stirring at room temperature for 4 hr. The progress of the reaction was monitored by TLC and upon completion of the reaction the mixture was partitioned between DCM (50 mL) and water (25 mL) and the organic layer was separated washed with water (2×25 mL), dried over sodium sulfate, filtered and the solvent was removed under reduced pressure to give crude residue, which was purified by column chromatography using silica gel to provide methyl-2-(9-[3-(morpholin-4-ylmethyl)phenyl]-1,4,5,6-tetrahydroazepino[4,5-b]indol-3(2H)-1-yl)pyrimidine-5-carboxylate (0.2 g).

To a 0° C. solution of methyl-2-(9-[3-(morpholin-4-ylmethyl)phenyl]-1,4,5,6-tetrahydroazepino[4,5-b]indol-3(2H)-1-yl)pyrimidine-5-carboxylate (0.2 g) in methanol:DCM (10 ml:4 ml) was added 50% aqueous hydroxylamine solution (4 mL) and to the mixture was added a solution of NaOH (0.12 g) in water (1 mL). The reaction mixture was stirred at room temperature for 1 hr and the progress of the reaction was monitored by TLC analysis and upon completion of the reaction the solvent was removed under reduced pressure. The pH of the mixture was adjusted to 7.5 using 1N HCl and the obtained solid was filtered and washed with water followed by diethyl ether and dried under vacuum to give Example 116; HPLC: (Rt=12.39); m/e=499 (M+1).

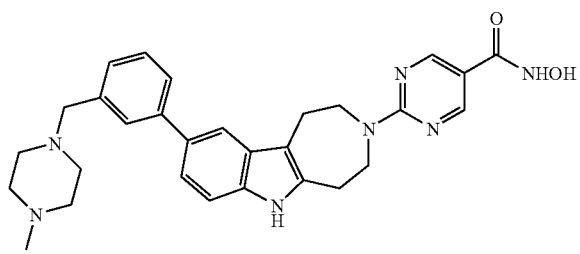

Example 117

N-hydroxy-2-(9-[3-((4-methylpiperazin-1-yl)methy)phenyl]-1,4,5,6-tetrahydroazepino[4,5-b]indol-3 (2H)-1-yl)pyrimidine-5-carboxamide Example 117 was synthesized in the same manner as Example 116 by substituting N-methylpiperazine for morpholine in the reaction sequence. A solid, HPLC: (Rt=11.81 min); m/e=512 (M+1).

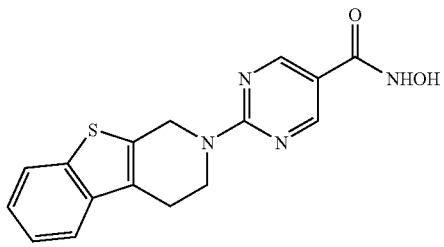

Example 118

2-(3,4-dihydro[1]benzothieno[2,3-c]pyridin-2(1H)-yl)-N-hydroxypyrimidine-5-carboxamide 1,2,3,4-Tetrahydro[1]benzothieno[2,3-c]pyridine was prepared as described by Wolf, G.; and Zymalkowski, F.; Arch. Pharm. 1976 (Weinheim Ger.), 309, 279-288. Hydrochloric acid was bubbled vigorously through a mixture of benzothiophene (5.0 g, 37.2 mmol), 37% aqueous formaldehyde (4.4 mL) and concentrated HCl (4.4 mL) until the reaction temperature rose to 65° C. At this time the flow of HCl gas was reduced to a slow stream and maintained for 1.5 h. The reaction mixture was diluted with water (10 mL) and subsequently extracted with ether (2×25 mL). The combined organic extracts were dried over anhydrous Na$_2$SO$_4$ and concentrated under reduced pressure and the residue was purified by silica gel column chromatography using ethyl acetate-hexane to furnish 3-(chloromethyl)-1-benzothiophene (4.5 g, 67%); $^1$H NMR (200 MHz, CDCl$_3$): δ 4.96 (s, 2H), 7.25 (s, 1H), 7.45 (m, 2H), 7.88 (m, 2H).

To a stirred solution of NaCN (1.4 g, 28.5 mmol) in DMSO (8 mL) was added 3-(chloromethyl)-1-benzothiophene (4 gm, 21.9 mmol) in DMSO (6 mL) over 15 min. The reaction mixture was stirred at room temperature for 18 h and then quenched with water and extracted with ether (2×50 mL). The organic layer was washed with brine, dried over anhydrous Na$_2$SO$_4$, filtered and concentrated under reduced pressure. The residue obtained was purified by silica gel column chromatography using ethyl acetate-hexane (1:1) to furnish 1-benzothien-3-ylacetonitrile (2.5 g, 65%). $^1$H NMR (200 MHz, CDCl$_3$): δ 3.69 (s, 2H), 7.25-7.91 (m, 5H).

To a slurry of lithium aluminium hydride (0.6 g, 15.16 mmol) in ether (25 mL) was added, under N$_2$, a slurry of aluminium chloride (2.1 g, 15.1 mmol) in dry ether. After 5 min, a solution of 1-benzothien-3-ylacetonitrile (2.5, 14.4 mmol) in ether (25 mL) was slowly added over 10 min. Upon completion of the addition, the resulting reaction mixture was refluxed for 18 h, cooled and neutralized with 6N NaOH and extracted with ethyl acetate (2×50 mL). The combined organic extracts were dried over anhydrous Na$_2$SO$_4$, filtered and concentrated under reduced pressure to yield a syrup. 2-(1-Benzothien-3-yl)ethanamine hydrochloride was obtained by treating the syrup with a solution of methanolic HCl (1.5 g, 50%); $^1$H NMR (200 MHz, CDCl$_3$): δ 1.43 (s, 2H), 3.00 (m, 4H), 7.11 (s, 1H), 7.36 (m, 2H), 7.72-7.86 (m, 2H).

A mixture of 2-(benzo[b]thien-3-yl)ethylamine hydrochloride (0.5 g, 2.34 mmol) and paraformaldehyde (0.125 g, 4.16 mmol) in methanol (15 mL) was refluxed for 24 h. The reaction mixture was concentrated under reduce pressure and the residue was neutralized with saturated NaHCO$_3$ (50 mL), and extracted with ethyl acetate (2×50 mL). The organic layer was dried over anhydrous sodium sulfate, filtered and concentrated to furnish 1,2,3,4-tetrahydro[1]benzothieno[2,3-c]pyridine (160 mg, 35%); $^1$H NMR (200 MHz, CDCl$_3$): δ 2.81 (m, 2H), 3.25 (m, 2H), 4.15 (s,2H), 7.30 (m, 2H), 7.69 (d, J=4.0 Hz, 1H), 7.79 ((d, J=4.0 Hz, 1H).

A mixture of 1,2,3,4-tetrahydro[1]benzothieno[2,3-c]pyridine (0.160 g, 0.855 mmol), Example 7 (0.280 g, 1.3 mmol) and K$_2$CO$_3$ (0.6 g, 4.27 mmol) in DMF (10 mL) was stirred at 90° C. for 3 h. The reaction mixture was cooled to room temperature, quenched by addition of water (50 mL) and extracted with ethyl acetate (2×25 mL). The organic layer was washed with water and brine, dried over anhydrous Na$_2$SO$_4$, filtered and concentrated under reduced pressure and the residue was purified by silica gel column chromatography using ethyl acetate-hexane (1:1) to furnish methyl-2-(3,4-dihydro [1]benzothieno[2,3-c]pyridin-2(1H)-yl)pyrimidine-5-carboxylate (0.08 g, 50%). ¹H NMR (200 MHz, CDCl₃): δ 2.99 (m, 2H), 3.89 (s, 3H), 4.35 (m, 2H), 5.20 (s, 2H), 7.35 (m, 2H), 7.61 (d, J=4.0 Hz, 1H), 7.81 ((d, J=4.0 Hz, 1H), 8.91 (s, 2H).

To a cooled (0° C.) solution of methyl-2-(3,4-dihydro[1] benzothieno[2,3-c]pyridin-2(1H)-yl)-pyrimidine-5-carboxylate (0.080 g, 0.28 mmol) in methanol:DCM (6 mL, 2:1) was added aqueous 50% NH₂OH solution (2 mL) and NaOH (0.08 g, 2.0 mmol) dissolved in 0.5 ml of water. The reaction mixture was stirred for 3 h at room temperature and the reaction mixture was concentrated under reduced pressure to give crude residue. The residue was neutralized with 2N HCl and the precipitated solid was filtered and dried to give pure Example 118 (0.030 g, 38%). ¹H NMR (200 MHz, CD₃OD): δ 2.97 (m, 2H), 4.36 (m, 2H), 5.20 (s, 2H), 7.29 (m, 2H), 7.64 (d, J=4.0 Hz, 1H), 7.84 (d, J=4.0 Hz, 1H), 8.95 (s ,2H); m/e=327 (M+1).

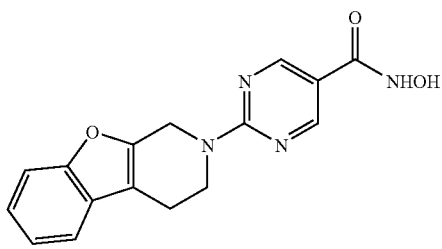

Example 119

2-(3,4-dihydro[1]benzofuro[2,3-c]pyridin-2(1)-yl)-N-hydroxypyrimidine-5-carboxamide 1,2,3,4-Tetrahydro[1]benzofuro[2,3-c]pyridine was prepared by the method described by Jaen, J. and Wise, L. D.; *J. Heterocycl. Chem.* 1987, 1317-1319. To a reaction mixture containing Mg turnings (0.85, 35.41 mmol), a pinch of iodine in THF (5 mL) under N₂ atmosphere was added a mixture of 2-bromoanisole (5.0 g, 26.7 mmol) and 1,2-dibromoethane (1.4 g, 8.8 mmol) in (10 mL) THF. When all the magnesium was consumed, a solution of 1-benzyl-4-piperidone (5.0 g, 28.24 mmol) in THF (10 mL) was added dropwise. Following the addition, the solution was refluxed for 20 minutes, and then stirred at room temperature for 2 h. The reaction mixture cooled to 0° C. and 10% HCl was added dropwise until the pH of the mixture was 1-2. The pH was adjusted to 10 with 2N NaOH and extracted with ether (2×100 mL). The organic extracts were dried over anhydrous Na₂SO₄, filtered and concentrated under reduced pressure to furnish 1-benzyl-4-(2-methoxyphenyl)piperidin-4-ol (4.5 g, 90%). ¹H NMR (200 MHz, CDCl₃): δ 2.20 (d, J=17 Hz, 2H), 2.60-3.15 (m, 2H), 3.20-3.50 (m, 4H), 3.90 (s, 3H), 4.20 (d, J=7 Hz, 2H), 6.90-7.05 (m, 2H), 7.20-7.35 (m, 2H), 7.35-7.55 (m, 3H), 7.60-7.80 (m, 2H); m/e=297.

1-Benzyl-4-(2-methoxyphenyl)piperidin-4-ol (4.5 g, 15.15 mmol) was mixed with anhydrous potassium bisulphate (8.0 g, 58.56 mmol) and heated to 160° C. under vacuum at 10 mm Hg for 0.5 h. The flask was cooled, the contents dissolved in water and the solution was saturated with sodium carbonate and extracted with ether (2×1100 mL). The organic layer was washed with brine, dried over anhydrous Na₂SO₄, filtered and concentrated under reduced pressure and the residue was purified by silica gel column chromatography using ethyl acetate-hexane (1:1) to furnish 1-benzyl-4-(2-methoxyphenyl)-1,2,3,6-tetrahydropyridine (2.0 g, 45%). ¹H NMR (200 MHz, CDCl₃): δ 2.551-2.573 (m, 2H), 2.67-2.71 (m, 2H), 3.16-3.19 (brs, 2H), 3.66 (s, 2H), 3.79 (s, 3H), 5.76-5.78 (brs, 1H), 6.83-6.92 (m, 2H), 7.15-7.41 (m, 7H); m/e=279 (M⁺).

Sodium borohydride (0.590 g, 15.94 mmol) was added at once to a solution of 1-benzyl-4-(2-methoxyphenyl)-1,2,3,6-tetrahydropyridine (2.0 g, 7.16 mmol) in (7 mL) anhydrous diglyme at 0° C. The reaction mixture was warmed to room temperature and a solution of borontrifluoride etherate (2.0 g 14.2 mmol) in (2 mL) diglyme was added dropwise under a N₂. The reaction mixture was stirred at room temperature for 2 h. Water (0.8 mL) was then added to the reaction mixture slowly followed by 6N NaOH (1.8 mL). The reaction mixture was heated to 50° C. for another 45 min. and then 30% H₂O₂ (1.7 mL, 14.7 mmol) was added. The reaction mixture was stirred for another 45 min., Concentrated HCl (1.7 mL) was added and the solvents were evaporated in vacuum. Water (7 mL) was added to the residue and the solvent again evaporation. The residue was quenched with saturated ammonium hydroxide solution and extracted with DCM (2×50 mL). The organic layer was dried over anhydrous Na₂SO₄, filtered and concentrated under reduced pressure to give 1-benzyl-4-(2-methoxyphenyl)piperidin-3-ol (1.0 g, 50%); ¹H NMR (200 MHz, CDCl₃): δ 1.79-2.18 (m, 5H), 2.91-3.045 (m, 2H), 3.184-3.256 (dd, J=10.4, 4.0 Hz, 2H), 3.615 (s, 2H), 3.827 (s, 3H), 3.785-3.949 (m, 1H), 6.892 (d, J=8.5 Hz, 2H), 6.974 (t, J=7.5 Hz, 1H), 7.188-7.416 (m, 7H); m/e=297 (M+1).

To a cooled (−78° C.) solution of oxalyl chloride (0.839 g, 6.73 mmol) in dry DCM (5 mL) was added dimethylsulfoxide (1.05 g, 13.46 mmol) dropwise. The mixture was stirred for 10 min at −78° C., 1-benzyl-4-(2-methoxyphenyl)piperidin-3-ol (1.0 g, 3.367 mmol) in DCM (10 mL) was added and stirring continued for a further 20 min at −78° C. Triethylamine (3.3 ml, 23.56 mmol) was added, the reaction mixture was stirred for 15 min at −78° C., warmed to room temperature and diluted with water. The organic layer washed with 2N HCl (50 mL), 10% aqueous sodium bicarbonate solution, brine and dried over anhydrous Na₂SO₄, filtered and concentrated under reduced pressure to afford 1-benzyl-4-(2-methoxyphenyl)piperidin-3-one (0.7 g, 70%) which was used in the next step without further purification. ¹H NMR (200 MHz, CDCl₃): δ 2.72 (m, 2H) 2.91-3.045 (m, 2H), 3.71 (m, 2H), 3.80 (s, 2H), 6.87-6.99 (m, 2H), 7.12 (dd, J=7.5, 1.7 Hz, 1H), 7.18-7.45 (m, 6H); m/e=295 (M+1).

The crude 1-benzyl-4-(2-methoxyphenyl)piperidin-3-one (0.7 g, 2.37 mmol) obtained in the previous step was dissolved in 4 mL of glacial acetic acid. To this solution, 48% hydrobromic acid (4 mL) was added, and the mixture was refluxed under N₂ for 4 h. After cooling to room temperature, the reaction mixture was poured over ice cold ethyl acetate (50 mL) and concentrated ammonium hydroxide solution (50 mL). The organic phase was washed with water, brine, dried over anhydrous Na₂SO₄, filtered and concentrated under reduced pressure and the residue was purified by silica gel column chromatography to give 2-benzyl-1,2,3,4-tetrahydro [1]benzofuro[2,3-c]pyridine (200 mg, 33%). ¹H NMR (200 MHz, CDCl₃): δ 2.70-2.76 (m, 2H) 2.85-2.91 (m, 2H), 3.67 (t, J=1.8 Hz, 2H), 3.78 (s, 2H), 7.18-7.45 (m, 9H); m/e=263 (M⁺).

A mixture of 2-benzyl-1,2,3,4-tetrahydro[1]benzofuro[2, 3-c]pyridine (0.2 g, 0.75 mmol) and methyl chloroformate (0.358 g, 3.787 mmol) in dichloroethane (15 mL) was refluxed for 1 h. The reaction mixture was cooled to room temperature and washed with saturated NaHCO₃ (25 mL). The organic layer was dried over anhydrous sodium sulfate, filtered and concentrated to furnish methyl 3,4-dihydro[1]benzofuro[2,3-c]pyridine-2(1H)-carboxylate (0.150 g, 85.7%). ¹H NMR (200 MHz, CDCl₃): δ 2.70-2.76 (m, 2H), 3.80 (s, 5H), 4.72 (m, 2H), 7.22 (m, 2H), 7.42 (m, 2H).

A mixture of methyl 3,4-dihydro[1]benzofuro[2,3-c]pyridine-2(1H)-carboxylate (0.150 g, 0.6493 mmol) and concentrated HCl (10 ml) was refluxed for 18 h. The reaction mixture was cooled to 0° C., quenched with saturated aqueous NaHCO₃ (100 mL), and extracted with ethyl acetate (2×50 mL), the organic layer was dried over anhydrous Na₂SO₄, filtered and concentrated under reduced pressure to furnish 1,2,3,4-tetrahydro[1]benzofuro[2,3-c]pyridine (0.1 g, 46%). ¹H NMR (200 MHz, CDCl₃): δ 3.15 (m, 4H), 4.40 (m, 2H), 7.35 (m, 2H), 7.51 (m, 2H). MS: 160 (M⁺).

A mixture of 1,2,3,4-tetrahydro[1]benzofuro[2,3-c]pyridine (0.1 g, 0.432 mmol), Example 7 (0.112 g, 0.519 mmol) and K₂CO₃ (0.298 g, 2.164 mmol) in DMF (5 mL) was stirred at 90° C. for 3 h. The reaction mixture was cooled to room temperature, quenched by addition of water (50 mL) and extracted with ethyl acetate (2×25 mL). The organic layer was washed with water and brine, dried over anhydrous Na₂SO₄, filtered and concentrated under reduced pressure and the residue was purified by silica gel column chromatography using ethyl acetate-hexane (1:1) to furnish methyl-2-(3,4-dihydro[1]benzofuro[2,3-c]pyridin-2(1H)-yl)-pyrimidine-5-carboxylate (0.08 g, 43%). ¹H NMR (200 MHz, CDCl₃): δ 2.82 (m, 2H), 3.90 (s, 3H), 4.31 (m, 2H), 5.09 (m, 2H), 7.52 (m, 4H), 8.91 (s, 2H).

To a cooled (0° C.) solution of methyl-2-(3,4-dihydro[1]benzofuro[2,3-c]pyridin-2(1H)-yl)-pyrimidine-5-carboxylate (0.08 g, 0.2179 mmol) in methanol:DCM (6 ml, 2:1) was added 50% aqueous hydroxylamine (2 mL) and NaOH (0.08 g, 2.0 mmol) dissolved in 0.5 ml of water. The reaction mixture was stirred for 3 h at room temperature and the reaction mixture was concentrated under reduced pressure to give crude residue. The residue was neutralized with 2N HCl until the pH is neutral, the precipitated solid was filtered and dried to give Example 119 (0.040 g, 50%). ¹H NMR (200 MHz, CD₃OD): δ 2.85 (m, 2H), 4.32 (m, 2H), 5.05 (s, 2H), 7.30 (m, 2H), 7.51 (m, 2H), 8.79 (s, 2H); m/e=311 (M+1).

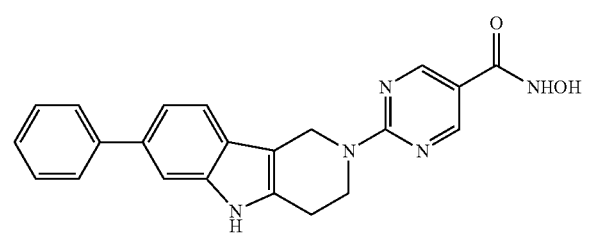

Example 120

N-hydroxy-2-{7-phenyl-1,3,4,5-tetrahydro-2H-pyrido[4,3-b]indol-2-yl}pyrimidine-5-carboxamide Methyl-2-(7-bromo-1,3,4,5-tetrahydro-2H-pyrido[4,3-b]indol-2-yl)pyrimidine-5-carboxylate was prepared in the same manner as Example 33 by substituting 3-bromophenylhydrazine for 4-bromophenylhydrazine. To a solution of the ester (1.0 g, 2.58 mmol) in THF:H₂0 (4:1) were added Cs₂CO₃ (6.71 g, 20.65 mmol) and phenylboronic acid (0.629 g, 5.16 mmol). The reaction mixture was thoroughly degassed and freshly prepared tetrakis(triphenylphosphine)palladium(0) (1.491 g, 1.29 mmol) was added under nitrogen atmosphere at room temperature. The reaction mixture temperature was raised to 80° C. and continued stirring for 12 hr. The progress of the reaction was monitored by TLC analysis and upon completion of the reaction the THF was removed under reduced pressure. The mixture was partitioned between ethyl acetate (100 mL) and water (15 mL). The organic layer was separated, dried over Na₂SO₄ filtered and the solvent was removed under reduced pressure to give crude residue, which was purified by column chromatography using silica gel to provide methyl-2-{7-phenyl-1,3,4,5-tetrahydro-2H-pyrido[4,3-b]indol-2-yl}pyrimidine-5-carboxylate (0.1 g, 10.09%).

To a 0° C. solution of methyl-2-{7-phenyl-1,3,4,5-tetrahydro-2H-pyrido[4,3-b]indol-2-yl}pyrimidine-5-carboxylate (0.1 g) in methanol:DCM (5:2 ml) was added 50% aqueous hydroxylamine solution (2 ml) and to the mixture was added solution of NaOH (0.08 g) in water (0.5 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the obtained solid was filtered and washed with water followed by diethyl ether and dried under vacuum to give Example 120 (0.025 g, 24.91%). HPLC: (Rt=14.77). ¹HNMR (DMSO-d₆, 200 MHz) δ: 11.03 (s, 1H), 8.72 (s, 2H), 7.62 (d, 2H), 7.56 (d.2H), 7.43 (m, 2H), 7.28 (d, 2H), 4.98 (s, 2H), 4.25 (m, 2H), 2.90 (m, 2H); m/e=386 (M+1).

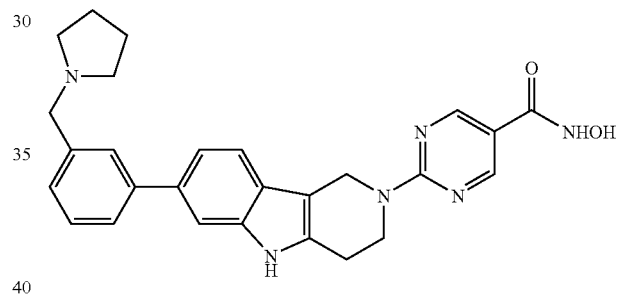

Example 121

N-hydroxy-2-{7-[3-(pyrrolidin-1-ylmethyl)phenyl]-1,3,4,5-tetrahydro-2H-pyrido[4,3-b]indol-2-yl}pyrimidine-5-carboxamide To a solution of methyl-2-(7-bromo-1,3,4,5-tetrahydro-2H-pyrido[4,3-b]indol-2-yl)pyrimidine-5-carboxylate (0.360 g, 0.93 mmol) in THF:H₂0 (4:1) were added Cs₂CO₃ (2.42 g, 7.44 mmol) and 3-formylphenylboronic acid (0.27 g, 1.86 mmol). The reaction mixture was thoroughly degassed and freshly prepared tetrakis(triphenylphosphine)palladium (0) (0.268 g, 0.23 mmol) was added under nitrogen atmosphere at room temperature. The reaction mixture temperature was raised to 80° C. and continued stirring for 12 hr. The progress of the reaction was monitored by TLC and upon completion of the reaction the THF was removed under reduced pressure. The mixture was partitioned between ethyl acetate (100 ml) and water (15 mL). The organic layer was separated, dried over Na₂SO₄ filtered and the solvent was removed under reduced pressure to give crude residue, which was purified by column chromatography using silica gel to provide methyl-2-{7-[3-(formyl)phenyl]-1,3,4,5-tetrahydro-2H-pyrido[4,3-b]indol-2-yl}pyrimidine-5-carboxylate (0.15 g, 39.13%).

To a 0° C. solution of methyl-2-{7-[3-(formyl)phenyl]-1,3,4,5-tetrahydro-2H-pyrido[4,3-b]indol-2-yl}pyrimidine-5-carboxylate (0.15 g, 0.36 mmol) in DCM (30 mL) was added Na(OAc)$_3$BH (0.154 g, 0.73 mmol) and stirred for 10 min. To the reaction mixture was added pyrrolidine (0.129 g, 1.82 mmol) under nitrogen atmosphere and the reaction mixture was continued stirring at room temperature for 4 hr. The progress of the reaction was monitored by TLC analysis and upon completion of the reaction the mixture was partitioned between DCM (50 mL) and water (25 mL) and the organic layer was separated, washed with water (2×25 mL), dried over sodium sulfate filtered and the solvent was removed under reduced pressure to give a crude residue, which was purified by column chromatography using silica gel to provide methyl-2-{7-[3-(pyrrolidin-1-ylmethyl)phenyl]-1,3,4,5-tetrahydro-2H-pyrido[4,3-b]indol-2-yl}pyrimidine-5-carboxylate (0.06 g, 35.39%).

To a 0° C. solution of methyl-2-{7-[3-(pyrrolidin-1-ylmethyl)phenyl]-1,3,4,5-tetrahydro-2H-pyrido[4,3-b]indol-2-yl}pyrimidine-5-carboxylate (0.05 g) in methanol:DCM (5:2 mL) was added 50% aqueous hydroxylamine solution (1 mL) and to the mixture was added solution of NaOH (0.04 g) in water (0.25 mL). The reaction mixture was stirred at room temperature for 1 hr and the progress of the reaction was monitored by TLC analysis and upon completion of the reaction the solvent was removed under reduced pressure. The pH of the mixture was adjusted to 7.5 using 1N HCl and the obtained solid was filtered and washed with water followed by diethyl ether and dried under vacuum to give Example 121 (0.005 g). HPLC (Rt=12.65); $^1$HNMR (DMSO-d$_6$, 200 MHz) δ: 11.017 (s, 1H), 8.73 (s, 2H), 7.23-7.56 (m, 8H), 4.99 (s, 2H), 4.25 (m, 2H), 3.63 (s, 2H), 2.90 (m, 2H), 2.49 (m, 4H), 1.69 (m, 4H); m/e=468 (M+1).

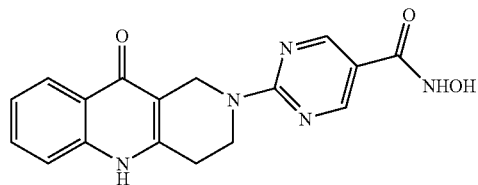

Example 122

N-hydroxy-2-(10-oxo-3,4,5,10-tetrahydrobenzo[b]-1,6-naphthyridin-2(1H)-yl)pyrimidine-5-carboxamide 1,3,4,5-Tetrahydrobenzo[b]-1,6-naphthyridin-10(2H)-one was prepared as described in *J. Am. Chem. Soc.* 1959, 81, 3098-3100. Further reaction of 1,3,4,5-tetrahydrobenzo[b]-1,6-naphthyridin-10(2H)-one with Example 7 and subsequent conversions as in Example 12 gave Example 122 as a yellow powder after hplc purification. $^1$H NMR (300 MHz, DMSO-d$_6$) δ: 2.90 (m, 2H), 4.15 (m, 2H), 4.68 (s, 2H), 7.26 (t, 1H), 7.49 (d, 1H), 7.61 (t, 1H), 8.09 (d, 1H), 8.72 (s, 2H), 9.0 (bs, 1H), 11.08 (s, 1H), 11.69 (s, 1H); m/e=338 (M+1).

Example 123

N-hydroxy-2-{8-[(4-methylpiperazin-1-yl)methyl]-1,3,4,5-tetrahydro-2H-pyrido[4,3-b]indol-2-yl}pyrimidine-5-carboxamide To a 0° C. cooled solution of 4-nitrobenzaldehyde in DCM (40 mL) was added Na(OAc)$_3$BH (10.526 gm, 49.66 mmol) and the reacton was stirred for 10 min. To the reaction mixture was added N-methylpiperazine (9.93 g, 99.3 mmol) under nitrogen atmosphere and the reaction mixture was continued stirring at room temperature for 4 h. The progress of the reaction was monitored by TLC and upon completion of the reaction, the mixture was partitioned between DCM (20 mL) and water (15 mL) and the organic layer was separated, washed with water (2×15 mL), dried over sodium sulphate, filtered and the solvent was removed under reduced pressure to give crude residue. Washing with ether gave 1-methyl-4-(4-nitrobenzyl)piperazine (4 g). $^1$H NMR (CDCl$_3$, 200 MHz) δ: 8.19 (2H, d, J=8.4 Hz), 7.53 (2H, d, J=8.4 Hz), 3.59 (2H, s), 2.47 (8H, bm), 2.29 (3H, s); m/e=236 (M+1).

To a solution of 1-methyl-4-(4-nitrobenzyl)piperazine (4.0 g) in methanol (100 mL) at room temperature under nitrogen atmosphere was added Raney nickel (1.6 gm). The reaction mixture was stirred for 2 hr under hydrogen atmosphere. The progress of the reaction was monitored by TLC and upon completion of the reaction, the mixture was filtered under nitrogen atmosphere and the solvent was removed under reduced pressure to give 4-[(4-methylpiperazin-1-yl)methyl] aniline (3.2 g). $^1$H NMR (CDCl$_3$, 200 MHz) δ: 7.13 (2H, d, J=8.4 Hz), 6.61 (2H, d, J=8.4 Hz), 3.41 (2H, s), 2.45 (8H, bm), 2.27 (3H, s); m/e=206 (M+1).

To a stirred solution of 4-[(4-methylpiperazin-1-yl)methyl]aniline (3.2 g, 15.57 mmol) in acetic acid: concentrated HCl (32:32 mL) at 10° C. was added NaNO$_2$ (1.30 g, 18.78 mmol) in water (16 mL) and stirred for 10 min. Freshly prepared SnCl$_2$.2H$_2$O (11.75 g, 51.97 mmol) in concentrated HCl (32 mL) was added at 10° C. The temperature of the reaction mixture was allowed to rise to room temperature and maintained there for 4 hr. After filtering the reaction mixture, the precipitate was washed with water and the solid obtained was dried under reduced pressure to obtain 1-(4-hydrazinobenzyl)-4-methylpiperazine (3.4 g). $^1$H NMR (CD$_3$OD, 200 MHz) δ: 7.66 (2H, d, J=8.4 Hz), 7.13 (2H, d, J=8.4 Hz), 4.46 (2H, s), 3.72 (8H, bm), 3.11 (3H, s);

To a solution of 1-(4-hydrazinobenzyl)-4-methylpiperazine (3.4 g, 13.25 mmol) in ethanol (50 mL) were added piperidone. HCl (2.51 g, 18.55 mmol). The reaction temperature was raised to 90° C. and continued stirring for 2 hrs. The progress of the reaction was monitored by TLC and upon completion of the reaction the mixture was cooled to rt and HCl gas was bubbled through the reaction mixture at 0° C. After the reaction mixture was saturated with HCl, the temperature was raised to 90° C. again and continued stirring for 2 hrs. The ethanolic HCl was removed under reduced pressure and the pH of the reaction mixture was adjusted to 12.0 with 10% NaOH solution. The mixture was partitioned between 20% MeOH:DCM and water (35 mL) and the organic layer was separated, dried over Na$_2$SO$_4$ filtered and the solvent was removed under reduced pressure to give crude residue. Washing with ether gave 8-[(4-methylpiperazin-1-yl)methyl]-2,3,4,5-tetrahydro-1H-pyrido[4,3-b]indole (1 g). $^1$H NMR (CD$_3$OD, 200 MHz) δ: 7.31 (1H, s), 7.27 (1H, d, J=8.6 Hz), 7.06 (1H, d, J=8.6 Hz), 4.01 (2H, s), 3.60 (2H, s), 3.21 (8H, bm), 2.86 (4H, m), 2.28 (3H, s); m/e=285 (M+1).

To a solution of 8-[(4-methylpiperazin-1-yl)methyl]-2,3,4,5-tetrahydro-1H-pyrido[4,3-b]indole (0.5 g, 1.76 mmol) in

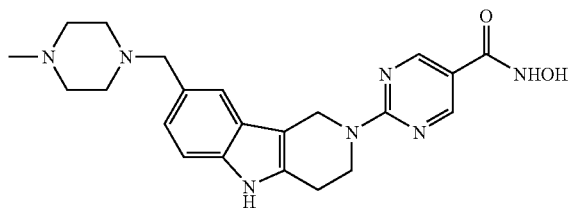

DMF (15 mL) at rt was added Example 7 (0.567 g, 2.64 mmol) and K$_2$CO$_3$ (0.731 g, 5.28 mmol). The reaction temperature was raised to 100° C. and continued stirring for 12 hr. The progress of the reaction was monitored by TLC and upon completion of the reaction DMF was removed under reduced pressure. The reaction mixture was partitioned between ethyl acetate (100 mL) and water (80 mL) and the organic layer was separated, dried over sodium sulphate, filtered and the solvent was removed under reduced pressure to give crude residue. Washing with ether gave methyl 2-{8-[(4-methylpiperazin-1-yl)methyl]-1,3,4,5-tetrahydro-2H-pyrido[4,3-b]indol-2-yl}pyrimidine-5-carboxylate (0.15 g). $^1$H NMR (DMSO-D$_6$, 200 MHz) δ: 8.84 (2H, s), 7.94 (1H,s), 7.67 (1H, d, J=8.6 Hz), 7.54 (1H, d, J=8.6 Hz), 5.01 (2H, s), 3.80-3.01 (10H, m), 2.87 (3H, s); m/e=421 (M+1).

To a 0° C. solution of methyl 2-{8-[(4-methylpiperazin-1-yl)methyl]-1,3,4,5-tetrahydro-2H-pyrido[4,3-b]indol-2-yl}pyrimidine-5-carboxylate (0.1 g) in MeOH:DCM (5:2 mL) was added 50% aqueous hydroxylamine solution (2 mL) and to the mixture was added a solution of NaOH (0.08 g) in water (1 mL). The reaction mixture was stirred at room temperature for 1 hr and the progress of the reaction was monitored by TLC and upon completion of the reaction the solvent was removed under reduced pressure. The pH of the mixture was adjusted to 7.5 using 1N HCl and the obtained solid was filtered and washed with water followed by diethyl ether. After filtering, the solid was dried under vacuum to give N-hydroxy-2-{8-[(4-methylpiperazin-1-yl)methyl]-1,3,4,5-tetrahydro-2H-pyrido[4,3-b]indol-2-yl}pyrimidine-5-carboxamide (0.075 g). $^1$H NMR (DMSO-D$_6$, 200 MHz) δ: 10.91 (2H, bm), 8.74 (2H, s), 7.64-7.01 (3H, m), 4.91 (2H, s), 4.19 (2H, s), 3.50-2.88 (10H, m), 2.87 (3H, s); m/e=422.9 (M+1).

BIOLOGICAL EXAMPLES

Example A

In Vitro Fluorescent Histone Deacetylase Assay

Histone deacetylase (HDAC) activity assays were performed using the HDAC fluorescent activity assay/drug discovery kit (Biomol Research Laboratories, Plymouth Meeting, Pa.) essentially according to the manufacturer's instructions. The included HeLa cell nuclear extract, which contains a mosaic of HDAC enzymes and other nuclear factors, was used as the source of HDAC activity. The final substrate concentration in the assay mixture was 50 μM. The reaction was allowed to proceed for 10 min at room temperature before stopping the reaction. Test compounds were prepared as 20 mM stock solutions in DMSO (Molecular Biology grade, Sigma-Aldrich Co., St. Louis, Mo.) and stored at −70° C. Serial dilutions of test compounds were prepared in assay buffer immediately prior to testing. DMSO was determined in a separate trial to have no significant effect on the activity of this assay at concentrations up to 5%; the final DMSO concentration in the wells was no more than 2% and therefore DMSO effects were safely neglected. Assays were performed in white polystyrene 96-well half-area assay plates (Corning, Corning, N.Y.) and measured on a Wallac 1420 fluorescent plate reader (Wallac Oy, Turku, Finland) with an excitation wavelength of 355 nm, an emission wavelength of 460 nm, and a 1 sec signal averaging time.

The following table shows the percent inhibition of HDAC produced by some of the examples of the present invention at a concentration of 100 μM.

TABLE 1

Inhibition of histone deacetylase at 100 μM concentration.

| Example Number | % Inhibition of HDAC @ 100 μM |
|---|---|
| 3 | 97.9 |
| 4 | 99.1 |
| 5 | 99.7 |
| 9 | 99.9 |
| 10 | 99.5 |
| 11 | 99.8 |
| 12 | 99.9 |
| 13 | 99.9 |
| 14 | 99.9 |
| 15 | 99.8 |
| 16 | 98.9 |
| 18 | 98.5 |
| 19 | 97.6 |
| 20 | 99.6 |
| 21 | 98.5 |
| 22 | 98.2 |
| 23 | 99.3 |
| 24 | 99 |
| 25 | 98 |
| 26 | 98.9 |
| 27 | 98.3 |
| 28 | 95.2 |
| 29 | 99.8 |
| 30 | 98.1 |
| 31 | 100 |
| 32 | 96.6 |
| 34 | 99.1 |
| 35 | 99.9 |
| 36 | 99.8 |
| 37 | 99.9 |
| 38 | 99.8 |
| 39 | 98.8 |
| 40 | 99.8 |
| 41 | 99.6 |
| 42 | 100 |
| 43 | 100 |
| 44 | 99.9 |
| 45 | 99.9 |
| 46 | 99.8 |
| 47 | 100 |
| 48 | 99.7 |
| 49 | 99.9 |
| 50 | 99.7 |
| 51 | 99.8 |
| 52 | 99.7 |
| 53 | 100 |
| 54 | 99.5 |
| 55 | 99.3 |
| 56 | 99.8 |
| 57 | 99.9 |
| 58 | 97.7 |
| 59 | 97.3 |
| 60 | 100 |
| 61 | 99.9 |
| 62 | 99.9 |
| 63 | 99.8 |
| 64 | 99.9 |
| 65 | 99.8 |
| 67 | 99.9 |
| 68 | 99.9 |
| 70 | 99.9 |
| 71 | 99.9 |
| 72 | 99.8 |
| 73 | 99.6 |
| 74 | 99.1 |
| 75 | 99.9 |
| 76 | 100 |
| 77 | 100 |
| 78 | 99.9 |
| 79 | 100 |
| 82 | 99.9 |
| 83 | 99.9 |
| 84 | 99.9 |
| 86 | 100 |

TABLE 1-continued

Inhibition of histone deacetylase at 100 μM concentration.

| Example Number | % Inhibition of HDAC @ 100 μM |
|---|---|
| 87 | 100 |
| 88 | 100 |
| 90 | 99.8 |
| 91 | 100 |
| 92 | 99.9 |
| 93 | 100 |
| 94 | 99.7 |
| 95 | 100 |
| 96 | 100 |
| 97 | 100 |
| 99 | 99.9 |
| 100 | 100 |
| 101 | 100 |
| 103 | 99.9 |
| 104 | 100 |
| 105 | 99.9 |
| 106 | 99.9 |
| 107 | 99.9 |
| 108 | 100 |
| 109 | 100 |
| 110 | 100 |
| 111 | 99.9 |
| 112 | 99.9 |
| 113 | 100 |
| 114 | 99.9 |
| 115 | 99.9 |
| 116 | 100 |
| 117 | 99.8 |
| 118 | 99.7 |
| 119 | 99.3 |
| 120 | 99.6 |
| 121 | 99.6 |
| 122 | 100 |
| 123 | 100 |

In some assays recombinant HDAC8 (Biomol) was used as the source of the enzyme activity; here the final substrate concentration was 250 μM, the final concentration of HDAC8 was 0.02 Units/μL and the reaction was allowed to proceed at 37° C. for 1 h before stopping. For all curves, $IC_{50}$ values were calculated with the GraFit curve-fitting program (Erithacus, Horley, Surrey, UK).

Example B

Whole Cell Cytotoxicity Assay:Sulforhodamine B

The following procedure can be found on the Developmental Therapeutics Program NCl/NIH web site at http://dtp.nci.nih.gov/brancehes/btb/ivclsp.html.

1. Human tumor cell lines of HT29, A549 and MCF7 are grown in DMEM containing 10% fetal bovine serum and 2 mM L-glutamine. Cells are plated in a 96 well plate at a density of 5000 cells per well in 100 μL of growth medium and incubated at 37° C., 5% $CO_2$, for 24 hours prior to the addition of experimental compounds.
2. Experimental drugs are solubilized in DMSO for a final concentration of 20 mM immediately prior to use. Drugs are further diluted in growth media for a total of nine drug concentrations and a growth control. At the 24 hour time point, one plate of cells is fixed in situ with TCA as a measurement of the cell population at time zero, or the time of drug addition.
3. The plates are further incubated with drug for an additional 48 hours.
4. The cells are fixed in situ by gently aspirating off the culture media and then adding 50 μL of ice cold 10% TCA per well and incubated at 4° C. for 60 minutes. The plates are washed with tap water five times and allowed to air dry for 5 minute.
5. 50 μL of a 0.4% (w/v) Sulforhodamine B solution in 1% (v/v) acetic acid is added per well and incubated for 30 minutes at room temperature.
6. Following staining, plates are washed five times with 1% acetic acid to remove any unbound dye and then allowed to air dry for 5 minutes.
7. Stain is solubilized with 100 μL of 10 mM Tris pH 10.5 per well and placed on an orbital rotator for 5 minutes.
8. Absorbance is read at 570 nm.

The following table shows the percent inhibition of MCF7 cell growth produced by some of the examples of the present invention at a concentration of 100 μM.

TABLE 2

Inhibition of HCT116 cell growth by examples at a 100 μM concentration.

| Example Number | % Inhibition of HCT116 cell growth @ 100 μM |
|---|---|
| 3 | 98.3 |
| 4 | 98.5 |
| 5 | 99.9 |
| 9 | 99.3 |
| 10 | 98.4 |
| 11 | 99 |
| 12 | 98.7 |
| 13 | 99.1 |
| 14 | 98.1 |
| 15 | 99 |
| 16 | 99 |
| 18 | 98.5 |
| 19 | 97.2 |
| 20 | 98.2 |
| 21 | 94 |
| 22 | 98.2 |
| 23 | 98.1 |
| 24 | 98.9 |
| 25 | 94 |
| 26 | 99 |
| 27 | 98.9 |
| 28 | 98.7 |
| 29 | 98 |
| 30 | 96.8 |
| 31 | 99.5 |
| 32 | 94.6 |
| 34 | 99.3 |
| 35 | 97.3 |
| 36 | 98.3 |
| 37 | 97.1 |
| 38 | 99.5 |
| 39 | 99.4 |
| 40 | 98.3 |
| 41 | 98.7 |
| 42 | 88.0 |
| 43 | 98.7 |
| 44 | 97.6 |
| 45 | 98.9 |
| 46 | 98.6 |
| 47 | 98.1 |
| 48 | 97.8 |
| 49 | 99.3 |
| 50 | 89.1 |
| 51 | 98.7 |
| 52 | 98.9 |
| 53 | 96.4 |
| 54 | 98.9 |
| 55 | 99.1 |

TABLE 2-continued

Inhibition of HCT116 cell growth by examples at a 100 μM concentration.

| Example Number | % Inhibition of HCT116 cell growth @ 100 μM |
|---|---|
| 56 | 99.0 |
| 57 | 98.2 |
| 58 | 96.3 |
| 59 | 97.5 |
| 60 | 99.0 |
| 61 | 98.2 |
| 62 | 96.2 |
| 63 | 98.9 |
| 64 | 98.7 |
| 65 | 98.4 |
| 67 | 98.2 |
| 68 | 98.9 |
| 70 | 97.9 |
| 71 | 98.6 |
| 72 | 95.6 |
| 73 | 99.4 |
| 74 | 93.6 |
| 75 | 98.4 |
| 76 | 98.9 |
| 77 | 98.1 |
| 78 | 85.1 |
| 79 | 95.7 |
| 82 | 97.0 |
| 83 | 94.7 |
| 84 | 93.2 |
| 86 | 99.1 |
| 87 | 83.1 |
| 88 | 98.4 |
| 90 | 93.1 |
| 91 | 98.6 |
| 92 | 98.9 |
| 93 | 98.0 |
| 94 | 98.5 |
| 95 | 98.2 |
| 96 | 98.7 |
| 97 | 98.1 |
| 99 | 93.8 |
| 100 | 96.6 |
| 101 | 97.9 |
| 103 | 98.9 |
| 104 | 92.0 |
| 105 | 97.0 |
| 106 | 98.3 |
| 107 | 92.7 |
| 108 | 99.1 |
| 109 | 91.7 |
| 110 | 98.7 |
| 111 | 97.7 |
| 112 | 98.7 |
| 113 | 98.7 |
| 114 | 99.3 |
| 115 | 98.8 |
| 116 | 98.6 |
| 117 | 98.6 |
| 118 | 98.9 |
| 119 | 98.6 |
| 120 | 97.6 |
| 121 | 97.5 |
| 122 | 44.4 |
| 123 | 97 |

What is claimed is:

1. A compound of formula I:

wherein

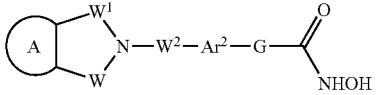

and the ring containing $W^1$ and W to which it is fused together form an optionally substituted 1,3,4,9-tetrahydro-2H-b-carbolin-2-yl or an optionally substituted 1,3,4,4a,9,9a-hexahydro-2H-b-carbolin-2-yl substituent;

$W^2$ is a bond or $[-C(R^1)(R^2)-]_p$;

$R^1$ and $R^2$ are independently selected from the group consisting of hydrogen, alkyl, substituted alkyl, aryl, substituted aryl, heteroaryl, substituted heteroaryl, heterocyclic, and substituted heterocyclic;

p is 1, 2, 3 or 4;

wherein $Ar^2$-G-C(O)NHOH, is 5-[-G-C(O)NHOH]-pyrimid-2-ylene

G is a bond; or a tautomer, stereoisomer, prodrug, or pharmaceutically acceptable salt thereof.

2. The compound according to claim 1, wherein $W^2$ is a bond.

3. The compound according to claim 2, wherein said compound is:

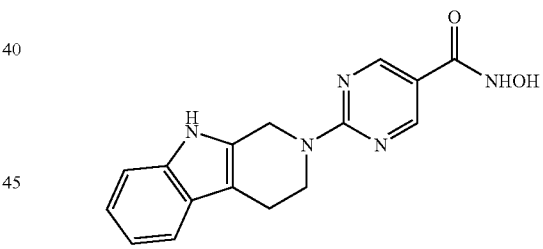

[N-hydroxy-2-(1,3,4,9-tetrahydro-2H-b-carbolin-2-yl)pyrimidine-5-carboxamide],

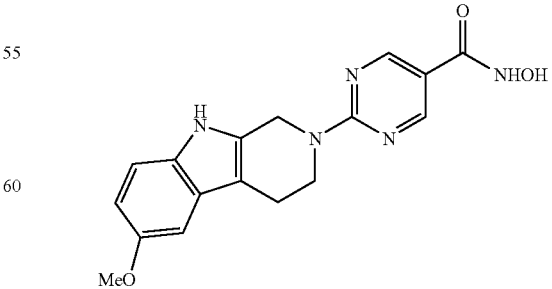

[N-hydroxy-2-(6-methoxy-1,3,4,9-tetrahydro-2H-b-carbolin-2-yl)pyrimidine-5-carboxamide],

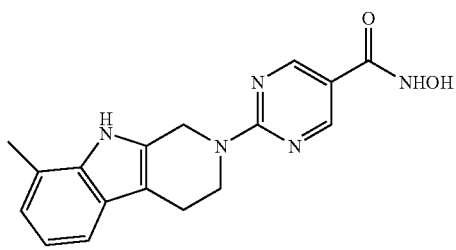

[N-hydroxy-2-(8-methyl-1,3,4,9-tetrahydro-2H-b-carbolin-2-yl)pyrimidine-5-carboxamide],

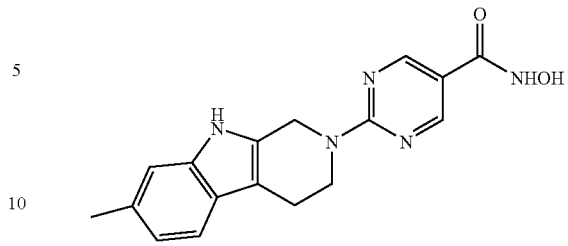

[N-hydroxy-2-(7-methyl-1,3,4,9-tetrahydro-2H-b-carbolin-2-yl)pyrimidine-5-carboxamide],

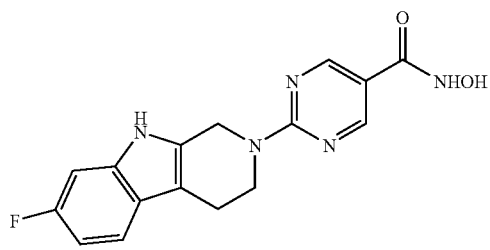

[N-hydroxy-2-(7-fluoro-1,3,4,9-tetrahydro-2H-b-carbolin-2-yl)pyrimidine-5-carboxamide],

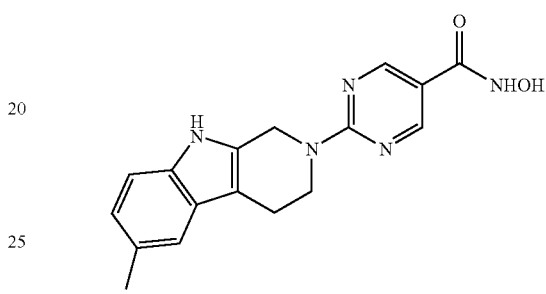

[N-hydroxy-2-(6-methyl-1,3,4,9-tetrahydro-2H-b-carbolin-2-yl)pyrimidine-5-carboxamide],

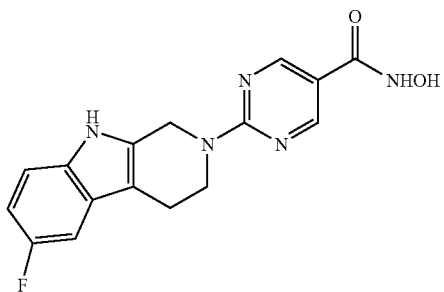

[N-hydroxy-2-(6-fluoro-1,3,4,9-tetrahydro-2H-b-carbolin-2-yl)pyrimidine-5-carboxamide],

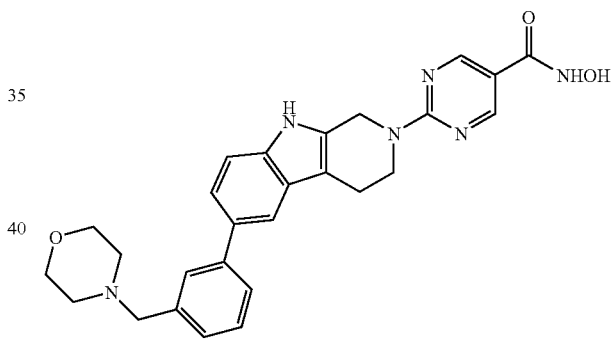

[N-hydroxy-2-{6-[3-(morpholin-4-ylmethyl)phenyl]-1,3,4,9-tetrahydro-2H-b-carbolin-2-yl}pyrimidine-5-carboxamide],

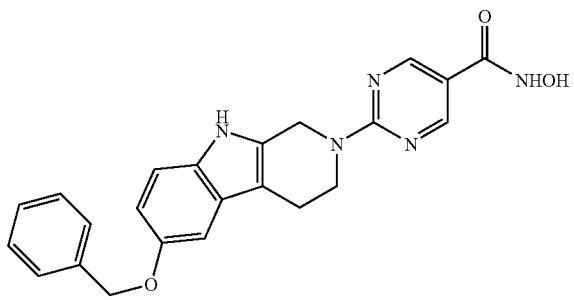

[N-hydroxy-2-(6-benzyloxy-1,3,4,9-tetrahydro-2H-b-carbolin-2-yl)pyrimidine-5-carboxamide],

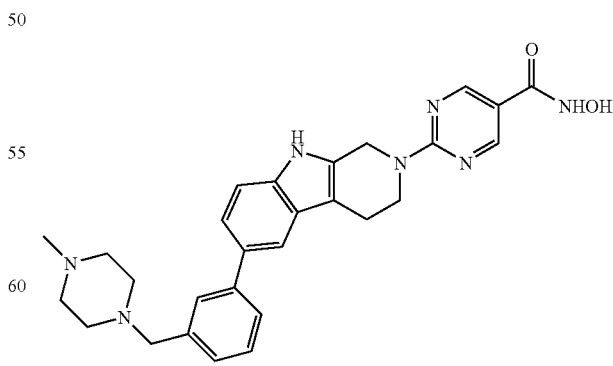

[N-hydroxy-2-{6-[3-((4-methylpiperazin-1-yl)methyl)phenyl]-1,3,4,9-tetrahydro-2H-b-carbolin-2-yl}pyrimidine-5-carboxamide],

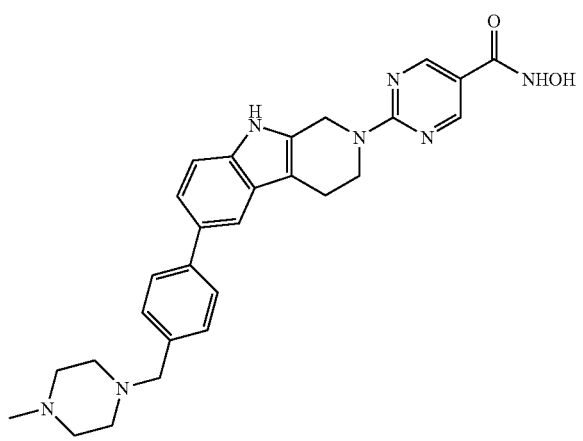

[N-hydroxy-2-{6-[4-((4-methylpiperazin-1-yl)methyl)phenyl]-1,3,4,9-tetrahydro-2H-b-carbolin-2-yl}pyrimidine-5-carboxamide],

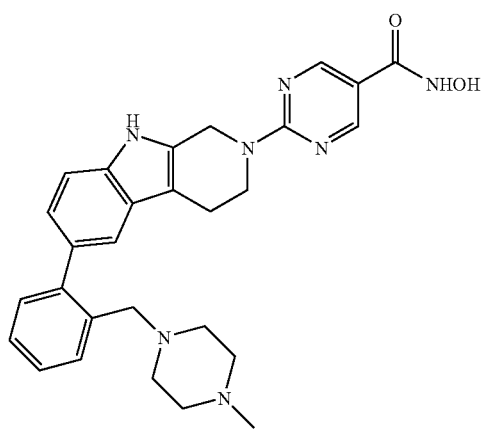

[N-hydroxy-2-{6-[2-((4-methylpiperazin-1-yl)methyl)phenyl]-1,3,4,9-tetrahydro-2H-b-carbolin-2-yl}pyrimidine-5-carboxamide],

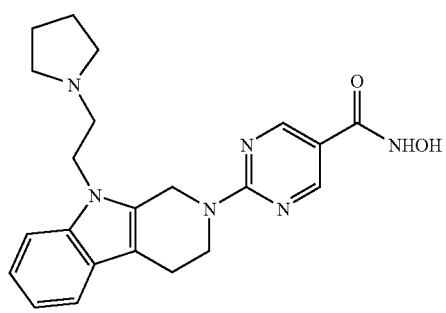

[N-hydroxy-2-{9-[2-pyrrolidin-1-ylethyl]-1,3,4,9-tetrahydro-2H-b- carbolin-2-yl}pyrimidine-5-carboxamide],

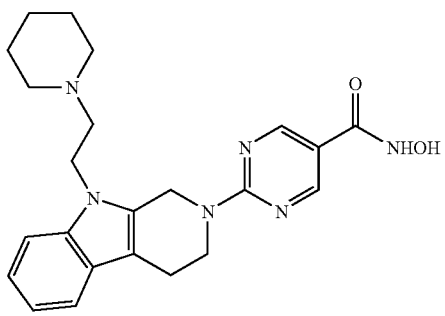

[N-hydroxy-2-[9-(2-piperidin-1-ylethyl)-1,3,4,9-tetrahydro-2H-b-carbolin-2-yl]pyrimidine-5-carboxamide],

[N-hydroxy-2-[9-(2-morpholin-4-ylethyl)-1,3,4,9-tetrahydro-2H-b- carbolin-2-yl]pyrimidine-5-carboxamide],

[N-hydroxy-2-[9-(phenylsulfonyl)-1,3,4,9-tetrahydro-2H-b-carbolin-2-yl]pyrimidine-5-carboxamide],

[N-hydroxy-2-(9-methyl-1,3,4,9-tetrahydro-2H-b-carbolin-2-yl)pyrimidine-5-carboxamide],

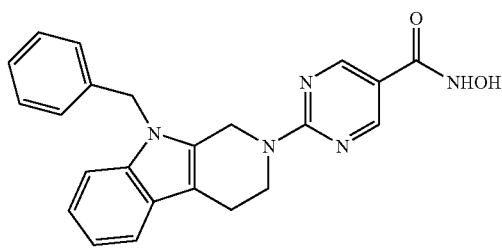

[N-hydroxy-2-(9-benzyl-1,3,4,9-tetrahydro-2H-b-carbolin-2-yl)pyrimidine-5-carboxamide],

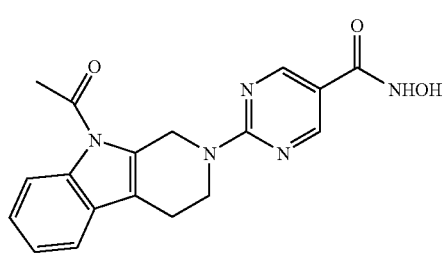

[2-(9-acetyl-1,3,4,9-tetrahydro-2H-b-carbolin-2-yl)-N-hydroxypyrimidine-5-carboxamide],

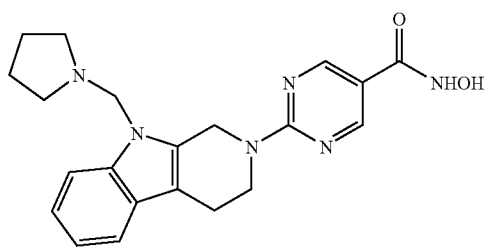

[N-hydroxy-2-{9-[2-pyrrolidin-1-ylmethyl]-1,3,4,9-tetrahydro-2H-b-carbolin-2-yl}pyrimidine-5-carboxamide],

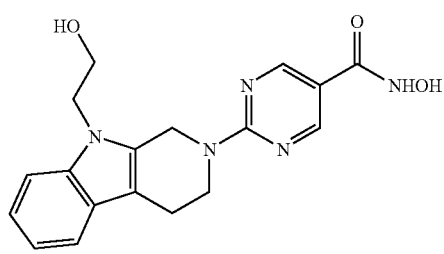

[N-hydroxy-2-[9-(2-hydroxyethyl)-1,3,4,9-tetrahydro-2H-b-carbolin-2-yl]pyrimidine-5-carboxamide],

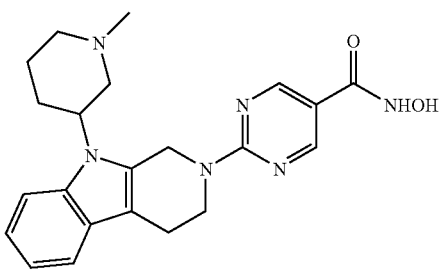

[N-hydroxy-2-[9-(1-methylpiperidin-3-yl)-1,3,4,9-tetrahydro-2H-b-carbolin-2-yl]pyrimidine-5-carboxamide] or

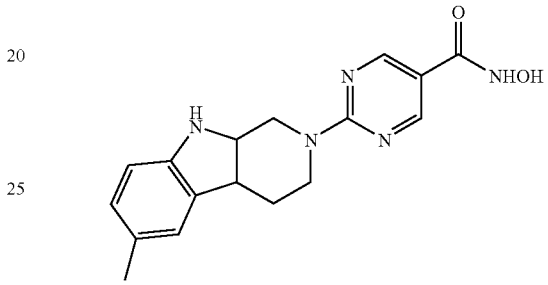

[N-hydroxy-2-(6-methyl-1,3,4,4a,9,9a-hexahydro-2H-b-carbolin-2-yl)pyrimidine-5-carboxamide].

4. A compound of formula I:

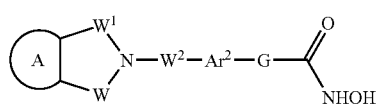

wherein

and the ring containing $W^1$ and W to which it is fused together form an optionally substituted 1,3,4,5-tetrahydro-2H-pyrido[4,3-b]indol-2-yl or an optionally substituted 1,1a,3,4,4a,5-hexahydro-2H-pyrido[4,3-b]indol-2-yl substituent;

$W^2$ is a bond or $[-C(R^1)(R^2)-]_p$;

$R^1$ and $R^2$ are independently selected from the group consisting of hydrogen, alkyl, substituted alkyl, aryl, substituted aryl, heteroaryl, substituted heteroaryl, heterocyclic, and substituted heterocyclic;

p is 1, 2, 3 or 4;

wherein $Ar^2$-G-C(O)NHOH, is 5-[-G-C(O)NHOH]-pyrimid-2-ylene G is a bond; or a tautomer, stereoisomer, prodrug, or pharmaceutically acceptable salt thereof.

5. The compound according to claim 4, wherein $W^2$ is a bond.

6. The compound according to claim 5, wherein said compound is:

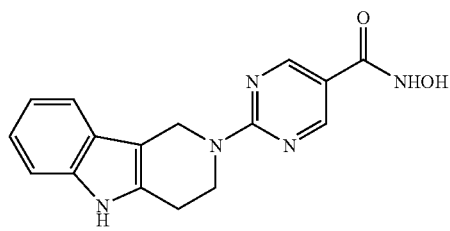

[N-hydroxy-2-(1,3,4,5-tetrahydro-2H-pyrido[4,3-b]indol-2-yl)pyrimidine-5-carboxamide],

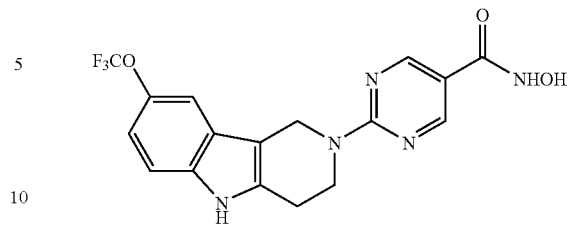

[N-hydroxy-2-[8-(trifluoromethoxy)-1,3,4,5-tetrahydro-2H-pyrido[4,3-b]indol-2-yl]pyrimidine-5-carboxamide],

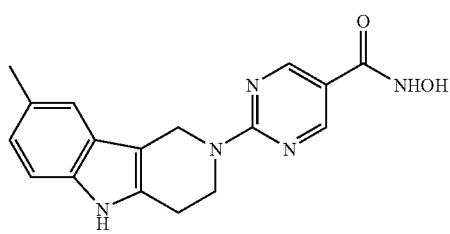

[N-hydroxy-2-(8-methyl-1,3,4,5-tetrahydro-2H-pyrido[4,3-b]indol-2-yl)pyrimidine-5-carboxamide],

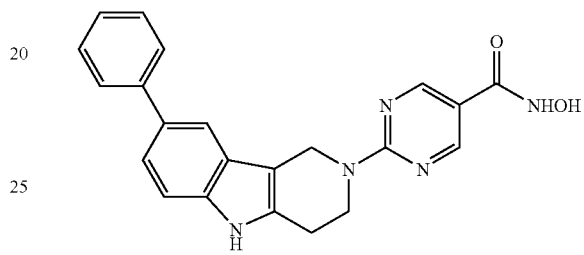
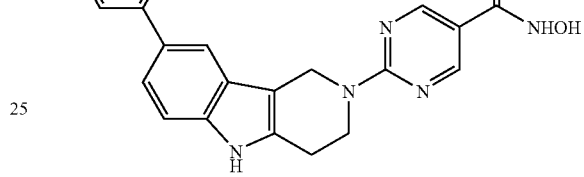

[N-hydroxy-2-(8-phenyl-1,3,4,5-tetrahydro-2H-pyrido[4,3-b]indol-2-yl)pyrimidine-5-carboxamide].

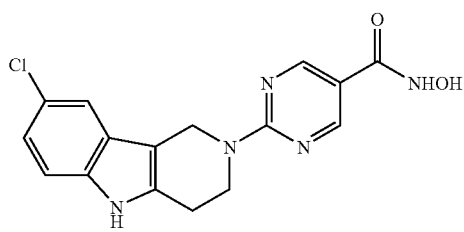

[2-(8-chloro-1,3,4,5-tetrahydro-2H-pyrido[4,3-b]indol-2-yl)-N-hydroxypyrimidine-5-carboxamide],

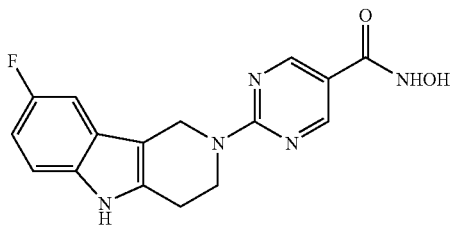

[N-hydroxy-2-(8-fluoro-1,3,4,5-tetrahydro-2H-pyrido[4,3-b]indol-2-yl)pyrimidine-5-carboxamide],

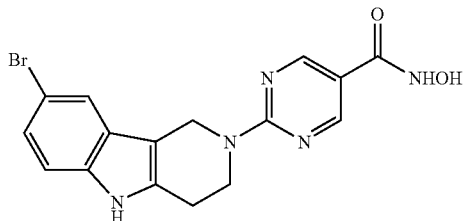

[2-(8-bromo-1,3,4,5-tetrahydro-2H-pyrido[4,3-b]indol-2-yl)-N-hydroxypyrimidine-5-carboxamide],

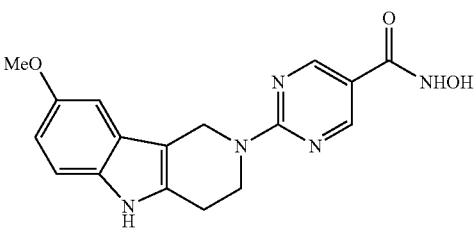
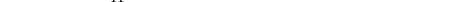

[N-hydroxy-2-(8-methoxy-1,3,4,5-tetrahydro-2H-pyrido[4,3-b]indol-2-yl)pyrimidine-5-carboxamide],

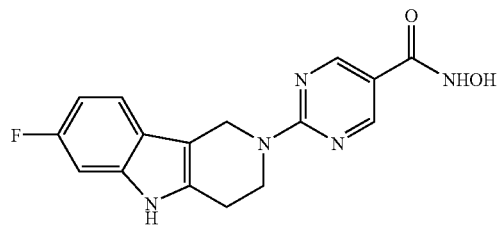

[N-hydroxy-2-(7-fluoro-1,3,4,5-tetrahydro-2H-pyrido[4,3-b]indol-2-yl)pyrimidine-5-carboxamide],

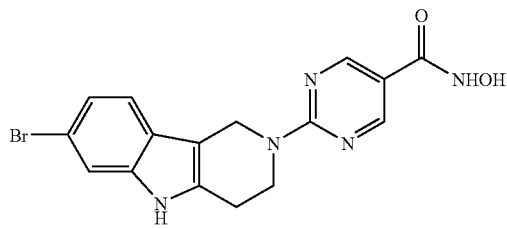

[N-hydroxy-2-(7-bromo-1,3,4,5-tetrahydro-2H-pyrido[4,3-b]indol-2-yl)pyrimidine-5-carboxamide],

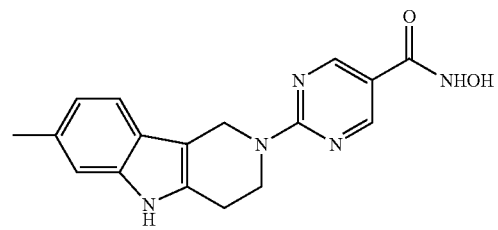

[N-hydroxy-2-(7-methyl-1,3,4,5-tetrahydro-2H-pyrido[4,3-b]indol-2-yl)pyrimidine-5-carboxamide],

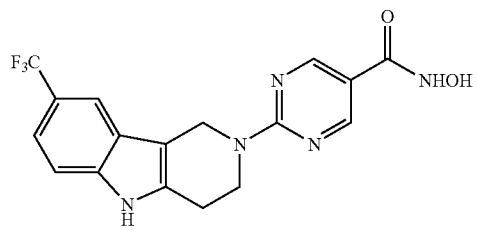

[N-hydroxy-2-(8-trifluoromethyl-1,3,4,5-tetrahydro-2H-pyrido[4,3-b]indol-2-yl)pyrimidine-5-carboxamide],

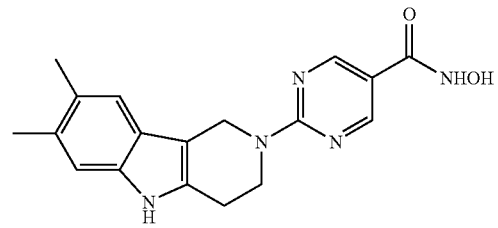

[N-hydroxy-2-(7,8-dimethyl-1,3,4,5-tetrahydro-2H-pyrido[4,3-b]indol-2-yl)pyrimidine-5-carboxamide],

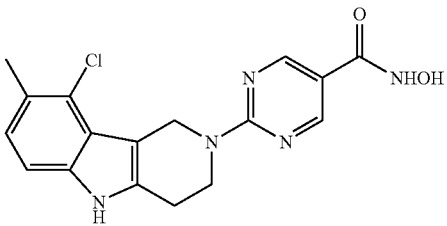

[N-hydroxy-2-(9-chloro-8-methyl-1,3,4,5-tetrahydro-2H-pyrido[4,3-b]indol-2-yl)pyrimidine-5-carboxamide],

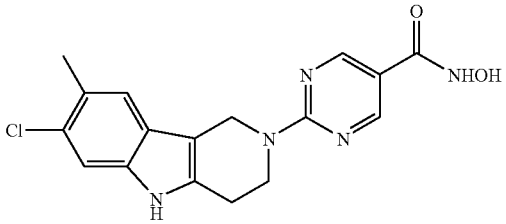

[N-hydroxy-2-(7-chloro-8-methyl-1,3,4,5-tetrahydro-2H-pyrido[4,3-b]indol-2-yl)pyrimidine-5-carboxamide],

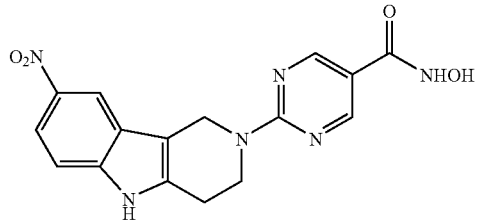

[N-hydroxy-2-(8-nitro-1,3,4,5-tetrahydro-2H-pyrido[4,3-b]indol-2-yl)pyrimidine-5-carboxamide].

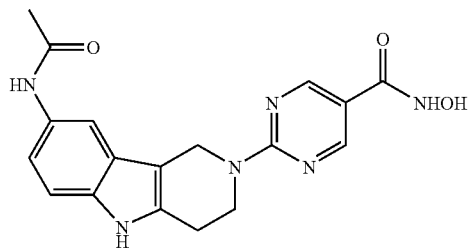

[N-hydroxy-2-(8-(N-acetamido)-1,3,4,5-tetrahydro-2H-pyrido[4,3-b]indol-2-yl)pyrimidine-5-carboxamide],

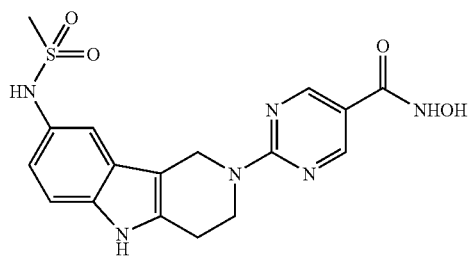

[N-hydroxy-2-(8-(N-methylsulfonamido)-1,3,4,5-tetrahydro-2H-pyrido[4,3-b]indol-2-yl)pyrimidine-5-carboxamide],

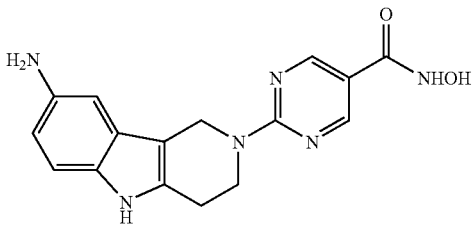

[N-hydroxy-2-(8-amino-1,3,4,5-tetrahydro-2H-pyrido[4,3-b]indol-2-yl)pyrimidine-5-carboxamide],

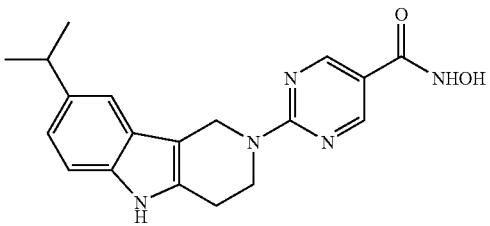

[N-hydroxy-2-{8-isopropyl-1,3,4,5-tetrahydro-2H-pyrido[4,3-b]indol-2-yl}pyrimidine-5-carboxamide],

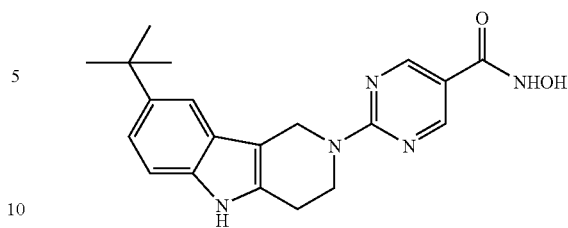

[N-hydroxy-2-{8-tert-butyl-1,3,4,5-tetrahydro-2H-pyrido[4,3-b]indol-2-yl}pyrimidine-5-carboxamide],

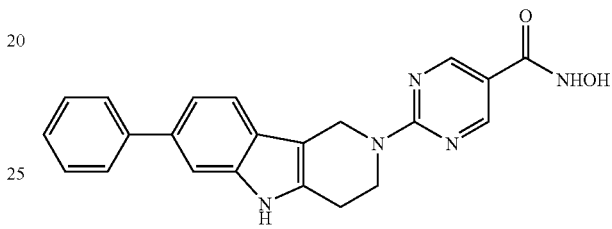

[N-hydroxy-2-{7-phenyl-1,3,4,5-tetrahydro-2H-pyrido[4,3-b]indol-2-yl}pyrimidine-5-carboxamide],

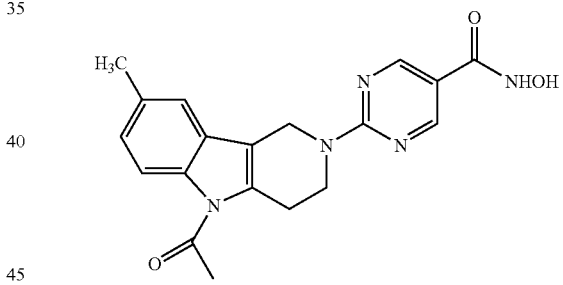

[N-hydroxy-2-{5-acetyl-8-methyl-1,3,4,5-tetrahydro-2H-pyrido[4,3-b]indol-2-yl}pyrimidine-5-carboxamide],

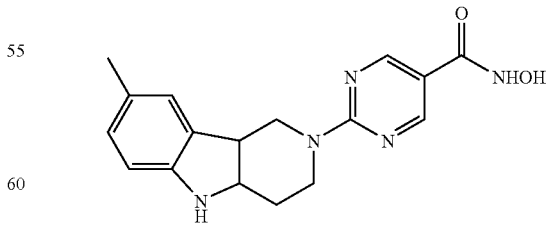

[N-hydroxy-2-(8-methyl-1,3,4,4a,5,9b-hexahydro-2H-pyrido[4,3-b]indol-2-yl)pyrimidine-5-carboxamide] or

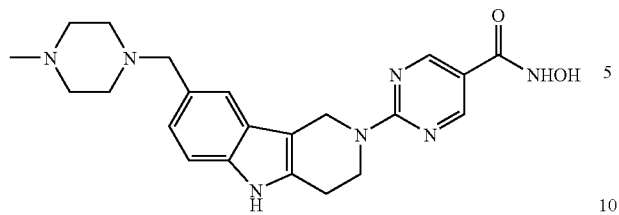

[N-hydroxy-2-{8-[(4-methylpiperazin-1-yl)methyl]-1,3,4,5-tetrahydro-2H-pyrido[4,3-b]indol-2-yl}pyrimidine-5-carboxamide].

7. The compound according to claim 4, wherein said compound is:

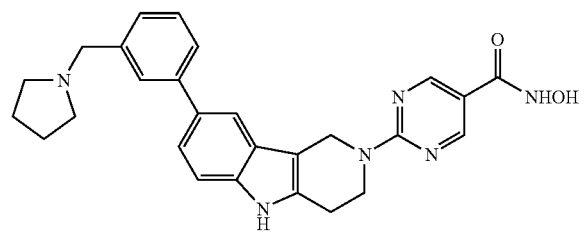

[N-hydroxy-2-{8-[3-(pyrrolidin-1-ylmethyl)phenyl]-1,3,4,5-tetrahydro-2H-pyrido[4,3-b]indol-2-yl}pyrimidine-5-carboxamide],

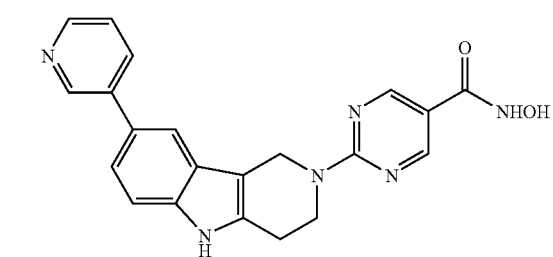

[N-hydroxy-2-{8-(pyridin-3-yl)-1,3,4,5-tetrahydro-2H-pyrido[4,3-b]indol-2-yl}pyrimidine-5-carboxamide],

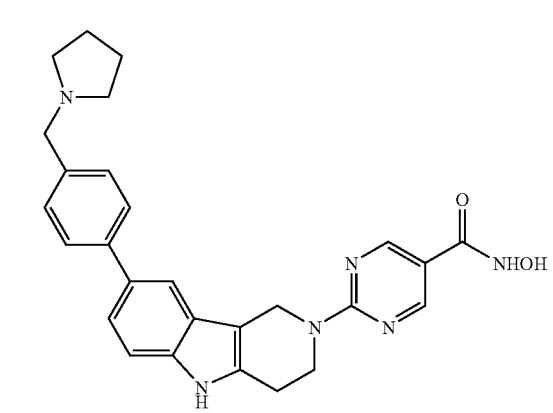

[N-hydroxy-2-{8-[4-(pyrrolidin-1-ylmethyl)phenyl]-1,3,4,5-tetrahydro-2H-pyrido[4,3-b]indol-2-yl}pyrimidine-5-carboxamide],

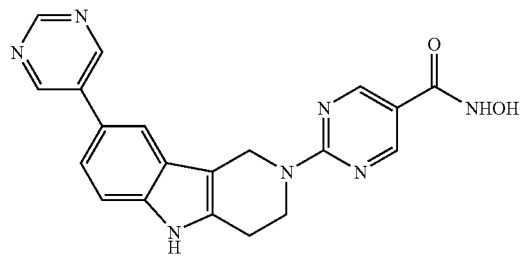

[N-hydroxy-2-{8-(pyrimidin-5-yl)-1,3,4,5-tetrahydro-2H-pyrido[4,3-b]indol-2-yl}pyrimidine-5-carboxamide],

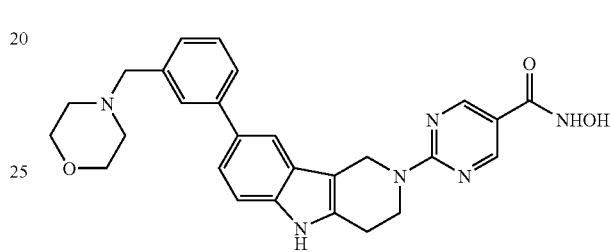

[N-hydroxy-2-{8-[3-(morpholin-4-ylmethyl)phenyl]-1,3,4,5-tetrahydro-2H-pyrido[4,3-b]indol-2-yl}pyrimidine-5-carboxamide],

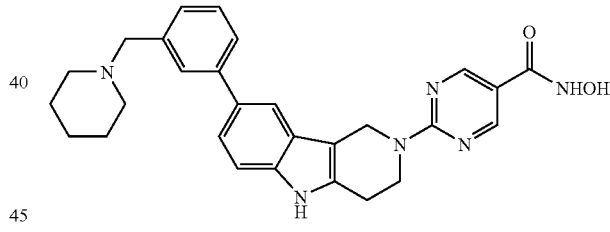

[N-hydroxy-2-{8-[3-(piperidin-1-ylmethyl)phenyl]-1,3,4,5-tetrahydro-2H-pyrido[4,3-b]indol-2-yl}pyrimidine-5-carboxamide],

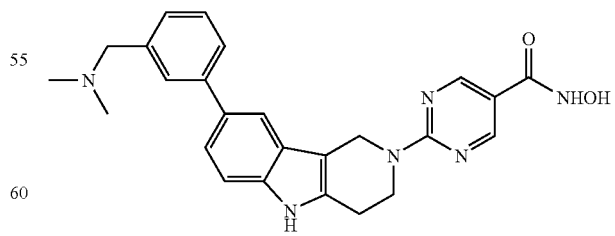

[N-hydroxy-2-{8-[3-(N,N-dimethylaminomethyl)phenyl]-1,3,4,5-tetrahydro-2H-pyrido[4,3-b]indol-2-yl}pyrimidine-5-carboxamide],

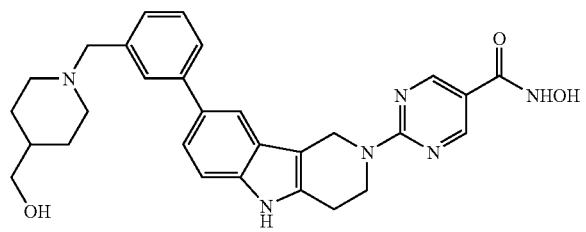

[N-hydroxy-2-{8-[3-((4-hydroxymethylpiperidin-1-yl)methyl)phenyl]-1,3,4,5-tetrahydro-2H-pyrido[4,3-b]indol-2-yl}pyrimidine-5-carboxamide],

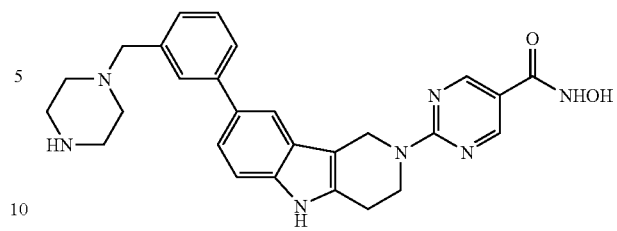

[N-hydroxy-2-{8-[3-(piperazin-1-ylmethyl)phenyl]-1,3,4,5-tetrahydro-2H-pyrido[4,3-b]indol-2-yl}pyrimidine-5-carboxamide],

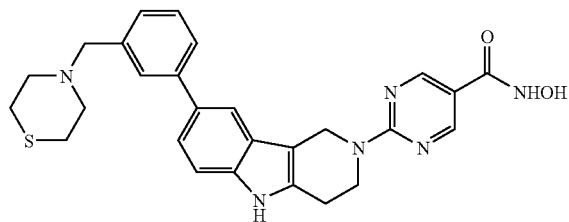

[N-hydroxy-2-{8-[3-(thiomorpholin-4-ylmethyl)phenyl]-1,3,4,5-tetrahydro-2H-pyrido[4,3-b]indol-2-yl}pyrimidine-5-carboxamide],

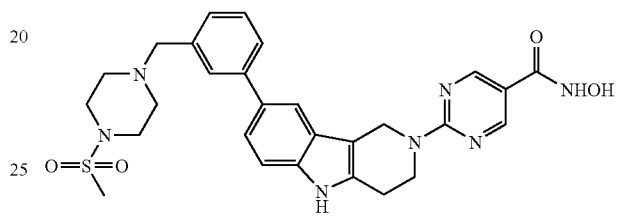

[N-hydroxy-2-{8-[3-((4-(methylsulfonyl)piperazin-1-yl)methyl)phenyl]-1,3,4,5-tetrahydro-2H-pyrido[4,3-b]indol-2-yl}pyrimidine-5-carboxamide],

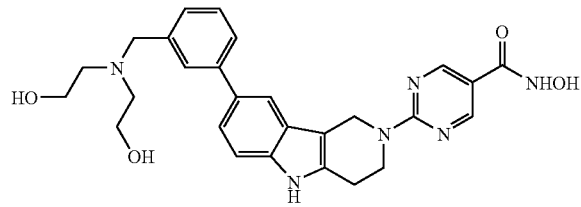

[N-hydroxy-2-{8-[3-(N,N-di(2-hydroxyethyl)aminomethyl)phenyl]-1,3,4,5-tetrahydro-2H-pyrido[4,3-b]indol-2-yl}pyrimidine-5-carboxamide],

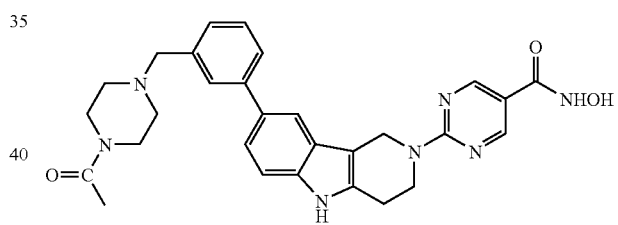

[N-hydroxy-2-{8-[3-((4-acetylpiperazin-1-yl)methyl)phenyl]-1,3,4,5-tetrahydro-2H-pyrido[4,3-b]indol-2-yl}pyrimidine-5-carboxamide],

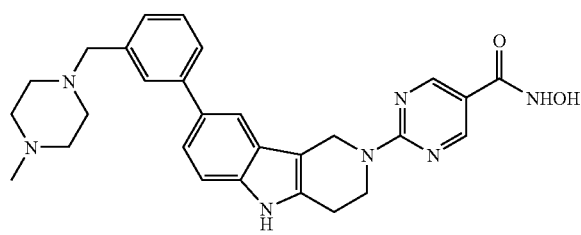

[N-hydroxy-2-{8-[3-((4-methylpiperazin-1-yl)methyl)phenyl]-1,3,4,5-tetrahydro-2H-pyrido[4,3-b]indol-2-yl}pyrimidine-5-carboxamide],

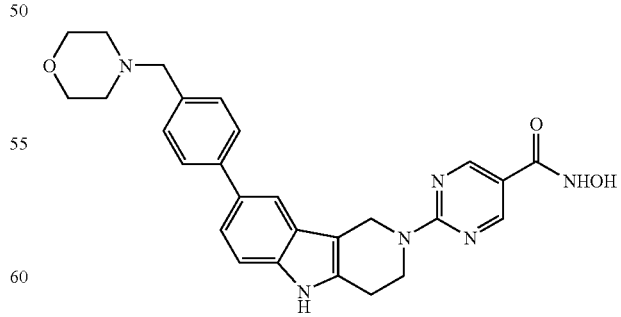

[N-hydroxy-2-{8-[4-(morpholin-4-ylmethyl)phenyl]-1,3,4,5-tetrahydro-2H-pyrido[4,3-b]indol-2-yl}pyrimidine-5-carboxamide],

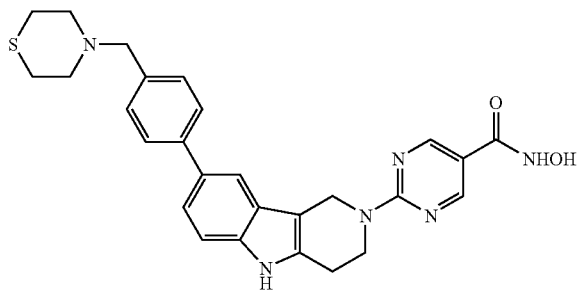

[N-hydroxy-2-{8-[4-(thiomorpholin-4-ylmethyl)phenyl]-1,3,4,5-tetrahydro-2H-pyrido[4,3-b]indol-2-yl}pyrimidine-5-carboxamide],

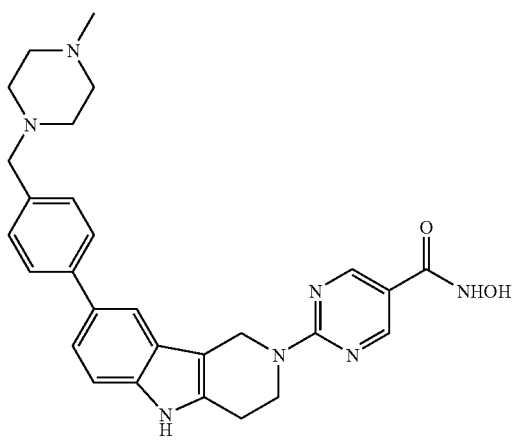

[N-hydroxy-2-{8-[4-((4-methylpiperazin-1-yl)methyl)phenyl]-1,3,4,5-tetrahydro-2H-pyrido[4,3-b]indol-2-yl}pyrimidine-5-carboxamide],

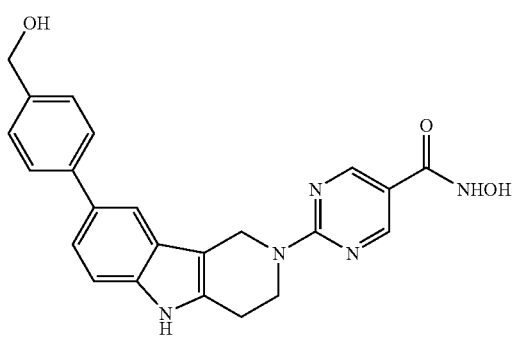

[N-hydroxy-2-{8-[4-(hydroxymethyl)phenyl]-1,3,4,5-tetrahydro-2H-pyrido[4,3-b]indol-2-yl}pyrimidine-5-carboxamide],

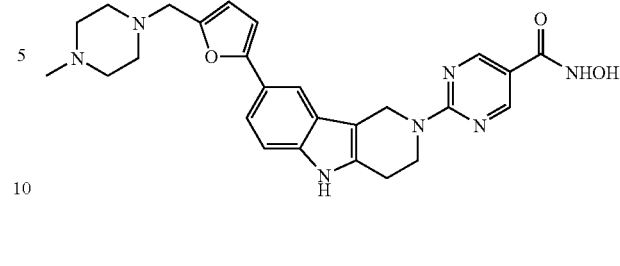

[N-hydroxy-2-{8-[5-((4-methylpiperazin-1-yl)methyl)-2-furyl]-1,3,4,5-tetrahydro-2H-pyrido[4,3-b]indol-2-yl}pyrimidine-5-carboxamide],

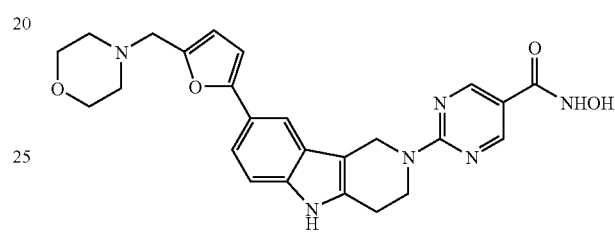

[N-hydroxy-2-{8-[5-(morpholin-4-yl)methyl-2-furyl]-1,3,4,5-tetrahydro-2H-pyrido[4,3-b]indol-2-yl}pyrimidine-5-carboxamide],

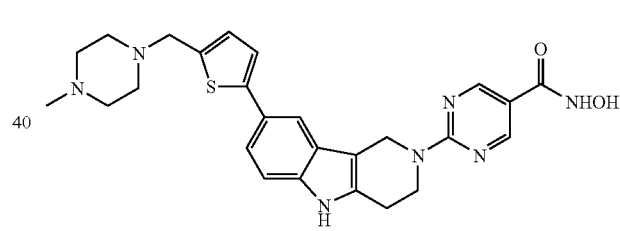

[N-hydroxy-2-{8-[5-((4-methylpiperazin-1-yl)methyl)-thien-2-yl]-1,3,4,5-tetrahydro-2H-pyrido[4,3-b]indol-2-yl}pyrimidine-5-carboxamide],

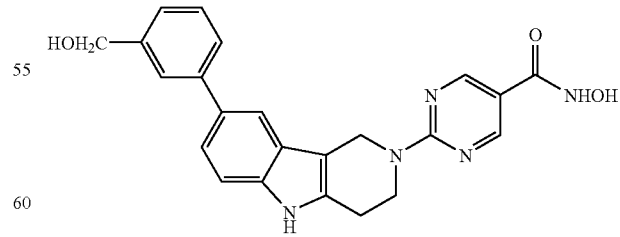

[N-hydroxy-2-{8-[3-(hydroxymethyl)phenyl]-1,3,4,5-tetrahydro-2H-pyrido[4,3-b]indol-2-yl}pyrimidine-5-carboxamide],

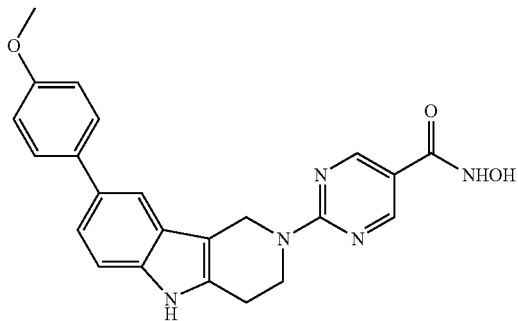

[N-hydroxy-2-{8-[4-methoxyphenyl]-1,3,4,5-tetrahydro-2H-pyrido[4,3-b]indol-2-yl}pyrimidine-5-carboxamide],

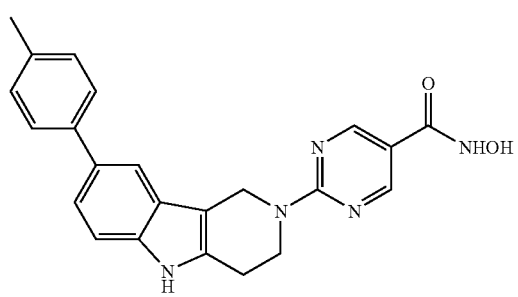

[N-hydroxy-2-{8-[4-methylphenyl]-1,3,4,5-tetrahydro-2H-pyrido[4,3-b]indol-2-yl}pyrimidine-5-carboxamide],

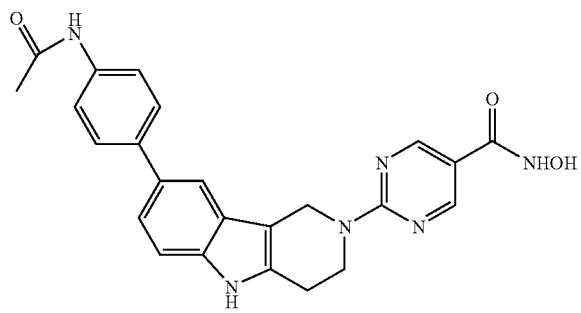

[N-hydroxy-2-{8-[4-(N-acetamido)phenyl]-1,3,4,5-tetrahydro-2H-pyrido[4,3-b]indol-2-yl}pyrimidine-5-carboxamide],

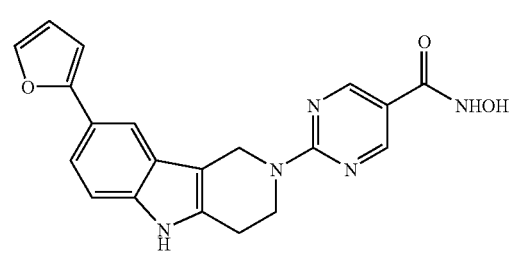

[N-hydroxy-2-{8-(fur-2-yl)-1,3,4,5-tetrahydro-2H-pyrido[4,3-b]indol-2-yl}pyrimidine-5-carboxamide],

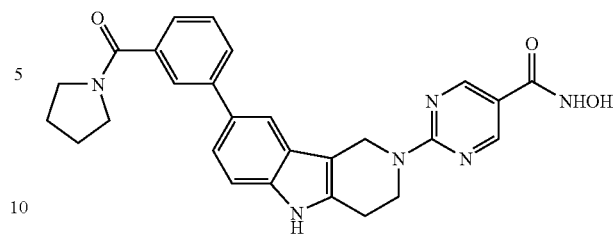

[N-hydroxy-2-{8-[3-(pyrrolidin-1-ylcarbonyl)phenyl]-1,3,4,5-tetrahydro-2H-pyrido[4,3-b]indol-2-yl}pyrimidine-5-carboxamide],

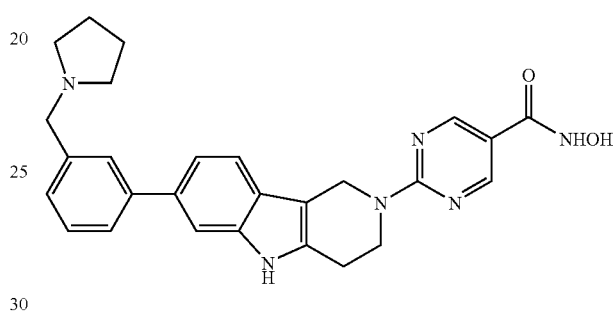

[N-hydroxy-2-{7-[3-(pyrrolidin-1-ylmethyl)phenyl]-1,3,4,5-tetrahydro-2H-pyrido[4,3-b]indol-2-yl}pyrimidine-5-carboxamide],

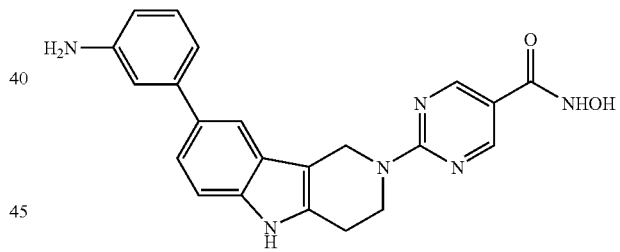

[N-hydroxy-2-{8-[3-aminophenyl]-1,3,4,5-tetrahydro-2H-pyrido[4,3-b]indol-2-yl}pyrimidine-5-carboxamide],

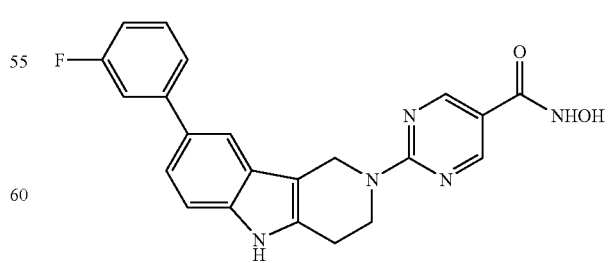

[N-hydroxy-2-{8-[3-fluorophenyl]-1,3,4,5-tetrahydro-2H-pyrido[4,3-b]indol-2-yl}pyrimidine-5-carboxamide],

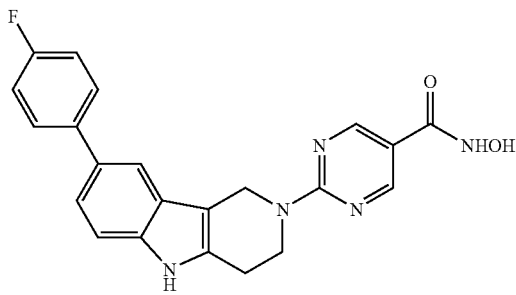

[N-hydroxy-2-{8-[4-fluorophenyl]-1,3,4,5-tetrahydro-2H-pyrido[4,3-b]indol-2-yl}pyrimidine-5-carboxamide],

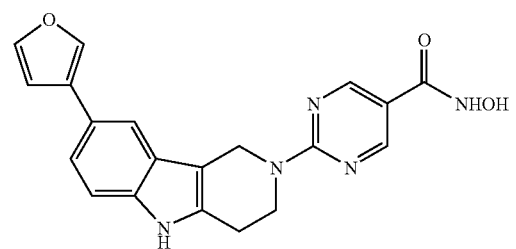

[N-hydroxy-2-{8-[fur-3-yl]-1,3,4,5-tetrahydro-2H-pyrido[4,3-b]indol-2-yl}pyrimidine-5-carboxamide],

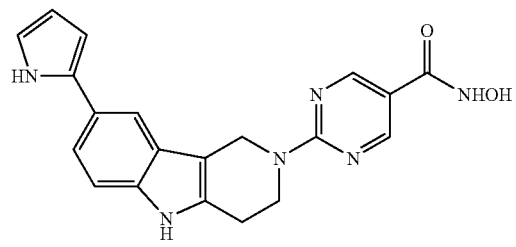

[N-hydroxy-2-{8-[1H-pyrrol-2-yl]-1,3,4,5-tetrahydro-2H-pyrido[4,3-b]indol-2-yl}pyrimidine-5-carboxamide],

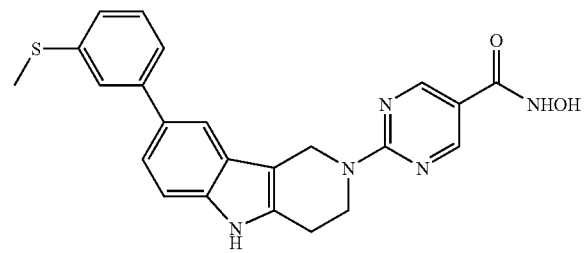

[N-hydroxy-2-{8-[3-(methylthio)phenyl]-1,3,4,5-tetrahydro-2H-pyrido[4,3-b]indol-2-yl}pyrimidine-5-carboxamide],

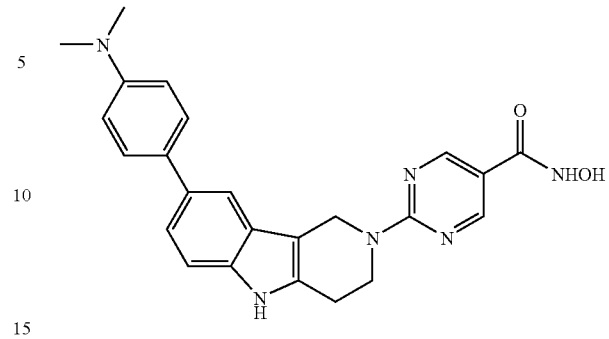

[N-hydroxy-2-{8-[4-dimethylaminophenyl]-1,3,4,5-tetrahydro-2H-pyrido[4,3-b]indol-2-yl}pyrimidine-5-carboxamide],

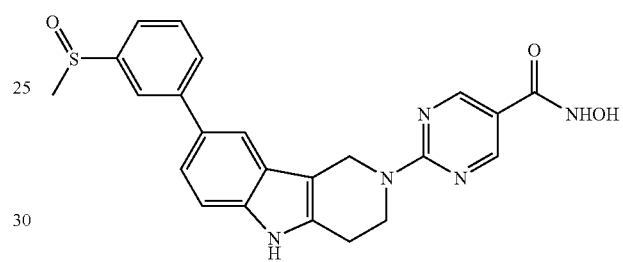

[N-hydroxy-2-{8-[3-(methylsulfinyl)phenyl]-1,3,4,5-tetrahydro-2H-pyrido[4,3-b]indol-2-yl}pyrimidine-5-carboxamide],

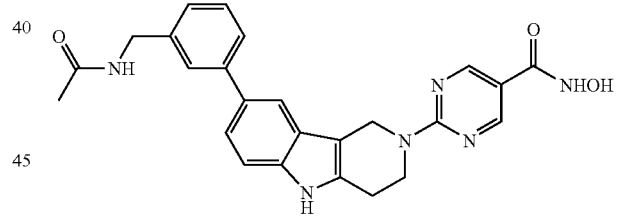

[N-hydroxy-2-{8-[3-(N-acetamidomethyl)phenyl]-1,3,4,5-tetrahydro-2H-pyrido[4,3-b]indol-2-yl}pyrimidine-5-carboxamide],

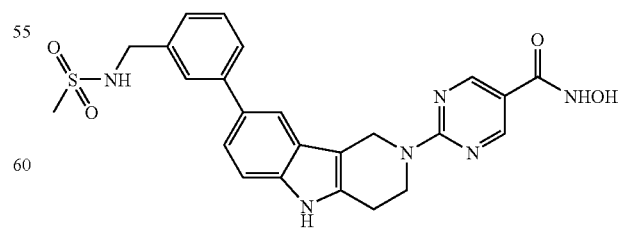

[N-hydroxy-2-{8-[3-(N-methylsulfonamidomethyl)phenyl]-1,3,4,5-tetrahydro-2H-pyrido[4,3-b]indol-2-yl}pyrimidine-5-carboxamide],

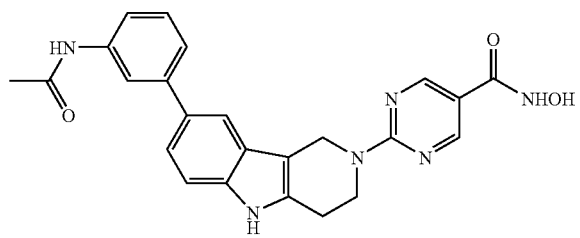

[N-hydroxy-2-{8-[3-(N-acetamido)phenyl]-1,3,4,5-tetrahydro-2H-pyrido[4,3-b]indol-2-yl}pyrimidine-5-carboxamide],

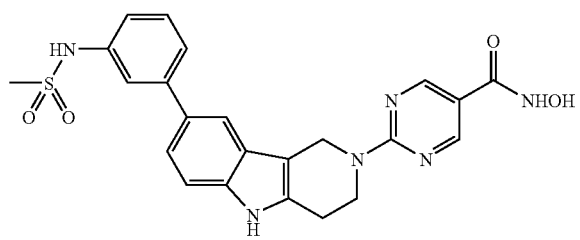

[N-hydroxy-2-{8-[3-(N-methylsulfonamido)phenyl]-1,3,4,5-tetrahydro-2H-pyrido[4,3-b]indol-2-yl}pyrimidine-5-carboxamide],

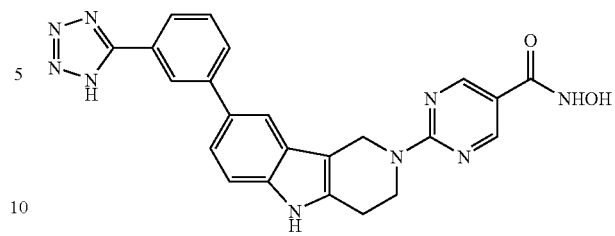

[N-hydroxy-2-{8-[3-(1H-tetrazol-5-yl)phenyl]-1,3,4,5-tetrahydro-2H-pyrido[4,3-b]indol-2-yl}pyrimidine-5-carboxamide] or

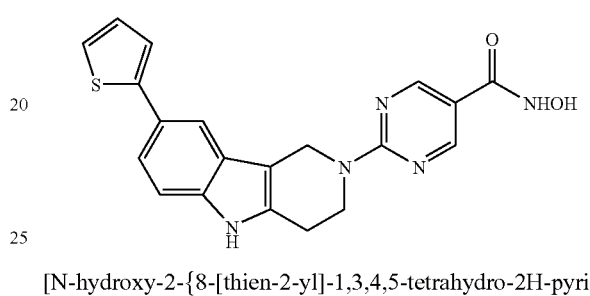

[N-hydroxy-2-{8-[thien-2-yl]-1,3,4,5-tetrahydro-2H-pyrido[4,3-b]indol-2-yl}pyrimidine-5-carboxamide].

8. A pharmaceutical composition comprising an effective amount of one or more compounds according to claim 1 or claim 4 and a pharmaceutically inert carrier.

* * * * *